US008637289B2

(12) United States Patent
Anthony et al.

(10) Patent No.: US 8,637,289 B2

(45) Date of Patent: Jan. 28, 2014

(54) EXPRESSION OF HEXOSE KINASE IN RECOMBINANT HOST CELLS

(75) Inventors: Larry Cameron Anthony, Aston, PA (US); Arthur Leo Kruckeberg, Wilmington, DE (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 12/980,607

(22) Filed: Dec. 29, 2010

(65) Prior Publication Data

US 2012/0015416 A1 Jan. 19, 2012

Related U.S. Application Data

(60) Provisional application No. 61/290,639, filed on Dec. 29, 2009.

(51) Int. Cl.
*C12N 9/12* (2006.01)
*C12N 1/00* (2006.01)

(52) U.S. Cl.
USPC .......................................... 435/194; 435/254.1

(58) Field of Classification Search
USPC ................................................ 435/194, 254.1
See application file for complete search history.

(56) References Cited

U.S. PATENT DOCUMENTS

| | | | |
|---|---|---|---|
| 4,683,202 | A | 7/1987 | Mullis et al. |
| 7,851,188 | B2 | 12/2010 | Donaldson et al. |
| 7,932,063 | B2 | 4/2011 | Dunson et al. |
| 2005/0059136 | A1 | 3/2005 | van Maris et al. |
| 2007/0031918 | A1 | 2/2007 | Dunson et al. |
| 2007/0031950 | A1 | 2/2007 | Winkler |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2008/0261230 | A1 | 10/2008 | Liao et al. |
| 2009/0155870 | A1 | 6/2009 | Donaldson et al. |
| 2009/0163376 | A1 | 6/2009 | Li et al. |
| 2009/0269823 | A1 | 10/2009 | Bramucci et al. |
| 2009/0305363 | A1 | 12/2009 | Anthony |
| 2010/0081154 | A1 | 4/2010 | Flint et al. |
| 2010/0081179 | A1 | 4/2010 | Anthony et al. |
| 2010/0120105 | A1 | 5/2010 | Anthony et al. |
| 2010/0197519 | A1 | 8/2010 | Li et al. |
| 2011/0124060 | A1 | 5/2011 | Anthony et al. |
| 2011/0136192 | A1 | 6/2011 | Paul et al. |
| 2012/0156735 | A1 | 6/2012 | Dauner et al. |
| 2012/0237988 | A1 | 9/2012 | Anthony et al. |

FOREIGN PATENT DOCUMENTS

| | | |
|---|---|---|
| EP | 1728854 | 6/2006 |
| WO | 9826079 | 6/1998 |
| WO | 0061722 | 10/2000 |
| WO | 2004099425 | 11/2004 |
| WO | 2008080124 | 7/2008 |
| WO | 2009046370 | 4/2009 |
| WO | 2009086423 | 7/2009 |

OTHER PUBLICATIONS

Bisson et al. 1983; Involvement of kinases in glucose and fructose uptake by *Saccharamyces cerevisiae*. PNAS 80: 1730-1734.*

Bonini et al. 2003; Uncoupling of the glucose growth defect and deregulation of glycolysis in *Saccharomyces cerevisiae* tps1 mutants expressing trehalose-6-phophate-insensitive hexokinase from *Schizosaccharomyces pombe*. Biochimica et Biophysica Acta 1606(1-3): 83-93.*

Karp et al. 2004; Cloning and biochemical characterization of hexokinase from the methylotrophic yeast *Hansenula polymorpha*. Current Genetics. 44: 268-276.*

Laht et al. 2002; Cloning and characterization of glucokinase from methylotrophic yeast *Hansenula polymorpha*: different effects on glucose repression in *H. polymorpha* and *Saccharomyces cerevisiae*. Gene. 296: 195-203.*

Petit et al. 2000; Hexokinase regulates kinetics of glucose transport and expression of genes encoding hexose transporters in *Saccharamyces cerevisiae*. J. Bacteriology. 182(23): 6815-6818.*

Prior et al. 1993; The hexokinase gene is required for transcriptional regulation of glucose transporter gene TAG1 in *Kluyveromyces lactis*. Molecular and Cellular Biology. 13(7): 3882-3889.*

Riera et al. 2008; Human pancreatic _-cell glucokinase: subcellular localization and glucose repression signaling function in yeast cell. Biochemical Journal. 415: 233-239.*

Rose 1995; Molecular and biochemical characterization of the hexokinase from the starch-utilizing yeast *Schwanniomyces occidentalis*. Current Genetics 27: 330-338.*

W. R. Pearson, Comput. Methods Genome Res., [Proc. Int. Symp.] (1994) Meeting Date 1992, 111 20. Editor(s): Suhai, Sandor. Plenum: New York, NY).

Sambrook, J., Fritsch, E. F. and Maniatis, T. Molecular Cloning: A Laboratory Manual, 2nd ed., Cold Spring Harbor Laboratory: Cold Spring Harbor, NY (1989), particularly Chapter 11 and Table 11.1.

Ullmann's Encyclopedia of Industrial Chemistry, 6th edition, 2003, Wiley-VCH Verlag GmbH and Co., Weinheim, Germany, vol. 5, pp. 716-719.

Voloch et al., "Fermentation Derived 2,3-Butanediol," in Comprehensive Biotechnology, Pergamon Press Ltd., England, vol. 2, Section 3:933-947 (1986).

U.S. Appl. No. 61/290,636, filed Dec. 29, 2009 now U.S. Appl. No. 12/980,597, filed Dec. 29, 2009.

U.S. Appl. No. 61/305,333, filed Feb. 17, 2010 now U.S. Appl. No. 13/029,558, filed Feb. 17, 2011.

U.S. Appl. No. 61/356,379, filed Jun. 18, 2010.

U.S. Appl. No. 61/380,563, filed Sep. 7, 2010.

U.S. Appl. No. 12/893,077, filed Sep. 29, 2010.

U.S. Appl. No. 12/893,089, filed Sep. 29, 2010.

(Continued)

*Primary Examiner* — Karen Cochrane Carlson

(74) *Attorney, Agent, or Firm* — Christine M. Lhulier

(57) ABSTRACT

The invention relates to a recombinant host cell having (a) a modification in an endogenous polynucleotide encoding a polypeptide having dual-role hexokinase activity; (b) a heterologous polynucleotide encoding a polypeptide having hexose kinase activity; and optionally (c) a modification in an endogenous polynucleotide encoding a polypeptide having pyruvate decarboxylase activity. Additionally, the invention relates to methods of making and using such recombinant host cells including, for example, methods of increasing glucose consumption, methods of improving redox balance, and/or methods of increasing the production of a product of a pyruvate-utilizing pathway.

30 Claims, 3 Drawing Sheets

(56) References Cited

OTHER PUBLICATIONS

Figure 1A:
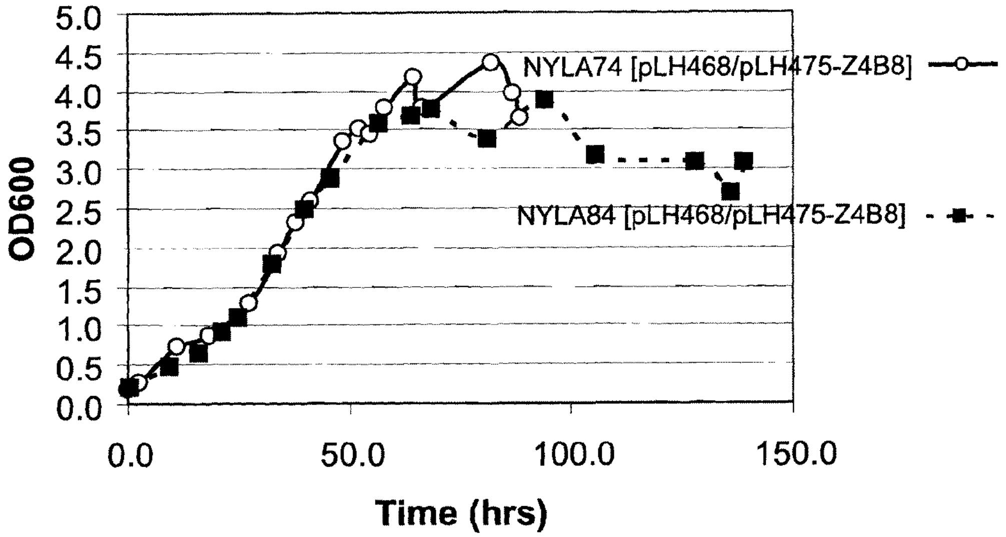

International Search Report and Written Opinion of corresponding PCT/US2010/062397 patent application mailed Apr. 5, 2011.
Laht et al., "Closing and characterization of glucokinase from a methylotrophic yeast *Hansenula polymorpha*: different effects on glucose repression in *H. polymorpha* and *Saccharomyces cerevisiae*", Gene 296 (202) pp. 195-203.
Prior et al., "The hexokinase gene is required for transcriptional regulation of the glucose transporter gene RAG1 in *Kluyveromyces lactis*" Molecular and Cellular Biology, Jul. 1993, p. 3882-3889.
GenBank Accession No. Z72775.1.
GenBank Accession No. CAA96973.1.
GenBank Accession No. AJ011524.1.
GenBank Accession No. CAA09674.1.
GenBank Accession No. S78714.1.
GenBank Accession No. AAB34892.1.
GenBank Accession No. NM_000162.3.
GenBank Accession No. NP_000153.1.
GenBank Accession No. NC_006040.
GenBank Accession No. XP_453567.
GenBank Accession No. AY034434.
GenBank Accession No. AAK60444.
GenBank Accession No. X92895.
GenBank Accession No. NP_593865.
Lopez, et al. Isocitrate lyase of the yeast *Kluyveromyces lactis* is subject to glucose repression but not to catabolite inactivation, Current Genetics, Jan. 2004, pp. 305-316, vol. 44.
Dong, et al., Glucose represses the lactose-galactose regulon in *Kluyveromyces lactis* through a SNF1 and MIG1—dependent pathway that modulates galactokinase (GAL1) gene expression, Nucleic Acids Research, Sep. 15, 1997, pp. 3657-3664, vol. 25, No. 18.
Suleau, et al., Transcriptomic Analysis of Extensive Changes in Metabolic Regulation in *Kluyveromyces lactis* Strains, Eukaryotic Cell, Aug. 2006, pp. 1360-1370, vol. 5, No. 8.
Elbing, et al., Role of hexose transport in control of glycolytic flux in *Saccharomyces cerevisiae*, Applied and Environmental Microbiology, vol. 70, No. 9, Sep. 2004, pp. 5323-5330.
Flick, et al., GRRI of *Saccharomyces cerevisiae* is required for glucose repression and encodes a protein with leucine-rich repeats, Molecular and Cellular Biology, vol. 11, No. 10, Oct. 1991, pp. 5101-5112.
Gancedo, Yeast carbon catabolite repression, Microbiology and Molecular Biology Reviews, vol. 62, No. 2, Jun. 1998, pp. 334-361.
Godon, et al., Branched-chain amino acid biosynthesis genes in *Lactococcus lactis* subsp. lactis, Journal of Bacteriology, Oct. 1992, vol. 174. No. 20, pp. 6580-6589.
Gollop, et al., Physiological implications of the substrate specificities of acetohydroxy acid synthases from vaired organisms, Journal of Bacteriology, Jun. 1990, vol. 172, No. 6, pp. 3444-3449.
Henricsson, et al., Engineering of a novel *Saccharomyces cerevisiae* wine strain with a respiratory phenotype at high external glucose concentrations, Applied and Environmental Microbiology, vol. 71, No. 10, Oct. 2005, pp. 6185-6192.
Holtzclaw, et al., Degradative acetolactate synthase of *Bacillus subtilis*: purification and properties, Journal of Bacteriology, 1975, vol. 121, No. 3, pp. 917-922.
Ma, et al., Plasmid construction by homologous recombination in yeast, Gene, 1987, 58, pp. 201-216.
Ye, et al. Growth and glucose repression are controlled by glucose transport in *Saccharomyces cerevisiae* cells containing only one glucose transporter, Journal of Bacteriology, vol. 181, No. 15, Aug. 1999, pp. 4673-4675.
Aden et al. Lignocellulosic Biomass to Ethanol Process Design and Economics Utilizing Co-current Dilute Acid Prehydrolysis and Enzymatic Hydrolysis for Corn Stover, Report NREL/TP-510-32438, National Renewable Energy Laboratory, Jun. 2002.
vanMaris, et al., Directed Evolution of Pyruvate Decarboxylase-Negative *Saccharomyces cerevisiae* Yielding a C2-Independent, Glucose-Tolerant, and Pyruvate-Hyperproducing Yeast, Applied and Environmental Microbiology, 2004, vol. 70, No. 1, pp. 159-166.
Stewart, et al. A Chemist's Perspective on the Use of Genetically Engineered Microbes as Reagents for Organic Synthesis, Biotechnology and Genetic Engineering Reviews, 1997, vol. 14: 67-143.
Ahuatzi et al., "The glucose-regulated nuclear localization of hexokinase 2 in *Saccharomyces cerevisiae* is mig1-dependent", J. Biol. Chem. 279(14):14440-6 (2004).
Altschul et al., "Basic Local Alignment Search Tool", J. Mol. Biol., (1990) vol. 215, pp. 403-410.
Bianchi et al., "The 'petite-negative' yeast *Kluyveromyces lactis* has a single gene expressing pyruvate decarboxylase activity", Molecular Microbiology (1996) vol. 19(1), pp. 27-36.
Carlini et al., "Guerbet condensation of methanol with n-propanol to isobutyl alcohol over heterogeneous copper chromite/Mg—Al mixed oxides catalysts", J. Mol. Catal. A: Chem., vol. 220 (2004) pp. 215-220.
Deshpande, "Ethanol Production from Cellulose by Coupled Saccharification/Fermentation using *Saccharomyces cerevisiae* and Cellulase Complex from *Sclerotium rolfsii* UV-8 Mutant*", Applied Biochemistry and Biotechnology, vol. 36 (1992) pp. 227-234.
Diderich, et al., "Physiological properties of *Saccharomyces cerevisiae* from which hexokinase II has been deleted", Applied and Environmental Microbiology, vol. 67, No. 4, Apr. 2001, pp. 1587-1593.
Durre, "New insights and novel developments in clostridial acetone/butanol/isopropanol fermentation", Appl. Microbiol. Biotechnol. (1998) vol. 49, pp. 639-648.
Flikweert et al., "Pyruvate decarboxylase: an indispensable enzyme for growth of *Saccharomyces cerevisiae* on glucose", Yeast (1996) vol. 12, pp. 247-257.
Groot et al., "Technologies for butanol recovery integrated with fermentations", Process Biochemistry, vol. 27 (1992) pp. 61-75.
Guo et al., "Pervaporation study on the dehydration of aqueous butanol solutions: a comparison of flux vs. permeance, separation factor vs. selectivity", Journal of Membrane Science 245 (2004) pp. 199-210.
Higgins et al., "Fast and sensitive multiple sequence alignments on a microcomputer", CABIOS Communications, vol. 5, No. 2 (1989) pp. 151-153.
Higgins et al., "Clustal V: improved software for multiple sequence alignment", CABIOS, vol. 8, No. 2 (1992) pp. 189-191.
Hohmann, "Characterisation of PDC2, a gene necessary for high level expression of pyruvate decarboxylase structural genes in *Saccharomyces cerevisiae*", Mol. Gen. Genet. (1993) vol. 241, pp. 657-666.
Horton et al., "Engineering hybrid genes without the use of restriction enzymes: gene splicing by overlap extension", Gene, 77 (1989) pp. 61-68.
Ishida et al., "Efficient production of L-lactic acid by metabolically engineered *Saccharomyces cerevisiae* with a genome-integrated L-lactate dehydrogenase gene", Applied and Environmental Microbiology, vol. 71, No. 4, Apr. 2005, pp. 1964-1970.
Kim et al., "Metabolic engineering of the nonmevalonate isopentenyl diphosphate synthesis pathway in *Escherichia coli* enhances lycopene production", Biotechnology and Bioengineering, vol. 72, No. 4, Feb. 20, 2001, pp. 408-415.
Lobo et al., "Yeast hexokinase genetics", Genetics, vol. 86, pp. 727-744 (1977).
Martin et al., "Engineering a mevalonate pathway in *Escherichia coli* for production of terpenoids", Nature Biotechnology, vol. 21, No. 7, Jul. 2003, pp. 796-802.
Mnaimneh et al., "Exploration of essential gene functions via titratable promoter alleles", Cell, vol. 118 (2004) pp. 31-44.
Nevoigt et al., "Reduced pyruvate decarboxylase and increased glycerol-3-phosphate dehydrogenase [NAD+] levels enhance glycerol production in *Saccharomyces cerevisiae*", Yeast, vol. 12 (1996) pp. 1331-1337.
Nystrom et al., "Reduction of organic compounds by lithium aluminum hydride", J. Am. Chem. Soc. (1947) vol. 69, p. 1198.
Rossell et al., "Mixed and diverse metabolic and gene-expression regulation of the glycolytic and fermentative pathways in response to a HXK2 deletion of *Saccharomyces cerevisiae*", FEMS Yeast Research, vol. 8 (2008) pp. 155-164.

(56) References Cited

OTHER PUBLICATIONS

Sutter et al., "Proliferation and metabolic significance of peroxisomes in *Candida boidinii* during growth on D-alanine or oleic acid as the sole carbon source", Arch. Microbial., vol. 153, pp. 485 489 (1990).

Tabor et al., "A bacteriophage T7 RNA polymerase/promoter system for controlled exclusive expression of specific genes", Proceedings of the National Academy of Sciences USA, vol. 82 (1985) pp. 1074-1078.

Vojtek et al., "Phosphorylation of yeast hexokinases", Eur. J. Biochem., vol. 190 pp. 371-375 (1990).

Wach et al., "New heterologous modules for classical or PCR-based gene disruptions in *Saccharomyces cerevisiae*", Yeast, vol. 10 (1994) pp. 1793-1808.

Walker et al., "Isothermal in vitro amplification of DNA by a restriction enzyme/DNA polymerase system", Proceedings of the National Academy of Sciences USA, vol. 89, Jan. 1992, pp. 392-396.

Winzeler, et al., "Functional characterization of the *S. cerevisiae* genome by gene deletion and parallel anaylsis", Science vol. 285, pp. 901-906 (1999).

Zelle et al., "Malic Acid Production by *Saccharomyces cerevisiae*: Engineering of Pyruvate Carboxylation, Oxaloacetate Reduction, and Malate Export", Applied and Environmental Microbiology, vol. 74, No. 9, May 2008, pp. 2766-2777.

Ausubel, F. M. et al., Current Protocols in Molecular Biology, published by Greene Publishing Assoc. and Wiley Interscience (1987).

Bellion et al., Microb. Growth C1 Compd., [Int. Symp.], 7th (1993), 415 32, Editor(s): Murrell, J. Collin; Kelly, Don. P. Publisher: Intercept, Andover, UK.

Methods in Yeast Genetics, 2005, Cold Spring Harbor Laboratory Press, Cold Spring Harbor, NY, pp. 201-202.

* cited by examiner

EXPRESSION OF HEXOSE KINASE IN RECOMBINANT HOST CELLS

CROSS-REFERENCE TO RELATED APPLICATIONS

This application claims the benefit of priority of U.S. Provisional Application No. 61/290,639 filed Dec. 29, 2009, the entirety of which is incorporated herein by reference.

FIELD OF THE INVENTION

The invention relates generally to the field of industrial microbiology and alcohol production. More specifically, the invention relates to a recombinant host cell comprising (a) a modification in an endogenous polynucleotide encoding a polypeptide having dual-role hexokinase activity in said recombinant host cell; (b) a heterologous polynucleotide encoding a polypeptide having hexose kinase activity; and optionally (c) a modification in an endogenous polynucleotide encoding a polypeptide having pyruvate decarboxylase activity. Additionally, the invention relates to methods of making and using such a recombinant host cell including, for example, methods of increasing glucose consumption, methods of enhancing redox balance, and methods of increasing the production of a product of a pyruvate-utilizing pathway.

BACKGROUND OF THE INVENTION

Global demand for liquid transportation fuel is projected to strain the ability to meet certain environmentally driven goals, for example, the conservation of oil reserves and limitation of greenhouse gas emissions. Such demand has driven the development of technology which allows utilization of renewable resources to mitigate the depletion of oil reserves and to minimize greenhouse gas emissions.

Butanol is an important industrial chemical, useful as a fuel additive, as a feedstock chemical in the plastics industry, and as a food grade extractant in the food and flavor industry. Each year 10 to 12 billion pounds of butanol are produced by petrochemical means and the need for this commodity chemical will likely increase in the future.

Methods for the chemical synthesis of isobutanol, an isomer of butanol, are known, such as oxo synthesis, catalytic hydrogenation of carbon monoxide (Ullmann's Encyclopedia of Industrial Chemistry, 6th edition, 2003, Wiley-VCH Verlag GmbH and Co., Weinheim, Germany, Vol. 5, pp. 716-719) and Guerbet condensation of methanol with n-propanol (Carlini et al., *J. Molec. Catal. A: Chem.* 220:215-220, 2004). These processes use starting materials derived from petrochemicals, are generally expensive, and are not environmentally friendly. The production of isobutanol from plant-derived raw materials would minimize greenhouse gas emissions and would represent an advance in the art.

2-Butanone, also referred to as methyl ethyl ketone (MEK), is a widely used solvent and is the most important commercially produced ketone, after acetone. It is used as a solvent for paints, resins, and adhesives, as well as a selective extractant, activator of oxidative reactions, and it can be chemically converted to 2-butanol by reacting with hydrogen in the presence of a catalyst (Nystrom, R. F. and Brown, W. G. (*J. Am. Chem. Soc.* (1947) 69:1198). 2,3-butanediol can be used in the chemical synthesis of butene and butadiene, important industrial chemicals currently obtained from cracked petroleum, and esters of 2,3-butanediol can be used as plasticizers (Voloch et al., "Fermentation Derived 2,3-Butanediol," in *Comprehensive Biotechnology*, Pergamon Press Ltd., England, Vol. 2, Section 3:933-947 (1986)).

Microorganisms can be engineered for the expression of biosynthetic pathways that utilize pyruvate to produce, for example, 2,3-butanediol, 2-butanone, 2-butanol and isobutanol. U.S. Patent Application Publication No. US 2007/0092957 A1 discloses the engineering of recombinant microorganisms for production of isobutanol. U.S. Patent Application Publication Nos. US 2007/0259410 A1 and US 2007/0292927 A1 disclose the engineering of recombinant microorganisms for production of 2-butanone or 2-butanol. Multiple pathways are disclosed for biosynthesis of isobutanol and 2-butanol, all of which initiate with cellular pyruvate. Butanediol is an intermediate in the 2-butanol pathway disclosed in U.S. Patent Application Publication No. US 2007/0292927 A1.

Engineering recombinant host cells for increased availability of pyruvate and/or for reduced glucose repression allows for increased formation of the products of pyruvate-utilizing biosynthetic pathways. For example, reducing glucose repression has been used to improve the respiratory capacity of yeast and to increase biomass production. Also, International Publication No. WO 1998/26079 A1 discloses overexpression of the Hap1 transcription factor to reduce glucose repression results in increased respiratory capacity and increased biomass production. European Patent No. 1728854 discloses a process for biomass production using yeast overexpressing the Hap1 transcription factor grown in aerobic conditions.

Functional deletion of the hexokinase 2 gene has been used to reduce glucose repression and to increase the availability of pyruvate for utilization in biosynthetic pathways. For example, International Publication No. WO 2000/061722 A1 discloses the production of yeast biomass by aerobically growing yeast having one or more functionally deleted hexokinase 2 genes or analogs. In addition, Rossell et al. (*Yeast Research* 8:155-164 (2008)) found that *Saccharomyces cerevisiae* with a deletion of the hexokinase 2 gene showed 75% reduction in fermentative capacity, defined as the specific rate of carbon dioxide production under sugar-excess and anaerobic conditions. After starvation, the fermentation capacity was similar to that of a strain without the hexokinase 2 gene deletion. Diderich et al. (*Applied and Environmental Microbiology* 67:1587-1593 (2001)) found that *S. cerevisiae* with a deletion of the hexokinase 2 gene had lower pyruvate decarboxylase activity.

Functional deletion of the pyruvate decarboxylase gene has also been used to increase the availability of pyruvate for utilization in biosynthetic pathways. For example, U.S. Application Publication No. US 2007/0031950 A1 discloses a yeast strain with a disruption of one or more pyruvate decarboxylase genes and expression of a D-lactate dehydrogenase gene, which is used for production of D-lactic acid. U.S. Application Publication No. US 2005/0059136 A1 discloses glucose tolerant two carbon source independent (GCSI) yeast strains with no pyruvate decarboxylase activity, which may have an exogenous lactate dehydrogenase gene. Nevoigt and Stahl (*Yeast* 12:1331-1337 (1996)) describe the impact of reduced pyruvate decarboxylase and increased NAD-dependent glycerol-3-phosphate dehydrogenase in *Saccharomyces cerevisiae* on glycerol yield. U.S. patent application Ser. No. 12/477,942 discloses increased conversion of pyruvate to acetolactate by engineering yeast for expression of a cytosol-localized acetolactate synthase and substantial elimination of pyruvate decarboxylase activity.

There remains a need to improve redox balance, glucose consumption and/or product formation of a pyruvate-utilizing biosynthetic pathway in recombinant host cells comprising a functional deletion of genes encoding dual-role hexokinases such as the hexokinase 2 gene.

BRIEF SUMMARY OF THE INVENTION

Provided herein are recombinant yeast cells comprising: (a) a modification in an endogenous polynucleotide encoding a polypeptide having dual-role hexokinase activity in the host cell wherein the activity of the polypeptide of (a) is reduced or substantially eliminated; and (b) a heterologous polynucleotide encoding a polypeptide having hexose kinase activity. In embodiments, the recombinant yeast cells have increased glucose consumption rates as compared to yeast cells with (a) but not (b). In embodiments, the modification of (a) is a deletion. In embodiments, the recombinant yeast cells have altered glucose repression as compared to yeast cells with (a) but not (b). In embodiments, the recombinant yeast cell further comprises (c) a modification in an endogenous polynucleotide encoding a polypeptide having pyruvate decarboxylase activity. In embodiments, pyruvate decarboxylase activity is reduced or substantially eliminated. In embodiments, the polypeptide of (a) is HXK2, and the recombinant yeast cell is *S. cerevisiae*. In embodiments, the polypeptide of (a) is RAG5, and the recombinant host cell is *K. lactis*; or the polypeptide of (a) is HPGLK1, and the recombinant host cell is *H. polymorpha*; or the polypeptide of (a) is HXK2, and the recombinant host cell is *S. pombe*. In another aspect of the invention, a polynucleotide or polypeptide of (b) corresponds to Enzyme Commission Number EC 2.7.1.1 and/or corresponds to Enzyme Commission EC 2.7.1.2. In embodiments, the polynucleotide of (b) contains a promoter such that the polypeptide of (b) is conditionally expressed. In embodiments, the conditional promoter comprises a sequence derived from the OLE1 promoter region. In embodiments, the polynucleotide of (b) contains a promoter such that the polypeptide of (b) is constitutively expressed. In embodiments, the heterologous polynucleotide of (b) comprises the polypeptide of (a) with a deletion of a protein interaction domain that prevents function as a transcriptional regulator. In embodiments, the heterologous polynucleotide of (b) encodes a polypeptide that has at least about 85% identity to SEQ ID NO: 2, 115, 117, 119, 4, 6, 8, 121, or 123. In embodiments, the heterologous polynucleotide of (b) comprises i) a promoter region derived from the *S. cerevisiae* ADH1 promoter region or ii) a promoter region having at least about 85% identity to SEQ ID NO: 131. In embodiments, the yeast cell is *S. cerevisiae* and the heterologous polynucleotide of (b) encodes a polypeptide of SEQ ID NO: 4, 6, 8, 121, or 123 or the heterologous polynucleotide of (b) encodes a polypeptide that has at least about 85% identity to SEQ ID NO: 4, 6, 8, 121, or 123. In embodiments, the heterologous polynucleotide of (b) encodes a polypeptide that has at least about 85% identity to SEQ ID NO: 130. In embodiments, the heterologous polynucleotide of (b) comprises a conditional promoter and encodes a polypeptide having at least 85% identity to SEQ ID NO: 4 or SEQ ID NO: 2.

One aspect of the invention relates to a recombinant host cell disclosed herein that expresses a pyruvate-utilizing biosynthetic pathway. In another aspect of the invention, such a pyruvate-utilizing biosynthetic pathway comprises a heterologous polynucleotide. In another aspect of the invention, such a pyruvate-utilizing biosynthetic pathway forms a product selected from 2,3-butanediol, isobutanol, 2-butanol, 1-butanol, 2-butanone, valine, leucine, lactic acid, malate, isoamyl alcohol, and isoprenoids. In another aspect of the invention, such a pyruvate-utilizing biosynthetic pathway is an isobutanol biosynthetic pathway comprising a polynucleotide encoding a polypeptide that catalyzes a substrate to product conversion of (i) pyruvate to acetolactate; (ii) acetolactate to 2,3-dihydroxyisovalerate; (iii) 2,3-dihydroxyisovalerate to 2-ketoisovalerate; (iv) 2-ketoisovalerate to isobutyraldehyde; and/or (v) isobutyraldehyde to isobutanol. In another aspect of the invention, such a pyruvate-utilizing biosynthetic pathway is a 2-butanone biosynthetic pathway comprising a polynucleotide encoding a polypeptide that catalyzes a substrate to product conversion of (i) pyruvate to acetolactate; (ii) acetolactate to acetoin; (iii) acetoin to 2,3-butanediol; and/or (iv) 2,3-butanediol to 2-butanone. In another aspect of the invention, such a pyruvate-utilizing biosynthetic pathway is a 2-butanol biosynthetic pathway comprising a polynucleotide encoding a polypeptide that catalyzes a substrate to product conversion of (i) pyruvate to acetolactate; (ii) acetolactate to acetoin; (iii) acetoin to 2,3-butanediol; (iv) 2,3-butanediol to 2-butanone; and/or (v) 2-butanone to 2-butanol. In another aspect of the invention, such a pyruvate-utilizing biosynthetic pathway is a 1-butanol biosynthetic pathway comprising a polynucleotide encoding a polypeptide that catalyzes a substrate to product conversion of (i) acetyl-CoA to acetoacetyl-CoA; (ii) acetoacetyl-CoA to 3-hydroxybutyryl-CoA; (iii) 3-hydroxybutyryl-CoA to crotonyl-CoA; (iv) crotonyl-CoA to butyryl-CoA; (v) butyryl-CoA to butyraldehyde; and/or (vi) butyraldehyde to 1-butanol.

One aspect of the invention relates to methods for the production of a product selected from 2,3-butanediol, isobutanol, 2-butanol, 1-butanol, 2-butanone, valine, leucine, lactic acid, malic acid, isoamyl alcohol, and isoprenoids comprising (a) growing a recombinant host cell disclosed herein under conditions wherein a product is produced; and (b) optionally recovering the product. In another aspect of the invention, such methods comprise an isobutanol biosynthetic pathway comprising a polynucleotide encoding a polypeptide that catalyzes a substrate to product conversion of (i) pyruvate to acetolactate; (ii) acetolactate to 2,3-dihydroxyisovalerate; (iii) 2,3-dihydroxyisovalerate to 2-ketoisovalerate; (iv) 2-ketoisovalerate to isobutyraldehyde; and/or (v) isobutyraldehyde to isobutanol. In another aspect of the invention, such methods comprise a 2-butanone biosynthetic pathway comprising a polynucleotide encoding a polypeptide that catalyzes a substrate to product conversion of (i) pyruvate to acetolactate; (ii) acetolactate to acetoin; (iii) acetoin to 2,3-butanediol; and/or (iv) 2,3-butanediol to 2-butanone. In another aspect of the invention, such methods comprise a 2-butanol biosynthetic pathway comprising a polynucleotide encoding a polypeptide that catalyzes a substrate to product conversion of (i) pyruvate to acetolactate; (ii) acetolactate to acetoin; (iii) acetoin to 2,3-butanediol; (iv) 2,3-butanediol to 2-butanone; and/or (v) 2-butanone to 2-butanol. In another aspect of the invention, such methods comprise a 1-butanol biosynthetic pathway comprising a polynucleotide encoding a polypeptide that catalyzes a substrate to product conversion of (i) acetyl-CoA to acetoacetyl-CoA; (ii) acetoacetyl-CoA to 3-hydroxybutyryl-CoA; (iii) 3-hydroxybutyryl-CoA to crotonyl-CoA; (iv) crotonyl-CoA to butyryl-CoA; (v) butyryl-CoA to butyraldehyde; and/or (vi) butyraldehyde to 1-butanol.

One aspect of the invention relates to methods of producing a recombinant host cell comprising (i) providing a recombinant host cell comprising a deletion, mutation, and/or substitution in an endogenous polynucleotide encoding a polypeptide having dual-role hexokinase activity; and (ii) transforming a recombinant host cell of (i) with a heterologous polynucleotide encoding a polypeptide having hexose kinase activity. In another aspect of the invention, such methods further comprise (iii) introducing a deletion, mutation, and/or substitution in an endogenous polynucleotide encoding a polypeptide having pyruvate decarboxylase activity.

One aspect of the invention relates to methods of increasing glucose consumption of a recombinant host cell comprising (i) providing a recombinant host cell comprising (a) a modification in an endogenous polynucleotide encoding a polypeptide having dual-role hexokinase activity; and (b) a heterologous polynucleotide encoding a polypeptide having hexose kinase activity; and (ii) growing the recombinant host cell of (i) under conditions wherein the heterologous polynucleotide of (b) is expressed in functional form. In another aspect of the invention, the glucose consumption of such a recombinant host cell is greater than the glucose consumption of a recombinant host cell comprising (a) but not (b).

One aspect of the invention relates to methods of increasing glucose consumption of a recombinant host cell comprising (i) providing a recombinant host cell comprising (a) a modification in an endogenous polynucleotide encoding a polypeptide having dual-role hexokinase activity; (b) a heterologous polynucleotide encoding a polypeptide having hexose kinase activity; and (c) a modification in an endogenous polynucleotide encoding a polypeptide having pyruvate decarboxylase activity; and (ii) growing the recombinant host cell of (i) under conditions wherein the heterologous polynucleotide of (b) is expressed in functional form. In another aspect of the invention, the glucose consumption of such a recombinant host cell is greater than the glucose consumption of a recombinant host cell comprising (a) and (c) but not (b).

One aspect of the invention relates to methods of improving the redox balance of a recombinant host cell comprising (i) providing a recombinant host cell comprising (a) a modification in an endogenous polynucleotide encoding a polypeptide having dual-role hexokinase activity; and (b) a heterologous polynucleotide encoding a polypeptide having hexose kinase activity; and (ii) growing the recombinant host cell of (i) under conditions wherein the heterologous polynucleotide of (b) is expressed in functional form. In another aspect of the invention, the redox balance of such a recombinant host cell is improved compared to the redox balance of a recombinant host cell comprising (a) but not (b).

One aspect of the invention relates to methods of improving the redox balance of a recombinant host cell comprising (i) providing a recombinant host cell comprising (a) a modification in an endogenous polynucleotide encoding a polypeptide having dual-role hexokinase activity; (b) a heterologous polynucleotide encoding a polypeptide having hexose kinase activity; and (c) a modification in an endogenous polynucleotide encoding a polypeptide having pyruvate decarboxylase activity; and (ii) growing the recombinant host cell of (i) under conditions wherein the heterologous polynucleotide of (b) is expressed in functional form. In another aspect of the invention, the redox balance of such a recombinant host cell is improved compared to the redox balance of a recombinant host cell comprising (a) and (c) but not (b).

One aspect of the invention relates to methods of increasing the formation of a product of a pyruvate-utilizing biosynthetic pathway comprising (i) providing a recombinant host cell comprising (a) a modification in an endogenous polynucleotide encoding a polypeptide having dual-role hexokinase activity; and (b) a heterologous polynucleotide encoding a polypeptide having hexose kinase activity; and (ii) growing the recombinant host cell of (i) under conditions wherein the product of the pyruvate-utilizing pathway is formed. In another aspect of the invention, the amount of product formed by such a recombinant host cell is greater than the amount of product formed by a recombinant host cell comprising (a) but not (b). In another aspect of the invention, the product is isobutanol, 2-butanol, or 1-butanol.

One aspect of the invention relates to methods of increasing the formation of a product of a pyruvate-utilizing biosynthetic pathway comprising (i) providing a recombinant host cell comprising (a) a modification in an endogenous polynucleotide encoding a polypeptide having dual-role hexokinase activity; (b) a heterologous polynucleotide encoding a polypeptide having hexose kinase activity; and (c) a modification in an endogenous polynucleotide encoding a polypeptide having pyruvate decarboxylase activity; and (ii) growing the recombinant host cell of (i) under conditions wherein the product of the pyruvate-utilizing pathway is formed. In another aspect of the invention, the amount of product formed by such a recombinant host cell is greater than the amount of product formed by a recombinant host cell comprising (a) and (c) but not (b). In another aspect of the invention, the product is isobutanol, 2-butanol, or 1-butanol.

REFERENCE TO A SEQUENCE LISTING SUBMITTED AS A TEXT FILE VIA EFS-WEB

The sequences in the accompanying sequence listing, filed electronically herewith and incorporated herein by reference, conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs: 1-2 and 114-119 are example dual-role hexokinases in *Saccharomyces cerevisiae*, described in Table 3.

SEQ ID NOs: 3-8 and 120-123 are example hexose kinase coding regions and proteins, described in Table 4.

SEQ ID NOs: 9-28 are pyruvate decarboxylase sequences described in Table 5.

SEQ ID NO: 30 is a sequence derived from the CUP1 promoter region.

SEQ ID NOs: 31 and 32 are *B. subtilis* acetolactate synthase coding region and protein sequences.

SEQ ID NOs: 33-36 are sequences derived from the CYC1 terminator region, ILV5 promoter region, ILV5 terminator region, and FBA1 promoter region, respectively.

SEQ ID NOs: 37 and 38 are the Pf5.IlvC-Z4B8 coding region and protein sequences.

SEQ ID NOs: 39 and 40 are the ILV5 coding region and protein sequences.

SEQ ID NOs: 41 and 42 are the Pf5.IlvC-JEA1 coding region and protein sequences.

SEQ ID NO: 44 and 47 is the *L. lactis* kivD coding region sequence codon optimized for *S. cerevisiae* and the encoded protein.

SEQ ID NO: 45 and 46 is the horse liver ADH coding region sequence codon optimized for *S. cerevisiae* and the encoded protein.

SEQ ID NO: 49, 53, and 54 are sequences derived from the TDH3 promoter region, GPM1 promoter region, and ADH1 terminator region, respectively.

SEQ ID NOs: 55 and 56 are the sadB coding region and protein sequences, respectively.

SEQ ID NOs: 60 and 61 are FBA terminator region derived and CYC1 terminator region derived sequences.

SEQ ID NOs: 62 and 63 are the ilvD coding region and protein sequences, respectively.

SEQ ID NOs: 124 and 125 are the nucleic acid and amino acid sequences of KlGlk1 from *K. lactis.*

SEQ ID NOs: 126 and 127 are the nucleic acid and amino acid sequences of HPHXK1 from *Hansenula polymorpha.*

SEQ ID NO: 131 is an ADH1 promoter region derived sequence.

SEQ ID NO: 140 and 141 are SNO1 and SNZ1 promoter region derived sequences.

SEQ ID NOs: 50-51, 57-58, 66-75, 77-80, 82-100, 104-105, 107-109, 112-113, 129, and 133-138 are primers used in the Examples.

The following correspond to synthetic constructs:

SEQ ID NO: 29 is the sequence of pLH475-Z4B8 plasmid.

SEQ ID NO: 43 is the sequence of the pLH468 plasmid.

SEQ ID NO: 48 is the sequence of vector pNY8.

SEQ ID NO: 52 is the sequence of vector pRS425::GPM-sadB.

SEQ ID NO: 59 is the sequence of pRS423 FBA ilvD (Strep).

SEQ ID NO: 64 is the GPM-sadB-ADHt segment sequence.

SEQ ID NO: 65 is the pUC19-URA3r sequence.

SEQ ID NO: 76 is the pdc1::PPDC1-ilvD-FBA1t-URA3r integration cassette sequence.

SEQ ID NO: 81 is the sequence of his3::URA3r2 cassette.

SEQ ID NO: 102 is the sequence of pUC19::loxP-URA3-loxP.

SEQ ID NO: 103 is the sequence of pLA25.

SEQ ID NO: 106 is the sequence of pLA31.

SEQ ID NO: 110 is the sequence of pRS423::PGAL1-cre.

SEQ ID NO: 111 is the sequence of pLA32.

SEQ ID NO: 128 is the pLH475-JEA1 plasmid.

SEQ ID NO: 130 is the HXK2(DLys6-Met15) sequence.

SEQ ID NO: 132 is a codon-optimized sequence encoding HXK2 with an internal deletion of the Lys6-Met15 region with ADH1 terminator region derived sequence.

SEQ ID NO: 139 is the sequence of pUC19::loxP-URA3-loxP-HXK2(Lys6-Met15)-ADH1t.

SEQ ID NO: 142 is the sequence of pLH467.

SEQ ID NO: 143 is the sequence of pLH435.

SEQ ID NO: 144 is the sequence of pLH441

BRIEF DESCRIPTION OF THE DRAWINGS/FIGURES

The various embodiments of the invention can be more fully understood from the following detailed description, the figures, and the accompanying sequence descriptions, which form a part of this application.

Figure 1B:
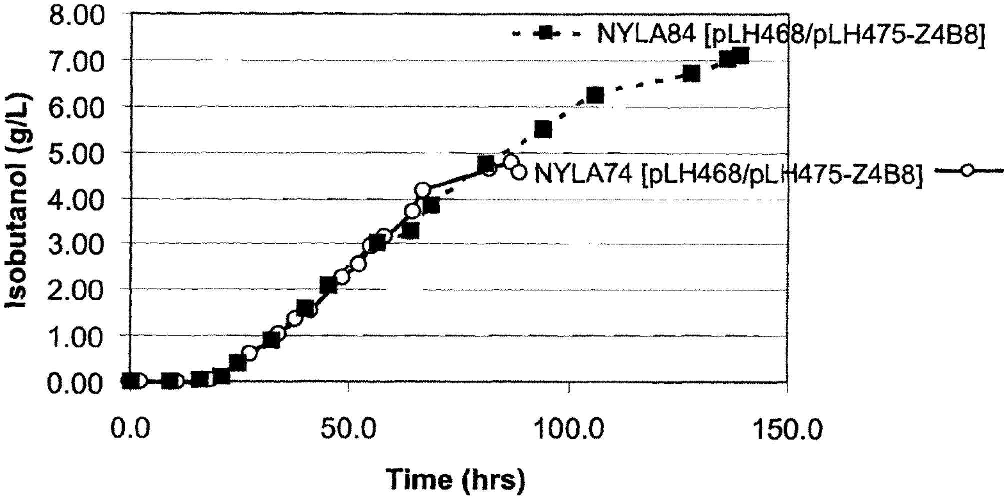

FIG. 1 depicts the growth (FIG. 1A) and isobutanol production (FIG. 1B) of a hexokinase 2 deletion yeast strain (NYLA84 [pLH468/pLH475-Z4B8]) as compared to a yeast strain without hexokinase 2 deletion (NYLA74 [pLH468/pLH475-Z4B8]), as described in Example 3.

Figure 2A:
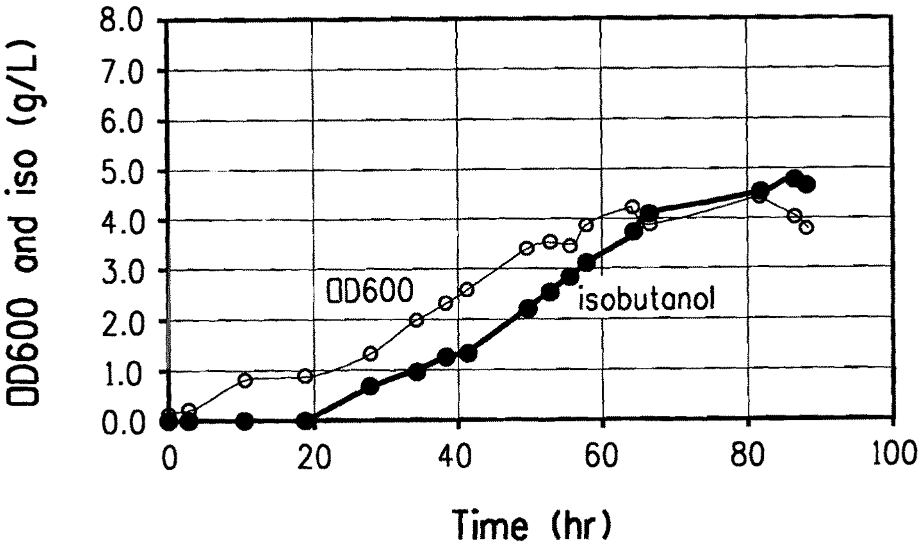
Figure 2B:
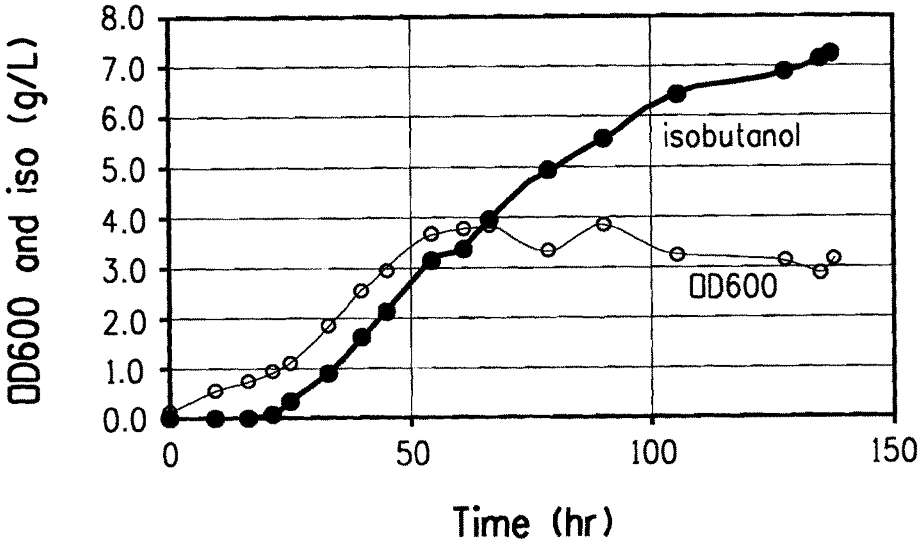

FIG. 2 depicts a comparison of growth and isobutanol production for a strain with a hexokinase 2 deletion (NYLA84 [pLH468/pLH475-Z4B8]; FIG. 2B) and a strain without hexokinase 2 deletion (NYLA74 [pLH468/pLH475-Z4B8]; FIG. 2A).

Figure 3:
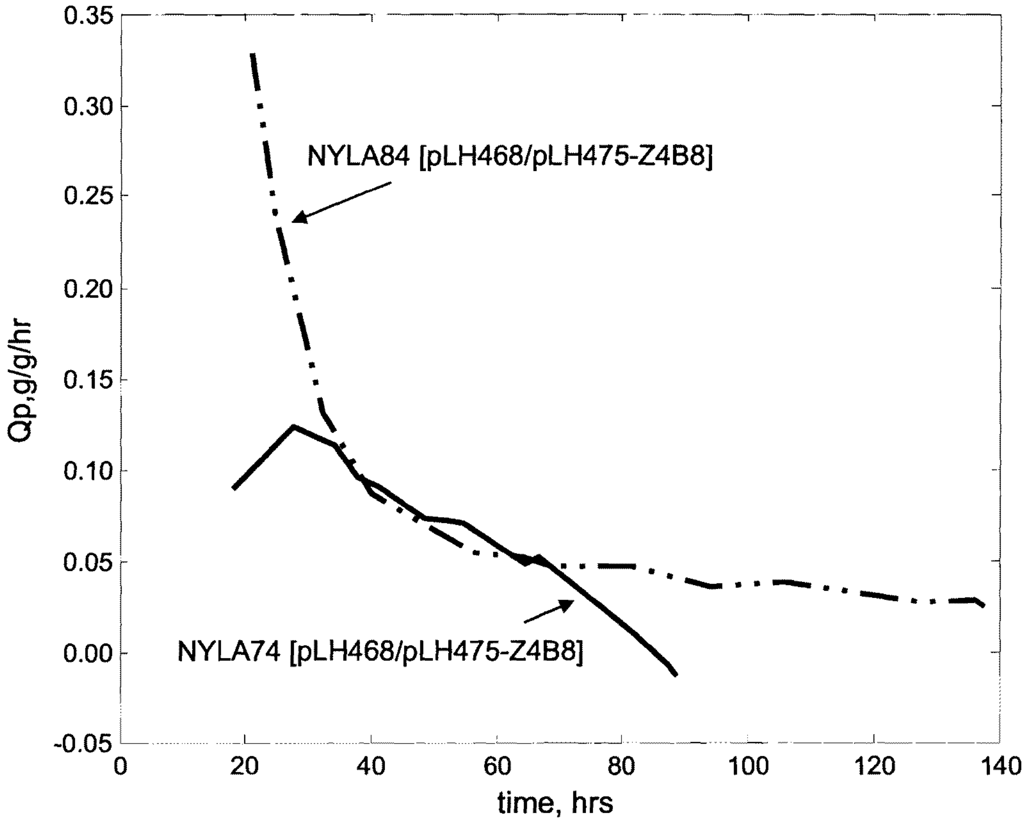

FIG. 3 depicts the specific productivity of a strain with a hexokinase 2 deletion (NYLA84 [pLH468/pLH475-Z4B8] and a strain without hexokinase 2 deletion (NYLA74 [pLH468/pLH475-Z4B8]) measured in grams of isobutanol produced per gram of cells over time.

The invention can be more fully understood from the following detailed description and the accompanying sequence descriptions which form a part of this application.

DETAILED DESCRIPTION OF THE INVENTION

This invention addresses the need for improved processes for the conversion of plant-derived raw materials to a product stream useful as a liquid transportation fuel. Such processes would satisfy both fuel demands and environmental concerns. Applicants have provided a means to improve redox balance, glucose consumption, and/or product formation of a pyruvate-utilizing biosynthetic pathway in a recombinant host cell comprising a modification in an endogenous polynucleotide encoding a polypeptide having dual-role hexokinase activity by introducing a heterologous polynucleotide encoding a polypeptide having hexose kinase activity. Such cells exhibit improved redox balance, increased glucose consumption, and/or increased product formation of a pyruvate-utilizing biosynthetic pathway compared to a recombinant host cell comprising a modification in an endogenous polynucleotide encoding a polypeptide having dual-role hexokinase activity without the introduction of a heterologous polynucleotide encoding a polypeptide having hexose kinase activity. Applicants have also provided methods of making and using such a recombinant host cell including, for example, methods of improving redox balance, methods of increasing glucose consumption, and methods of increasing the production of a product of a pyruvate-utilizing biosynthetic pathway.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

Although methods and materials similar or equivalent to those disclosed herein can be used in practice or testing of the present invention, suitable methods and materials are disclosed below. The materials, methods and examples are illustrative only and are not intended to be limiting. Other features and advantages of the invention will be apparent from the detailed description and from the claims.

In order to further define this invention, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as disclosed in the application.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 2-butanol, 1-butanol, isobutanol, or mixtures thereof.

The term "pyruvate-utilizing biosynthetic pathway" refers to an enzyme pathway to produce a biosynthetic product from pyruvate.

The term "isobutanol biosynthetic pathway" refers to an enzyme pathway to produce isobutanol from pyruvate.

The term "2-butanone biosynthetic pathway" refers to an enzyme pathway to produce 2-butanone from pyruvate.

The term "2-butanol biosynthetic pathway" refers to an enzyme pathway to produce 2-butanol from pyruvate.

The term "1-butanol biosynthetic pathway" refers to an enzyme pathway to produce 1-butanol from pyruvate.

The terms "hxk2 mutant," "HXK2 knockout," or "HXK2-KO" as used herein refer to a *S. cerevisiae* host cell that has a genetic modification to inactivate or reduce expression of a gene encoding hexokinase 2 so that the cell substantially or completely lacks hexokinase 2 enzyme activity.

The terms "pdc mutant," "PDC knockout," or "PDC-KO" as used herein refer to a cell that has a genetic modification to inactivate or reduce expression of a gene encoding pyruvate decarboxylase (Pdc) so that the cell substantially or completely lacks pyruvate decarboxylase enzyme activity. If the cell has more than one expressed (active) PDC gene, then each of the active PDC genes may be inactivated or have minimal expression.

The term "carbon substrate" refers to a carbon source capable of being metabolized by the recombinant host cells disclosed herein. Non-limiting examples of carbon substrates are provided herein and include, but are not limited to, monosaccharides including, but not limited to, glucose, fructose, xylose, and arabinose; oligosaccharides including, but not limited to, sucrose and maltose; polysaccharides; and non-carbohydrate carbon sources including, but not limited to, ethanol, lactate, succinate, glycerol, carbon dioxide, methanol, or mixtures thereof.

The term "polynucleotide" is intended to encompass a singular nucleic acid as well as plural nucleic acids, and refers to a nucleic acid molecule or construct, e.g., messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

A polynucleotide sequence may be referred to as "isolated," in which it has been removed from its native environment. For example, a heterologous polynucleotide encoding a polypeptide or polypeptide fragment contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA may be comprised of one or more segments of cDNA, genomic DNA or synthetic DNA.

The term "gene" refers to a nucleic acid fragment that is capable of being expressed as a specific protein, optionally including regulatory sequences preceding (5' non-coding sequences) and following (3' non-coding sequences) the coding sequence.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner, including by chemical synthesis.

As used herein, "hexose kinase activity" refers to the activity of any polypeptide having a biological function of a hexose kinase, including the examples provided herein. Such polypeptides include glucokinases and hexokinases. Such polypeptides also include a polypeptide that catalyzes the conversion of hexose to hexose-6-phosphate, the conversion of D-glucose to D-glucose 6-phosphate, D-fructose to D-fructose 6-phosphate, and D-mannose to D-mannose 6-phosphate. Such polypeptides also include a polypeptide that corresponds to Enzyme Commission Number EC 2.7.1.1 or to Enzyme Commission Number EC 2.7.1.2. Such polypeptides can be determined by methods well known in the art and disclosed herein.

As used herein, "hexokinase 2 activity" refers to the activity of any polypeptide having a biological function of a *Saccharomyces cerevisiae* hexokinase 2 enzyme, including the examples provided herein. Such polypeptides include a polypeptide that catalyzes the conversion of hexose to hexose-6-phosphate, the conversion of D-glucose to D-glucose 6-phosphate, D-fructose to D-fructose 6-phosphate, and D-mannose to D-mannose 6-phosphate. Such polypeptides also include a polypeptide that corresponds to Enzyme Commission Number EC 2.7.1.1. Such polypeptides can be determined by methods well known in the art.

As used herein, "dual-role hexokinase activity" refers to the activity of any polypeptide having a biological function of a hexose kinase enzyme and exerting a glucose repression phenotype in the cell in which it is expressed. Such polypeptides include a polypeptide that catalyzes the conversion of hexose to hexose-6-phosphate, the conversion of D-glucose to D-glucose 6-phosphate, D-fructose to D-fructose 6-phosphate, and D-mannose to D-mannose 6-phosphate. The second role that a hexose kinase may have is regulatory: A hexokinase is dual-role in a yeast host if it functions to exert glucose repression on glucose-repressible genes. This may be demonstrated by relief from glucose repression in a strain with a mutation in the gene encoding that hexokinase. The dual-role is specific to a particular host cell, thus, a hexose kinase having both hexose kinase activity and glucose repression activity in one species may not express the glucose repression function in another. Hexose kinases including dual-function hexokinases are known in the art.

As used herein, "pyruvate decarboxylase activity" refers to any polypeptide having a biological function of a pyruvate decarboxylase enzyme, including the examples provided herein. Such polypeptides include a polypeptide that catalyzes the conversion of pyruvate to acetaldehyde. Such polypeptides also include a polypeptide that corresponds to Enzyme Commission Number 4.1.1.1. Such polypeptides can be determined by methods well known in the art and disclosed herein.

As used herein, "reduced activity" refers to any measurable decrease in a known biological activity of a polypeptide when compared to the same biological activity of the polypeptide prior to the change resulting in the reduced activity. Such a change can include a modification of a polypeptide or a polynucleotide encoding a polypeptide as described herein. A reduced activity of a polypeptide disclosed herein can be determined by methods well known in the art and disclosed herein.

As used herein, "substantially eliminated activity" refers to measurable decrease in a known biological activity of a polypeptide that results in nearly complete abolishment of the activity when compared to the same biological activity of the polypeptide prior to the change resulting in the substantially eliminated activity. Such a change can include a modification of a polypeptide or a polynucleotide encoding a polypeptide as described herein. A substantially eliminated activity of a polypeptide disclosed herein can be determined by methods well known in the art and disclosed herein.

As used herein, "eliminated activity" refers to the complete abolishment of a known biological activity of a polypeptide when compared to the same biological activity of the polypeptide prior to the change resulting in the eliminated activity. Such a change can include a modification of a polypeptide or a polynucleotide encoding a polypeptide as described herein. An eliminated activity includes a biological activity of a polypeptide that is not measurable when compared to the same biological activity of the polypeptide prior to the change resulting in the eliminated activity. An eliminated activity of a polypeptide disclosed herein can be determined by methods well known in the art and disclosed herein.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, "native" refers to the form of a polynucleotide, gene or polypeptide as found in nature with its own regulatory sequences, if present.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism.

As used herein, "heterologous" refers to a polynucleotide, gene or polypeptide not normally found in the host organism but that is introduced into the host organism or is otherwise modified from its native state. "Heterologous polynucleotide" includes a native coding region from the host organism, or portion thereof, that is reintroduced into or is otherwise modified from the host organism in a form that is different from the corresponding native polynucleotide as well as a coding region from a different organism, or portion thereof. "Heterologous gene" includes a native coding region, or portion thereof, that is reintroduced or otherwise modified in the source organism in a form that is different from the corresponding native gene as well as a coding region from a different organism. For example, a heterologous gene may include a native coding region that is a portion of a chimeric gene including non-native regulatory regions that is reintroduced into the native host. "Heterologous polypeptide" includes a native polypeptide that is in a form that is different from the corresponding native polypeptide as well as a polypeptide from another organism. A polypeptide that is altered such that the expression pattern (such as transcriptional or translational profile or cellular localization) is different from that of the native polypeptide is considered heterologous.

As used herein, the term "modification" refers to a change in a polynucleotide or polypeptide that results in reduced, substantially eliminated or eliminated activity of a polypeptide encoded by the polynucleotide, as well as a change in a polypeptide disclosed herein that results in reduced, substantially eliminated or eliminated activity of the polypeptide. Such changes can be made by methods well known in the art, including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof. Guidance in determining which nucleotides or amino acid residues can be modified can be found by comparing the sequence of the particular polynucleotide or polypeptide with that of homologous polynucleotides or polypeptides, e.g., yeast or bacterial, and maximizing the number of modifications made in regions of high homology (conserved regions) or consensus sequences. Other modifications to polynucleotides may result in increased expression, such as in the case of biosynthetic pathways for the production of a product.

As used herein, the term "variant" refers to a polypeptide differing from a specifically recited polypeptide of the invention by amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences.

Alternatively, recombinant polynucleotide variants encoding these same or similar polypeptides may be synthesized or selected by making use of the "redundancy" in the genetic code. Various codon substitutions, such as silent changes which produce various restriction sites, may be introduced to optimize cloning into a plasmid or viral vector for expression. Mutations in the polynucleotide sequence may be reflected in the polypeptide or domains of other peptides added to the polypeptide to modify the properties of any part of the polypeptide.

Amino acid "substitutions" may be the result of replacing one amino acid with another amino acid having similar structural and/or chemical properties, i.e., conservative amino acid replacements, or they may be the result of replacing one amino acid with an amino acid having different structural and/or chemical properties, i.e., non-conservative amino acid replacements. "Conservative" amino acid substitutions may be made on the basis of similarity in polarity, charge, solubility, hydrophobicity, hydrophilicity, or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions may be made by selecting the differences in polarity, charge, solubility, hydrophobicity, hydrophilicity, or the amphipathic nature of any of these amino acids. "Insertions" or "deletions" may be within the range of variation as structurally or functionally tolerated by the recombinant proteins. The variation allowed may be experimentally determined by systematically making insertions, deletions, or substitutions of amino acids in a polypeptide molecule using recombinant DNA techniques and assaying the resulting recombinant variants for activity.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

The term "overexpression," as used herein, refers to expression that is higher than endogenous expression of the same or related gene. A heterologous gene is overexpressed if its expression is higher than that of a comparable endogenous gene.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" as used herein, refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA **Stop** | TGA **Stop** |
| | TTG Leu (L) | TCG Ser (S) | TAG **Stop** | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | **ATG** Met (M) | ACT Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at http://www.kazusa.or.jp/codon/ (visited Mar. 20, 2008), and these tables can be adapted in a number of ways. See Nakamura, Y., et al. *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. Table 2 has been adapted so that frequencies are calculated for each amino acid, rather than for all 64 codons.

TABLE 2

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the Vector NTI Suite, available from InforMax, Inc., Bethesda, Md., and the "backtranslate" function in the GCG-Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Apr. 15, 2008) and the "backtranseq" function available at http://bioinfo.pbi.nrc.ca:8090/EMBOSS/index.html (visited Jul. 9, 2002). Constructing a rudimentary algorithm to assign codons based on a given frequency can also easily be accomplished with basic mathematical functions by one of ordinary skill in the art.

Codon-optimized coding regions can be designed by various methods known to those skilled in the art including software packages such as "synthetic gene designer" (http://phenotype.biosci.umbc.edu/codon/sgd/index.php).

A polynucleotide or nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementarity, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.,* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as provided herein, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence*

*Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (disclosed by Higgins and Sharp, *CABIOS.* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, such as from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% may be useful in describing the present invention, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

The genetic manipulations of a recombinant host cell disclosed herein can be performed using standard genetic techniques and screening and can be made in any host cell that is suitable for genetic manipulation (*Methods in Yeast Genetics,* 2005, Cold Spring Harbor Laboratory Press, Cold Spring Harbor, N.Y., pp. 201-202). In embodiments, a recombinant host cell disclosed herein can be any yeast or fungi host useful for genetic modification and recombinant gene expression. In other embodiments, a recombinant host cell can be a member of the genera *Saccharomyces, Zygosaccharomyces, Schizosaccharomyces, Dekkera, Torulopsis, lssatchenkia, Brettanomyces, Torulaspora, Hanseniaspora, Kluyveromyces*, and some species of *Candida.* In another embodiment, a recombinant host cell can be *S. cerevisiae.*

Modification of Dual-Role Hexokinase

Recombinant yeast cells disclosed herein can comprise a modification in an endogenous polynucleotide encoding a polypeptide having dual-role hexokinase activity in said host cell and/or a modification in a polypeptide having dual-role hexokinase activity in said host cell. In embodiments, a recombinant host cell disclosed herein can have a modification or disruption of one or more polynucleotides, genes or polypeptides encoding dual-role hexokinases. In embodiments, a recombinant host cell comprises a deletion, mutation, and/or substitution in one or more endogenous polynucleotides or genes encoding a polypeptide having dual-role hexokinase activity, or in one or more endogenous polypeptides having dual-role hexokinase activity. Such modifications, disruptions, deletions, mutations, and/or substitutions can result in dual-role hexokinase activity that is reduced or substantially eliminated, resulting, for example, in a dual-role hexokinase knockout phenotype.

In embodiments, a polypeptide having dual-role hexokinase activity can catalyze the conversion of hexose to hexose-6-phosphate, and/or can catalyze the conversion of D-glucose to D-glucose 6-phosphate, D-fructose to D-fructose 6-phosphate, and/or D-mannose to D-mannose 6-phosphate. In other embodiments, a polynucleotide, gene or polypeptide having dual-role hexokinase activity can correspond to Enzyme Commission Number EC 2.7.1.1.

In embodiments, a recombinant host cell can be *S. cerevisiae* and a polynucleotide, gene or polypeptide having dual-role hexokinase activity can be hexokinase 2 (HXK2). In embodiments, a recombinant host cell can be *K. lactis* and a polynucleotide, gene or polypeptide having dual-role hexokinase activity can be RAG5. In other embodiments, a recombinant host cell can be *H. polymorpha* and a polynucleotide, gene or polypeptide having dual-role hexokinase activity can be HPGLK1. In other embodiments, a recombinant host cell can be *S. pombe* and a polynucleotide, gene or polypeptide having dual-role hexokinase activity can be HXK2. Hexokinase 2 knockout strains are known in the art (Vojtek and Fraenkel, Eur. J. Biochem. 190: 371-375, 1990; Lobo and Maitra, Genetics 86: 727-744, 1977; Winzeler, et al. Science 285: 901-906, 1999; and American Type Culture Collection #4004620, #4014620, #4024620, and #4034620).

Other examples of dual-role hexokinase polynucleotides, genes and polypeptides that can be targeted for modification or inactivation in a recombinant host cell disclosed herein include, but are not limited to, dual-role hexokinase polynucleotides, genes and/or polypeptides having at least about 70% to about 75%, about 75% to about 80%, about 80% to about 85%, about 85% to about 90%, about 90% to about 95%, about 96%, about 97%, about 98%, or about 99% sequence identity to any one of the sequences disclosed herein, wherein such a polynucleotide or gene encodes, or such a polypeptide has, dual-role hexokinase activity. Still other examples of dual-role hexokinase polynucleotides, genes and polypeptides that can be targeted for modification or inactivation in a recombinant host cell disclosed herein include, but are not limited to, an active variant, fragment or derivative of any one of the sequences disclosed herein, wherein such a polynucleotide or gene encodes, or such a polypeptide has, dual-role hexokinase activity.

In embodiments, the sequences of other dual-role hexokinase polynucleotides, genes and/or polypeptides can be identified in the literature and candidates can be identified in bioinformatics databases well known to the skilled person using sequences disclosed herein and available in the art. For example, such sequences can be identified through BLAST searching of publicly available databases with known hexose kinase encoding polynucleotide or polypeptide sequences. In such a method, identities can be based on the Clustal W method of alignment using the default parameters of GAP PENALTY=10, GAP LENGTH PENALTY=0.1, and Gonnet 250 series of protein weight matrix.

Additionally, the dual-role hexokinase polynucleotide or polypeptide sequences disclosed herein or known the art can be used to identify other candidate hexose kinase homologs in nature. For example, each of the hexose kinase encoding nucleic acid fragments disclosed herein can be used to isolate genes encoding homologous proteins. Isolation of homologous genes using sequence-dependent protocols is well known in the art. Examples of sequence-dependent protocols include, but are not limited to (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker et al., *Proc. Natl. Acad. Sci. U.S.A.,* 89:392 (1992)]; and (3) methods of library construction and screening by complementation.

Whether or not a particular hexose kinase is a dual-role hexokinase is specific to the host cell in which the hexose kinase is expressed. For example, while *Hansenula polymorpha* HPGLK1 is a dual-role hexokinase in the native organism, it is not associated with glucose repression in *S. cerevisiae*. Additional examples of hexose kinases that are dual-role in *S. cerevisiae* are given in Table 3. The dual-role nature of certain hexose kinases is known in the art, and, whether or not a hexose kinase is a dual-role hexokinase in a particular host cell can be readily determined from the art and/or using methods known to those of skill in the art. For example, one of the roles of any hexose kinase is enzymatic activity to phosphorylate hexoses, as per E.C. definition 2.7.1.1 or 2.7.1.2, and such activity can be confirmed by assays known in the art. The second role that a dual-role hexokinase will have is regulatory: that is, it is exerts glucose repression on glucose-repressible genes. This is demonstrated by relief from glucose repression in a strain with a mutation in the gene encoding that hexose kinase. Glucose repression relief in the mutant strain can be demonstrated by methods known in the art, including, but not limited, to:

1. measuring expression of the enzymatic activity of an enzyme(s) known to be glucose-repressed in that host (e.g. in *S. cerevisiae*, invertase; maltase; galactokinase) when the cells are grown in glucose-containing medium (if the genetic system involves induction as well as repression, the cognate non-glucose carbon source must be added too, e.g. galactose, maltose);

2. measuring transcription of a gene(s) known to be glucose-repressed in that host when the cells are grown in glucose-containing medium (if the genetic system involves induction as well as repression, the cognate non-glucose carbon source must be added too, e.g. galactose, maltose). Transcription can be measured by Northern blot, RT-PCR, run-on transcription, etc. Transcription can be measured by expression of a reporter gene (e.g. GFP, lacZ, gusB) placed under control of a promoter from a glucose-repressible gene;

3. measuring the ability of the mutant strain to co-consume glucose and a carbon source whose consumption is normally repressed by glucose (e.g. in *S. cerevisiae*: sucrose, maltose, galactose);

4. testing the ability of the mutant strain to grow on a carbon source whose consumption is normally repressed by glucose, when the growth medium also contains a gratuitous glucose repressor (e.g. 2-deoxyglucose, 5-thioglucose).

All of the tests mentioned above could be done with the non-mutant strain as well, for reference.

In embodiments, dual-role hexokinase polynucleotides, genes and/or polypeptides related to a recombinant host cell disclosed herein can be modified or disrupted. Many methods for genetic modification and disruption of target genes to reduce or eliminate expression are known to one of ordinary skill in the art and can be used to create a recombinant host cell disclosed herein. Modifications that can be used include, but are not limited to, deletion of the entire gene or a portion of the gene encoding a dual-role hexokinase protein, inserting a DNA fragment into the encoding gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less active protein is expressed. In other embodiments, expression of a target gene can be blocked by expression of an antisense RNA or an interfering RNA, and constructs can be introduced that result in cosuppression. In other embodiments, the synthesis or stability of the transcript can be lessened by mutation. In embodiments, the efficiency by which a protein is translated from mRNA can be modulated by mutation. All of these methods can be readily practiced by one skilled in the art making use of the known or identified sequences encoding target proteins.

In other embodiments, DNA sequences surrounding a target dual-role hexokinase coding sequence are also useful in some modification procedures and are available, for example, for yeast such as *Saccharomyces cerevisiae* in the complete genome sequence coordinated by Genome Project ID9518 of Genome Projects coordinated by NCBI (National Center for Biotechnology Information) with identifying GOPID #13838. An additional non-limiting example of yeast genomic sequences is that of *Candida albicans*, which is included in GPID #10771, #10701 and #16373. Other yeast genomic sequences can be readily found by one of skill in the art in publicly available databases.

In other embodiments, DNA sequences surrounding a target dual-role hexokinase coding sequence can be useful for modification methods using homologous recombination. In a non-limiting example of this method, dual-role hexokinase gene flanking sequences can be placed bounding a selectable marker gene to mediate homologous recombination whereby the marker gene replaces the dual-role hexokinase gene. In another non-limiting example, partial dual-role hexokinase gene sequences and dual-role hexokinase gene flanking sequences bounding a selectable marker gene can be used to mediate homologous recombination whereby the marker gene replaces at least a portion of the target dual-role hexokinase gene. In embodiments, the selectable marker can be bounded by site-specific recombination sites, so that following expression of the corresponding site-specific recombinase, the resistance gene is excised from the dual-role hexokinase gene without reactivating the latter. In embodiments, the site-specific recombination leaves behind a recombination site which disrupts expression of the dual-role hexokinase protein. In other embodiments, the homologous recombination vector can be constructed to also leave a deletion in the dual-role hexokinase gene following excision of the selectable marker, as is well known to one skilled in the art.

In other embodiments, deletions can be made to a dual-role hexokinase target gene using mitotic recombination as described by Wach et al. (*Yeast,* 10:1793-1808; 1994). Such a method can involve preparing a DNA fragment that contains a selectable marker between genomic regions that can be as short as 20 bp, and which bound a target DNA sequence. In other embodiments, this DNA fragment can be prepared by PCR amplification of the selectable marker gene using as primers oligonucleotides that hybridize to the ends of the marker gene and that include the genomic regions that can recombine with the yeast genome. In embodiments, the linear DNA fragment can be efficiently transformed into yeast and recombined into the genome resulting in gene replacement including with deletion of the target DNA sequence (as disclosed, for example, in *Methods in Enzymology*, Volume 194, Guide to Yeast Genetics and Molecular and Cell Biology (Part A, 2004, Christine Guthrie and Gerald R. Fink (Eds.), Elsevier Academic Press, San Diego, Calif.).

Moreover, promoter replacement methods can be used to exchange the endogenous transcriptional control elements allowing another means to modulate expression such as described by Mnaimneh et al. ((2004) *Cell* 118(1):31-44).

In other embodiments, the dual-role hexokinase target gene encoded activity can be disrupted using random mutagenesis, which can then be followed by screening to identify strains with reduced or substantially eliminated activity. In this type of method, the DNA sequence of the target gene encoding region, or any other region of the genome affecting carbon substrate dependency for growth, need not be known. In embodiments, a screen for cells with reduced dual-role hexokinase activity, or other mutants having reduced dual-role hexokinase activity, can be useful as recombinant host cells of the invention.

Methods for creating genetic mutations are common and well known in the art and can be applied to the exercise of creating mutants. Commonly used random genetic modification methods (reviewed in *Methods in Yeast Genetics,* 2005, Cold Spring Harbor Laboratory Press, Cold Spring Harbor, N.Y.) include spontaneous mutagenesis, mutagenesis caused by mutator genes, chemical mutagenesis, irradiation with UV or X-rays, or transposon mutagenesis.

Chemical mutagenesis of host cells can involve, but is not limited to, treatment with one of the following DNA mutagens: ethyl methanesulfonate (EMS), nitrous acid, diethyl sulfate, or N-methyl-N'-nitro-N-nitroso-guanidine (MNNG). Such methods of mutagenesis have been reviewed in Spencer et al. (Mutagenesis in Yeast, 1996, *Yeast Protocols: Methods in Cell and Molecular Biology*. Humana Press, Totowa, N.J.). In embodiments, chemical mutagenesis with EMS can be performed as disclosed in *Methods in Yeast Genetics,* 2005, Cold Spring Harbor Laboratory Press, Cold Spring Harbor, N.Y. Irradiation with ultraviolet (UV) light or X-rays can also be used to produce random mutagenesis in yeast cells. The primary effect of mutagenesis by UV irradiation is the formation of pyrimidine dimers which disrupt the fidelity of DNA replication. Protocols for UV-mutagenesis of yeast can be found in Spencer et al. (Mutagenesis in Yeast, 1996, *Yeast Protocols: Methods in Cell and Molecular Biology*. Humana Press, Totowa, N.J.). In embodiments, the introduction of a mutator phenotype can also be used to generate random chromosomal mutations in host cells. In embodiments, common mutator phenotypes can be obtained through disruption of one or more of the following genes: PMS1, MAG1, RAD18 or RAD51. In other embodiments, restoration of the non-mutator phenotype can be obtained by insertion of the wildtype allele. In other embodiments, collections of modified cells produced from any of these or other known random mutagenesis processes may be screened for reduced or eliminated dual-role hexokinase activity.

Genomes have been completely sequenced and annotated and are publicly available for the following yeast strains: *Ashbya gossypii* ATCC 10895, *Candida glabrata* CBS 138, *Kluyveromyces lactis* NRRL Y-1140, *Pichia stipitis* CBS 6054, *Saccharomyces cerevisiae* S288c, *Schizosaccharomyces pombe* 972h–, and *Yarrowia lipolytica* CLIB122. Typically BLAST (described above) searching of publicly available databases with known dual-role hexokinase polynucleotide or polypeptide sequences, such as those provided herein, is used to identify candidate dual-role hexokinase-encoding sequences of other host cells, such as yeast cells.

Accordingly, it is within the scope of the invention to provide dual-role hexokinase polynucleotides, genes and polypeptides having at least about 70% to about 75%, about 75% to about 80%, about 80% to about 85%, about 85% to about 90%, about 90% to about 95%, about 96%, about 97%, about 98%, or about 99% sequence identity to any of the hexokinase polynucleotides or polypeptides disclosed herein. Identities are based on the Clustal W method of alignment using the default parameters of GAP PENALTY=10, GAP LENGTH PENALTY=0.1, and Gonnet 250 series of protein weight matrix.

The modification of a dual-role hexokinase in a recombinant host cell disclosed herein to reduce or eliminate dual-role hexokinase activity can be confirmed using methods known in the art. For example, one can screen for disruption of hexokinase 2 in *S. cerevisiae* by PCR (for example, looking for lack of a PCR product with primers such as those listed in Example 2) or by Southern blotting using a probe designed to the hexokinase 2 sequence. Alternatively, one can screen for decreased glucose consumption and higher yield of biomass which is phenotypically indicative of a hexokinase 2 disruption.

Introduction of Hexose Kinase Activity

Applicants have found that the inclusion of a heterologous polynucleotide encoding a polypeptide having hexose kinase activity in a recombinant host cell comprising a modification in an endogenous polynucleotide, gene or polypeptide having dual-role hexokinase activity wherein the activity of the dual-role hexokinase is reduced or eliminated can result in altered glucose repression in the recombinant host cell. The introduction of a heterologous polynucleotide encoding a polypeptide having hexose kinase activity may result in an improved redox balance, increased glucose consumption and/or increased product formation by a pyruvate-utilizing biosynthetic pathway.

Hexose kinase polynucleotides, genes or polypeptides known in the art or that are identified as disclosed herein can be expressed in a recombinant host cell disclosed herein.

Suitable hexose kinase polypeptides include, but are not limited to those that are typically dual-role hexokinases in the host cell but have been modified to reduce or eliminate the glucose repression function. Such hexose kinase polypeptides may be encoded by a polynucleotide comprising a conditional promoter such that the expression of the polypeptide is conditional. As an example, dual-role hexokinase polynucleotides, genes and polypeptides in *Saccharomyces cerevisiae* include, but are not limited to, those in Table 3.

TABLE 3

Example hexose kinases that are dual-role hexokinases in *S. cerevisiae*

| Description | Nucleic Acid GenBank Accession No. | Nucleic Acid SEQ ID NO | Protein GenBank Accession No. | Protein SEQ ID NO |
|---|---|---|---|---|
| HXK2 (hexokinase 2) from *S. cerevisiae* | Z72775.1 | 1 | CAA96973.1 | 2 |
| *Yarrowia lipolytica* YIHXK1 | AJ011524.1 | 114 | CAA09674.1 | 115 |
| *Schwanniomyces occidentalis* SoXHK | S78714.1 | 116 | AAB34892.1 | 117 |
| Human pancreatic glucokinase (hexokinase 4; GCK) | NM_000162.3 | 118 | NP_000153.1 | 119 |

In embodiments, suitable heterologous polynucleotides encode hexose kinases which are dual-function hexokinases in a particular host cell but are expressed in said host cell under the control of a conditional promoter such that glucose repression is altered under conditions where the promoter is not activated or not activated to a significant extent. In embodiments, HXK2 is expressed in *S. cerevisiae* under the control of a conditional promoter. In embodiments, a dual-function hexokinase having at least 85%, at least 90%, or at least 95% identity to SEQ ID NO: 2, 115, 117, or 119 (see Table 3) is encoded in *S. cerevisiae* by a polynucleotide comprising a conditional promoter sequence. In embodiments, a dual-function hexokinase of SEQ ID NO: 2, 115, 117, or 119 (see Table 3) is encoded in *S. cerevisiae* by a polynucleotide comprising a conditional promoter sequence. In embodiments, the conditional promoter sequence is derived from the OLE1 promoter region. In embodiments, the promoter sequence is at least 95% identical to SEQ ID NO: 98. In embodiments, the promoter sequence comprises SEQ ID NO: 98. In embodiments, the promoter is SNO1 (SEQ ID NO: 140) or SNZ1 (SEQ ID NO: 141). In embodiments, the promoter sequence is at least about 95% identical to SEQ ID NO: 140 or 141.

In embodiments, a polynucleotide encoding a dual-role hexokinase disclosed herein or known in the art can be modified using methods disclosed herein such that the glucose repression activity is reduced or eliminated by altering the cellular localization od rhw wnxosws polypeptide. For example, a decapeptide at the N-terminus of hexokinase 2 (Lys6-Met15) has been implicated as a domain involved with MIG1 binding, and it is believed that the hexokinase 2-MIG1 complex is imported into the nucleus where both genes can function as transcriptional regulators. Ahuatzi et al. describes a Lys6-Met15 deletion mutant of HXK2 could no longer bind MIG1 and was localized to the cytosol and could not enter the nucleus (Ahuatzi et al. (2004) The Glucose-regulated Nuclear Localization of Hexokinase 2 in *Saccharomyces cerevisiae* Is Mig1-dependent. JBC 279(14):14440-6).

Thus, deletion or mutation of the MIG1-interaction domain from hexokinase 2 (or related hexokinases) using molecular biology methods known in the art would allow the enzyme to function as a glycolytic enzyme but prevent the enzyme from being translocated to the nucleus and functioning as a transcriptional regulator. In a recombinant host cell comprising reduced or substantially eliminated hexokinase 2 activity, with this modification, one could obtain the growth benefit of the hexokinase 2 reduction, but also high glucose uptake rates akin to the wildtype strain. Therefore, provided herein is a heterologous polynucleotide encoding a polypeptide having hexose kinase activity comprising a mutation or deletion in a protein binding domain necessary for nuclear translocation. In embodiments, the domain is the MIG1-interaction domain. In embodiments, the polynucleotide has at least about 85%, at least about 90%, or at least about 95% identity to SEQ ID NO: 132. In embodiments, the polynucleotide is SEQ ID NO: 132. In embodiments, the polypeptide has at least about 85%, at least about 90%, or at least about 95% identity to SEQ ID NO: 130. In embodiments, the polypeptide is SEQ ID NO: 130.

In embodiments, a heterologous polynucleotide encoding a polypeptide having hexose kinase activity is overexpressed, or expressed at a level that is higher than endogenous expression of the same or related endogenous gene, if any. In other embodiments, a polypeptide having hexose kinase activity is native to a recombinant host cell. In other embodiments, a polypeptide having hexose kinase activity is not native to a recombinant host cell.

In embodiments, the heterologous polynucleotide encoding a polypeptide having hexose kinase activity comprises a constitutive promoter sequence. In embodiments, the constitutive promoter sequence is derived from the ADH1 promoter region. In embodiments, the constitutive promoter sequence has at least 95% identity to SEQ ID NO: 131. In embodiments, the constitutive promoter sequence is SEQ ID NO: 131.

In embodiments, a polypeptide having hexose kinase activity catalyzes the conversion of hexose to hexose-6-phosphate. In other embodiments, a polypeptide having hexose kinase activity catalyzes the conversion of D-glucose to D-glucose 6-phosphate, D-fructose to D-fructose 6-phosphate, and/or D-mannose to D-mannose 6-phosphate.

In embodiments, such a polynucleotide, gene and/or polypeptide can be *K. lactis* RAG5, *H. polymorpha* HPGLK1, *S. pombe* HXK2, or combinations thereof.

In embodiments, a polynucleotide, gene and/or polypeptide encoding hexose kinase activity corresponds to the Enzyme Commission Number EC 2.7.1.1. In other embodiments, a polynucleotide, gene and/or polypeptide encoding hexose kinase can include, but is not limited to, a sequence selected from the following Table 4 or from Table 3. Hexose kinases suitable for expression in *S. cerevisiae* include those disclosed in Table 4. The hexose kinases disclosed in Table 4 are not dual-function hexokinases when expressed in *S. cerevisiae*, but one of skill in the art will recognize that certain of the hexose kinases suitable for expression in *S. cerevisiae*, will be dual-function hexokinases in other types of host cells.

TABLE 4

Example hexose kinase coding regions and proteins and source organism

| Target gene and source organism | Nucleic Acid GenBank Accession No. or Gene ID No. | Nucleic acid SEQ ID NO: | Amino acid GenBank Accession No. | Protein SEQ ID NO: |
|---|---|---|---|---|
| RAG5 from *K. lactis* | NC_006040 REGION: 973371 . . . 974828 | 3 | XP_453567 | 4 |
| HPGLK1 from *H. polymorpha* | AY034434 | 5 | AAK60444 | 6 |
| HXK2 from *S. pombe* | X92895 | 7 | NP_593865 | 8 |
| *S. cerevisiae* HXK1 | Entrez GeneID: 850614 | 120 | — | 121 |
| *S. cerevisiae* GLK1 | Entrez GeneID: 850317 | 122 | — | 123 |

In other embodiments, a polynucleotide, gene and/or polypeptide encoding a hexose kinase can have at least about 70% to about 75%, about 75% to about 80%, about 80% to about 85%, about 85% to about 90%, about 90% to about 95%, about 96%, about 97%, about 98%, or about 99% sequence identity to that of any one of the sequences of Table 3 or Table 4, wherein such a polynucleotide or gene encodes, or such a polypeptide has, hexose kinase activity. Still other examples of hexose kinase polynucleotides, genes and polypeptides that can be expressed in a recombinant host cell disclosed herein include, but are not limited to, an active variant, fragment or derivative of any one of the sequences of Table 3 or Table 4, wherein such a polynucleotide or gene encodes, or such a polypeptide has, hexose kinase activity. Still other examples of hexose kinase polynucleotides, genes and polypeptides that can be expressed in a recombinant host cell disclosed herein include, but are not limited to, an active variant, fragment or derivative of any one of the sequences of *K. lactis* KIGLK1 (Nucleic acid SEQ ID NO: 124; Amino acid SEQ ID NO: 125) or *Hansenula polymorpha* HPHXK1 (Nucleic acid SEQ ID NO: 126; Amino acid SEQ ID NO: 127), wherein such a polynucleotide or gene encodes, or such a polypeptide has, hexose kinase activity.

In other embodiments, a polynucleotide, gene and/or polypeptide encoding hexose kinase can be used to identify another hexose kinase polynucleotide, gene and/or polypeptide sequences and/or can be used to identify a hexose kinase homolog in other cells, as disclosed above for dual-role hexokinases. Such hexose kinase encoding sequences can be identified, for example, in the literature and/or in bioinformatics databases well known to the skilled person. For example, the identification of a hexose kinase encoding sequence in another cell type using bioinformatics can be accomplished through BLAST (as disclosed above) searching of publicly available databases with a known hexose kinase encoding DNA and polypeptide sequence, such as any of those provided herein. Identities are based on the Clustal W method of alignment using the default parameters of GAP PENALTY=10, GAP LENGTH PENALTY=0.1, and Gonnet 250 series of protein weight matrix.

Modification of Pyruvate Decarboxylase

In embodiments, a recombinant host cell disclosed herein can comprise a modification in an endogenous polynucleotide encoding a polypeptide having pyruvate decarboxylase (PDC) activity or a modification in an endogenous polypeptide having PDC activity. In embodiments, a recombinant host cell disclosed herein can have a modification or disruption of one or more polynucleotides, genes and/or polypeptides encoding PDC. In embodiments, a recombinant host cell comprises a deletion, mutation, and/or substitution in one or more endogenous polynucleotides or genes encoding a polypeptide having PDC activity, or in one or more endogenous polypeptides having PDC activity. Such modifications, disruptions, deletions, mutations, and/or substitutions can result in PDC activity that is reduced or substantially eliminated, resulting, for example, in a PDC knock-out (PDC-KO) phenotype.

In embodiments, the endogenous pyruvate decarboxylase activity of a recombinant host cell disclosed herein converts pyruvate to acetaldehyde, which can then be converted to ethanol or to acetyl-CoA via acetate. In other embodiments, a recombinant host cell is *Kluyveromyces lactis* containing one gene encoding pyruvate decarboxylase, *Candida glabrata* containing one gene encoding pyruvate decarboxylase, or *Schizosaccharomyces pombe* containing one gene encoding pyruvate decarboxylase.

In other embodiments, the recombinant host cell is *Saccharomyces cerevisiae* containing three isozymes of pyruvate decarboxylase encoded by the PDC1, PDC5, and PDC6 genes, as well as a pyruvate decarboxylase regulatory gene, PDC2. In a non-limiting example in *S. cerevisiae*, the PDC1 and PDC5 genes, or the PDC1, PDC5, and PDC6 genes, are disrupted. In another non-limiting example in *S. cerevisiae*, pyruvate decarboxylase activity can be reduced by disrupting the PDC2 regulatory gene. In another non-limiting example, expression of the PDC1 and PDC5 genes, or the PDC1, PDC5, and PDC6 genes are reduced. In another non-limiting example in *S. cerevisiae*, polynucleotides or genes encoding pyruvate decarboxylase proteins such as those having about 70% to about 75%, about 75% to about 80%, about 80% to about 85%, about 85% to about 90%, about 90% to about 95%, about 96%, about 97%, about 98%, or about 99% sequence identity to PDC1, PDC2, PDC5 and/or PDC6 can be disrupted.

In embodiments, a polypeptide having PDC activity or a polynucleotide or gene encoding a polypeptide having PDC activity corresponds to Enzyme Commission Number EC 4.1.1.1. In other embodiments, a PDC gene of a recombinant host cell disclosed herein is not active under the fermentation conditions used, and therefore such a gene would not need to be modified or inactivated.

Examples of a recombinant host cell with reduced pyruvate decarboxylase activity due to disruption of pyruvate decarboxylase encoding genes have been reported, such as for *Saccharomyces* in Flikweert et al. (*Yeast* (1996) 12:247-257), for *Kluyveromyces* in Bianchi et al. (*Mol. Microbiol.* (1996) 19(1):27-36), and disruption of the regulatory gene in Hohmann (*Mol. Gen. Genet.* (1993) 241:657-666). *Saccharomyces* strains having no pyruvate decarboxylase activity are available from the ATCC with Accession #200027 and #200028.

Examples of PDC polynucleotides, genes and/or polypeptides that can be targeted for modification or inactivation in the recombinant host cells disclosed herein include, but are not limited to, those of the following Table 5.

TABLE 5

Pyruvate decarboxylase target gene coding regions and proteins.

| Description | SEQ ID NO: Nucleic acid | SEQ ID NO: Amino acid |
|---|---|---|
| PDC1 pyruvate decarboxylase from *Saccharomyces cerevisiae* | 9 | 10 |
| PDC5 pyruvate decarboxylase from *Saccharomyces cerevisiae* | 11 | 12 |
| PDC6 pyruvate decarboxylase from *Saccharomyces cerevisiae* | 13 | 14 |
| pyruvate decarboxylase from *Candida glabrata* | 15 | 16 |
| PDC1 pyruvate decarboxylase from *Pichia stipitis* | 17 | 18 |
| PDC2 pyruvate decarboxylase from *Pichia stipitis* | 19 | 20 |
| pyruvate decarboxylase from *Kluyveromyces lactis* | 21 | 22 |
| pyruvate decarboxylase from *Yarrowia lipolytica* | 23 | 24 |
| pyruvate decarboxylase from *Schizosaccharomyces pombe* | 25 | 26 |
| pyruvate decarboxylase from *Zygosaccharomyces rouxii* | 27 | 28 |

Other examples of PDC polynucleotides, genes and polypeptides that can be targeted for modification or inactivation in a recombinant host cell disclosed herein include, but are not limited to, PDC polynucleotides, genes and/or polypeptides having at least about 70% to about 75%, about 75% to about 80%, about 80% to about 85%, about 85% to about 90%, about 90% to about 95%, about 96%, about 97%, about 98%, or about 99% sequence identity to any one of the sequences of Table 5, wherein such a polynucleotide or gene encodes, or such a polypeptide has, Pdc activity. Still other examples of PDC polynucleotides, genes and polypeptides that can be targeted for modification or inactivation in a recombinant host cell disclosed herein include, but are not limited to, an active variant, fragment or derivative of any one of the sequences of Table 5, wherein such a polynucleotide or gene encodes, or such a polypeptide has, Pdc activity.

In embodiments, a polynucleotide, gene and/or polypeptide encoding a PDC sequence disclosed herein or known in the art can be modified, as disclosed above for hexokinases. In other embodiments, a polynucleotide, gene and/or polypeptide encoding PDC can be used to identify another PDC polynucleotide, gene and/or polypeptide sequence or to identify a PDC homolog in other cells, as disclosed above for hexokinases. Such a PDC encoding sequence can be identified, for example, in the literature and/or in bioinformatics databases well known to the skilled person. For example, the identification of a PDC encoding sequence in other cell types using bioinformatics can be accomplished through BLAST (as described above) searching of publicly available databases with a known PDC encoding DNA and polypeptide sequence, such as those provided herein. Identities are based on the Clustal W method of alignment using the default parameters of GAP PENALTY=10, GAP LENGTH PENALTY=0.1, and Gonnet 250 series of protein weight matrix.

The modification of PDC in a recombinant host cell disclosed herein to reduce or eliminate PDC activity can be confirmed using methods known in the art. For example, one can screen for disruption of pyruvate decarboxylase by lack of a PCR product with primers listed in Example 2 or by Southern blotting using a probe designed to a PDC sequence.

Gene Expression in Recombinant Host Cells

Methods for gene expression in recombinant host cells, including, but not limited to, yeast cells are known in the art (see, for example, *Methods in Enzymology, Volume* 194, Guide to Yeast Genetics and Molecular and Cell Biology (Part A, 2004, Christine Guthrie and Gerald R. Fink (Eds.), Elsevier Academic Press, San Diego, Calif.). In embodiments, the coding region for the hexose kinase genes to be expressed can be codon optimized for the target host cell, as well known to one skilled in the art. Expression of genes in recombinant host cells, including but not limited to yeast cells, can require a promoter operably linked to a coding region of interest, and a transcriptional terminator. A number of promoters can be used in constructing expression cassettes for genes, including, but not limited to, the following constitutive promoters suitable for use in yeast: FBA1, TDH3 (GPD), ADH1, GPM1, and TEF1; and the following inducible promoters suitable for use in yeast: GAL1, GAL10 and CUP1. Suitable for conditional expression is the OLE1 promoter, for which transcription of the gene is induced under anaerobic conditions. While not wishing to be bound by theory, it is believed that anaerobic conditions often prevail during stationary phase, especially in industrial fermentations. Other promoters with stationary-phase expression are known in the art and would also be suitable, such as SNO1 and SNZ1. Suitable transcriptional terminators that can be used in a chimeric gene construct for expression include, but are not limited to, FBA1t, TDH3t, GPM1t, ERG10t, GAL1t, CYC1t, and ADH1t.

Recombinant polynucleotides are typically cloned for expression using the coding sequence as part of a chimeric gene used for transformation, which includes a promoter operably linked to the coding sequence as well as a ribosome binding site and a termination control region. The coding region may be from the host cell for transformation and combined with regulatory sequences that are not native to the natural gene encoding hexose kinase. Alternatively, the coding region may be from another host cell.

Vectors useful for the transformation of a variety of host cells are common and disclosed in the literature. Typically the vector contains a selectable marker and sequences allowing autonomous replication or chromosomal integration in the desired host. In addition, suitable vectors can comprise a promoter region which harbors transcriptional initiation controls and a transcriptional termination control region, between which a coding region DNA fragment may be inserted, to provide expression of the inserted coding region. Both control regions can be derived from genes homologous to the transformed host cell, although it is to be understood that such control regions can also be derived from genes that are not native to the specific species chosen as a production host.

In embodiments, suitable promoters, transcriptional terminators, and hexose kinase coding regions can be cloned into *E. coli*-yeast shuttle vectors, and transformed into yeast cells. Such vectors allow plasmid propagation in both *E. coli* and yeast strains, and can contain a selectable marker and sequences allowing autonomous replication or chromosomal integration in the desired host. Typically used plasmids in yeast include, but are not limited to, shuttle vectors pRS423, pRS424, pRS425, and pRS426 (American Type Culture Collection, Rockville, Md.), which contain an *E. coli* replication origin (e.g., pMB1), a yeast 2-micron origin of replication, and a marker for nutritional selection. The selection markers for these four vectors are HIS3 (vector pRS423), TRP1 (vector pRS424), LEU2 (vector pRS425) and URA3 (vector pRS426).

In embodiments, construction of expression vectors with a chimeric gene encoding the disclosed hexose kinases can be performed by the gap repair recombination method in yeast. The gap repair cloning approach takes advantage of the highly efficient homologous recombination in yeast. In embodiments, a yeast vector DNA is digested (e.g., in its multiple cloning site) to create a "gap" in its sequence. A number of insert DNAs of interest are generated that contain an approximately 21 bp sequence at both the 5' and the 3' ends that sequentially overlap with each other, and with the 5' and 3' terminus of the vector DNA. For example, to construct a yeast expression vector for "Gene X," a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g., TOP10, followed by mini preps and restriction mapping to further verify the plasmid construct. Finally the construct can be verified by sequence analysis.

Like the gap repair technique, integration into the yeast genome also takes advantage of the homologous recombination system in yeast. In embodiments, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding region X-terminator construct is PCR amplified from a plasmid DNA construct and joined to an auxotrophic marker (such as URA3) by either SOE PCR or by common restriction digests and cloning. The full cassette, containing the promoter-coding regionX-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA.

A recombinant host cell disclosed herein can be cultured using standard laboratory techniques known in the art (see, e.g., *Methods in Yeast Genetics,* 2005, Cold Spring Harbor Laboratory Press, Cold Spring Harbor, N.Y., pp. 201-202). The growth of the recombinant host cells disclosed herein can be measured by methods known in the art (see, e.g., *Methods in Yeast Genetics,* 2005, Cold Spring Harbor Laboratory Press, Cold Spring Harbor, N.Y., pp. 201-202).

Applicants have provided a recombinant host cell comprising (a) a modification in an endogenous polynucleotide encoding a polypeptide having dual-role hexokinase activity; (b) a heterologous polynucleotide encoding a polypeptide having hexose kinase activity; and optionally (c) a modification in an endogenous polynucleotide encoding a polypeptide having pyruvate decarboxylase activity. In embodiments, such a recombinant host cell can have an improved redox balance, increased glucose consumption and/or increased formation of a product of a pyruvate-utilizing biosynthetic pathway. As such, Applicants have also provided methods of improving redox balance, increasing glucose consumption and/or increasing formation of a product of a pyruvate-utilizing biosynthetic pathway of a recombinant host cell comprising (a) a modification in an endogenous polynucleotide encoding a polypeptide having dual-role activity; (b) a heterologous polynucleotide encoding a polypeptide having hexose kinase activity; and optionally (c) a modification in an endogenous polynucleotide encoding a polypeptide having pyruvate decarboxylase activity.

Redox balance and glucose consumption of a recombinant host cell disclosed herein can be measured by methods known in the art (see, e.g., *Methods in Yeast Genetics,* 2005, Cold Spring Harbor Laboratory Press, Cold Spring Harbor, N.Y., pp. 201-202). In a non-limiting example, glucose consumption can be measured by quantitating the amount of glucose in culture media by HPLC. Redox balance can be assessed indirectly, for example, by measuring glycerol formation, wherein more glycerol formation implies greater imbalance. Alternatively, redox balance can be assessed by direct analysis of NAD/NADH and NADP/NADPH pools by methods known in the art.

In other embodiments, methods of producing a recombinant host cell are provided comprising (i) providing a recombinant host cell comprising a deletion, mutation, and/or substitution in an endogenous polynucleotide encoding a polypeptide having dual-role hexokinase activity; (ii) transforming said recombinant host cell with a heterologous polynucleotide encoding a polypeptide having hexose kinase activity; and optionally (iii) introducing a deletion, mutation, and/or substitution in an endogenous polynucleotide encoding a polypeptide having pyruvate decarboxylase activity.

In other embodiments, methods for the conversion of hexose into hexose-6-phosphate comprising (i) providing a recombinant host cell comprising a deletion, mutation, and/or substitution in an endogenous polynucleotide encoding a polypeptide having dual-role hexokinase activity; (ii) transforming said recombinant host cell with a heterologous polynucleotide encoding a polypeptide having hexose kinase activity; and optionally (iii) introducing a deletion, mutation, and/or substitution in an endogenous polynucleotide encoding a polypeptide having pyruvate decarboxylase activity. In other embodiments, methods for the conversion of D-glucose into D-glucose 6-phosphate, D-fructose into D-fructose 6-phosphate, and/or D-mannose into D-mannose 6-phosphate are provided comprising (i) providing a recombinant host cell comprising a deletion, mutation, and/or substitution in an endogenous polynucleotide encoding a polypeptide having dual-role hexokinase activity; (ii) transforming said recombinant host cell with a heterologous polynucleotide encoding a polypeptide having hexose kinase activity; and optionally (iii) introducing a deletion, mutation, and/or substitution in an endogenous polynucleotide encoding a polypeptide having pyruvate decarboxylase activity.

Engineered Biosynthetic Pathways Using Pyruvate.

In embodiments, a recombinant host cell comprising (a) a modification (e.g., a deletion, mutation, and/or substitution) in an endogenous polynucleotide encoding a polypeptide having dual-role hexokinase activity; (b) a heterologous polynucleotide encoding a polypeptide having hexose kinase activity; and optionally (c) a modification (e.g., a deletion, mutation, and/or substitution) in an endogenous polynucleotide encoding a polypeptide having pyruvate decarboxylase activity can be engineered to have a biosynthetic pathway for the production of a product of a biosynthetic pathway utilizing pyruvate. Such a recombinant host cell can exhibit an increased production of a product of a biosynthetic pathway utilizing pyruvate. As such, in embodiments, methods for the increased production of a product of a biosynthetic pathway utilizing pyruvate are also provided comprising (i) providing a recombinant host cell comprising (a) a modification (e.g., a deletion, mutation, and/or substitution) in an endogenous polynucleotide encoding a polypeptide having dual-role hexokinase activity; and (b) a heterologous polynucleotide encoding a polypeptide having hexose kinase activity; and (ii) growing the recombinant host cell under conditions wherein the product of the pyruvate-utilizing pathway is formed; wherein the amount of product formed by the recombinant host cell is greater than the amount of product formed by a recombinant host cell comprising (a) but not (b).

In other embodiments, methods for the increased production of a product of a biosynthetic pathway utilizing pyruvate are provided comprising (i) providing a recombinant host cell comprising (a) a modification (e.g., a deletion, mutation, and/or substitution) in an endogenous polynucleotide encoding a polypeptide having dual-role hexokinase activity; (b) a heterologous polynucleotide encoding a polypeptide having hexose kinase activity; and (c) a modification (e.g., a deletion, mutation, and/or substitution) in an endogenous polynucleotide encoding a polypeptide having pyruvate decarboxylase activity; and (ii) growing the recombinant host cell under conditions wherein the product of the pyruvate-utilizing pathway is formed; wherein the amount of product formed by the recombinant host cell is greater than the amount of product formed by a recombinant host cell comprising (a) and (c) but not (b).

A product from a pyruvate-utilizing biosynthetic pathway used in relation to a recombinant host cell disclosed herein includes, but is not limited to, 2,3-butanediol, isobutanol, 2-butanol, 1-butanol, 2-butanone, valine, leucine, lactic acid, malic acid, isoamyl alcohol, and/or isoprenoids. The features of any pyruvate-utilizing biosynthetic pathway can be engineered in a recombinant host cell disclosed herein in any order. Any product made using a biosynthetic pathway that has pyruvate as the initial substrate can be produced with greater effectiveness in a recombinant host cell disclosed herein. The biosynthetic pathway of a recombinant host cell disclosed herein can be any pathway that utilizes pyruvate and produces a desired product. In some embodiments at least one polynucleotide encoding a polypeptide that catalyzes a substrate to product conversion in biosynthetic pathway is heterologous. In some embodiments, one, two, three, four, or five substrate to product conversions of a biosynthetic pathway are catalyzed by polypeptides encoded by polynucleotides heterologous to the host cell. In some embodiments, the biosynthetic pathway comprises more than one polynucleotide that is heterologous to the yeast cell. In some embodiments, each substrate to product conversion of a biosynthetic pathway is catalyzed by polypeptides encoded by polynucleotides that are heterologous to the host cell. In some embodiments, the polypeptides are heterologous.

An example of a biosynthetic pathway for producing 2,3-butanediol can be engineered in a recombinant host cell disclosed herein, as disclosed in U.S. patent application Ser. No. 12/477,942. The 2,3-butanediol pathway is a portion of the 2-butanol biosynthetic pathway that is disclosed in U.S. Patent Application Publication No. US 2007/0292927 A1. Such pathway steps include, but are not limited to, conversion of pyruvate to acetolactate, for example by acetolactate synthase, conversion of acetolactate to acetoin, for example by acetolactate decarboxylase, and conversion of acetoin to 2,3-butanediol, for example by butanediol dehydrogenase. Butanediol dehydrogenase requires NADH and thereby contributes to redox balance. The skilled person will appreciate that polypeptides having the activity of such pathway steps can be isolated from a variety of sources can be used in the recombinant host cells disclosed herein.

In addition, examples of biosynthetic pathways for production of 2-butanone or 2-butanol that can be engineered in a recombinant host cell disclosed herein are disclosed in U.S. Patent Application Publication Nos. US 2007/0292927 A1 and US 2007/0259410 A1. The pathway in U.S. Patent Application Publication No. US 2007/0292927 A1 is the same as disclosed for butanediol production with the addition of the following steps:

- 2,3-butanediol to 2-butanone as catalyzed for example by diol dehydratase or glycerol dehydratase; and
- 2-butanone to 2-butanol as catalyzed for example by butanol dehydrogenase.

Disclosed in U.S. Patent Application Publication No. US 2009/0155870 A1, is the construction of chimeric genes and genetic engineering of yeast for 2-butanol production using the U.S. Patent Application Publication No. US 2007/0292927 A1 disclosed biosynthetic pathway. Further description for gene construction and expression related to these pathways can be found, for example, in International Publication No. WO 2009/046370 (e.g., butanediol dehydratases); and U.S. Patent Application Publication No. US 2009/0269823 A1 (e.g., butanol dehydrogenase) and U.S. Patent Application Publication No. US 20070259410 A1. The skilled person will appreciate that polypeptides having the activity of such pathway steps can be isolated from a variety of sources and can be used in the recombinant host cells disclosed herein.

Examples of biosynthetic pathways for production of isobutanol that can be engineered in a recombinant host cell disclosed herein are also provided in U.S. Patent Application Publication No. US 2007/0092957 A1. As disclosed in U.S. Patent Application Publication No. US 2007/0092957 A1, steps in an example isobutanol biosynthetic pathway include conversion of:

- pyruvate to acetolactate as catalyzed by acetolactate synthase
- acetolactate to 2,3-dihydroxyisovalerate as catalyzed for example by acetohydroxy acid isomeroreductase, also called ketol-acid reductoisomerase;
- 2,3-dihydroxyisovalerate to 2-ketoisovalerate as catalyzed for example by acetohydroxy acid dehydratase, also called dihydroxy-acid dehydratase;
- 2-ketoisovalerate to isobutyraldehyde as catalyzed for example by branched-chain α-keto acid decarboxylase; and
- isobutyraldehyde to isobutanol as catalyzed for example by branched-chain alcohol dehydrogenase.

Further description for gene construction and expression related to this pathway can be found, for example, in U.S. Patent Application Publication Nos. US 2008/0261230 A1 and US 2009/0269823 A1. The skilled person will appreciate that polypeptides having the activity of such pathway steps can be isolated from a variety of sources and can be used in a recombinant host cell disclosed herein. Suitable proteins having the ability to catalyze the indicated substrate to product conversions are described in the art. For example, US Published Patent Application Nos. US20080261230 and US20090163376, US20100197519, and U.S. application Ser. No. 12/893,077 describe acetohydroxy acid isomeroreductases; US20070092957 and US20100081154, describe suitable dihydroxyacid dehydratases; suitable alcohol dehydrogenases are described in US Published Patent Application US20090269823 and U.S. Provisional Patent Application No. 61/290,636.

An example of a biosynthetic pathway for production of 1-butanol that can be engineered in a recombinant host cell disclosed herein is disclosed in U.S. Patent Application Publication No. US 2008/0182308 A1. As disclosed this publication, steps in the disclosed 1-butanol biosynthetic pathway include conversion of:

- acetyl-CoA to acetoacetyl-CoA, as catalyzed for example by acetyl-CoA acetyltransferase;
- acetoacetyl-CoA to 3-hydroxybutyryl-CoA, as catalyzed for example by 3-hydroxybutyryl-CoA dehydrogenase;
- 3-hydroxybutyryl-CoA to crotonyl-CoA, as catalyzed for example by crotonase;
- crotonyl-CoA to butyryl-CoA, as catalyzed for example by butyryl-CoA dehydrogenase;
- butyryl-CoA to butyraldehyde, as catalyzed for example by butyraldehyde dehydrogenase; and
- butyraldehyde to 1-butanol, as catalyzed for example by butanol dehydrogenase.

Genes that may be used for expression of these enzymes are disclosed, for example, in U.S. Patent Application Publication No. US 2008/0182308 A1, and additional genes that can be used can be identified by one skilled in the art.

An example of a biosynthetic pathway for production of valine that can be engineered in a recombinant host cell disclosed herein includes the steps of acetolactate conversion to 2,3-dihydroxy-isovalerate by acetohydroxyacid reductoisomerase (ILV5), conversion of 2,3-dihydroxy-isovalerate to 2-keto-isovalerate by dihydroxy-acid dehydratase (ILV3), and conversion of 2-keto-isovalerate to valine by branched-chain amino acid transaminase (BAT2) and branched-chain amino acid aminotransferase (BAT1). Biosynthesis of leucine includes the same steps to 2-keto-isovalerate, followed by conversion of 2-keto-isovalerate to alpha-isopropylmalate by alpha-isopropylmalate synthase (LEU9, LEU4), conversion of alpha-isopropylmalate to beta-isopropylmalate by isopropylmalate isomerase (LEU1), conversion of beta-isopropylmalate to alpha-ketoisocaproate by beta-IPM dehydrogenase (LEU2), and finally conversion of alpha-ketoisocaproate to leucine by branched-chain amino acid transaminase (BAT2) and branched-chain amino acid aminotransferase (BAT1). It is desired for production of valine or leucine to overexpress at least one of the enzymes in these disclosed pathways.

An example of a biosynthetic pathway for production of isoamyl alcohol that can be engineered in a recombinant host cell disclosed herein includes the steps of leucine conversion to alpha-ketoisocaproate by branched-chain amino acid transaminase (BAT2) and branched-chain amino acid aminotransferase (BAT1), conversion of alpha-ketoisocaproate to 3-methylbutanal by ketoisocaproate decarboxylase (THI3) or decarboxylase ARO10, and finally conversion of 3-methylbutanal to isoamyl alcohol by an alcohol dehydrogenase such as ADH1 or SFA1. Production of isoamyl alcohol benefits from increased production of leucine or the alpha-ketoisocaproate intermediate by overexpression of one or more enzymes in biosynthetic pathways for these chemicals. In addition, one or both enzymes for the final two steps can be overexpressed.

An example of a biosynthetic pathway for production of lactic acid that can be engineered in a recombinant host cell disclosed herein includes pyruvate conversion to lactic acid by lactate dehydrogenase. Engineering yeast for lactic acid production using lactate dehydrogenase, known as EC 1.1.1.27, is well known in the art such as in Ishida et al. (*Appl. Environ. Microbiol.* 71:1964-70 (2005)).

An example of a biosynthetic pathway for production of malate that can be engineered in a recombinant host cell disclosed herein includes pyruvate conversion to oxaloacetate by pyruvate carboxylase, and conversion of oxaloacetate to malate by malate dehydrogenase as disclosed in Zelle et al. (*Appl. Environ. Microbiol.* 74:2766-77 (2008)). In addition, a malate transporter can be expressed.

Examples of biosynthetic pathways for production of isoprenoids can also be engineered in a recombinant host cell disclosed herein. In a non-limiting example, a mevalonate pathway can be used (Martin et al. (2003) *Nature Biotech.* 21:796-802) which includes the conversion of pyruvate to acetyl-CoA, which is converted to acetoacetyl-CoA, which is converted to 3-hydroxy-3-methylglutaryl-CoA, which is converted to mevalonate and then to isoprenoids. In another non-limiting example, a non-mevalonate pathway is described by Kim and Keisling (*Biotechnol. Bioeng.* 72:408-15 (2001)).

The skilled person will appreciate that polypeptides having activities of the above-mentioned biosynthetic pathways can be isolated from a variety of sources can be used in a recombinant host cell disclosed herein.

Additional Modifications

Additional modifications that may be useful in cells provided herein include modifications to reduce glycerol-3-phosphate dehydrogenase activity as described in US Patent Application Publication No. 20090305363 (incorporated herein by reference), modifications to a host cell that provide for increased carbon flux through an Entner-Doudoroff Pathway or reducing equivalents balance as described in US Patent Application Publication No. 20100120105 (incorporated herein by reference). Yeast strains with increased activity of heterologous proteins that require binding of an Fe—S cluster for their activity are described in US Application Publication No. 20100081179 (incorporated herein by reference). Other modifications include integration of at least one polynucleotide encoding a polypeptide that catalyzes a step in a pyruvate-utilizing biosynthetic pathway described in U.S. Provisional Application No. 61/380,563 (both referenced provisional applications are incorporated herein by reference in their entirety). Additional modifications that may be suitable for embodiments herein are described in U.S. application Ser. No. 12/893,089.

Additionally, host cells comprising at least one deletion, mutation, and/or substitution in an endogenous gene encoding a polypeptide affecting Fe—S cluster biosynthesis are described in U.S. Provisional Patent Application No. 61/305,333 (incorporated herein by reference), and host cells comprising a heterologous polynucleotide encoding a polypeptide with phosphoketolase activity and host cells comprising a heterologous polynucleotide encoding a polypeptide with phosphotransacetylase activity are described in U.S. Provisional Patent Application No. 61/356,379.

Growth for Production

A recombinant host cell disclosed herein is grown in fermentation media which contains a suitable carbon substrate. Carbon substrates can include, but are not limited to, monosaccharides such as fructose or galactose, oligosaccharides such as lactose, maltose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally a carbon substrate can also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1-Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention can encompass a wide variety of carbon containing substrates and will only be limited by the choice of organism.

Although it is contemplated that all of the above mentioned carbon substrates and mixtures thereof are suitable in the present invention, in some embodiments, a carbon substrates can be glucose, fructose, and sucrose, or mixtures of these with C5 sugars such as xylose and/or arabinose for yeast cells modified to use C5 sugars. Sucrose can be derived from renewable sugar sources such as sugar cane, sugar beets, cassava, sweet sorghum, and mixtures thereof. Glucose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. US 20070031918 A1.

Biomass refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media can contain suitable minerals, salts, cofactors, buffers and other components, known to those skilled in the art, suitable for the growth of the cultures.

Culture Conditions

Typically cells are grown at a temperature in the range of about 20° C. to about 40° C. in an appropriate medium. Suitable growth media in the present invention are common commercially prepared media such as Luria Bertani (LB) broth, Sabouraud Dextrose (SD) broth, Yeast Medium (YM) broth, or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, can also be incorporated into the fermentation medium.

Suitable pH ranges for the fermentation are between about pH 5.0 to about pH 9.0. In one embodiment, about pH 6.0 to about pH 8.0 can be used for the initial condition. Suitable pH ranges for the fermentation of yeast are typically between about pH 3.0 to about pH 9.0. In one embodiment, about pH 5.0 to about pH 8.0 can be used for the initial condition. Suitable pH ranges for the fermentation of other microorganisms are between about pH 3.0 to about pH 7.5. In one embodiment, about pH 4.5 to about pH 6.5 can be used for the initial condition.

Fermentations can be performed under aerobic or anaerobic conditions. In one embodiment, anaerobic or microaerobic conditions can be used for fermentations.

Industrial Batch and Continuous Fermentations

The recombinant host cells disclosed herein can be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992).

A product of a pyruvate-utilizing biosynthetic pathway related to a recombinant host cell disclosed herein can also be produced using continuous fermentation methods. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that a product of a pyruvate-utilizing biosynthetic pathway can be practiced using batch, fed-batch or continuous processes and that any known mode of fermentation would be suitable. Additionally, it is contemplated that a recombinant host cell disclosed herein can be immobilized on a substrate as whole cell catalysts and subjected to fermentation conditions for isobutanol production.

Methods for Product Isolation from the Fermentation Medium

A product of a pyruvate-utilizing biosynthetic pathway can be isolated from the fermentation medium using methods known in the art for acetone-butanol-ethanol (ABE) fermentations (see, e.g., Durre, *Appl. Microbiol. Biotechnol.* 49:639-648 (1998), Groot et al., *Process. Biochem.* 27:61-75 (1992), and references therein). For example, solids can be removed from the fermentation medium by centrifugation, filtration, decantation, or the like. Then, the product can be isolated from the fermentation medium using methods such as distillation, azeotropic distillation, liquid-liquid extraction, adsorption, gas stripping, membrane evaporation, or pervaporation.

Where a product has a low boiling point (e.g., isobutanol), azeotropic mixture with water, distillation can be used to separate the mixture up to its azeotropic composition. Distillation can be used in combination with another separation method to obtain separation around the azeotrope. Methods that can be used in combination with distillation to isolate and purify butanol include, but are not limited to, decantation, liquid-liquid extraction, adsorption, and membrane-based techniques. Additionally, butanol may be isolated using azeotropic distillation using an entrainer (see, e.g., Doherty and Malone, *Conceptual Design of Distillation Systems*, McGraw Hill, N.Y., 2001).

The butanol-water mixture forms a heterogeneous azeotrope so that distillation can be used in combination with decantation to isolate and purify the isobutanol. In this method, the isobutanol containing fermentation broth is distilled to near the azeotropic composition. Then, the azeotropic mixture is condensed, and the isobutanol is separated from the fermentation medium by decantation. The decanted aqueous phase can be returned to the first distillation column as reflux. The isobutanol-rich decanted organic phase can be further purified by distillation in a second distillation column.

A product of a pyruvate-utilizing biosynthetic pathway can also be isolated from the fermentation medium using liquid-liquid extraction in combination with distillation. In this method, the product (e.g., isobutanol) can be extracted from the fermentation broth using liquid-liquid extraction with a suitable solvent. The product-containing organic phase can then be distilled to separate the product from the solvent.

Distillation in combination with adsorption can also be used to isolate a product (e.g., isobutanol) from the fermentation medium. In this method, the fermentation broth containing the product is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation can be used to isolate and purify a product (e.g., isobutanol) from the fermentation medium. In this method, the fermentation broth containing the product is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987), and by *Methods in Yeast Genetics,* 2005, Cold Spring Harbor Laboratory Press, Cold Spring Harbor, N.Y.

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of microbial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified. Microbial strains were obtained from The American Type Culture Collection (ATCC), Manassas, Va., unless otherwise noted. The oligonucleotide primers used in the following Examples are given in the following Tables. All the oligonucleotide primers were synthesized by Sigma-Genosys (Woodlands, Tex.) or Integrated DNA Technologies (Coralsville, Iowa).

Synthetic complete medium is described by Amberg, Burke and Strathern, 2005, Methods in Yeast Genetics, Cold Spring Harbor Laboratory Press, Cold Spring Harbor, N.Y.

GC Method

The GC method utilized a ZB-WAXplus column (30 m×0.25 mm ID, 0.25 μm film) from Phenomenex (Torrance, Calif.). The carrier gas was helium at a constant flow rate of 2.3 mL/min; injector split was 1:20 at 250° C.; oven temperature was 70° C. for 1 min, 70° C. to 160° C. at 10° C./min, and 160° C. to 240° C. at 30° C./min. FID detection was used at 260° C. with 40 ml/min helium makeup gas. Culture broth samples were filtered through 0.2 μm spin filters before injection. Depending on analytical sensitivity desired, either 0.1 μl or 0.5 μl injection volumes were used. Calibrated standard curves were generated for the following compounds: ethanol, isobutanol, acetoin, meso-2,3-butanediol, and (2S,3S)-2,3-butanediol. (2S,3S)-2,3-butanediol retention time is 6.8 minutes. meso-2,3-butanediol retention time is 7.2 minutes. Analytical standards were also utilized to identify retention times for isobutryaldehyde, isobutyric acid, and isoamyl alcohol.

HPLC Method

Analysis for glucose and fermentation by-product composition is well known to those skilled in the art. For example, one high performance liquid chromatography (HPLC) method utilizes a Shodex SH-1011 column with a Shodex SH-G guard column (both available from Waters Corporation, Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol retention time is 47.6 minutes.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmol" means micromole(s), "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "wt %" means percent by weight, "HPLC" means high performance liquid chromatography, and "GC" means gas chromatography. The term "molar selectivity" is the number of moles of product produced per mole of sugar substrate consumed and is reported as a percent. "SLPM" stands for Standard Liters per Minute (of air), "dO" is dissolved oxygen, Qp is "specific productivity" measured in grams isobutanol per gram of cells over time. The term "nt" means nucleotides.

Example 1

Construction of Expression Vectors for Isobutanol Pathway Gene Expression in *S. cerevisiae* pLH475-Z4B8 Construction

The pLH475-Z4B8 plasmid (SEQ ID NO: 29) was constructed for expression of ALS and KARI in yeast. pLH475-Z4B8 is a pHR81 vector (ATCC #87541) containing the following chimeric genes: A) CUP1 promoter region derived sequence (SEQ ID NO: 30), acetolactate synthase coding region from *Bacillus subtilis* (AlsS; SEQ ID NOs: 31 and 32) and a CYC1 terminator region derived sequence ("CYC1 terminator 2"; SEQ ID NO: 33); B) ILV5 promoter region derived sequence (SEQ ID NO: 34), Pf5.IlvC-Z4B8 coding region (SEQ ID NOs: 37 and 38) and ILV5 terminator region derived sequence (SEQ ID NO: 35); and C) FBA1 promoter region derived sequence (SEQ ID NO: 36), *S. cerevisiae* KARI coding region (ILV5; SEQ ID NOs: 39 and 40) and CYC1 terminator region derived sequence.

The Pf5.IlvC-Z4B8 coding region is a sequence encoding KARI derived from *Pseudomonas fluorescens* with certain mutations, as disclosed in U.S. Patent Application Publication No. US 2009-0163376 A1. More specifically, the Pf5.IlvC-Z4B8 encoded KARI (SEQ ID NO: 38) has the following amino acid changes as compared to the natural *Pseudomonas fluorescens* KARI:

C33L: cysteine at position 33 changed to leucine,
R47Y: arginine at position 47 changed to tyrosine,
S50A: serine at position 50 changed to alanine,
T52D: threonine at position 52 changed to asparagine,
V53A: valine at position 53 changed to alanine,
L61F: leucine at position 61 changed to phenylalanine,
T80I: threonine at position 80 changed to isoleucine,
A156V: alanine at position 156 changed to threonine, and
G170A: glycine at position 170 changed to alanine.

The Pf5.IlvC-Z4B8 coding region (SEQ ID NO: 37) was synthesized by DNA 2.0 (Palo Alto, Calif.; based on codons that were optimized for expression in *Saccharomyces cerevisiae*.

pLH475-JEA1 Construction

The pLH475-JEA1 plasmid (SEQ ID NO:128) was constructed for expression of ALS and KARI in yeast. pLH475-JEA1 is a pHR81 vector (ATCC #87541) containing the following chimeric genes: 1) the CUP1 promoter (SEQ ID NO: 30), acetolactate synthase coding region from *Bacillus subtilis* (AlsS; (SEQ ID NOs: 31 and 32)) and CYC1 terminator 2 (SEQ ID NO: 33)); 2) an ILV5 promoter (SEQ ID NO: 34, Pf5.IlvC-JEA1 coding region and ILV5 terminator (SEQ ID NO: 35); and 3) the FBA1 promoter (SEQ ID NO: 36)*S. cerevisiae* KARI coding region (ILV5; SEQ ID NOs: 39 and 40) and CYC1 terminator.

The Pf5.IlvC-JEA1 coding region is a sequence encoding KARI derived from *Pseudomonas fluorescens* with certain mutations, as disclosed in U.S. Patent Application Publication 20090163376A1. More specifically, the Pf5.IlvC-JEA1 encoded KARI (nucleic acid and amino acid sequences of SEQ ID NOs: 41 and 42, respectively) has the following amino acid changes as compared to the natural *Pseudomonas fluorescens* KARI:

Y24F: tyrosine at position 24 changed to phenylalanine
C33L: cysteine at position 33 changed to leucine,
R47P: arginine at position 47 changed to proline,
S50F: serine at position 50 changed to phenylalanine,
T52D: threonine at position 52 changed to asparagine,
L61F: leucine at position 61 changed to phenylalanine,
T80I: threonine at position 80 changed to isoleucine,
A156V: alanine at position 156 changed to threonine.

Expression Vector pLH468

The pLH468 plasmid (SEQ ID NO: 43) was constructed for expression of DHAD, KivD and HADH in yeast. Coding regions for *Lactococcus lactis* ketoisovalerate decarboxylase (KivD) and horse liver alcohol dehydrogenase (HADH) were synthesized by DNA2.0 based on codons that were optimized for expression in *Saccharomyces cerevisiae* (SEQ ID NO: 44 and 45) and provided in plasmids pKivDy-DNA2.0 and pHadhy-DNA2.0. The encoded proteins are (SEQ ID NOs 47 and 46, respectively. Individual expression vectors for KivD and HADH were constructed. To assemble pLH467 (pRS426::$P_{TDH3}$-kivDy-TDH3t), vector pNY8 (SEQ ID NO: 48; also named pRS426.GPD-ald-GPDt, disclosed in U.S. Patent Application Publication No. US 2008/0182308 A1, Example 17) was digested with AscI and SfiI enzymes, thus excising the GPD promoter region derived sequence and the ald coding region. A TDH3 promoter region derived sequence fragment (SEQ ID NO: 49) from pNY8 was PCR amplified to add an AscI site at the 5' end, and an SpeI site at the 3' end, using 5' primer OT1068 and 3' primer OT1067 (SEQ ID NO: 50 and 51). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::$P_{TDH3}$-kivDy-TDH3t). pLH467 (SEQ ID NO: 142) was verified by restriction mapping and sequencing.

pLH435 (pRS425::$P_{GPM1}$-Hadhy-ADH1t) was derived from vector pRS425::GPM-sadB (SEQ ID NO: 52) which is disclosed in U.S. Provisional Patent Application No. 61/058, 970, Example 3. pRS425::GPM-sadB is the pRS425 vector (ATCC #77106) with a chimeric gene containing a GPM1 promoter region derived sequence (SEQ ID NO: 53), a coding region from a butanol dehydrogenase of *Achromobacter xylosoxidans* (sadB; SEQ ID NO: 55, disclosed in U.S. Patent Application No. 61/048,291; amino acid SEQ ID NO: 56), and an ADH1 terminator region derived sequence (SEQ ID NO: 54). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NO: 57 and 58) to generate vector pRS425-GPMp-sadB-NheI, which was verified by sequencing. pRS425::$P_{GPM1}$-sadB-NheI was digested with NheI and PacI to drop out the sadB coding region, and ligated with the NheI-PacI fragment containing the codon optimized HADH coding region from vector pHadhy-DNA2.0 to create pLH435 (SEQ ID NO: 143).

To combine KivD and HADH expression cassettes in a single vector, yeast vector pRS411 (ATCC #87474) was digested with SacI and NotI, and ligated with the SacI-SalI fragment from pLH467 that contains the $P_{TDH3}$-kivDy-TDH3t cassette together with the SalI-NotI fragment from pLH435 that contains the $P_{GPM1}$-Hadhy-ADH1t cassette in a triple ligation reaction. This yielded the vector pRS411::$P_{TDH3}$-kivDy-$P_{GPM}$1-Hadhy (pLH441 SEQ ID NO: 144), which was verified by restriction mapping.

In order to generate a co-expression vector for all three genes in the lower isobutanol pathway: ilvD, kivDy and Hadhy, we used pRS423 FBA ilvD(Strep) (SEQ ID NO: 59), which is disclosed in U.S. Patent Application No. 61/100,792, as the source of the ilvD gene. This shuttle vector contains an F1 origin of replication (nt 1423 to 1879) for maintenance in *E. coli* and a 2 micron origin (nt 8082 to 9426) for replication in yeast. The vector has an FBA1 promoter region derived sequence (nt 2111 to 3108; ((SEQ ID NO: 36) and FBA1 terminator region derived sequence (nt 4861 to 5860; SEQ ID NO: 60). In addition, it carries the HIS3 marker (nt 504 to 1163) for selection in yeast and ampicillin resistance marker (nt 7092 to 7949) for selection in *E. coli*. The ilvD coding region (nt 3116 to 4828; (ilvD coding region of vector is SEQ ID NO: 62 and wild-type protein sequence of ilvD is SEQ ID NO: 63) from *Streptococcus mutans* UA159 (ATCC #700610) is between the FBA1 promoter region derived sequence and FBA1 terminator region derived sequence forming a chimeric gene for expression. In addition there is a lumio tag fused to the ilvD coding region (nt 4829-4849).

The first step was to linearize pRS423::FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-IlvD (*Streptococcus mutans*)-Lumio. This generated vector pLH468 (pRS423::$P_{FBA1}$-ilvD(Strep)Lumio-FBA/t-$P_{TDH3}$-kivDy-TDH3t-$P_{GPM1}$-hadhy-ADH1t), which was confirmed by restriction mapping and sequencing.

Example 2

Pyruvate Decarboxylase and Hexokinase 2 Gene Inactivation

This example describes insertion-inactivation of endogenous PDC1, PDC5, and PDC6 genes of *S. cerevisiae*. PDC1, PDC5, and PDC6 genes encode the three major isozymes of pyruvate decarboxylase. The resulting PDC inactivation strain was used as a host for expression vectors pLH475-Z4B8 and pLH468 that were described in Example 1.

Construction of pdc6::$P_{GPM1}$-sadB Integration Cassette and PDC6 Deletion:

A pdc6::$P_{GPM1}$-sadB-ADH1t-URA3r integration cassette was made by joining the GPM-sadB-ADHt segment (SEQ ID NO: 64) from pRS425::GPM-sadB (described above) to the URA3r gene from pUC19-URA3r. pUC19-URA3r (SEQ ID NO: 65) contains the URA3 marker from pRS426 (ATCC #77107) flanked by 75 bp homologous repeat sequences to allow homologous recombination in vivo and removal of the URA3 marker. The two DNA segments were joined by SOE PCR (as described by Horton et al. (1989) *Gene* 77:61-68) using as template pRS425::GPM-sadB and pUC19-URA3r plasmid DNAs, with Phusion DNA polymerase (New England Biolabs Inc., Beverly, Mass.; catalog no. F-540S) and primers 114117-11A through 114117-11D (SEQ ID NOs: 66-69), and 114117-13A and 114117-13B (SEQ ID NOs: 70 and 71). The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC #200866) and transformants were maintained on synthetic complete media lacking uracil and supplemented with 2% glucose at 30° C. using standard genetic techniques (*Methods in Yeast Genetics,* 2005, Cold Spring Harbor Laboratory Press, Cold Spring Harbor, N.Y., pp. 201-202). Transformants were screened by PCR using primers 112590-34G and 112590-34H (SEQ ID NOs: 72 and 73), and 112590-34F and 112590-49E (SEQ ID NOs: 74 and 75) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD URA-media to verify the absence of growth. The resulting identified strain has the genotype: BY4700 pdc6::$P_{GPM1}$-sadB-ADH1t.

Construction of pdc1::$P_{PDC1}$-ilvD Integration Cassette and PDC1 Deletion:

A pdc1::$P_{PDC1}$-ilvD-FBA1t-URA3r integration cassette was made by joining the ilvD-FBA1t segment (SEQ ID NO: 76) from pLH468 (described above) to the URA3r gene from pUC19-URA3r by SOE PCR (as described by Horton et al. (1989) *Gene* 77:61-68) using as template pLH468 and pUC19-URA3r plasmid DNAs, with Phusion DNA polymerase (New England Biolabs Inc., Beverly, Mass.; catalog no. F-540S) and primers 114117-27A through 114117-27D (SEQ ID NOs: 77-80).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::$P_{GPM1}$-sadB-ADH1t and transformants were maintained on synthetic complete media lacking uracil and supplemented with 2% glucose at 30° C. using standard genetic techniques (*Methods in Yeast Genetics,* 2005, Cold Spring Harbor Laboratory Press, Cold Spring Harbor, N.Y., pp. 201-202). Transformants were screened by PCR using primers 114117-36D and 135 (SEQ ID NOs:82 and 83), and primers 112590-49E and 112590-30F (SEQ ID NOs: 75 and 129) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6::$P_{GPM1}$-sadB-ADH1t pdc1::_$P_{PDC1}$-ilvD-FBA1t.

HIS3 Deletion

To delete the endogenous HIS3 coding region, a his3::URA3r2 cassette was PCR-amplified from URA3r2 template DNA (SEQ ID NO: 81). URA3r2 contains the URA3 marker from pRS426 (ATCC #77107) flanked by 500 bp homologous repeat sequences to allow homologous recombination in vivo and removal of the URA3 marker. PCR was done using Phusion DNA polymerase and primers 114117-45A and 114117-45B (SEQ ID NOs: 84 and 85) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (*Methods in Yeast Genetics,* 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6::$P_{GPM1}$-sadB-ADH1t pdc1::$P_{PDC1}$-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion DNA polymerase and primers PDC5::KanMXF and PDC5::KanMXR (SEQ ID NOs: 86 and 87) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (*Methods in Yeast Genetics,* 2005, Cold Spring Harbor Laboratory Press, Cold Spring Harbor, N.Y., pp. 201-202) and transformants were selected on YP media supplemented with 1% ethanol and geneticin (200 μg/ml) at 30° C. Transformants were screened by PCR to verify correct integration at the PDC locus with replacement of the PDC5 coding region using primers PDC5kofor and N175 (SEQ ID NOs: 88 and 89). The identified correct transformants have the genotype: BY4700 pdc6::$P_{GPM1}$-sadB-ADH1t pdc1::$P_{PDC1}$-ilvD-FBA1t Δhis3 pdc5::kanMX4. The strain was named NYLA74.

Deletion of Hexokinase 2:

A hxk2::URA3r cassette was PCR-amplified from URA3r2 template (described above) using Phusion DNA polymerase and primers 384 and 385 (SEQ ID NOs: 90 and 91) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (*Methods in Yeast Genetics,* 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NO: 92 and 93). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NO: 94 and 95). The resulting identified strain named NYLA83 has the genotype: BY4700 pdc6::$P_{GPM1}$-sadB-ADH1t pdc1::$P_{PDC1}$-ilvD-FBA1t Δhis3 Δhxk2.

Construction of pdc5::kanMX Integration Cassette and PDC5 Deletion

A pdc5::kanMX4 cassette was PCR-amplified as described above. The PCR fragment was transformed into NYLA83, and transformants were selected and screened as described above. The identified correct transformants named NYLA84 have the genotype: BY4700 pdc6::$P_{GPM1}$-sadB-ADH1t pdc1::$P_{PDC1}$-ilvD-FBA1t Δhis3 Δhxk2 pdc5::kanMX4.

Plasmid vectors pLH468 and pLH475-Z4B8 were simultaneously transformed into strain NYLA84 (BY4700 pdc6::$P_{GPM1}$-sadB-ADH1t pdc1::$P_{PDC1}$-ilvD-FBA1t Δhis3 Δhxk2 pdc5::kanMX4) using standard genetic techniques (*Methods in Yeast Genetics,* 2005, Cold Spring Harbor Laboratory Press, Cold Spring Harbor, N.Y.) and the resulting strain was maintained on synthetic complete media lacking histidine and uracil, and supplemented with 1% ethanol at 30° C.

Example 3

Production of Isobutanol

The purpose of this example is to describe the production of isobutanol in the yeast strain NYLA84. The yeast strain comprises deletions of PDC1, PDC5, and PDC6, genes encoding three isozymes of pyruvate decarboxylase, and constructs for heterologous expression of AlsS (acetolactate synthase), KARI (keto acid reductoisomerase), DHAD (dihydroxy acid dehydratase), KivD (ketoisovalerate decarboxylase), and SadB (secondary alcohol dehydrogenase).

Strain Construction

Plasmids pLH468 and pLH475-Z4B8 were introduced into NYLA74 or NYLA84, described in Example 2, by standard PEG/lithium acetate-mediated transformation methods. Transformants were selected on synthetic complete medium lacking glucose, histidine and uracil. Ethanol (1% v/v) was used as the carbon source. After three days, transformants were patched to synthetic complete medium lacking histidine and uracil supplemented with both 2% glucose and 1% ethanol as carbon sources. Fermentation seed vials were made by inoculation of cultures into synthetic complete medium lacking histidine and uracil supplemented with both 0.2% glucose and 0.5% ethanol. Glycerol was added to final concentration of 15% (v/v) and vials were stored at −80° C.

Production of Isobutanol

Fermentation inoculum was grown in synthetic complete medium lacking histidine and uracil supplemented with 1% ethanol as a carbon source at 30° C. and shaking at 250 rpm.

Inoculation volume for the fermenters was 80 ml. The 80 ml of inoculum in the 800 ml fermentation medium described below resulted in the presence of 0.1% ethanol.

The NYLA84/pLH468+pLH475-Z4B8 strain fermenter was prepared and sterilized with 0.4 L water. After cooling, filter sterilized media was added to give the following final concentrations in 800 mL post-inoculation:

Medium (Final Concentration):

6.7 g/L Yeast Nitrogen Base w/o amino acids (Difco)

2.8 g/L Yeast Synthetic Drop-out Medium Supplement Without Histidine, Leucine, Tryptophan and Uracil (Sigma Y2001)

20 mL/L of 1% (w/v) L-Leucine 4 mL/L of 1% (w/v) L-Tryptophan 10 g/L glucose 1 mL/L 1% ergosterol in 50% (v/v) Tween-80/ethanol solution 0.2 mL/L Sigma DF204 antifoam The fermenter was set to control at pH 5.5 with KOH, initial dO (dissolved oxygen) 30% by stirring, temperature 30° C., and airflow of 0.2 SLPM (or, 0.25 vvm). At inoculation, the airflow was set to 0.01 SLPM initially, then increased to 0.2 SLPM. Glucose was maintained at 5-15 g/L throughout.

The NYLA74/pLH468+pLH475-Z4B8 strain fermenter was prepared as for the NYLA84/pLH468+pLH475-Z4B8 strain fermenter except that 1 mL/L ergosterol/tween/ethanol solution and 0.2 mL/L Sigma DF204 antifoam were omitted, and glucose was 2 g/L. Initial ethanol concentration in the fermenter was 0.1%.

The fermenter was set to control at pH 5.5 with KOH, initial dO 30% by stirring, temperature 30° C., and airflow of 0.2 SLPM (or, 0.25 vvm). At inoculation, the airflow was set to 0.01 SLPM initially, then increased to 0.2 SLPM. Glucose was maintained at 0.1-2 g/L throughout.

Samples were taken periodically and measured for growth by OD600, and for isobutanol content by HPLC as described in General Methods. FIG. 1 shows the results comparing strains with and without hexokinase 2 deletion for growth (1A) and isobutanol production (1B). FIG. 2 shows a comparison of growth and isobutanol production for the strain without hexokinase 2 deletion (2A) and the strain with hexokinase 2 deletion (2B). FIG. 3 plots the results as "specific productivity" (Qp) measured in grams isobutanol per gram of cells over time. For the strain without deletion of hexokinase 2, the cell specific productivity dropped from 60-90 hours when there was no longer growth, while for hexokinase 2 deletion strain, the specific productivity was relatively well maintained from 60-140 hours showing that the strain is capable of better non-growth associated production.

Example 4

Prophetic

Regulated Expression of Hexokinase in a *S. cerevisiae* Strain Devoid of Pyruvate Decarboxylase and Hexokinase 2 Activity This example describes insertion of hexokinase enzyme under a controlled expression in a *S. cerevisiae* strain where pyruvate decarboxylase (Δpdc1/5/6) and hexokinase 2 (Δhxk2) activity have been removed. Creation of the NYLA84 (Δpdc1/5/6 Δhxk2) strain was described in Example 2.

The HXK2 gene and native terminator from *S. cerevisiae* (SEQ ID NO: 101) was PCR amplified from genomic DNA from strain BY4700 (ATCC #200866) using Phusion DNA polymerase and primers LA588 (SEQ ID NO: 96) and LA589 (SEQ ID NO: 97), and digested with XbaI and BamHI restriction enzymes. The OLE1 promoter region derived sequence (SEQ ID NO: 98) was PCR amplified from BY4700 genomic DNA using Phusion DNA polymerase and primers LA586 (SEQ ID NO: 99) and LA587 (SEQ ID NO: 100), and digested with HindIII and XbaI restriction enzymes. The HXK2 and $P_{OLE1}$ products were ligated and subcloned into pUC19::loxP-URA3-loxP which was previously digested with HindIII and BamHI. pUC19::loxP-URA3-loxP (SEQ ID NO: 102) contains the URA3 marker from (ATCC #77107) flanked by loxP recombinase sites. The resulting vector was named pLA25 (SEQ ID NO: 103).

The RAG5 gene from *K. lactis* (SEQ ID NO: 3) was PCR amplified from genomic DNA from strain GG799 (#01001S; New England Biolabs, Ipswich, Mass.) using Phusion DNA polymerase and primers LA593 and LA594 (SEQ ID NO: 104 and 105), and was digested with HindIII and XbaI restriction enzymes. The gel-purified RAG5 product was ligated with the OLE1 promoter region derived sequence from above, and subcloned into pUC19::loxP-URA3-loxP which was previously digested with HindIII and BamHI. The resulting vector was named pLA31 (SEQ ID NO: 106).

In order to integrate into the TRP1 locus, the $P_{OLE1}$-HXK2-loxP-URA3-loxP and $P_{OLE1}$-RAG5-loxP-URA3-loxP cassettes is PCR amplified from plasmids pLA25 and pLA31 using Phusion DNA polymerase and primers BK600 and BK601 (SEQ ID NOs: 107 and 108). The TRP1 portion of each primer is derived from the 5' region upstream of the TRP1 promoter and 3' region downstream of the coding region such that integration of the $P_{OLE1}$-HXK2-loxP-URA3-loxP or $P_{OLE1}$-RAG5-loxP-URA3-loxP cassette results in replacement of the TRP1 coding region. The PCR product is transformed into NYLA84 using standard genetic techniques (*Methods in Yeast Genetics,* 2005, Cold Spring Harbor Laboratory Press, Cold Spring Harbor, N.Y., pp. 201-202) and transformants are selected on synthetic complete media lacking uracil and supplemented with 2% glucose at 30° C. Transformants are screened by PCR to verify correct integration at the TRP1 locus with replacement of the TRP1 coding region using primers 112590-49E (SEQ ID NO: 75) and LA606 (SEQ ID NO: 109). The URA3 marker is recycled by transformation with pRS423::$P_{GAL1}$-cre (SEQ ID NO: 110) and plating on synthetic complete media lacking histidine supplemented with 1% ethanol at 30° C. Colonies are patched onto YP (1% galactose) plates at 30° C. to induce URA3 marker excision and are transferred onto YP (1 ethanol) plates at 30° C. for recovery. Removal of the URA3 marker is confirmed by patching colonies from the YP (1% ethanol) plates onto synthetic complete media lacking uracil supplemented with 1% ethanol to verify the absence of growth.

Example 5

Prophetic

Constitutive Expression of Hexokinase in a *S. cerevisiae* Strain Devoid of Pyruvate Decarboxylase and Hexokinase 2 Activity This example describes insertion of hexokinase enzyme under control of the constitutive ADH1-derived promoter sequence in a *S. cerevisiae* strain where pyruvate decarboxylase (Δpdc1/5/6) and hexokinase 2 (Δhxk2) activity have been removed. Creation of the NYLA84 (Δpdc1/5/6 Δhxk2) strain was described in Example 2.

The RAG5 gene from *K. lactis* (SEQ ID NO: 3) was PCR amplified from genomic DNA from strain GG799 (#C1001 S; New England Biolabs, Ipswich, Mass.) using Phusion DNA polymerase and primers LA593 and LA594 (SEQ ID NOs: 104 and 105), and was digested with HindIII and XbaI restriction enzymes. The ADH1 promoter region derived sequence (SEQ ID NO: 131) was PCR amplified from BY4700 genomic DNA using Phusion DNA polymerase and primers LA595 and LA597 (SEQ ID NOs: 112 and 113), and digested with HindIII and XbaI restriction enzymes. The gel-purified RAG5 product was ligated with the ADH1 promoter fragment, and subcloned into pUC19::loxP-URA3-loxP which was previously digested with HindIII and BamHI. The resulting vector was named pLA32 (SEQ ID NO: 111).

In order to integrate into the TRP1 locus, the $P_{ADH1}$-RAG5-loxP-URA3-loxP cassette is PCR amplified from plasmid pLA32 using Phusion DNA polymerase and primers BK600 and BK601 (SEQ ID NOs 107 and 108). The TRP1 portion of each primer is derived from the 5' region upstream of the TRP1 promoter and 3' region downstream of the coding region such that integration of the $P_{ADH1}$-RAG5-loxP-URA3-loxP cassette results in replacement of the TRP1 coding region. The PCR product is transformed into NYLA84 using standard genetic techniques (*Methods in Yeast Genetics,* 2005, Cold Spring Harbor Laboratory Press, Cold Spring Harbor, N.Y., pp. 201-202) and transformants are selected on synthetic complete media lacking uracil and supplemented with 2% glucose at 30° C. Transformants are screened by PCR to verify correct integration at the TRP1 locus with replacement of the TRP1 coding region using primers 112590-49E (SEQ ID NO: 75) and LA606 (SEQ ID NO: 109). The URA3 marker is recycled by transformation with pRS423::$P_{GAL1}$-cre (SEQ ID NO: 110) and plating on synthetic complete media lacking histidine supplemented with 1% ethanol at 30° C. Colonies are patched onto YP (1% galactose) plates at 30° C. to induce URA3 marker excision and are transferred onto YP (1% ethanol) plates at 30° C. for recovery. Removal of the URA3 marker is confirmed by patching colonies from the YP (1% ethanol) plates onto synthetic complete media lacking uracil supplemented with 1% ethanol to verify the absence of growth.

Example 6

Prophetic

Isobutanol Production Using NYLA84 Strains with Regulated Expression of Hexose Kinase Isobutanol Strain and Production The expression constructs pLH475-JEA1 and pLH468 (described in Example 1) are transformed into strains NYLA84, NYLA84 trp1:$P_{OLE1}$-HXK2 and NYLA84 trp1: $P_{OLE1}$-RAG5 (described in Example 4) by standard PEG/lithium acetate-mediated transformation methods. Transformants are selected on synthetic complete medium lacking glucose, histidine and uracil. Ethanol (1% v/v) is used as the carbon source. After three days, transformants are patched to synthetic complete medium lacking histidine and uracil supplemented with both 2% glucose and 1% ethanol as carbon sources. Seed vials are made by inoculation of cultures into synthetic complete medium lacking histidine and uracil supplemented with both 0.2% glucose and 0.5% ethanol. Glycerol is added to final concentration of 15% (v/v) and vials are stored at −80° C.

Isobutanol Production

Seed vials of NYLA84 pLH475-JEA1, NYLA84 trp1::$P_{OLE1}$-HXK2, and NYLA84 trp1::$P_{OLE1}$-RAG5 are inoculated into 80 mL of synthetic complete medium lacking histidine and uracil supplemented with both 0.25% glucose and 0.5% ethanol as carbon sources at 30° C. A 1 liter fermenter is prepared and sterilized with 0.4 L water. After cooling, filter sterilized medium is added to give the following final concentrations in 800 mL post-inoculation:

Medium (Final Concentration):

6.7 g/L, Yeast Nitrogen Base w/o amino acids (Difco)

2.8 g/L, Yeast Synthetic Drop-out Medium Supplement Without Histidine, Leucine, Tryptophan and Uracil (Sigma Y2001)

20 mL/L of 1% (w/v) L-Leucine 4 mL/L of 1% (w/v) L-Tryptophan 1 mL/L ergosterol/tween/ethanol solution 0.2 mL/L Sigma DF204

10 g/L glucose

The fermenter is set to control at pH 5.5 with KOH, 30% dO, temperature 30° C., and airflow of 0.2 SLPM (or, 0.25 vvm). At inoculation, the airflow is set to 0.01 SLPM initially, then increased to 0.2 SLPM once growth was established. Glucose is maintained at 5-15 g/L throughout by manual addition. Alternatively, the fermenter is set to control at pH 5.5 with KOH, 3-5% dO, temperature 30° C., and airflow of 0.2 SLPM (or 0.25 vvm). At inoculation, the airflow is set to 0.01 SLPM initially, increased to 0.2 SLPM once growth is established.

To quantify the loss of isobutanol due to stripping, the off-gas from the fermentor is directly sent to a mass spectrometer (Prima dB mass spectrometer, Thermo Electron Corp., Madison, Wis.) to quantify the amount of isobutanol in the gas stream. The isobutanol peaks at mass to charge ratios of 74 or 42 are monitored continuously to quantify the amount of isobutanol in the gas stream. Glucose and organic acids in the aqueous phase are monitored during the fermentation using HPLC. Glucose is also monitored quickly using a glucose analyzer (YSI, Inc., Yellow Springs, Ohio). Isobutanol and isobutyric acid in the aqueous phase are quantified by HPLC as described in the General Methods Section herein above after the aqueous phase is removed periodically from the fermentor.

Example 7

Prophetic

Modification of Hexose Kinase Function

The purpose of this example is to describe how the function of hexose kinase can be altered by deletion of a protein interaction domain that prevents function as a transcriptional regulator. The MIG1-interaction domain (Lys6-Met15) is removed from *S. cerevisiae* HXK2 which allows function as a glycolytic enzyme but prevents translocation to the nucleus.

In order to remove the N-terminal MIG1-interaction domain from *S. cerevisiae* HXK2, an integration cassette is constructed using the pUC19::loxP-URA3-loxP plasmid. The gene encoding HXK2 with an internal deletion of the Lys6-Met15 region (bp 19-48) and ADH1 terminator region derived sequence is synthesized by DNA 2.0 with codon-optimization for *S. cerevisiae* (SEQ ID NO: 132). The HXK2 (ΔLys6-Met15)-ADH1t cassette is PCR-amplified using Phusion DNA polymerase and primers E001 and E002 (SEQ ID NOS: 133 and 134) and subcloned into pUC19::loxP- URA3-loxP via HindIII BamHI sites, creating plasmid pUC19::loxP-URA3-loxP-HXK2(Lys6-Met15)-ADH1t (SEQ ID NO: 139).

The HXK2(ΔLys6-Met15)ADH1t-loxP-URA3-loxP cassette is PCR amplified using Phusion DNA polymerase and primers E003 and E004 (SEQ ID NOS: 135 and 136). Primer E003 contains sequence from the HXK2 promoter region and primer E004 contains sequence from the HXK2 terminator, such that integration of the HXK2(ΔLys6-Met15)ADH1t-loxP-URA3-loxP cassette results in replacement of the native HXK2 coding sequence. The PCR product is transformed into NYLA74 using standard genetic techniques (*Methods in Yeast Genetics,* 2005, Cold Spring Harbor Laboratory Press, Cold Spring Harbor, N.Y., pp. 201-202) and transformants are selected on synthetic complete media lacking uracil and supplemented with 2% glucose at 30° C. Transformants are screened by PCR to verify correct integration at the HXK2 locus using primers E005 and E006 (SEQ ID NOS: 137 and 138). The URA3 marker is recycled by transformation with pRS423::$P_{GAL1}$-cre (SEQ ID NO: 110) and plating on synthetic complete media lacking histidine supplemented with 1% ethanol at 30° C. Colonies are patched onto YP (1% galactose) plates at 30° C. to induce URA3 marker excision and are transferred onto YP (1% ethanol) plates at 30° C. for recovery. Removal of the URA3 marker is confirmed by patching colonies from the YP (1% ethanol) plates onto synthetic complete media lacking uracil supplemented with 1% ethanol to verify the absence of growth.

Example 8

Prophetic

Isobutanol Production Using NYLA44 Strains with Modified Function of Hexose Kinase Isobutanol Strain and Production The expression constructs pLH475-JEA1 and pLH468 (described in Example 1) are transformed into strains NYLA74 hxk2Δ::HXK2(ΔLys6-Met15) (described in Example 7) by standard PEG/lithium acetate-mediated transformation methods. Transformants are selected on synthetic complete medium lacking glucose, histidine and uracil. Ethanol (1% v/v) is used as the carbon source. After three days, transformants are patched to synthetic complete medium lacking histidine and uracil supplemented with both 2% glucose and 1% ethanol as carbon sources. Seed vials are made by inoculation of cultures into synthetic complete medium lacking histidine and uracil supplemented with both 0.2% glucose and 0.5% ethanol. Glycerol is added to final concentration of 15% (v/v) and vials are stored at −80° C.

Isobutanol Production

Seed vials of NYLA74 hxk2Δ::HXK2(ΔLys6-Met15) pLH468 pLH475-JEA1 are inoculated into 80 mL of synthetic complete medium lacking histidine and uracil supplemented with both 0.25% glucose and 0.5% ethanol as carbon sources at 30° C. A 1 liter fermenter is prepared and sterilized with 0.4 L water. After cooling, filter sterilized medium is added to give the following final concentrations in 800 mL post-inoculation:

Medium (Final Concentration):

6.7 g/L, Yeast Nitrogen Base w/o amino acids (Difco)
2.8 g/L, Yeast Synthetic Drop-out Medium Supplement Without Histidine, Leucine, Tryptophan and Uracil (Sigma Y2001)
20 mL/L of 1% (w/v) L-Leucine
4 mL/L of 1% (w/v) L-Tryptophan
1 mL/L ergosterol/tween/ethanol solution
0.2 mL/L Sigma DF204
10 g/L glucose The fermenter is set to control at pH 5.5 with KOH, 30% dO, temperature 30° C., and airflow of 0.2 SLPM (or, 0.25 vvm). At inoculation, the airflow is set to 0.01 SLPM initially, then increased to 0.2 SLPM once growth was established. Glucose is maintained at 5-15 g/L throughout by manual addition. Alternatively, the fermenter is set to control at pH 5.5 with KOH, 3-5% dO, temperature 30° C., and airflow of 0.2 SLPM (or 0.25 vvm). At inoculation, the airflow is set to 0.01 SLPM initially, increased to 0.2 SLPM once growth is established.

To quantify the loss of isobutanol due to stripping, the off-gas from the fermentor is directly sent to a mass spectrometer (Prima dB mass spectrometer, Thermo Electron Corp., Madison, Wis.) to quantify the amount of isobutanol in the gas stream. The isobutanol peaks at mass to charge ratios of 74 or 42 are monitored continuously to quantify the amount of isobutanol in the gas stream. Glucose and organic acids in the aqueous phase are monitored during the fermentation using HPLC. Glucose is also monitored quickly using a glucose analyzer (YSI, Inc., Yellow Springs, Ohio). Isobutanol and isobutyric acid in the aqueous phase are quantified by HPLC as described in the General Methods Section herein above after the aqueous phase is removed periodically from the fermentor.

What is claimed is:

1. A recombinant yeast host cell comprising:

(a) a modification in an endogenous polynucleotide encoding a polypeptide having dual-role hexokinase activity in the host cell wherein the activity of the polypeptide of (a) is reduced or substantially eliminated; and (b) a heterologous polynucleotide encoding a polypeptide having hexose kinase activity; and (c) a modification in an endogenous polynucleotide encoding a polypeptide having pyruvate decarboxylase activity wherein pyruvate decarboxylase activity is reduced or substantially eliminated.

2. The recombinant host cell of claim 1 wherein the glucose consumption rate is increased as compared to that of the host cell comprising (a) but not (b).

3. The recombinant host cell of claim 1 wherein the modification of (a) is a deletion.

4. The recombinant host of claim 1 wherein the polypeptide of (a) is HXK2, and wherein the recombinant host cell is *S. cerevisiae.*

5. The recombinant host cell of claim 4 wherein the heterologous polynucleotide of (b) encodes a polypeptide of SEQ ID NO: 4, 6, 8, 121, or 123.

6. The recombinant host cell of claim 4 wherein the heterologous polynucleotide of (b) encodes a polypeptide that has at least about 85% identity to SEQ ID NO: 4, 6, 8, 121, or 123.

7. The recombinant host cell of claim 4 wherein the heterologous polynucleotide of (b) en codes a polypeptide that has at least about 85% identity to SEQ ID NO: 130.

8. The recombinant host cell of claim 4 wherein the heterologous polynucleotide of (b) comprises a conditional promoter and encodes a polypeptide having at least 85% identity to SEQ ID NO: 4 or SEQ ID NO: 2.

9. The recombinant host cell of claim 8 wherein the conditional promoter comprises a sequence derived from the OLE1 promoter region.

10. The recombinant host cell of claim 4 comprising an isobutanol biosynthetic pathway, the isobutanol biosynthetic pathway comprising a heterologous polynucleotide encoding a polypeptide that catalyzes a substrate to product conversion of:

(i) pyruvate to acetolactate;
(ii) acetolactate to 2,3-dihydroxyisovalerate;
(iii) 2,3-dihydroxyisovalerate to 2-ketoisovalerate;
(iv) 2-ketoisovalerate to isobutyraldehyde; and
(v) isobutyraldehyde to isobutanol; and
wherein the host cell produces isobutanol.

11. The recombinant host cell of claim 1, wherein the polypeptide of (a) is RAG5, and wherein the recombinant host cell is *K. lactis*, or wherein the polypeptide of (a) is HPGLK1, and wherein the recombinant host cell is *H. polymorpha*, or wherein the polypeptide of (a) is HXK2, and wherein the recombinant host cell is *S. pombe.*

12. The recombinant host cell of claim 1 wherein the polynucleotide of (b) comprises a promoter such that the polypeptide of (b) is conditionally expressed.

13. The recombinant host cell of claim 1 wherein the polynucleotide of (b) comprises a promoter such that the polypeptide of (b) is constitutively expressed.

14. The recombinant host cell of claim 1 wherein the heterologous polynucleotide of (b) comprises the polypeptide of (a) having a deletion of a protein interaction domain that prevents function as a transcriptional regulator.

15. The recombinant host cell of claim 1 wherein the heterologous polynucleotide of (b) encodes a polypeptide that has at least about 85% identity to SEQ ID NO: 2, 115, 117, 119, 4, 6, 8, 121, or 123.

16. The recombinant host cell of claim 1 wherein the polypeptide encoded by the heterologous polynucleotide of (b) is constitutively expressed.

17. The recombinant host cell of claim 1 wherein the heterologous polynucleotide of (b) comprises i) a promoter region derived from *S. cerevisiae* ADH1 promoter region or ii) a promoter region having at least about 85% identity to SEQ ID NO: 131.

18. The recombinant host cell of claim 1 further comprising a pyruvate-utilizing biosynthetic pathway which forms a product selected from the group consisting of: 2,3-butanediol, isobutanol, 2-butanol, 1-butanol, 2-butanone, valine, leucine, lactic acid, malate, isoamyl alcohol, and isoprenoids.

19. The recombinant host cell of claim 18 wherein the product is isobutanol.

20. The recombinant host cell of claim 18 wherein the pyruvate-utilizing biosynthetic pathway is an isobutanol biosynthetic pathway comprising a heterologous polynucleotide encoding a polypeptide for each of the following substrate to product conversions:

(i) pyruvate to acetolactate;
(ii) acetolactate to 2,3-dihydroxyisovalerate;
(iii) 2,3-dihydroxyisovalerate to 2-ketoisovalerate;
(iv) 2-ketoisovalerate to isobutyraldehyde; and
(v) isobutyraldehyde to isobutanol; and
wherein the host cell produces sobutanol.

21. The recombinant host cell of claim 19 wherein the pyruvate-utilizing biosynthetic pathway is a 2-butanone biosynthetic pathway comprising a heterologous polynucleotide encoding a polypeptide for each the following substrate to product conversions:

(i) pyruvate to acetolactate:
(ii) acetolactate to acetoin;
(iii) acetoin to 2,3-butanediol; and
(iv) 2,3-butanediol to 2-butanone; and
wherein the host cell produces 2-butanone.

22. The recombinant host cell of claim 18 wherein the pyruvate-utilizing biosynthetic pathway is a 2-butanol biosynthetic pathway comprising a heterologous polynucleotide encoding a polypeptide for each the following substrate to product conversions:

(i) pyruvate to acetolactate;
(ii) acetolactate to acetoin;
(iii) acetoin to 2,3-butanediol;
(iv) 2,3-butanediol to 2-butanone; and
(v) 2-butanone to 2-butanol; and
wherein the host cell produces 2-butanol.

23. The recombinant host cell of claim 18 wherein the pyruvate-utilizing biosynthetic pathway is a 1-butanol biosynthetic pathway comprising a heterologous polynucleotide encoding a polypeptide for each the following substrate to product conversions:

(i) acetyl-CoA to acetoacetyl-CoA;
(ii) acetoacetyl-CoA to 3-hydroxybutyryl-CoA;
(iii) 3-hydroxybutyryl-CoA to crotonyl-CoA;
(iv) crotonyl-CoA to butyryl-CoA;
(v) butyryl-CoA to butyraldehyde; and
(vi) butyraldehyde to 1-butanol; and
wherein the host cell produces isobutanol.

24. A method for the production of isobutanol comprising:

(a) providing a recombinant host cell of claim 10; and
(b) growing the recombinant host cell of claim 10 under conditions wherein isobutanol is produced.

25. A method of increasing glucose consumption of a recombinant host cell comprising:

(i) providing the recombinant host cell of claim 1; and (ii) growing the recombinant host cell under conditions wherein the heterologous polynucleotide of (b) is expressed in functional form;

wherein the glucose consumption of the recombinant host cell is greater than the glucose consumption of a host cell comprising (a) but not (b).

26. A method of increasing the formation of a product of a pyruvate-utilizing biosynthetic pathway comprising:

(i) providing the recombinant host cell of claim 18, or combinations thereof; and (ii) growing the recombinant host cell under conditions wherein the product of the pyruvate-utilizing pathway is formed;

wherein the amount of product formed by the recombinant host cell is greater than the amount of product formed by a host cell comprising (a) but not (b).

27. The method of claim 26 wherein the product is butanol.

28. The method of claim 27, wherein said butanol is isobutanol.

29. A method for improving the redox balance of a recombinant host cell comprising:

(i) providing the recombinant host cell of claim 1; and (ii) growing the recombinant host cell of (i) under conditions wherein the heterologous polynucleotide of (b) is expressed in functional form wherein the redox balance of such a recombinant host cell is improved compared to the redox balance of a recombinant host cell comprising (i)(a) but not (i)(b).

30. A method for the production of isobutanol comprising:

(a) providing a recombinant host cell of claim 20; and (b) growing the recombinant host cell of claim 20 under conditions wherein isobutanol is produced.

* * * * *

SEQUENCE LISTING

```
<160> NUMBER OF SEQ ID NOS: 144

<210> SEQ ID NO 1
<211> LENGTH: 1461
<212> TYPE: DNA
<213> ORGANISM: Saccharomyces cerevisiae

<400> SEQUENCE: 1

atggttcatt taggtccaaa aaaaccacaa gccagaaagg gttccatggc cgatgtgcca      60

aaggaattga tgcaacaaat tgagaatttt gaaaaaattt tcactgttcc aactgaaact     120

ttacaagccg ttaccaagca cttcatttcc gaattggaaa agggtttgtc caagaagggt     180

ggtaacattc caatgattcc aggttgggtt atggatttcc caactggtaa ggaatccggt     240
```

-continued

```
gatttcttgg ccattgattt gggtggtacc aacttgagag ttgtcttagt caagttgggc    300

ggtgaccgta cctttgacac cactcaatct aagtacagat taccagatgc tatgagaact    360

actcaaaatc cagacgaatt gtgggaattt attgccgact ctttgaaagc ttttattgat    420

gagcaattcc cacaaggtat ctctgagcca attccattgg gtttcacctt ttctttccca    480

gcttctcaaa acaaaatcaa tgaaggtatc ttgcaaagat ggactaaagg ttttgatatt    540

ccaaacattg aaaaccacga tgttgttcca atgttgcaaa agcaaatcac taagaggaat    600

atcccaattg aagttgttgc tttgataaac gacactaccg gtactttggt tgcttcttac    660

tacactgacc cagaaactaa gatgggtgtt atcttcggta ctggtgtcaa tggtgcttac    720

tacgatgttt gttccgatat cgaaaagcta caaggaaaac tatctgatga cattccacca    780

tctgctccaa tggccatcaa ctgtgaatac ggttccttcg ataatgaaca tgtcgttttg    840

ccaagaacta aatacgatat caccattgat gaagaatctc caagaccagg ccaacaaacc    900

tttgaaaaaa tgtcttctgg ttactactta ggtgaaattt tgcgtttggc cttgatggac    960

atgtacaaac aaggtttcat cttcaagaac caagacttgt ctaagttcga caagcctttc   1020

gtcatggaca cttcttaccc agccagaatc gaggaagatc cattcgagaa cctagaagat   1080

accgatgact tgttccaaaa tgagttcggt atcaacacta ctgttcaaga acgtaaattg   1140

atcagacgtt tatctgaatt gattggtgct agagctgcta gattgtccgt ttgtggtatt   1200

gctgctatct gtcaaaagag aggttacaag accggtcaca tcgctgcaga cggttccgtt   1260

tacaacagat acccaggttt caaagaaaag gctgccaatg ctttgaagga catttacggc   1320

tggactcaaa cctcactaga cgactaccca atcaagattg ttcctgctga agatggttcc   1380

ggtgctggtg ccgctgttat tgctgctttg gcccaaaaaa gaattgctga aggtaagtcc   1440

gttggtatca tcggtgctta a                                             1461


<210> SEQ ID NO 2
<211> LENGTH: 486
<212> TYPE: PRT
<213> ORGANISM: Saccharomyces cerevisiae

<400> SEQUENCE: 2

Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Thr Leu Gln Ala Val Thr Lys His Phe
        35                  40                  45

Ile Ser Glu Leu Glu Lys Gly Leu Ser Lys Lys Gly Gly Asn Ile Pro
    50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160
```

```
Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
    290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
        355                 360                 365

Phe Gly Ile Asn Thr Thr Val Gln Glu Arg Lys Leu Ile Arg Arg Leu
    370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
        435                 440                 445

Tyr Pro Ile Lys Ile Val Pro Ala Glu Asp Gly Ser Gly Ala Gly Ala
    450                 455                 460

Ala Val Ile Ala Ala Leu Ala Gln Lys Arg Ile Ala Glu Gly Lys Ser
465                 470                 475                 480

Val Gly Ile Ile Gly Ala
                485
```

<210> SEQ ID NO 3
<211> LENGTH: 1458
<212> TYPE: DNA
<213> ORGANISM: Kluyveromyces lactis

<400> SEQUENCE: 3

```
atggttcgtt taggtccaaa gaagcctcca gccagaaagg ggtccatggc agatgtgcca     60

gctaatttga tggaacaaat ccacggtttg gaaactttgt tcaccgtctc ttcagaaaaa    120

atgagaagca ttgtcaagca tttcatcagt gaattggaca aaggtttgtc caaaaagggt    180

ggtaacattc ctatgattcc aggttgggtt gttgagtatc caactggtaa ggaaactggt    240

gatttcttag ctcttgattt gggtggtacc aacttgagag ttgtgttggt taaattgggt    300
```

```
ggtaatcatg atttcgacac cactcaaaac aagtacagat taccagacca tttgagaact    360

ggtacttctg aacaattgtg gtcatttatt gcaaagtgtt tgaaggaatt cgtcgatgaa    420

tggtacccag atggtgtttc tgaaccattg ccattgggtt tcactttctc ataccctgca    480

tctcaaaaga agatcaattc cggtgtgttg caacgttgga ccaagggttt cgatattgaa    540

ggtgttgaag gtcacgatgt tgttccaatg ctacaagaac agattgaaaa gctgaatatc    600

ccaatcaatg tcgttcgatt gatcaacgat accactggta ccttggttgc ctctttgtac    660

actgatcctc aaactaagat gggtatcatt atcggtactg gtgtcaacgg tgcttactac    720

gatgttgttt ctggtattga gaaattggaa ggtttgttgc cagaagatat cggtccagat    780

tctccaatgg caatcaactg tgaatatggt tccttcgata acgaacattt ggtgttgcca    840

agaaccaaat acgatgttat aatcgatgaa gaatctccaa gaccaggtca acaagctttc    900

gaaaagatga cttctggtta ctatctaggt gaaatcatgc gtctagtact attggacttg    960

tacgacagtg gtttcatctt taaggaccaa gatatctcca agttgaaaga ggcttacgtc   1020

atggacacca gttatccatc taagatcgaa gatgatccat tcgaaaactt ggaagacact   1080

gacgatctgt tcaagactaa cttgaacatc gaaactaccg ttgttgagag aaagttgatt   1140

agaaaattag ccgaattggt cggaacaaga gctgcaagat tgactgtttg tggtgtttct   1200

gctatctgtg acaagagagg ctacaagact gctcacattg cagctgatgg ttctgtcttc   1260

aacagatacc caggttacaa ggaaaaggcc gctcaagcct tgaaggatat ctacaactgg   1320

gatgtcgaaa agatggaaga ccacccaatc caattggtgg ctgctgaaga tggttccggt   1380

gttggtgctg ctatcattgc ttgtttgact caaaagagat tggctgccgg taagtctgtt   1440

ggtattaaag gcgaatag                                                 1458
```

<210> SEQ ID NO 4
<211> LENGTH: 485
<212> TYPE: PRT
<213> ORGANISM: Kluyveromyces lactis

<400> SEQUENCE: 4

```
Met Val Arg Leu Gly Pro Lys Lys Pro Pro Ala Arg Lys Gly Ser Met
1               5                   10                  15

Ala Asp Val Pro Ala Asn Leu Met Glu Gln Ile His Gly Leu Glu Thr
            20                  25                  30

Leu Phe Thr Val Ser Ser Glu Lys Met Arg Ser Ile Val Lys His Phe
        35                  40                  45

Ile Ser Glu Leu Asp Lys Gly Leu Ser Lys Lys Gly Gly Asn Ile Pro
    50                  55                  60

Met Ile Pro Gly Trp Val Val Glu Tyr Pro Thr Gly Lys Glu Thr Gly
65                  70                  75                  80

Asp Phe Leu Ala Leu Asp Leu Gly Gly Thr Asn Leu Arg Val Val Leu
                85                  90                  95

Val Lys Leu Gly Gly Asn His Asp Phe Asp Thr Thr Gln Asn Lys Tyr
            100                 105                 110

Arg Leu Pro Asp His Leu Arg Thr Gly Thr Ser Glu Gln Leu Trp Ser
        115                 120                 125

Phe Ile Ala Lys Cys Leu Lys Glu Phe Val Asp Glu Trp Tyr Pro Asp
    130                 135                 140

Gly Val Ser Glu Pro Leu Pro Leu Gly Phe Thr Phe Ser Tyr Pro Ala
145                 150                 155                 160

Ser Gln Lys Lys Ile Asn Ser Gly Val Leu Gln Arg Trp Thr Lys Gly
```

-continued

```
                165                 170                 175

Phe Asp Ile Glu Gly Val Glu Gly His Asp Val Val Pro Met Leu Gln
            180                 185                 190

Glu Gln Ile Glu Lys Leu Asn Ile Pro Ile Asn Val Val Arg Leu Ile
        195                 200                 205

Asn Asp Thr Thr Gly Thr Leu Val Ala Ser Leu Tyr Thr Asp Pro Gln
    210                 215                 220

Thr Lys Met Gly Ile Ile Ile Gly Thr Gly Val Asn Gly Ala Tyr Tyr
225                 230                 235                 240

Asp Val Val Ser Gly Ile Glu Lys Leu Glu Gly Leu Leu Pro Glu Asp
                245                 250                 255

Ile Gly Pro Asp Ser Pro Met Ala Ile Asn Cys Glu Tyr Gly Ser Phe
            260                 265                 270

Asp Asn Glu His Leu Val Leu Pro Arg Thr Lys Tyr Asp Val Ile Ile
        275                 280                 285

Asp Glu Glu Ser Pro Arg Pro Gly Gln Gln Ala Phe Glu Lys Met Thr
    290                 295                 300

Ser Gly Tyr Tyr Leu Gly Glu Ile Met Arg Leu Val Leu Leu Asp Leu
305                 310                 315                 320

Tyr Asp Ser Gly Phe Ile Phe Lys Asp Gln Asp Ile Ser Lys Leu Lys
                325                 330                 335

Glu Ala Tyr Val Met Asp Thr Ser Tyr Pro Ser Lys Ile Glu Asp Asp
            340                 345                 350

Pro Phe Glu Asn Leu Glu Asp Thr Asp Asp Leu Phe Lys Thr Asn Leu
        355                 360                 365

Asn Ile Glu Thr Thr Val Val Glu Arg Lys Leu Ile Arg Lys Leu Ala
    370                 375                 380

Glu Leu Val Gly Thr Arg Ala Ala Arg Leu Thr Val Cys Gly Val Ser
385                 390                 395                 400

Ala Ile Cys Asp Lys Arg Gly Tyr Lys Thr Ala His Ile Ala Ala Asp
                405                 410                 415

Gly Ser Val Phe Asn Arg Tyr Pro Gly Tyr Lys Glu Lys Ala Ala Gln
            420                 425                 430

Ala Leu Lys Asp Ile Tyr Asn Trp Asp Val Glu Lys Met Glu Asp His
        435                 440                 445

Pro Ile Gln Leu Val Ala Ala Glu Asp Gly Ser Gly Val Gly Ala Ala
    450                 455                 460

Ile Ile Ala Cys Leu Thr Gln Lys Arg Leu Ala Ala Gly Lys Ser Val
465                 470                 475                 480

Gly Ile Lys Gly Glu
                485


<210> SEQ ID NO 5
<211> LENGTH: 1416
<212> TYPE: DNA
<213> ORGANISM: Hansenula polymorpha

<400> SEQUENCE: 5

atgagtttgg atactgaagt cgataagatt gtgtcggagt ttgccgtcac ccaggagaca      60

ctccaaaagg gtgtggagcg tttcattgag cttgcaactg ccggactgaa tagtgatgag     120

gacaagtatg gtctgccaat gatcccaact tttgttacct ccatcccaac cggtaaagag     180

aagggcattc tttttgccgc agacttggga ggaaccaatt tcagagtttg ctctgttgcc     240

ttgaacggag atcacacttt caaactgatc cagcagaagt cacatattcc tgccgaactg     300
```

-continued

```
atgacctcca cctcggacga attgttttcg tatcttgcaa gcaaggtcaa gaatttctta    360

gagactcatc atgaaggggc tgttacttct acaggaagcc agaaattcaa gatgggtttc    420

actttcagtt tccctgtctc gcagaccgcc ttaaacgccg gtactttgct aagatggacc    480

aagggattca atattccgga tactgttggt caagaggttg tttctctatt ccaaatgcat    540

ttagacgccc aggaaattcc tgttactgtg tctgccctgt ccaacgatac tgtgggaacc    600

cttcttgcaa gatcctacac gggttccaat aaggagggca ctactgttct aggatgcatc    660

ttcggaacgg gaacaaacgg tgcttacaac gagaagctcg agaatatcaa gaagcttccg    720

gccgaggtga gagagaagct gaaggctcaa ggtgtcaccc acatggtcat taatactgaa    780

tggggttcct tcgataacca gctcaaggtt ttgccaaata cgaagtatga cgctcaagtt    840

gacgaactta ccggcaataa gggcttccac atgtttgaaa agcgtgtttc cggaatgttc    900

ttgggtgaga ttctgagaca tattttggtc gaccttcact ctaagggagt gctatttact    960

cagtacgcca gctacgaatc cctgccccac agattgagga cgccgtggga tctggactct   1020

gaggttctct cactgattga gatcgacgaa tccaccaatt tgcaggccac tgagctgtct   1080

ttgaaacagg cattgagact gccaactact actgaggaga gacttgctat tcaaaaactt   1140

actcgtgctg tggccaagag atctgcctat cttgctgcta ttcctattgc tgctattcta   1200

cacatgaccg agtcttttaa gggccacaac gttgaggtgg acgttggagc agacgggtct   1260

gtggttgagt tctaccctgg attcagaact atgatgagag acgccattgc gcagacgcag   1320

ataggtgcca aaggagagag aagactgcac attaacattg ccaaagacgg ctcatctgtg   1380

ggcgctgcat tgtgcgcatt aagcgagaaa gactaa                              1416
```

```
<210> SEQ ID NO 6
<211> LENGTH: 471
<212> TYPE: PRT
<213> ORGANISM: Hansenula polymorpha

<400> SEQUENCE: 6

Met Ser Leu Asp Thr Glu Val Asp Lys Ile Val Ser Glu Phe Ala Val
1               5                   10                  15

Thr Gln Glu Thr Leu Gln Lys Gly Val Glu Arg Phe Ile Glu Leu Ala
            20                  25                  30

Thr Ala Gly Leu Asn Ser Asp Glu Asp Lys Tyr Gly Leu Pro Met Ile
        35                  40                  45

Pro Thr Phe Val Thr Ser Ile Pro Thr Gly Lys Glu Lys Gly Ile Leu
    50                  55                  60

Phe Ala Ala Asp Leu Gly Gly Thr Asn Phe Arg Val Cys Ser Val Ala
65                  70                  75                  80

Leu Asn Gly Asp His Thr Phe Lys Leu Ile Gln Gln Lys Ser His Ile
                85                  90                  95

Pro Ala Glu Leu Met Thr Ser Thr Ser Asp Glu Leu Phe Ser Tyr Leu
            100                 105                 110

Ala Ser Lys Val Lys Asn Phe Leu Glu Thr His His Glu Gly Ala Val
        115                 120                 125

Thr Ser Thr Gly Ser Gln Lys Phe Lys Met Gly Phe Thr Phe Ser Phe
    130                 135                 140

Pro Val Ser Gln Thr Ala Leu Asn Ala Gly Thr Leu Leu Arg Trp Thr
145                 150                 155                 160

Lys Gly Phe Asn Ile Pro Asp Thr Val Gly Gln Glu Val Val Ser Leu
                165                 170                 175

Phe Gln Met His Leu Asp Ala Gln Glu Ile Pro Val Thr Val Ser Ala
```

-continued

```
            180                 185                 190

Leu Ser Asn Asp Thr Val Gly Thr Leu Leu Ala Arg Ser Tyr Thr Gly
        195                 200                 205

Ser Asn Lys Glu Gly Thr Thr Val Leu Gly Cys Ile Phe Gly Thr Gly
    210                 215                 220

Thr Asn Gly Ala Tyr Asn Glu Lys Leu Glu Asn Ile Lys Lys Leu Pro
225                 230                 235                 240

Ala Glu Val Arg Glu Lys Leu Lys Ala Gln Gly Val Thr His Met Val
                245                 250                 255

Ile Asn Thr Glu Trp Gly Ser Phe Asp Asn Gln Leu Lys Val Leu Pro
            260                 265                 270

Asn Thr Lys Tyr Asp Ala Gln Val Asp Glu Leu Thr Gly Asn Lys Gly
        275                 280                 285

Phe His Met Phe Glu Lys Arg Val Ser Gly Met Phe Leu Gly Glu Ile
    290                 295                 300

Leu Arg His Ile Leu Val Asp Leu His Ser Lys Gly Val Leu Phe Thr
305                 310                 315                 320

Gln Tyr Ala Ser Tyr Glu Ser Leu Pro His Arg Leu Arg Thr Pro Trp
                325                 330                 335

Asp Leu Asp Ser Glu Val Leu Ser Leu Ile Glu Ile Asp Glu Ser Thr
            340                 345                 350

Asn Leu Gln Ala Thr Glu Leu Ser Leu Lys Gln Ala Leu Arg Leu Pro
        355                 360                 365

Thr Thr Thr Glu Glu Arg Leu Ala Ile Gln Lys Leu Thr Arg Ala Val
    370                 375                 380

Ala Lys Arg Ser Ala Tyr Leu Ala Ala Ile Pro Ile Ala Ala Ile Leu
385                 390                 395                 400

His Met Thr Glu Ser Phe Lys Gly His Asn Val Glu Val Asp Val Gly
                405                 410                 415

Ala Asp Gly Ser Val Val Glu Phe Tyr Pro Gly Phe Arg Thr Met Met
            420                 425                 430

Arg Asp Ala Ile Ala Gln Thr Gln Ile Gly Ala Lys Gly Glu Arg Arg
        435                 440                 445

Leu His Ile Asn Ile Ala Lys Asp Gly Ser Ser Val Gly Ala Ala Leu
    450                 455                 460

Cys Ala Leu Ser Glu Lys Asp
465                 470


<210> SEQ ID NO 7
<211> LENGTH: 1634
<212> TYPE: DNA
<213> ORGANISM: Schizosaccharomyces pombe

<400> SEQUENCE: 7

aacacttttc gcctcacttg cgaatctacg aaaggaatat ataggtggtt cacccctttt      60

cttttcattt cgtgttttta atagttattt acatcaacag agataactat ttctgttaac     120

gatttttttt cccacttgtt ttcttccttt tttggtgaat tttaattaat ttataataag     180

caatggaggc taattttcaa caagctgtta aaaagttagt caatgacttt gaatacccta     240

ccgagtcctt gagagaggcc gttaaggagt ttgacgaatt acgtcaaaag ggtttacaaa     300

agaatggtga ggtgcttgct atggctcctg cctttatctc tacccttccc accggcgctg     360

aaactggtga cttcttggcc cttgactttg gtggtaccaa cttgcgtgtt tgttggatcc     420

aacttctcgg tgacggcaag tatgagatga agcacagcaa gtccgtcttg ccccgtgaat     480
```

-continued

```
gcgttcgtaa cgagtctgtt aagcccatca ttgactttat gagtgaccat gttgagcttt    540

tcatcaagga gcacttccct tccaagtttg gctgccctga ggaggaatac cttcctatgg    600

gtttcacctt ttcttatccc gccaaccaag tttccatcac cgagagctac ttgcttcgtt    660

ggaccaaggg tcttaacatt cctgaggcca tcaacaagga ctttgcccaa tttttgactg    720

aaggtttcaa ggctcgtaac cttcctatta gaatcgaggc tgtcatcaac gataccgtcg    780

gtactctcgt tacccgtgct tatacttcaa aggagagcga cacctttatg ggtatcattt    840

tcggaaccgg taccaacggt gcttacgtcg agcaaatgaa ccaaattccc aagcttgctg    900

gcaagtgtac tggtgatcat atgcttatca acatggaatg gggagcaact gatttctctt    960

gccttcactc cactcgttat gatttacttc ttgatcatga tactcccaat gctggtcgtc   1020

aaatctttga gaagcgcgtt ggtggtatgt atctcggtga gcttttccgc cgtgccttat   1080

tccacttgat caaggtttac aacttcaacg aaggtatttt ccctccttcc attactgatg   1140

cttggtcttt ggaaacttct gttctttcca gaatgatggt tgaacgttct gctgagaatg   1200

ttcgtaacgt tcttagtaca ttcaagttcc gtttccgcag cgacgaagag gctttgtacc   1260

tttgggatgc tgctcatgca attggccgtc gtgctgctcg tatgtctgcc gttcccattg   1320

cttctttgta tctttctacc ggccgcgctg gtaagaagag tgatgttggt gttgatggtt   1380

ctttagtcga acactatcct cactttgttg acatgctccg tgaagccttg cgtgagctta   1440

tcggtgataa cgaaaaattg atttccattg gtattgccaa ggatggcagt ggtattggtg   1500

ccgctctttg cgccctccaa gctgttaagg aaaagaaagg cttggcctaa atcatgttag   1560

atgtctgtta gctttttttg aattgtacgt agaaatgagc atgtaaatat gaaattgctt   1620

tttaacagct ttta                                                     1634
```

```
<210> SEQ ID NO 8
<211> LENGTH: 455
<212> TYPE: PRT
<213> ORGANISM: Schizosaccharomyces pombe

<400> SEQUENCE: 8

Met Glu Ala Asn Phe Gln Gln Ala Val Lys Lys Leu Val Asn Asp Phe
1               5                   10                  15

Glu Tyr Pro Thr Glu Ser Leu Arg Glu Ala Val Lys Glu Phe Asp Glu
            20                  25                  30

Leu Arg Gln Lys Gly Leu Gln Lys Asn Gly Glu Val Leu Ala Met Ala
        35                  40                  45

Pro Ala Phe Ile Ser Thr Leu Pro Thr Gly Ala Glu Thr Gly Asp Phe
    50                  55                  60

Leu Ala Leu Asp Phe Gly Gly Thr Asn Leu Arg Val Cys Trp Ile Gln
65                  70                  75                  80

Leu Leu Gly Asp Gly Lys Tyr Glu Met Lys His Ser Lys Ser Val Leu
                85                  90                  95

Pro Arg Glu Cys Val Arg Asn Glu Ser Val Lys Pro Ile Ile Asp Phe
            100                 105                 110

Met Ser Asp His Val Glu Leu Phe Ile Lys Glu His Phe Pro Ser Lys
        115                 120                 125

Phe Gly Cys Pro Glu Glu Glu Tyr Leu Pro Met Gly Phe Thr Phe Ser
    130                 135                 140

Tyr Pro Ala Asn Gln Val Ser Ile Thr Glu Ser Tyr Leu Leu Arg Trp
145                 150                 155                 160

Thr Lys Gly Leu Asn Ile Pro Glu Ala Ile Asn Lys Asp Phe Ala Gln
                165                 170                 175
```

Phe Leu Thr Glu Gly Phe Lys Ala Arg Asn Leu Pro Ile Arg Ile Glu
            180                 185                 190

Ala Val Ile Asn Asp Thr Val Gly Thr Leu Val Thr Arg Ala Tyr Thr
        195                 200                 205

Ser Lys Glu Ser Asp Thr Phe Met Gly Ile Ile Phe Gly Thr Gly Thr
    210                 215                 220

Asn Gly Ala Tyr Val Glu Gln Met Asn Gln Ile Pro Lys Leu Ala Gly
225                 230                 235                 240

Lys Cys Thr Gly Asp His Met Leu Ile Asn Met Glu Trp Gly Ala Thr
                245                 250                 255

Asp Phe Ser Cys Leu His Ser Thr Arg Tyr Asp Leu Leu Leu Asp His
            260                 265                 270

Asp Thr Pro Asn Ala Gly Arg Gln Ile Phe Glu Lys Arg Val Gly Gly
        275                 280                 285

Met Tyr Leu Gly Glu Leu Phe Arg Arg Ala Leu Phe His Leu Ile Lys
    290                 295                 300

Val Tyr Asn Phe Asn Glu Gly Ile Phe Pro Pro Ser Ile Thr Asp Ala
305                 310                 315                 320

Trp Ser Leu Glu Thr Ser Val Leu Ser Arg Met Met Val Glu Arg Ser
                325                 330                 335

Ala Glu Asn Val Arg Asn Val Leu Ser Thr Phe Lys Phe Arg Phe Arg
            340                 345                 350

Ser Asp Glu Glu Ala Leu Tyr Leu Trp Asp Ala Ala His Ala Ile Gly
        355                 360                 365

Arg Arg Ala Ala Arg Met Ser Ala Val Pro Ile Ala Ser Leu Tyr Leu
    370                 375                 380

Ser Thr Gly Arg Ala Gly Lys Lys Ser Asp Val Gly Val Asp Gly Ser
385                 390                 395                 400

Leu Val Glu His Tyr Pro His Phe Val Asp Met Leu Arg Glu Ala Leu
                405                 410                 415

Arg Glu Leu Ile Gly Asp Asn Glu Lys Leu Ile Ser Ile Gly Ile Ala
            420                 425                 430

Lys Asp Gly Ser Gly Ile Gly Ala Ala Leu Cys Ala Leu Gln Ala Val
        435                 440                 445

Lys Glu Lys Lys Gly Leu Ala
    450                 455

<210> SEQ ID NO 9
<211> LENGTH: 1689
<212> TYPE: DNA
<213> ORGANISM: Saccharomyces cerevisiae

<400> SEQUENCE: 9
atgtctgaaa ttactttggg taaatatttg ttcgaaagat taaagcaagt caacgttaac 60
accgttttcg gtttgccagg tgacttcaac ttgtccttgt tggacaagat ctacgaagtt 120
gaaggtatga gatgggctgg taacgccaac gaattgaacg ctgcttacgc cgctgatggt 180
tacgctcgta tcaagggtat gtcttgtatc atcaccacct tcggtgtcgg tgaattgtct 240
gctttgaacg gtattgccgg ttcttacgct gaacacgtcg gtgttttgca cgttgttggt 300
gtcccatcca tctctgctca agctaagcaa ttgttgttgc accacacctt gggtaacggt 360
gacttcactg ttttccacag aatgtctgcc aacatttctg aaaccactgc tatgatcact 420
gacattgcta ccgccccagc tgaaattgac agatgtatca gaaccactta cgtcacccaa 480
agaccagtct acttaggttt gccagctaac ttggtcgact tgaacgtccc agctaagttg 540

```
ttgcaaactc caattgacat gtctttgaag ccaaacgatg ctgaatccga aaaggaagtc    600

attgacacca tcttggcttt ggtcaaggat gctaagaacc cagttatctt ggctgatgct    660

tgttgttcca gacacgacgt caaggctgaa actaagaagt tgattgactt gactcaattc    720

ccagctttcg tcaccccaat gggtaagggt tccattgacg aacaacaccc aagatacggt    780

ggtgtttacg tcggtacctt gtccaagcca gaagttaagg aagccgttga atctgctgac    840

ttgattttgt ctgtcggtgc tttgttgtct gatttcaaca ccggttcttt ctcttactct    900

tacaagacca agaacattgt cgaattccac tccgaccaca tgaagatcag aaacgccact    960

ttcccaggtg tccaaatgaa attcgttttg caaaagttgt tgaccactat tgctgacgcc   1020

gctaagggtt acaagccagt tgctgtccca gctagaactc cagctaacgc tgctgtccca   1080

gcttctaccc cattgaagca agaatggatg tggaaccaat tgggtaactt cttgcaagaa   1140

ggtgatgttg tcattgctga aaccggtacc tccgctttcg gtatcaacca aaccactttc   1200

ccaaacaaca cctacggtat ctctcaagtc ttatggggtt ccattggttt caccactggt   1260

gctaccttgg gtgctgcttt cgctgctgaa gaaattgatc caaagaagag agttatctta   1320

ttcattggtg acggttcttt gcaattgact gttcaagaaa tctccaccat gatcagatgg   1380

ggcttgaagc catacttgtt cgtcttgaac aacgatggtt acaccattga aaagttgatt   1440

cacggtccaa aggctcaata caacgaaatt caaggttggg accacctatc cttgttgcca   1500

actttcggtg ctaaggacta tgaaacccac agagtcgcta ccaccggtga atgggacaag   1560

ttgacccaag acaagtcttt caacgacaac tctaagatca gaatgattga aatcatgttg   1620

ccagtcttcg atgctccaca aaacttggtt gaacaagcta agttgactgc tgctaccaac   1680

gctaagcaa                                                           1689
```

<210> SEQ ID NO 10
<211> LENGTH: 563
<212> TYPE: PRT
<213> ORGANISM: Saccharomyces cerevisiae

<400> SEQUENCE: 10

```
Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
```

-continued

```
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 11
<211> LENGTH: 1689
<212> TYPE: DNA

-continued

<213> ORGANISM: Saccharomyces cerevisiae

<400> SEQUENCE: 11

```
atgtctgaaa taaccttagg taaatattta tttgaaagat tgagccaagt caactgtaac     60
accgtcttcg gtttgccagg tgactttaac ttgtctcttt tggataagct ttatgaagtc    120
aaaggtatga gatgggctgg taacgctaac gaattgaacg ctgcctatgc tgctgatggt    180
tacgctcgta tcaagggtat gtcctgtatt attaccacct tcggtgttgg tgaattgtct    240
gctttgaatg gtattgccgg ttcttacgct gaacatgtcg gtgttttgca cgttgttggt    300
gttccatcca tctcttctca agctaagcaa ttgttgttgc atcatacctt gggtaacggt    360
gacttcactg ttttccacag aatgtctgcc aacatttctg aaaccactgc catgatcact    420
gatattgcta acgctccagc tgaaattgac agatgtatca gaaccaccta cactacccaa    480
agaccagtct acttgggttt gccagctaac ttggttgact tgaacgtccc agccaagtta    540
ttggaaactc caattgactt gtctttgaag ccaaacgacg ctgaagctga agctgaagtt    600
gttagaactg ttgttgaatt gatcaaggat gctaagaacc cagttatctt ggctgatgct    660
tgtgcttcta gacatgatgt caaggctgaa actaagaagt tgatggactt gactcaattc    720
ccagtttacg tcaccccaat gggtaagggt gctattgacg aacaacaccc aagatacggt    780
ggtgtttacg ttggtacctt gtctagacca gaagttaaga aggctgtaga atctgctgat    840
ttgatattgt ctatcggtgc tttgttgtct gatttcaata ccggttcttt ctcttactcc    900
tacaagacca aaaatatcgt tgaattccac tctgaccaca tcaagatcag aaacgccacc    960
ttcccaggtg ttcaaatgaa atttgccttg caaaaattgt tggatgctat tccagaagtc   1020
gtcaaggact acaaacctgt tgctgtccca gctagagttc caattaccaa gtctactcca   1080
gctaacactc caatgaagca agaatggatg tggaaccatt tgggtaactt cttgagagaa   1140
ggtgatattg ttattgctga aaccggtact tccgccttcg gtattaacca aactactttc   1200
ccaacagatg tatacgctat cgtccaagtc ttgtggggtt ccattggttt cacagtcggc   1260
gctctattgg gtgctactat ggccgctgaa gaacttgatc caaagaagag agttatttta   1320
ttcattggtg acggttctct acaattgact gttcaagaaa tctctaccat gattagatgg   1380
ggtttgaagc catacatttt tgtcttgaat aacaacggtt acaccattga aaaattgatt   1440
cacggtcctc atgccgaata taatgaaatt caaggttggg accacttggc cttattgcca   1500
acttttggtg ctagaaacta cgaaacccac agagttgcta ccactggtga atgggaaaag   1560
ttgactcaag acaaggactt ccaagacaac tctaagatta gaatgattga agttatgttg   1620
ccagtctttg atgctccaca aaacttggtt aaacaagctc aattgactgc cgctactaac   1680
gctaaacaa                                                           1689
```

<210> SEQ ID NO 12
<211> LENGTH: 563
<212> TYPE: PRT
<213> ORGANISM: Saccharomyces cerevisiae

<400> SEQUENCE: 12

```
Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
```

```
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Glu Val Val Arg Thr Val Val Glu Leu Ile
        195                 200                 205

Lys Asp Ala Lys Asn Pro Val Ile Leu Ala Asp Ala Cys Ala Ser Arg
    210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
        355                 360                 365

Trp Met Trp Asn His Leu Gly Asn Phe Leu Arg Glu Gly Asp Ile Val
    370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
                405                 410                 415

Phe Thr Val Gly Ala Leu Leu Gly Ala Thr Met Ala Ala Glu Glu Leu
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Ile Phe Val Leu Asn Asn Asn Gly Tyr Thr Ile Glu Lys Leu Ile
465                 470                 475                 480
```

-continued

```
His Gly Pro His Ala Glu Tyr Asn Glu Ile Gln Gly Trp Asp His Leu
                485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
        515                 520                 525

Asp Asn Ser Lys Ile Arg Met Ile Glu Val Met Leu Pro Val Phe Asp
    530                 535                 540

Ala Pro Gln Asn Leu Val Lys Gln Ala Gln Leu Thr Ala Ala Thr Asn
545                 550                 555                 560

Ala Lys Gln


<210> SEQ ID NO 13
<211> LENGTH: 1599
<212> TYPE: DNA
<213> ORGANISM: Saccharomyces cerevisiae

<400> SEQUENCE: 13

atgtctgaaa ttactcttgg aaaatactta tttgaaagat tgaagcaagt taatgttaac     60

accatttttg ggctaccagg cgacttcaac ttgtccctat tggacaagat ttacgaggta    120

gatggattga gatgggctgg taatgcaaat gagctgaacg ccgcctatgc cgccgatggt    180

tacgcacgca tcaagggttt atctgtgctg gtaactactt ttggcgtagg tgaattatcc    240

gccttgaatg gtattgcagg atcgtatgca gaacacgtcg gtgtactgca tgttgttggt    300

gtcccctcta tctccgctca ggctaagcaa ttgttgttgc atcatacctt gggtaacggt    360

gattttaccg tttttcacag aatgtccgcc aatatctcag aaactacatc aatgattaca    420

gacattgcta cagccccttc agaaatcgat aggttgatca ggacaacatt tataacacaa    480

aggcctagct acttggggtt gccagcgaat ttggtagatc taaaggttcc tggttctctt    540

ttggaaaaac cgattgatct atcattaaaa cctaacgatc ccgaagctga aaaggaagtt    600

attgataccg tactagaatt gatccagaat tcgaaaaacc ctgttatact atcggatgcc    660

tgtgcttcta ggcacaacgt taaaaaagaa acccagaagt taattgattt gacgcaattc    720

ccagcttttg tgacacctct aggtaaaggg tcaatagatg aacagcatcc cagatatggc    780

ggtgtttatg tgggaacgct gtccaaacaa gacgtgaaac aggccgttga gtcggctgat    840

ttgatccttt cggtcggtgc tttgctctct gattttaaca caggttcgtt ttcctactcc    900

tacaagacta aaaatgtagt ggagtttcat tccgattacg taaaggtgaa gaacgctacg    960

ttcctcggtg tacaaatgaa atttgcacta caaaacttac tgaaggttat tcccgatgtt   1020

gttaagggct acaagagcgt tcccgtacca accaaaactc ccgcaaacaa aggtgtacct   1080

gctagcacgc ccttgaaaca agagtggttg tggaacgaat tgtccaaatt cttgcaagaa   1140

ggtgatgtta tcatttccga gaccggcacg tctgccttcg gtatcaatca aactatcttt   1200

cctaaggacg cctacggtat ctcgcaggtg ttgtgggggt ccatcggttt tacaacagga   1260

gcaactttag gtgctgcctt tgccgctgag gagattgacc ccaacaagag agtcatctta   1320

ttcataggtg acgggtcttt gcagttaacc gtccaagaaa tctccaccat gatcagatgg   1380

gggttaaagc cgtatctttt tgtccttaac aacgacggct acactatcga aaagctgatt   1440

catgggcctc acgcagagta caacgaaatc cagacctggg atcacctcgc cctgttgccc   1500

gcatttggtg cgaaaaagta cgaaaatcac aagatcgcca ctacgggtga gtgggatgcc   1560

ttaaccactg attcagagtt ccagaaaaac tcggtgatc                          1599
```

<210> SEQ ID NO 14
<211> LENGTH: 533
<212> TYPE: PRT
<213> ORGANISM: Saccharomyces cerevisiae

<400> SEQUENCE: 14

```
Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
```

-continued

```
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile
    530


<210> SEQ ID NO 15
<211> LENGTH: 1692
<212> TYPE: DNA
<213> ORGANISM: Candida glabrata

<400> SEQUENCE: 15

atgtctgaga ttactttggg tagatacttg ttcgagagat tgaaccaagt cgacgttaag     60

accatcttcg gtttgccagg tgacttcaac ttgtccctat tggacaagat ctacgaagtt    120

gaaggtatga gatgggctgg taacgctaac gaattgaacg ctgcttacgc tgctgacggt    180

tacgctagaa tcaagggtat gtcctgtatc atcaccacct tcggtgtcgg tgaattgtct    240

gccttgaacg gtattgccgg ttcttacgct gaacacgtcg gtgtcttgca cgtcgtcggt    300

gtcccatcca tctcctctca agctaagcaa ttgttgttgc accacacctt gggtaacggt    360

gacttcactg tcttccacag aatgtccgct aacatctctg agaccaccgc tatggtcact    420

gacatcgcta ccgctccagc tgagatcgac agatgtatca gaaccaccta catcacccaa    480

agaccagtct acttgggtct accagctaac ttggtcgacc taaaggtccc agccaagctt    540

ttggaaaccc caattgactt gtccttgaag ccaaacgacc cagaagccga aactgaagtc    600

gttgacaccg tcttggaatt gatcaaggct gctaagaacc cagttatctt ggctgatgct    660

tgtgcttcca gacacgacgt caaggctgaa accaagaagt tgattgacgc cactcaattc    720

ccatccttcg ttaccccaat gggtaagggt tccatcgacg aacaacaccc aagattcggt    780

ggtgtctacg tcggtacctt gtccagacca gaagttaagg aagctgttga atccgctgac    840

ttgatcttgt ctgtcggtgc tttgttgtcc gatttcaaca ctggttcttt ctcttactct    900

tacaagacca agaacatcgt cgaattccac tctgactaca tcaagatcag aaacgctacc    960

ttcccaggtg tccaaatgaa gttcgctttg caaaagttgt tgaacgccgt cccagaagct   1020

atcaagggtt acaagccagt ccctgtccca gctagagtcc cagaaaacaa gtcctgtgac   1080

ccagctaccc cattgaagca agaatggatg tggaaccaag tttccaagtt cttgcaagaa   1140

ggtgatgttg ttatcactga aaccggtacc tccgcttttg gtatcaacca aaccccattc   1200

ccaaacaacg cttacggtat ctcccaagtt ctatggggtt ccatcggttt caccaccggt   1260

gcttgtttgg gtgccgcttt cgctgctgaa gaaatcgacc caaagaagag agttatcttg   1320
```

```
ttcattggtg acggttcttt gcaattgact gtccaagaaa tctccaccat gatcagatgg   1380

ggcttgaagc catacttgtt cgtcttgaac aacgacggtt acaccatcga aagattgatt   1440

cacggtgaaa aggctggtta caacgacatc caaaactggg accacttggc tctattgcca   1500

accttcggtg ctaaggacta cgaaaaccac agagtcgcca ccaccggtga atgggacaag   1560

ttgacccaag acaaggaatt caacaagaac tccaagatca gaatgatcga agttatgttg   1620

ccagttatgg acgctccaac ttccttgatt gaacaagcta agttgaccgc ttccatcaac   1680

gctaagcaag aa                                                         1692


<210> SEQ ID NO 16
<211> LENGTH: 564
<212> TYPE: PRT
<213> ORGANISM: Candida glabrata

<400> SEQUENCE: 16

Met Ser Glu Ile Thr Leu Gly Arg Tyr Leu Phe Glu Arg Leu Asn Gln
1               5                   10                  15

Val Asp Val Lys Thr Ile Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Val Thr Asp Ile Ala Thr
    130                 135                 140

Ala Pro Ala Glu Ile Asp Arg Cys Ile Arg Thr Thr Tyr Ile Thr Gln
145                 150                 155                 160

Arg Pro Val Tyr Leu Gly Leu Pro Ala Asn Leu Val Asp Leu Lys Val
                165                 170                 175

Pro Ala Lys Leu Leu Glu Thr Pro Ile Asp Leu Ser Leu Lys Pro Asn
            180                 185                 190

Asp Pro Glu Ala Glu Thr Glu Val Val Asp Thr Val Leu Glu Leu Ile
        195                 200                 205

Lys Ala Ala Lys Asn Pro Val Ile Leu Ala Asp Ala Cys Ala Ser Arg
    210                 215                 220

His Asp Val Lys Ala Glu Thr Lys Lys Leu Ile Asp Ala Thr Gln Phe
225                 230                 235                 240

Pro Ser Phe Val Thr Pro Met Gly Lys Gly Ser Ile Asp Glu Gln His
                245                 250                 255

Pro Arg Phe Gly Gly Val Tyr Val Gly Thr Leu Ser Arg Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300
```

-continued

```
Asn Ile Val Glu Phe His Ser Asp Tyr Ile Lys Ile Arg Asn Ala Thr
305                 310                 315                 320

Phe Pro Gly Val Gln Met Lys Phe Ala Leu Gln Lys Leu Leu Asn Ala
                325                 330                 335

Val Pro Glu Ala Ile Lys Gly Tyr Lys Pro Val Pro Val Pro Ala Arg
            340                 345                 350

Val Pro Glu Asn Lys Ser Cys Asp Pro Ala Thr Pro Leu Lys Gln Glu
        355                 360                 365

Trp Met Trp Asn Gln Val Ser Lys Phe Leu Gln Glu Gly Asp Val Val
    370                 375                 380

Ile Thr Glu Thr Gly Thr Ser Ala Phe Gly Ile Asn Gln Thr Pro Phe
385                 390                 395                 400

Pro Asn Asn Ala Tyr Gly Ile Ser Gln Val Leu Trp Gly Ser Ile Gly
                405                 410                 415

Phe Thr Thr Gly Ala Cys Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Glu Lys Ala Gly Tyr Asn Asp Ile Gln Asn Trp Asp His Leu
                485                 490                 495

Ala Leu Leu Pro Thr Phe Gly Ala Lys Asp Tyr Glu Asn His Arg Val
            500                 505                 510

Ala Thr Thr Gly Glu Trp Asp Lys Leu Thr Gln Asp Lys Glu Phe Asn
        515                 520                 525

Lys Asn Ser Lys Ile Arg Met Ile Glu Val Met Leu Pro Val Met Asp
    530                 535                 540

Ala Pro Thr Ser Leu Ile Glu Gln Ala Lys Leu Thr Ala Ser Ile Asn
545                 550                 555                 560

Ala Lys Gln Glu
```

<210> SEQ ID NO 17
<211> LENGTH: 1788
<212> TYPE: DNA
<213> ORGANISM: Pichia stipitis

<400> SEQUENCE: 17

```
atggctgaag tctcattagg aagatatctc ttcgagagat tgtaccaatt gcaagtgcag      60

accatcttcg gtgtccctgg tgatttcaac ttgtcgcttt tggacaagat ctacgaagtg     120

gaagatgccc atggcaagaa ttcgtttaga tgggctggta atgccaacga attgaatgca     180

tcgtacgctg ctgacggtta ctcgagagtc aagcgtttag ggtgtttggt cactaccttt     240

ggtgtcggtg aattgtctgc tttgaatggt attgccggtt cttatgccga acatgttggt     300

ttgcttcatg tcgtaggtgt tccatcgatt tcctcgcaag ctaagcaatt gttacttcac     360

cacactttgg gtaatggtga tttcactgtt ttccatagaa tgtccaacaa catttctcag     420

accacagcct ttatctccga tatcaactcg gctccagctg aaattgatag atgtatcaga     480

gaggcctacg tcaaacaaag accagtttat atcgggttac cagctaactt agttgatttg     540

aatgttccgg cctctttgct tgagtctcca atcaacttgt cgttggaaaa gaacgaccca     600

gaggctcaag atgaagtcat tgactctgtc ttagacttga tcaaaaagtc gctgaaccca     660
```

-continued

```
atcatcttgg tcgatgcctg tgcctcgaga catgactgta aggctgaagt tactcagttg    720

attgaacaaa cccaattccc agtatttgtc actccaatgg gtaaaggtac cgttgatgag    780

ggtggtgtag acggagaatt gttagaagat gatcctcatt tgattgccaa ggtcgctgct    840

aggttgtctg ctggcaagaa cgctgcctct agattcggag gtgtttatgt cggaaccttg    900

tcgaagcccg aagtcaagga cgctgtagag agtgcagatt tgattttgtc tgtcggtgcc    960

cttttgtctg atttcaacac tggttcattt tcctactcct acagaaccaa gaacatcgtc   1020

gaattccatt ctgattacac taagattaga caagccactt tcccaggtgt gcagatgaag   1080

gaagccttgc aagaattgaa caagaaagtt tcatctgctg ctagtcacta tgaagtcaag   1140

cctgtgccca agatcaagtt ggccaataca ccagccacca gagaagtcaa gttaactcag   1200

gaatggttgt ggaccagagt gtcttcgtgg ttcagagaag gtgatattat tatcaccgaa   1260

accggtacat cctccttcgg tatagttcaa tccagattcc caaacaacac catcggtatc   1320

tcccaagtat tgtggggttc tattggtttc tctgttggtg ccactttggg tgctgccatg   1380

gctgcccaag aactcgaccc taacaagaga accatcttgt ttgttggaga tggttctttg   1440

caattgaccg ttcaggaaat ctccaccata atcagatggg gtaccacacc ttacctttc    1500

gtgttgaaca atgacggtta caccatcgag cgtttgatcc acggtgtaaa tgcctcatat   1560

aatgacatcc aaccatggca aaacttggaa atcttgccta ctttctcggc caagaactac   1620

gacgctgtga gaatctccaa catcggagaa gcagaagata tcttgaaaga caaggaattc   1680

ggaaagaact ccaagattag attgatagaa gtcatgttac caagattgga tgcaccatct   1740

aaccttgcca aacaagctgc cattacagct gccaccaacg ccgaagct                1788


<210> SEQ ID NO 18
<211> LENGTH: 596
<212> TYPE: PRT
<213> ORGANISM: Pichia stipitis

<400> SEQUENCE: 18

Met Ala Glu Val Ser Leu Gly Arg Tyr Leu Phe Glu Arg Leu Tyr Gln
1               5                   10                  15

Leu Gln Val Gln Thr Ile Phe Gly Val Pro Gly Asp Phe Asn Leu Ser
            20                  25                  30

Leu Leu Asp Lys Ile Tyr Glu Val Glu Asp Ala His Gly Lys Asn Ser
        35                  40                  45

Phe Arg Trp Ala Gly Asn Ala Asn Glu Leu Asn Ala Ser Tyr Ala Ala
    50                  55                  60

Asp Gly Tyr Ser Arg Val Lys Arg Leu Gly Cys Leu Val Thr Thr Phe
65                  70                  75                  80

Gly Val Gly Glu Leu Ser Ala Leu Asn Gly Ile Ala Gly Ser Tyr Ala
                85                  90                  95

Glu His Val Gly Leu Leu His Val Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Asn Ile Ser Gln Thr Thr Ala Phe
    130                 135                 140

Ile Ser Asp Ile Asn Ser Ala Pro Ala Glu Ile Asp Arg Cys Ile Arg
145                 150                 155                 160

Glu Ala Tyr Val Lys Gln Arg Pro Val Tyr Ile Gly Leu Pro Ala Asn
                165                 170                 175

Leu Val Asp Leu Asn Val Pro Ala Ser Leu Leu Glu Ser Pro Ile Asn
```

-continued

```
            180                 185                 190

Leu Ser Leu Glu Lys Asn Asp Pro Glu Ala Gln Asp Glu Val Ile Asp
        195                 200                 205

Ser Val Leu Asp Leu Ile Lys Lys Ser Ser Asn Pro Ile Ile Leu Val
    210                 215                 220

Asp Ala Cys Ala Ser Arg His Asp Cys Lys Ala Glu Val Thr Gln Leu
225                 230                 235                 240

Ile Glu Gln Thr Gln Phe Pro Val Phe Val Thr Pro Met Gly Lys Gly
                245                 250                 255

Thr Val Asp Glu Gly Gly Val Asp Gly Glu Leu Leu Glu Asp Asp Pro
            260                 265                 270

His Leu Ile Ala Lys Val Ala Ala Arg Leu Ser Ala Gly Lys Asn Ala
        275                 280                 285

Ala Ser Arg Phe Gly Gly Val Tyr Val Gly Thr Leu Ser Lys Pro Glu
    290                 295                 300

Val Lys Asp Ala Val Glu Ser Ala Asp Leu Ile Leu Ser Val Gly Ala
305                 310                 315                 320

Leu Leu Ser Asp Phe Asn Thr Gly Ser Phe Ser Tyr Ser Tyr Arg Thr
                325                 330                 335

Lys Asn Ile Val Glu Phe His Ser Asp Tyr Thr Lys Ile Arg Gln Ala
            340                 345                 350

Thr Phe Pro Gly Val Gln Met Lys Glu Ala Leu Gln Glu Leu Asn Lys
        355                 360                 365

Lys Val Ser Ser Ala Ala Ser His Tyr Glu Val Lys Pro Val Pro Lys
    370                 375                 380

Ile Lys Leu Ala Asn Thr Pro Ala Thr Arg Glu Val Lys Leu Thr Gln
385                 390                 395                 400

Glu Trp Leu Trp Thr Arg Val Ser Ser Trp Phe Arg Glu Gly Asp Ile
                405                 410                 415

Ile Ile Thr Glu Thr Gly Thr Ser Ser Phe Gly Ile Val Gln Ser Arg
            420                 425                 430

Phe Pro Asn Asn Thr Ile Gly Ile Ser Gln Val Leu Trp Gly Ser Ile
        435                 440                 445

Gly Phe Ser Val Gly Ala Thr Leu Gly Ala Ala Met Ala Ala Gln Glu
    450                 455                 460

Leu Asp Pro Asn Lys Arg Thr Ile Leu Phe Val Gly Asp Gly Ser Leu
465                 470                 475                 480

Gln Leu Thr Val Gln Glu Ile Ser Thr Ile Ile Arg Trp Gly Thr Thr
                485                 490                 495

Pro Tyr Leu Phe Val Leu Asn Asn Asp Gly Tyr Thr Ile Glu Arg Leu
            500                 505                 510

Ile His Gly Val Asn Ala Ser Tyr Asn Asp Ile Gln Pro Trp Gln Asn
        515                 520                 525

Leu Glu Ile Leu Pro Thr Phe Ser Ala Lys Asn Tyr Asp Ala Val Arg
    530                 535                 540

Ile Ser Asn Ile Gly Glu Ala Glu Asp Ile Leu Lys Asp Lys Glu Phe
545                 550                 555                 560

Gly Lys Asn Ser Lys Ile Arg Leu Ile Glu Val Met Leu Pro Arg Leu
                565                 570                 575

Asp Ala Pro Ser Asn Leu Ala Lys Gln Ala Ala Ile Thr Ala Ala Thr
            580                 585                 590

Asn Ala Glu Ala
        595
```

<210> SEQ ID NO 19
<211> LENGTH: 1707
<212> TYPE: DNA
<213> ORGANISM: Pichia stipitis

<400> SEQUENCE: 19
atggtatcaa cctacccaga atcagaggtt actctaggaa ggtacctctt tgagcgactc 60
caccaattga aagtggacac cattttcggc ttgccgggtg acttcaacct ttccttattg 120
gacaaagtgt atgaagttcc ggatatgagg tgggctggaa atgccaacga attgaatgct 180
gcctatgctg ccgatggtta ctccagaata aagggattgt cttgcttggt cacaactttt 240
ggtgttggtg aattgtctgc tttaaacgga gttggtggtg cctatgctga acacgtagga 300
cttctacatg tcgttggagt tccatccata tcgtcacagg ctaaacagtt gttgctccac 360
cataccttgg gtaatggtga cttcactgtt tttcacagaa tgtccaatag catttctcaa 420
actacagcat ttctctcaga tatctctatt gcaccaggtc aaatagatag atgcatcaga 480
gaagcatatg ttcatcagag accagtttat gttggtttac cggcaaatat ggttgatctc 540
aaggttcctt ctagtctctt agaaactcca attgatttga aattgaaaca aaatgatcct 600
gaagctcaag aagttgttga aacagtcctg aagttggtgt cccaagctac aaaccccatt 660
atcttggtag acgcttgtgc cctcagacac aattgcaaag aggaagtcaa acaattggtt 720
gatgccacta attttcaagt ctttacaact ccaatgggta aatctggtat ctccgaatct 780
catccaagat tgggcggtgt ctatgtcggg acaatgtcga gtcctcaagt caaaaaagcc 840
gttgaaaatg ccgatcttat actatctgtt ggttcgttgt tatcggactt caatacaggt 900
tcattttcat actcctacaa gacgaagaat gttgttgaat tccactctga ctatatgaaa 960
atcagacagg ccaccttccc aggagttcaa atgaaagaag ccttgcaaca gttgataaaa 1020
agggtctctt cttacatcaa tccaagctac attcctactc gagttcctaa aaggaaacag 1080
ccattgaaag ctccatcaga agctcctttg acccaagaat atttgtggtc taaagtatcc 1140
ggctggttta gagagggtga tattatcgta accgaaactg gtacatctgc tttcggaatt 1200
attcaatccc attttcccag caacactatc ggtatatccc aagtcttgtg gggctcaatt 1260
ggtttcacag taggtgcaac agttggtgct gccatggcag cccaggaaat cgaccctagc 1320
aggagagtaa ttttgttcgt cggtgatggt tcattgcagt tgacggttca ggaaatctct 1380
acgttgtgta aatgggattg taacaatact tatctttacg tgttgaacaa tgatggttac 1440
actatagaaa ggttgatcca cggcaaaagt gccagctaca acgatataca gccttggaac 1500
catttatcct tgcttcgctt attcaatgct aagaaatacc aaaatgtcag agtatcgact 1560
gctggagaat tggactcttt gttctctgat aagaaatttg cttctccaga taggataaga 1620
atgattgagg tgatgttatc gagattggat gcaccagcaa atcttgttgc tcaagcaaag 1680
ttgtctgaac gggtaaacct tgaaaat 1707

<210> SEQ ID NO 20
<211> LENGTH: 569
<212> TYPE: PRT
<213> ORGANISM: Pichia stipitis

<400> SEQUENCE: 20

Met Val Ser Thr Tyr Pro Glu Ser Glu Val Thr Leu Gly Arg Tyr Leu
1 5 10 15

Phe Glu Arg Leu His Gln Leu Lys Val Asp Thr Ile Phe Gly Leu Pro
20 25 30

-continued

```
Gly Asp Phe Asn Leu Ser Leu Leu Asp Lys Val Tyr Glu Val Pro Asp
        35                  40                  45

Met Arg Trp Ala Gly Asn Ala Asn Glu Leu Asn Ala Ala Tyr Ala Ala
    50                  55                  60

Asp Gly Tyr Ser Arg Ile Lys Gly Leu Ser Cys Leu Val Thr Thr Phe
65                  70                  75                  80

Gly Val Gly Glu Leu Ser Ala Leu Asn Gly Val Gly Gly Ala Tyr Ala
                85                  90                  95

Glu His Val Gly Leu Leu His Val Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Ser Ile Ser Gln Thr Thr Ala Phe
    130                 135                 140

Leu Ser Asp Ile Ser Ile Ala Pro Gly Gln Ile Asp Arg Cys Ile Arg
145                 150                 155                 160

Glu Ala Tyr Val His Gln Arg Pro Val Tyr Val Gly Leu Pro Ala Asn
                165                 170                 175

Met Val Asp Leu Lys Val Pro Ser Ser Leu Leu Glu Thr Pro Ile Asp
            180                 185                 190

Leu Lys Leu Lys Gln Asn Asp Pro Glu Ala Gln Glu Val Val Glu Thr
        195                 200                 205

Val Leu Lys Leu Val Ser Gln Ala Thr Asn Pro Ile Ile Leu Val Asp
    210                 215                 220

Ala Cys Ala Leu Arg His Asn Cys Lys Glu Glu Val Lys Gln Leu Val
225                 230                 235                 240

Asp Ala Thr Asn Phe Gln Val Phe Thr Thr Pro Met Gly Lys Ser Gly
                245                 250                 255

Ile Ser Glu Ser His Pro Arg Leu Gly Gly Val Tyr Val Gly Thr Met
            260                 265                 270

Ser Ser Pro Gln Val Lys Lys Ala Val Glu Asn Ala Asp Leu Ile Leu
        275                 280                 285

Ser Val Gly Ser Leu Leu Ser Asp Phe Asn Thr Gly Ser Phe Ser Tyr
    290                 295                 300

Ser Tyr Lys Thr Lys Asn Val Val Glu Phe His Ser Asp Tyr Met Lys
305                 310                 315                 320

Ile Arg Gln Ala Thr Phe Pro Gly Val Gln Met Lys Glu Ala Leu Gln
                325                 330                 335

Gln Leu Ile Lys Arg Val Ser Ser Tyr Ile Asn Pro Ser Tyr Ile Pro
            340                 345                 350

Thr Arg Val Pro Lys Arg Lys Gln Pro Leu Lys Ala Pro Ser Glu Ala
        355                 360                 365

Pro Leu Thr Gln Glu Tyr Leu Trp Ser Lys Val Ser Gly Trp Phe Arg
    370                 375                 380

Glu Gly Asp Ile Ile Val Thr Glu Thr Gly Thr Ser Ala Phe Gly Ile
385                 390                 395                 400

Ile Gln Ser His Phe Pro Ser Asn Thr Ile Gly Ile Ser Gln Val Leu
                405                 410                 415

Trp Gly Ser Ile Gly Phe Thr Val Gly Ala Thr Val Gly Ala Ala Met
            420                 425                 430

Ala Ala Gln Glu Ile Asp Pro Ser Arg Arg Val Ile Leu Phe Val Gly
        435                 440                 445

Asp Gly Ser Leu Gln Leu Thr Val Gln Glu Ile Ser Thr Leu Cys Lys
    450                 455                 460
```

```
Trp Asp Cys Asn Asn Thr Tyr Leu Tyr Val Leu Asn Asn Asp Gly Tyr
465                 470                 475                 480

Thr Ile Glu Arg Leu Ile His Gly Lys Ser Ala Ser Tyr Asn Asp Ile
                485                 490                 495

Gln Pro Trp Asn His Leu Ser Leu Leu Arg Leu Phe Asn Ala Lys Lys
            500                 505                 510

Tyr Gln Asn Val Arg Val Ser Thr Ala Gly Glu Leu Asp Ser Leu Phe
        515                 520                 525

Ser Asp Lys Lys Phe Ala Ser Pro Asp Arg Ile Arg Met Ile Glu Val
    530                 535                 540

Met Leu Ser Arg Leu Asp Ala Pro Ala Asn Leu Val Ala Gln Ala Lys
545                 550                 555                 560

Leu Ser Glu Arg Val Asn Leu Glu Asn
                565
```

<210> SEQ ID NO 21
<211> LENGTH: 1692
<212> TYPE: DNA
<213> ORGANISM: Kluyveromyces lactis

<400> SEQUENCE: 21

```
atgtctgaaa ttacattagg tcgttacttg ttcgaaagat taaagcaagt cgaagttcaa     60

accatctttg gtctaccagg tgatttcaac ttgtccctat tggacaatat ctacgaagtc    120

ccaggtatga gatgggctgg taatgccaac gaattgaacg ctgcttacgc tgctgatggt    180

tacgccagat taaagggtat gtcctgtatc atcaccacct tcggtgtcgg tgaattgtct    240

gctttgaacg gtattgccgg ttcttacgct gaacacgttg gtgtcttgca cgttgtcggt    300

gttccatccg tctcttctca agctaagcaa ttgttgttgc accacacctt gggtaacggt    360

gacttcactg ttttccacag aatgtgctcc aacatttctg aaaccactgc tatgatcacc    420

gatatcaaca ctgccccagc tgaaatcgac agatgtatca gaaccactta cgtttcccaa    480

agaccagtct acttgggttt gccagctaac ttggtcgact tgactgtccc agcttctttg    540

ttggacactc caattgattt gagcttgaag ccaaatgacc cagaagccga agaagaagtc    600

atcgaaaacg tcttgcaact gatcaaggaa gctaagaacc cagttatctt ggctgatgct    660

tgttgttcca gacacgatgc caaggctgag accaagaagt tgatcgactt gactcaattc    720

ccagccttcg ttaccccaat gggtaagggt tccattgacg aaaagcaccc aagattcggt    780

ggtgtctacg tcggtaccct atcttctcca gctgtcaagg aagccgttga atctgctcac    840

ttggttctat cggtcggtgc tctattgtcc gatttcaaca ctggttcttt ctcttactct    900

tacaagacca agaacattgt cgaattccac tctgactaca ccaagatcag aaggcctacc    960

ttcccaggtg tccaaatgaa gttcgcttta caaaaattgt tgactaaggt tgccgatgct   1020

gctaagggtt acaagccagt tccagttcca tctgaaccag aacacaacga agatgtcgct   1080

gactccactc cattgaagca agaatgggtc tggactcaag tcggtgaatt cttgagagaa   1140

ggtgatgttg ttatcactga aaccggtacc tctgccttcg gtatcaacca aactcatttc   1200

ccaaacaaca catacggtat ctctcaagtt ttatggggtt ccattggttt caccactggt   1260

gctaccttgg gtgctgcctt cgctgccgaa gaaattgatc caaagaagag agttatctta   1320

ttcattggtg acggttcttt gcaattgact gttcaagaaa tctccaccat gatcagatgg   1380

ggcttgaagc catacttgtt cgtattgaac aacgacggtt acaccattga aagattgatt   1440

cacggtgaaa ccgctcaata caactgtatc caaaactggc aacacttgga attattgcca   1500
```

-continued actttcggtg ccaaggacta cgaagctgtc agagtttcca ccactggtga atggaacaag 1560
ttgaccactg acgaaaagtt ccaagacaac accagaatca gattgatcga agttatgttg 1620
ccaactatgg atgctccatc taacttggtt aagcaagctc aattgactgc tgcatccaac 1680
gctaagaact aa 1692

<210> SEQ ID NO 22
<211> LENGTH: 563
<212> TYPE: PRT
<213> ORGANISM: Kluyveromyces lactis

<400> SEQUENCE: 22

Met Ser Glu Ile Thr Leu Gly Arg Tyr Leu Phe Glu Arg Leu Lys Gln
1 5 10 15

Val Glu Val Gln Thr Ile Phe Gly Leu Pro Gly Asp Phe Asn Leu Ser
20 25 30

Leu Leu Asp Asn Ile Tyr Glu Val Pro Gly Met Arg Trp Ala Gly Asn
35 40 45

Ala Asn Glu Leu Asn Ala Ala Tyr Ala Ala Asp Gly Tyr Ala Arg Leu
50 55 60

Lys Gly Met Ser Cys Ile Ile Thr Thr Phe Gly Val Gly Glu Leu Ser
65 70 75 80

Ala Leu Asn Gly Ile Ala Gly Ser Tyr Ala Glu His Val Gly Val Leu
85 90 95

His Val Val Gly Val Pro Ser Val Ser Ser Gln Ala Lys Gln Leu Leu
100 105 110

Leu His His Thr Leu Gly Asn Gly Asp Phe Thr Val Phe His Arg Met
115 120 125

Ser Ser Asn Ile Ser Glu Thr Thr Ala Met Ile Thr Asp Ile Asn Thr
130 135 140

Ala Pro Ala Glu Ile Asp Arg Cys Ile Arg Thr Thr Tyr Val Ser Gln
145 150 155 160

Arg Pro Val Tyr Leu Gly Leu Pro Ala Asn Leu Val Asp Leu Thr Val
165 170 175

Pro Ala Ser Leu Leu Asp Thr Pro Ile Asp Leu Ser Leu Lys Pro Asn
180 185 190

Asp Pro Glu Ala Glu Glu Glu Val Ile Glu Asn Val Leu Gln Leu Ile
195 200 205

Lys Glu Ala Lys Asn Pro Val Ile Leu Ala Asp Ala Cys Cys Ser Arg
210 215 220

His Asp Ala Lys Ala Glu Thr Lys Lys Leu Ile Asp Leu Thr Gln Phe
225 230 235 240

Pro Ala Phe Val Thr Pro Met Gly Lys Gly Ser Ile Asp Glu Lys His
245 250 255

Pro Arg Phe Gly Gly Val Tyr Val Gly Thr Leu Ser Ser Pro Ala Val
260 265 270

Lys Glu Ala Val Glu Ser Ala Asp Leu Val Leu Ser Val Gly Ala Leu
275 280 285

Leu Ser Asp Phe Asn Thr Gly Ser Phe Ser Tyr Ser Tyr Lys Thr Lys
290 295 300

Asn Ile Val Glu Phe His Ser Asp Tyr Thr Lys Ile Arg Ser Ala Thr
305 310 315 320

Phe Pro Gly Val Gln Met Lys Phe Ala Leu Gln Lys Leu Leu Thr Lys
325 330 335

Val Ala Asp Ala Ala Lys Gly Tyr Lys Pro Val Pro Val Pro Ser Glu

-continued

```
            340                 345                 350

Pro Glu His Asn Glu Ala Val Ala Asp Ser Thr Pro Leu Lys Gln Glu
        355                 360                 365

Trp Val Trp Thr Gln Val Gly Glu Phe Leu Arg Glu Gly Asp Val Val
    370                 375                 380

Ile Thr Glu Thr Gly Thr Ser Ala Phe Gly Ile Asn Gln Thr His Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Glu Thr Ala Gln Tyr Asn Cys Ile Gln Asn Trp Gln His Leu
                485                 490                 495

Glu Leu Leu Pro Thr Phe Gly Ala Lys Asp Tyr Glu Ala Val Arg Val
            500                 505                 510

Ser Thr Thr Gly Glu Trp Asn Lys Leu Thr Thr Asp Glu Lys Phe Gln
        515                 520                 525

Asp Asn Thr Arg Ile Arg Leu Ile Glu Val Met Leu Pro Thr Met Asp
    530                 535                 540

Ala Pro Ser Asn Leu Val Lys Gln Ala Gln Leu Thr Ala Ala Thr Asn
545                 550                 555                 560

Ala Lys Asn


<210> SEQ ID NO 23
<211> LENGTH: 1716
<212> TYPE: DNA
<213> ORGANISM: Yarrowia lipolytica

<400> SEQUENCE: 23

atgagcgact ccgaacccca aatggtcgac ctgggcgact atctctttgc ccgattcaag      60

cagctaggcg tggactccgt ctttggagtg cccggcgact tcaacctcac cctgttggac     120

cacgtgtaca atgtcgacat gcggtgggtt gggaacacaa acgagctgaa tgccggctac     180

tcggccgacg gctactcccg ggtcaagcgg ctggcatgtc ttgtcaccac ctttggcgtg     240

ggagagctgt ctgccgtggc tgctgtggca ggctcgtacg ccgagcatgt gggcgtggtg     300

catgttgtgg gcgttcccag cacctctgct gagaacaagc atctgctgct gcaccacaca     360

ctcggtaacg gcgacttccg ggtctttgcc cagatgtcca aactcatctc cgagtacacc     420

caccatattg aggaccccag cgaggctgcc gacgtaatcg acaccgccat ccgaatcgcc     480

tacacccacc agcggcccgt ttacattgct gtgccctcca acttctccga ggtcgatatt     540

gccgaccagg ctagactgga taccccccctg gacctttcgc tgcagcccaa cgaccccgag     600

agccagtacg aggtgattga ggagatttgc tcgcgtatca aggccgccaa gaagcccgtg     660

attctcgtcg acgcctgcgc ttcgcgatac agatgtgtgg acgagaccaa ggagctggcc     720

aagatcacca actttgccta ctttgtcact cccatgggta agggttctgt ggacgaggat     780

actgaccggt acggaggaac atacgtcgga tcgctgactg ctcctgctac tgccgaggtg     840

gttgagacag ctgatctcat catctccgta ggagctcttc tgtcggactt caacaccggt     900
```

```
tccttctcgt actcctactc caccaaaaac gtggtggaat tgcattcgga ccacgtcaaa    960

atcaagtccg ccacctacaa caacgtcggc atgaaaatgc tgttcccgcc cctgctcgaa   1020

gccgtcaaga aactggttgc cgagacccct gactttgcat ccaaggctct ggctgttccc   1080

gacaccactc ccaagatccc cgaggtaccc gatgatcaca ttacgaccca ggcatggctg   1140

tggcagcgtc tcagttactt tctgaggccc accgacatcg tggtcaccga gaccggaacc   1200

tcgtcctttg gaatcatcca gaccaagttc cccacaacg tccgaggtat ctcgcaggtg   1260

ctgtggggct ctattggata ctcggtggga gcagcctgtg gagcctccat tgctgcacag   1320

gagattgacc cccagcagcg agtgattctg tttgtgggcg acggctctct tcagctgacg   1380

gtgaccgaga tctcgtgcat gatccgcaac aacgtcaagc cgtacatttt tgtgctcaac   1440

aacgacggct acaccatcga gaggctcatt cacggcgaaa acgcctcgta caacgatgtg   1500

cacatgtgga agtactccaa gattctcgac acgttcaacg ccaaggccca cgagtcgatt   1560

gtggtcaaca ccaagggcga gatggacgct ctgttcgaca acgaagagtt tgccaagccc   1620

gacaagatcc ggctcattga ggtcatgtgc gacaagatgg acgcgcctgc ctcgttgatc   1680

aagcaggctg agctctctgc caagaccaac gtttag                              1716


<210> SEQ ID NO 24
<211> LENGTH: 571
<212> TYPE: PRT
<213> ORGANISM: Yarrowia lipolytica

<400> SEQUENCE: 24

Met Ser Asp Ser Glu Pro Gln Met Val Asp Leu Gly Asp Tyr Leu Phe
1               5                   10                  15

Ala Arg Phe Lys Gln Leu Gly Val Asp Ser Val Phe Gly Val Pro Gly
            20                  25                  30

Asp Phe Asn Leu Thr Leu Leu Asp His Val Tyr Asn Val Asp Met Arg
        35                  40                  45

Trp Val Gly Asn Thr Asn Glu Leu Asn Ala Gly Tyr Ser Ala Asp Gly
    50                  55                  60

Tyr Ser Arg Val Lys Arg Leu Ala Cys Leu Val Thr Thr Phe Gly Val
65                  70                  75                  80

Gly Glu Leu Ser Ala Val Ala Ala Val Ala Gly Ser Tyr Ala Glu His
                85                  90                  95

Val Gly Val Val His Val Val Gly Val Pro Ser Thr Ser Ala Glu Asn
            100                 105                 110

Lys His Leu Leu Leu His His Thr Leu Gly Asn Gly Asp Phe Arg Val
        115                 120                 125

Phe Ala Gln Met Ser Lys Leu Ile Ser Glu Tyr Thr His His Ile Glu
    130                 135                 140

Asp Pro Ser Glu Ala Ala Asp Val Ile Asp Thr Ala Ile Arg Ile Ala
145                 150                 155                 160

Tyr Thr His Gln Arg Pro Val Tyr Ile Ala Val Pro Ser Asn Phe Ser
                165                 170                 175

Glu Val Asp Ile Ala Asp Gln Ala Arg Leu Asp Thr Pro Leu Asp Leu
            180                 185                 190

Ser Leu Gln Pro Asn Asp Pro Glu Ser Gln Tyr Glu Val Ile Glu Glu
        195                 200                 205

Ile Cys Ser Arg Ile Lys Ala Ala Lys Lys Pro Val Ile Leu Val Asp
    210                 215                 220

Ala Cys Ala Ser Arg Tyr Arg Cys Val Asp Glu Thr Lys Glu Leu Ala
```

-continued

```
225                 230                 235                 240

Lys Ile Thr Asn Phe Ala Tyr Phe Val Thr Pro Met Gly Lys Gly Ser
                245                 250                 255

Val Asp Glu Asp Thr Asp Arg Tyr Gly Gly Thr Tyr Val Gly Ser Leu
            260                 265                 270

Thr Ala Pro Ala Thr Ala Glu Val Val Glu Thr Ala Asp Leu Ile Ile
        275                 280                 285

Ser Val Gly Ala Leu Leu Ser Asp Phe Asn Thr Gly Ser Phe Ser Tyr
    290                 295                 300

Ser Tyr Ser Thr Lys Asn Val Val Glu Leu His Ser Asp His Val Lys
305                 310                 315                 320

Ile Lys Ser Ala Thr Tyr Asn Asn Val Gly Met Lys Met Leu Phe Pro
                325                 330                 335

Pro Leu Leu Glu Ala Val Lys Lys Leu Val Ala Glu Thr Pro Asp Phe
            340                 345                 350

Ala Ser Lys Ala Leu Ala Val Pro Asp Thr Thr Pro Lys Ile Pro Glu
        355                 360                 365

Val Pro Asp Asp His Ile Thr Thr Gln Ala Trp Leu Trp Gln Arg Leu
    370                 375                 380

Ser Tyr Phe Leu Arg Pro Thr Asp Ile Val Val Thr Glu Thr Gly Thr
385                 390                 395                 400

Ser Ser Phe Gly Ile Ile Gln Thr Lys Phe Pro His Asn Val Arg Gly
                405                 410                 415

Ile Ser Gln Val Leu Trp Gly Ser Ile Gly Tyr Ser Val Gly Ala Ala
            420                 425                 430

Cys Gly Ala Ser Ile Ala Ala Gln Glu Ile Asp Pro Gln Gln Arg Val
        435                 440                 445

Ile Leu Phe Val Gly Asp Gly Ser Leu Gln Leu Thr Val Thr Glu Ile
    450                 455                 460

Ser Cys Met Ile Arg Asn Asn Val Lys Pro Tyr Ile Phe Val Leu Asn
465                 470                 475                 480

Asn Asp Gly Tyr Thr Ile Glu Arg Leu Ile His Gly Glu Asn Ala Ser
                485                 490                 495

Tyr Asn Asp Val His Met Trp Lys Tyr Ser Lys Ile Leu Asp Thr Phe
            500                 505                 510

Asn Ala Lys Ala His Glu Ser Ile Val Val Asn Thr Lys Gly Glu Met
        515                 520                 525

Asp Ala Leu Phe Asp Asn Glu Glu Phe Ala Lys Pro Asp Lys Ile Arg
    530                 535                 540

Leu Ile Glu Val Met Cys Asp Lys Met Asp Ala Pro Ala Ser Leu Ile
545                 550                 555                 560

Lys Gln Ala Glu Leu Ser Ala Lys Thr Asn Val
                565                 570


<210> SEQ ID NO 25
<211> LENGTH: 1716
<212> TYPE: DNA
<213> ORGANISM: Schizosaccharomyces pombe

<400> SEQUENCE: 25

atgagtgggg atattttagt cggtgaatat ctattcaaaa ggcttgaaca attaggggtc      60

aagtccattc ttggtgttcc aggagatttc aatttagctc tacttgactt aattgagaaa     120

gttggagatg agaaatttcg ttgggttggc aataccaatg agttgaatgg tgcttatgcc     180

gctgatggtt atgctcgtgt taatggtctt tcagccattg ttacaacgtt cggcgtggga     240
```

-continued

```
gagctttccg ctattaatgg agtggcaggt tcttatgcgg agcatgtccc agtagttcat    300
attgttggaa tgccttccac aaaggtgcaa gatactggag ctttgcttca tcatacttta    360
ggagatggag actttcgcac tttcatggat atgtttaaga aagtttctgc ctacagtata    420
atgatcgata acggaaacga tgcagctgaa aagatcgatg aagccttgtc gatttgttat    480
aaaaaggcta ggcctgttta cattggtatt ccttctgatg ctggctactt caaagcatct    540
tcatcaaatc ttgggaaaag actaaagctc gaggaggata ctaacgatcc agcagttgag    600
caagaagtca tcaatcatat ctcggaaatg gttgtcaatg caaagaaacc agtgatttta    660
attgacgctt gtgctgtaag acatcgtgtc gttccagaag tacatgagct gattaaattg    720
acccatttcc ctacatatgt aactcccatg ggtaaatctg caattgacga aacttcgcaa    780
tttttgacg gcgtttatgt tggttcaatt tcagatcctg aagttaaaga cagaattgaa    840
tccactgatc tgttgctatc catcggtgct ctcaaatcag actttaacac gggttccttc    900
tcttaccacc tcagccaaaa gaatgccgtt gagtttcatt cagaccacat gcgcattcga    960
tatgctcttt atccaaatgt agccatgaag tatattcttc gcaaactgtt gaaagtactt   1020
gatgcttcta tgtgtcattc caaggctgct cctaccattg gctacaacat caagcctaag   1080
catgcggaag gatattcttc caacgagatt actcattgct ggttttggcc taaatttagt   1140
gaatttttga agccccgaga tgttttgatc accgagactg gaactgcaaa ctttggtgtc   1200
cttgattgca ggtttccaaa ggatgtaaca gccatttccc aggtattatg gggatctatt   1260
ggatactccg ttggtgcaat gtttggtgct gttttggccg tccacgattc taaagagccc   1320
gatcgtcgta ccattcttgt agtaggtgat ggatccttac aactgacgat tacagagatt   1380
tcaacctgca ttcgccataa cctcaaacca attattttca taattaacaa cgacggttac   1440
accattgagc gtttaattca tggtttgcat gctagctata acgaaattaa cactaaatgg   1500
ggctaccaac agattcccaa gtttttcgga gctgctgaaa accacttccg cacttactgt   1560
gttaaaactc ctactgacgt tgaaaagttg tttagcgaca aggagtttgc aaatgcagat   1620
gtcattcaag tagttgagct tgtaatgcct atgttggatg cacctcgtgt cctagttgag   1680
caagccaagt tgacgtctaa gatcaataag caatga                             1716
```

```
<210> SEQ ID NO 26
<211> LENGTH: 571
<212> TYPE: PRT
<213> ORGANISM: Schizosaccharomyces pombe

<400> SEQUENCE: 26

Met Ser Gly Asp Ile Leu Val Gly Glu Tyr Leu Phe Lys Arg Leu Glu
1               5                   10                  15

Gln Leu Gly Val Lys Ser Ile Leu Gly Val Pro Gly Asp Phe Asn Leu
            20                  25                  30

Ala Leu Leu Asp Leu Ile Glu Lys Val Gly Asp Glu Lys Phe Arg Trp
        35                  40                  45

Val Gly Asn Thr Asn Glu Leu Asn Gly Ala Tyr Ala Ala Asp Gly Tyr
    50                  55                  60

Ala Arg Val Asn Gly Leu Ser Ala Ile Val Thr Thr Phe Gly Val Gly
65                  70                  75                  80

Glu Leu Ser Ala Ile Asn Gly Val Ala Gly Ser Tyr Ala Glu His Val
                85                  90                  95

Pro Val Val His Ile Val Gly Met Pro Ser Thr Lys Val Gln Asp Thr
            100                 105                 110
```

-continued

```
Gly Ala Leu Leu His His Thr Leu Gly Asp Gly Asp Phe Arg Thr Phe
        115                 120                 125

Met Asp Met Phe Lys Lys Val Ser Ala Tyr Ser Ile Met Ile Asp Asn
    130                 135                 140

Gly Asn Asp Ala Ala Glu Lys Ile Asp Glu Ala Leu Ser Ile Cys Tyr
145                 150                 155                 160

Lys Lys Ala Arg Pro Val Tyr Ile Gly Ile Pro Ser Asp Ala Gly Tyr
                165                 170                 175

Phe Lys Ala Ser Ser Ser Asn Leu Gly Lys Arg Leu Lys Leu Glu Glu
            180                 185                 190

Asp Thr Asn Asp Pro Ala Val Glu Gln Glu Val Ile Asn His Ile Ser
        195                 200                 205

Glu Met Val Val Asn Ala Lys Lys Pro Val Ile Leu Ile Asp Ala Cys
    210                 215                 220

Ala Val Arg His Arg Val Val Pro Glu Val His Glu Leu Ile Lys Leu
225                 230                 235                 240

Thr His Phe Pro Thr Tyr Val Thr Pro Met Gly Lys Ser Ala Ile Asp
                245                 250                 255

Glu Thr Ser Gln Phe Phe Asp Gly Val Tyr Val Gly Ser Ile Ser Asp
            260                 265                 270

Pro Glu Val Lys Asp Arg Ile Glu Ser Thr Asp Leu Leu Leu Ser Ile
        275                 280                 285

Gly Ala Leu Lys Ser Asp Phe Asn Thr Gly Ser Phe Ser Tyr His Leu
    290                 295                 300

Ser Gln Lys Asn Ala Val Glu Phe His Ser Asp His Met Arg Ile Arg
305                 310                 315                 320

Tyr Ala Leu Tyr Pro Asn Val Ala Met Lys Tyr Ile Leu Arg Lys Leu
                325                 330                 335

Leu Lys Val Leu Asp Ala Ser Met Cys His Ser Lys Ala Ala Pro Thr
            340                 345                 350

Ile Gly Tyr Asn Ile Lys Pro Lys His Ala Glu Gly Tyr Ser Ser Asn
        355                 360                 365

Glu Ile Thr His Cys Trp Phe Trp Pro Lys Phe Ser Glu Phe Leu Lys
    370                 375                 380

Pro Arg Asp Val Leu Ile Thr Glu Thr Gly Thr Ala Asn Phe Gly Val
385                 390                 395                 400

Leu Asp Cys Arg Phe Pro Lys Asp Val Thr Ala Ile Ser Gln Val Leu
                405                 410                 415

Trp Gly Ser Ile Gly Tyr Ser Val Gly Ala Met Phe Gly Ala Val Leu
            420                 425                 430

Ala Val His Asp Ser Lys Glu Pro Asp Arg Arg Thr Ile Leu Val Val
        435                 440                 445

Gly Asp Gly Ser Leu Gln Leu Thr Ile Thr Glu Ile Ser Thr Cys Ile
    450                 455                 460

Arg His Asn Leu Lys Pro Ile Ile Phe Ile Ile Asn Asn Asp Gly Tyr
465                 470                 475                 480

Thr Ile Glu Arg Leu Ile His Gly Leu His Ala Ser Tyr Asn Glu Ile
                485                 490                 495

Asn Thr Lys Trp Gly Tyr Gln Gln Ile Pro Lys Phe Phe Gly Ala Ala
            500                 505                 510

Glu Asn His Phe Arg Thr Tyr Cys Val Lys Thr Pro Thr Asp Val Glu
        515                 520                 525

Lys Leu Phe Ser Asp Lys Glu Phe Ala Asn Ala Asp Val Ile Gln Val
    530                 535                 540
```

Val Glu Leu Val Met Pro Met Leu Asp Ala Pro Arg Val Leu Val Glu
545 550 555 560

Gln Ala Lys Leu Thr Ser Lys Ile Asn Lys Gln
565 570

<210> SEQ ID NO 27
<211> LENGTH: 1689
<212> TYPE: DNA
<213> ORGANISM: Zygosaccharomyces rouxii

<400> SEQUENCE: 27
atgtctgaaa ttactctagg tcgttacttg ttcgaaagat taaagcaagt tgacactaac 60
accatcttcg gtgttccagg tgacttcaac ttgtccttgt tggacaaggt ctacgaagtg 120
caaggtctaa gatgggctgg taacgctaac gaattgaacg ctgcctacgc tgctgacggt 180
tacgccagag ttaagggttt ggctgctttg atcaccacct tcggtgtcgg tgaattgtct 240
gctttgaacg gtattgcagg ttcttacgct gaacacgttg gtgttttgca cattgttggt 300
gttccatctg tctcttctca agctaagcaa ttgttgttgc accacacctt gggtaacggt 360
gacttcactg ttttccacag aatgtccgcc aacatctctg aaaccaccgc tatgttgacc 420
gacatcactg ctgctccagc tgaaattgac cgttgcatca gagttgctta cgtcaaccaa 480
agaccagtct acttgggtct accagctaac ttggttgacc aaaaggtccc agcttctttg 540
ttgaacactc caattgatct atctctaaag gagaacgacc cagaagctga aaccgaagtt 600
gttgacaccg ttttggaatt gatcaaggaa gctaagaacc cagttatctt ggctgatgct 660
tgctgctcca gacacgacgt caaggctgaa accaagaagt tgatcgactt gactcaattc 720
ccatctttcg ttactcctat gggtaagggt tccatcgacg aacaaaaccc aagattcggt 780
ggtgtctacg tcggtactct atccagccca gaagttaagg aagctgttga atctgctgac 840
ttggttctat ctgtcggtgc tctattgtcc gatttcaaca ctggttcttt ctcttactct 900
tacaagacca agaacgttgt tgaattccac tctgaccaca tcaagatcag aaacgctacc 960
ttcccaggtg ttcaaatgaa attcgttttg aagaaactat tgcaagctgt cccagaagct 1020
gtcaagaact acaagccagg tccagtccca gctccgccat ctccaaacgc tgaagttgct 1080
gactctacca ccttgaagca agaatggtta tggagacaag tcggtagctt cttgagagaa 1140
ggtgatgttg ttattaccga aactggtacc tctgctttcg gtatcaacca aactcacttc 1200
cctaaccaaa cttacggtat ctctcaagtc ttgtggggtt ctattggtta caccactggt 1260
tccactttgg gtgctgcctt cgctgctgaa gaaattgacc ctaagaagag agttatcttg 1320
ttcattggtg acggttctct acaattgacc gttcaagaaa tctccaccat gatcagatgg 1380
ggtctaaagc catacttgtt cgttttgaac aacgatggtt acaccattga aagattgatt 1440
cacggtgaaa ccgctgaata caactgtatc caaccatgga agcacttgga attgttgaac 1500
accttcggtg ccaaggacta cgaaaaccac agagtctcca ctgtcggtga atggaacaag 1560
ttgactcaag atccaaaatt caacgaaaac tctagaatta gaatgatcga agttatgctt 1620
gaagtcatgg acgctccatc ttctttggtc gctcaagctc aattgaccgc tgctactaac 1680
gctaagcaa 1689

<210> SEQ ID NO 28
<211> LENGTH: 563
<212> TYPE: PRT
<213> ORGANISM: Zygosaccharomyces rouxii

<400> SEQUENCE: 28

-continued

```
Met Ser Glu Ile Thr Leu Gly Arg Tyr Leu Phe Glu Arg Leu Lys Gln
1               5                   10                  15

Val Asp Thr Asn Thr Ile Phe Gly Val Pro Gly Asp Phe Asn Leu Ser
            20                  25                  30

Leu Leu Asp Lys Val Tyr Glu Val Gln Gly Leu Arg Trp Ala Gly Asn
        35                  40                  45

Ala Asn Glu Leu Asn Ala Ala Tyr Ala Ala Asp Gly Tyr Ala Arg Val
    50                  55                  60

Lys Gly Leu Ala Ala Leu Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Ile Val Gly Val Pro Ser Val Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Leu Thr Asp Ile Thr Ala
    130                 135                 140

Ala Pro Ala Glu Ile Asp Arg Cys Ile Arg Val Ala Tyr Val Asn Gln
145                 150                 155                 160

Arg Pro Val Tyr Leu Gly Leu Pro Ala Asn Leu Val Asp Gln Lys Val
                165                 170                 175

Pro Ala Ser Leu Leu Asn Thr Pro Ile Asp Leu Ser Leu Lys Glu Asn
            180                 185                 190

Asp Pro Glu Ala Glu Thr Glu Val Val Asp Thr Val Leu Glu Leu Ile
        195                 200                 205

Lys Glu Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ser Phe Val Thr Pro Met Gly Lys Gly Ser Ile Asp Glu Gln Asn
                245                 250                 255

Pro Arg Phe Gly Gly Val Tyr Val Gly Thr Leu Ser Ser Pro Glu Val
            260                 265                 270

Lys Glu Ala Val Glu Ser Ala Asp Leu Val Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp His Ile Lys Ile Arg Asn Ala Thr
305                 310                 315                 320

Phe Pro Gly Val Gln Met Lys Phe Val Leu Lys Lys Leu Leu Gln Ala
                325                 330                 335

Val Pro Glu Ala Val Lys Asn Tyr Lys Pro Gly Pro Val Pro Ala Pro
            340                 345                 350

Pro Ser Pro Asn Ala Glu Val Ala Asp Ser Thr Thr Leu Lys Gln Glu
        355                 360                 365

Trp Leu Trp Arg Gln Val Gly Ser Phe Leu Arg Glu Gly Asp Val Val
    370                 375                 380

Ile Thr Glu Thr Gly Thr Ser Ala Phe Gly Ile Asn Gln Thr His Phe
385                 390                 395                 400

Pro Asn Gln Thr Tyr Gly Ile Ser Gln Val Leu Trp Gly Ser Ile Gly
                405                 410                 415

Tyr Thr Thr Gly Ser Thr Leu Gly Ala Ala Phe Ala Ala Glu Glu Ile
```

-continued

```
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Glu Thr Ala Glu Tyr Asn Cys Ile Gln Pro Trp Lys His Leu
                485                 490                 495

Glu Leu Leu Asn Thr Phe Gly Ala Lys Asp Tyr Glu Asn His Arg Val
            500                 505                 510

Ser Thr Val Gly Glu Trp Asn Lys Leu Thr Gln Asp Pro Lys Phe Asn
        515                 520                 525

Glu Asn Ser Arg Ile Arg Met Ile Glu Val Met Leu Glu Val Met Asp
    530                 535                 540

Ala Pro Ser Ser Leu Val Ala Gln Ala Gln Leu Thr Ala Ala Thr Asn
545                 550                 555                 560

Ala Lys Gln


<210> SEQ ID NO 29
<211> LENGTH: 16387
<212> TYPE: DNA
<213> ORGANISM: artificial sequence
<220> FEATURE:
<223> OTHER INFORMATION: synthetic construct

<400> SEQUENCE: 29

tcccattacc gacatttggg cgctatacgt gcatatgttc atgtatgtat ctgtatttaa     60

aacacttttg tattattttt cctcatatat gtgtataggt ttatacggat gatttaatta    120

ttacttcacc accctttatt tcaggctgat atcttagcct tgttactagt tagaaaaaga    180

catttttgct gtcagtcact gtcaagagat tcttttgctg gcatttcttc tagaagcaaa    240

aagagcgatg cgtcttttcc gctgaaccgt tccagcaaaa aagactacca acgcaatatg    300

gattgtcaga atcatataaa agagaagcaa ataactcctt gtcttgtatc aattgcatta    360

taatatcttc ttgttagtgc aatatcatat agaagtcatc gaaatagata ttaagaaaaa    420

caaactgtac aatcaatcaa tcaatcatcg ctgaggatgt tgacaaaagc aacaaaagaa    480

caaaaatccc ttgtgaaaaa cagaggggcg gagcttgttg ttgattgctt agtggagcaa    540

ggtgtcacac atgtatttgg cattccaggt gcaaaaattg atgcggtatt tgacgcttta    600

caagataaag gacctgaaat tatcgttgcc cggcacgaac aaaacgcagc attcatggcc    660

caagcagtcg gccgtttaac tggaaaaccg ggagtcgtgt tagtcacatc aggaccgggt    720

gcctctaact tggcaacagg cctgctgaca gcgaacactg aaggagaccc tgtcgttgcg    780

cttgctggaa acgtgatccg tgcagatcgt ttaaaacgga cacatcaatc tttggataat    840

gcggcgctat tccagccgat tacaaaatac agtgtagaag ttcaagatgt aaaaaatata    900

ccggaagctg ttacaaatgc atttaggata gcgtcagcag ggcaggctgg ggccgctttt    960

gtgagctttc cgcaagatgt tgtgaatgaa gtcacaaata cgaaaaacgt gcgtgctgtt   1020

gcagcgccaa aactcggtcc tgcagcagat gatgcaatca gtgcggccat agcaaaaatc   1080

caaacagcaa aacttcctgt cgttttggtc ggcatgaaag gcggaagacc ggaagcaatt   1140

aaagcggttc gcaagctttt gaaaaaggtt cagcttccat ttgttgaaac atatcaagct   1200

gccggtaccc tttctagaga tttagaggat caatattttg gccgtatcgg tttgttccgc   1260
```

-continued

```
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga aagtggaatt tgcagagcgt   1500
gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgctc tagaactagt accacaggtg   2460
ttgtcctctg aggacataaa atacacaccg agattcatca actcattgct ggagttagca   2520
tatctacaat tgggtgaaat ggggagcgat ttgcaggcat ttgctcggca tgccggtaga   2580
ggtgtggtca ataagagcga cctcatgcta tacctgagaa agcaacctga cctacaggaa   2640
agagttactc aagaataaga attttcgttt taaaacctaa gagtcacttt aaaatttgta   2700
tacacttatt tttttataa cttatttaat aataaaaatc ataaatcata agaaattcgc   2760
ttactcttaa ttaatcaagc atctaaaaca caaccgttgg aagcgttgga aaccaactta   2820
gcatacttgg atagagtacc tcttgtgtaa cgaggtggag gtgcaaccca actttgttta   2880
cgttgagcca tttccttatc agagactaat aggtcaatct tgttattatc agcatcaatg   2940
ataatctcat cgccgtctct gaccaacccg ataggaccac cttcagcggc ttcgggaaca   3000
atgtggccga ttaagaaccc gtgagaacca ccagagaatc taccatcagt caacaatgca   3060
acatctttac ccaaaccgta acccatcaga gcagaggaag gctttagcat ttcaggcata   3120
cctggtgcac ctcttggacc ttcatatctg ataacaacaa cggttttttc acccttcttg   3180
atttcacctc tttccaaggc ttcaataaag gcaccttcct cttcgaacac acgtgctcta   3240
cccttgaagt aagtaccttc cttaccggta attttaccca cagctccacc tggtgccaat   3300
gaaccgtaca gaatttgcaa gtgaccgttg gccttgattg ggtgggagag tggcttaata   3360
atctcttgtc cttcaggtag gcttggtgct ttctttgcac gttctgccaa agtgtcaccg   3420
gtaacagtca ttgtgttacc gtgcaacatg ttgttttcat atagatactt aatcacagat   3480
tgggtaccac caacgttaat caaatcggcc atgacgtatt taccagaagg tttgaagtca   3540
ccgatcaatg gtgtagtatc actgattctt tggaaatcat ctggtgacaa cttgacaccc   3600
gcagagtgag caacagccac caaatgcaaa acagcattag tggacccacc ggttgcaacg   3660
```

-continued

```
acataagtaa tggcgttttc aaaagcctct tttgtgagga tatcacgagg taaaataccc   3720
aattccattg tcttcttgat gtattcacca atgttgtcac actcagctaa cttctccttg   3780
gaaacggctg ggaaggaaga ggagtttgga atggtcaaac ctagcacttc agcggcagaa   3840
gccattgtgt tggcagtata cataccacca caagaaccag gacctgggca tgcatgttcc   3900
acaacatctt ctctttcttc ttcagtgaat tgcttggaaa tatattcacc gtaggattgg   3960
aacgcagaga cgatatcgat gtttttagag atcctgttaa aacctctagt ggagtagtag   4020
atgtaatcaa tgaagcggaa gccaaaagac cagagtagag gcctatagaa gaaactgcga   4080
taccttttgt gatggctaaa caaacagaca tctttttata tgtttttact tctgtatatc   4140
gtgaagtagt aagtgataag cgaatttggc taagaacgtt gtaagtgaac aagggacctc   4200
ttttgccttt caaaaaagga ttaaatggag ttaatcattg agatttagtt ttcgttagat   4260
tctgtatccc taaataactc ccttacccga cgggaaggca caaaagactt gaataatagc   4320
aaacggccag tagccaagac caaataatac tagagttaac tgatggtctt aaacaggcat   4380
tacgtggtga actccaagac caatatacaa aatatcgata agttattctt gcccaccaat   4440
ttaaggagcc tacatcagga cagtagtacc attcctcaga gaagaggtat acataacaag   4500
aaaatcgcgt gaacacctta tataacttag cccgttattg agctaaaaaa ccttgcaaaa   4560
tttcctatga ataagaatac ttcagacgtg ataaaaattt actttctaac tcttctcacg   4620
ctgcccctat ctgttcttcc gctctaccgt gagaaataaa gcatcgagta cggcagttcg   4680
ctgtcactga actaaaacaa taaggctagt tcgaatgatg aacttgcttg ctgtcaaact   4740
tctgagttgc cgctgatgtg acactgtgac aataaattca aaccggttat agcggtctcc   4800
tccggtaccg gttctgccac ctccaataga gctcagtagg agtcagaacc tctgcggtgg   4860
ctgtcagtga ctcatccgcg tttcgtaagt tgtgcgcgtg cacatttcgc ccgttcccgc   4920
tcatcttgca gcaggcggaa attttcatca cgctgtagga cgcaaaaaaa aaataattaa   4980
tcgtacaaga atcttggaaa aaaaattgaa aaattttgta taaaagggat gacctaactt   5040
gactcaatgg cttttacacc cagtattttc cctttccttg tttgttacaa ttatagaagc   5100
aagacaaaaa catatagaca acctattcct aggagttata ttttttacc ctaccagcaa    5160
tataagtaaa aaactagtat gaaggtgttt tacgataaag actgcgatct gagcatcatc   5220
cagggaaaga aggttgctat tataggatat ggttcccaag gacacgcaca agccttgaac   5280
ttgaaagatt ctggggtcga cgtgacagta ggtctgtata aaggtgctgc tgatgcagca   5340
aaggctgaag cacatggctt taaagtcaca gatgttgcag cggctgttgc tggcgctgat   5400
ttagtcatga ttttaattcc agatgaattt caatcgcaat tgtacaaaaa tgaaatagaa   5460
ccaaacatta agaagggcgc taccttggcc ttcagtcatg gatttgccat tcattacaat   5520
caagtagtcc ccagggcaga tttggacgtt attatgattg cacctaaggc tccggggcat   5580
actgttagga gcgaatttgt taagggtggt ggtattccag atttgatcgc tatataccaa   5640
gacgttagcg gaaacgctaa gaatgtagct ttaagctacg cagcaggagt tggtggcggg   5700
agaacgggta taatagaaac cacttttaaa gacgagactg agacagattt atttggagaa   5760
caagcggttc tgtgcggagg aactgttgaa ttggttaaag caggctttga gacgcttgtc   5820
gaagcagggt acgctcccga aatggcatac ttcgaatgtc tacatgaatt gaagttgata   5880
gtagacttaa tgtatgaagg tggtatagct aatatgaact attccatttc aaataatgca   5940
gaatatggtg agtatgtcac cggacctgaa gtcattaacg cagaatcaag acaagccatg   6000
agaaatgcct tgaaacgtat ccaggacggt gaatacgcta agatgttcat aagtgaaggc   6060
```

-continued

```
gctacgggtt acccgagtat gactgctaaa agaagaaaca atgcagcaca tggtatcgaa   6120
attattggtg aacagttaag gtctatgatg ccctggatcg gtgctaataa gatcgtagac   6180
aaggcgaaaa attaaggccc tgcaggccta tcaagtgctg gaaacttttt ctcttggaat   6240
ttttgcaaca tcaagtcata gtcaattgaa ttgacccaat ttcacattta agattttttt   6300
tttttcatcc gacatacatc tgtacactag gaagccctgt ttttctgaag cagcttcaaa   6360
tatatatatt ttttacatat ttattatgat tcaatgaaca atctaattaa atcgaaaaca   6420
agaaccgaaa cgcgaataaa taatttattt agatggtgac aagtgtataa gtcctcatcg   6480
ggacagctac gatttctctt tcggttttgg ctgagctact ggttgctgtg acgcagcggc   6540
attagcgcgg cgttatgagc taccctcgtg gcctgaaaga tggcgggaat aaagcggaac   6600
taaaaattac tgactgagcc atattgaggt caatttgtca actcgtcaag tcacgtttgg   6660
tggacggccc ctttccaacg aatcgtatat actaacatgc gcgcgcttcc tatatacaca   6720
tatacatata tatatatata tatatgtgtg cgtgtatgtg tacacctgta tttaatttcc   6780
ttactcgcgg gtttttcttt tttctcaatt cttggcttcc tctttctcga gtatataatt   6840
tttcaggtaa aatttagtac gatagtaaaa tacttctcga actcgtcaca tatacgtgta   6900
cataatgtct gaaccagctc aaaagaaaca aaaggttgct aacaactctc tagagcggcc   6960
gcccgcaaat taaagccttc gagcgtccca aaaccttctc aagcaaggtt ttcagtataa   7020
tgttacatgc gtacacgcgt ctgtacagaa aaaaaagaaa aatttgaaat ataaataacg   7080
ttcttaatac taacataact ataaaaaaat aaatagggac ctagacttca ggttgtctaa   7140
ctccttcctt ttcggttaga gcggatgtgg ggggagggcg tgaatgtaag cgtgacataa   7200
ctaattacat gattaattaa ttattggttt tctggtctca actttctgac ttccttacca   7260
accttccaga tttccatgtt tctgatggtg tctaattcct tttctagctt ttctctgtag   7320
tcaggttgag agttgaattc caaagatctc ttggtttcgg taccgttctt ggtagattcg   7380
tacaagtctt ggaaaacagg cttcaaagca ttcttgaaga ttgggtacca gtccaaagca   7440
cctcttctgg cggtggtgga acaagcatcg tacatgtaat ccataccgta cttaccgatc   7500
aatgggtata gagattgggt agcttcttcg acggtttcgt tgaaagcttc agatggggag   7560
tgaccgtttt ctctcaagac gtcgtattga gccaagaaca taccgtggat accacccatt   7620
aaacaacctc tttcaccgta caagtcagag ttgacttctc tttcgaaagt ggtttggtaa   7680
acgtaaccgg aaccaatggc aacggccaaa gcttgggcct tttcgtgagc cttaccggtg   7740
acatcgttcc agacggcgta agaagagtta ataccacgac cttccttgaa caaagatctg   7800
acagttctac cggaaccctt tggagcaacc aagataacat ctaagtcctt tggtggttca   7860
acgtgagtca agtccttgaa gactggggag aaaccgtggg agaagtacaa agtcttaccc   7920
ttggtcaaca atggcttgat agcaggccag gtttctgatt gagcggcatc ggacaacaag   7980
ttcataacgt aactacctct cttgatagca tcttcaacag tgaacaagtt cttgcctgga   8040
acccaaccgt cttcgatggc agccttccaa gaagcaccat ctttacggac accaatgata   8100
acgttcaaac cgttgtctct caagttcaaa ccttgaccgt aaccttggga accgtaaccg   8160
atcaaagcaa aagtgtcgtt cttgaagtag tccaacaact tttctcttgg ccagtcagct   8220
ctttcgtaga cggtttcaac agtaccaccg aagttgattt gcttcaacat cctcagctct   8280
agatttgaat atgtattact tggttatggt tatatatgac aaaagaaaaa gaagaacaga   8340
agaataacgc aaggaagaac aataactgaa attgatagag aagtattatg tctttgtctt   8400
tttataataa atcaagtgca gaaatccgtt agacaacatg agggataaaa tttaacgtgg   8460
```

-continued

```
gcgaagaaga aggaaaaaag tttttgtgag ggcgtaattg aagcgatctg ttgattgtag   8520
atttttttt tttgaggagt caaagtcaga agagaacaga caaatggtat taaccatcca   8580
atactttttt ggagcaacgc taagctcatg cttttccatt ggttacgtgc tcagttgtta   8640
gatatggaaa gagaggatgc tcacggcagc gtgactccaa ttgagcccga aagagaggat   8700
gccacgtttt cccgacggct gctagaatgg aaaaaggaaa aatagaagaa tcccattcct   8760
atcattattt acgtaatgac ccacacattt ttgagatttt caactattac gtattacgat   8820
aatcctgctg tcattatcat tattatctat atcgacgtat gcaacgtatg tgaagccaag   8880
taggcaatta tttagtactg tcagtattgt tattcatttc agatctatcc gcggtggagc   8940
tcgaattcac tggccgtcgt tttacaacgt cgtgactggg aaaaccctgg cgttacccaa   9000
cttaatcgcc ttgcagcaca tccccctttc gccagctggc gtaatagcga agaggcccgc   9060
accgatcgcc cttcccaaca gttgcgcagc ctgaatggcg aatggcgcct gatgcggtat   9120
tttctcctta cgcatctgtg cggtatttca caccgcatac gtcaaagcaa ccatagtacg   9180
cgccctgtag cggcgcatta agcgcggcgg gtgtggtggt tacgcgcagc gtgaccgcta   9240
cacttgccag cgccttagcg cccgctcctt tcgctttctt cccttccttt ctcgccacgt   9300
tcgccggctt tccccgtcaa gctctaaatc gggggctccc tttagggttc cgatttagtg   9360
ctttacggca cctcgacccc aaaaaacttg atttgggtga tggttcacgt agtgggccat   9420
cgccctgata gacggttttt cgccctttga cgttggagtc cacgttcttt aatagtggac   9480
tcttgttcca aactggaaca acactcaact ctatctcggg ctattctttt gatttataag   9540
ggattttgcc gatttcggtc tattggttaa aaaatgagct gatttaacaa aaatttaacg   9600
cgaattttaa caaaatatta acgtttacaa ttttatggtg cactctcagt acaatctgct   9660
ctgatgccgc atagttaagc cagccccgac acccgccaac acccgctgac gcgccctgac   9720
gggcttgtct gctcccggca tccgcttaca gacaagctgt gaccgtctcc gggagctgca   9780
tgtgtcagag gttttcaccg tcatcaccga aacgcgcgag acgaaagggc ctcgtgatac   9840
gcctattttt ataggttaat gtcatgataa taatggtttc ttagacgtca ggtggcactt   9900
ttcggggaaa tgtgcgcgga acccctattt gtttattttt ctaaatacat tcaaatatgt   9960
atccgctcat gagacaataa ccctgataaa tgcttcaata atattgaaaa aggaagagta  10020
tgagtattca acatttccgt gtcgccctta ttcccttttt tgcggcattt tgccttcctg  10080
tttttgctca cccagaaacg ctggtgaaag taaaagatgc tgaagatcag ttgggtgcac  10140
gagtgggtta catcgaactg gatctcaaca gcggtaagat ccttgagagt tttcgccccg  10200
aagaacgttt tccaatgatg agcactttta aagttctgct atgtggcgcg gtattatccc  10260
gtattgacgc cgggcaagag caactcggtc gccgcataca ctattctcag aatgacttgg  10320
ttgagtactc accagtcaca gaaaagcatc ttacggatgg catgacagta agagaattat  10380
gcagtgctgc cataaccatg agtgataaca ctgcggccaa cttacttctg acaacgatcg  10440
gaggaccgaa ggagctaacc gctttttgc acaacatggg ggatcatgta actcgccttg  10500
atcgttggga accggagctg aatgaagcca taccaaacga cgagcgtgac accacgatgc  10560
ctgtagcaat ggcaacaacg ttgcgcaaac tattaactgg cgaactactt actctagctt  10620
cccggcaaca attaatagac tggatggagg cggataaagt tgcaggacca cttctgcgct  10680
cggcccttcc ggctggctgg tttattgctg ataaatctgg agccggtgag cgtgggtctc  10740
gcggtatcat tgcagcactg gggccagatg gtaagccctc ccgtatcgta gttatctaca  10800
cgacggggag tcaggcaact atggatgaac gaaatagaca gatcgctgag ataggtgcct  10860
```

-continued

```
cactgattaa gcattggtaa ctgtcagacc aagtttactc atatatactt tagattgatt  10920
taaaacttca tttttaattt aaaaggatct aggtgaagat cctttttgat aatctcatga  10980
ccaaaatccc ttaacgtgag ttttcgttcc actgagcgtc agaccccgta gaaaagatca  11040
aaggatcttc ttgagatcct ttttttctgc gcgtaatctg ctgcttgcaa acaaaaaaac  11100
caccgctacc agcggtggtt tgtttgccgg atcaagagct accaactctt tttccgaagg  11160
taactggctt cagcagagcg cagataccaa atactgttct tctagtgtag ccgtagttag  11220
gccaccactt caagaactct gtagcaccgc ctacatacct cgctctgcta atcctgttac  11280
cagtggctgc tgccagtggc gataagtcgt gtcttaccgg gttggactca agacgatagt  11340
taccggataa ggcgcagcgg tcgggctgaa cggggggttc gtgcacacag cccagcttgg  11400
agcgaacgac ctacaccgaa ctgagatacc tacagcgtga gctatgagaa agcgccacgc  11460
ttcccgaagg gagaaaggcg gacaggtatc cggtaagcgg cagggtcgga acaggagagc  11520
gcacgaggga gcttccaggg ggaaacgcct ggtatcttta tagtcctgtc gggtttcgcc  11580
acctctgact tgagcgtcga tttttgtgat gctcgtcagg ggggcggagc ctatggaaaa  11640
acgccagcaa cgcggccttt ttacggttcc tggccttttg ctggcctttt gctcacatgt  11700
tctttcctgc gttatcccct gattctgtgg ataaccgtat taccgccttt gagtgagctg  11760
ataccgctcg ccgcagccga acgaccgagc gcagcgagtc agtgagcgag gaagcggaag  11820
agcgcccaat acgcaaaccg cctctccccg cgcgttggcc gattcattaa tgcagctggc  11880
acgacaggtt tcccgactgg aaagcgggca gtgagcgcaa cgcaattaat gtgagttagc  11940
tcactcatta ggcaccccag gctttacact ttatgcttcc ggctcgtatg ttgtgtggaa  12000
ttgtgagcgg ataacaattt cacacaggaa acagctatga ccatgattac gccaagcttt  12060
ttctttccaa tttttttttt ttcgtcatta taaaaatcat tacgaccgag attcccgggt  12120
aataactgat ataattaaat tgaagctcta atttgtgagt ttagtataca tgcatttact  12180
tataatacag tttttttagtt ttgctggccg catcttctca aatatgcttc ccagcctgct  12240
tttctgtaac gttcaccctc taccttagca tcccttccct ttgcaaatag tcctcttcca  12300
acaataataa tgtcagatcc tgtagagacc acatcatcca cggttctata ctgttgaccc  12360
aatgcgtctc ccttgtcatc taaacccaca ccgggtgtca taatcaacca atcgtaacct  12420
tcatctcttc cacccatgtc tctttgagca ataaagccga taacaaaatc tttgtcgctc  12480
ttcgcaatgt caacagtacc cttagtatat tctccagtag atagggagcc cttgcatgac  12540
aattctgcta acatcaaaag gcctctaggt tcctttgtta cttcttctgc cgcctgcttc  12600
aaaccgctaa caatacctgg gcccaccaca ccgtgtgcat tcgtaatgtc tgcccattct  12660
gctattctgt atacacccgc agagtactgc aatttgactg tattaccaat gtcagcaaat  12720
tttctgtctt cgaagagtaa aaaattgtac ttggcggata atgcctttag cggcttaact  12780
gtgccctcca tggaaaaatc agtcaagata tccacatgtg tttttagtaa acaaattttg  12840
ggacctaatg cttcaactaa ctccagtaat tccttggtgg tacgaacatc caatgaagca  12900
cacaagtttg tttgcttttc gtgcatgata ttaaatagct tggcagcaac aggactagga  12960
tgagtagcag cacgttcctt atatgtagct ttcgacatga tttatcttcg tttcctgcag  13020
gtttttgttc tgtgcagttg ggttaagaat actgggcaat ttcatgtttc ttcaacacta  13080
catatgcgta tatataccaa tctaagtctg tgctccttcc ttcgttcttc cttctgttcg  13140
gagattaccg aatcaaaaaa atttcaagga aaccgaaatc aaaaaaaaga ataaaaaaaa  13200
aatgatgaat tgaaaagctt gcatgcctgc aggtcgactc tagtatactc cgtctactgt  13260
```

-continued

```
acgatacact tccgctcagg tccttgtcct ttaacgaggc cttaccactc ttttgttact  13320
ctattgatcc agctcagcaa aggcagtgtg atctaagatt ctatcttcgc gatgtagtaa  13380
aactagctag accgagaaag agactagaaa tgcaaaaggc acttctacaa tggctgccat  13440
cattattatc cgatgtgacg ctgcattttt tttttttttt tttttttttt tttttttttt  13500
tttttttttt tttttttgta caaatatcat aaaaaaagag aatcttttta agcaaggatt  13560
ttcttaactt cttcggcgac agcatcaccg acttcggtgg tactgttgga accacctaaa  13620
tcaccagttc tgatacctgc atccaaaacc tttttaactg catcttcaat ggctttacct  13680
tcttcaggca agttcaatga caatttcaac atcattgcag cagacaagat agtggcgata  13740
gggttgacct tattctttgg caaatctgga gcggaaccat ggcatggttc gtacaaacca  13800
aatgcggtgt tcttgtctgg caaagaggcc aaggacgcag atggcaacaa acccaaggag  13860
cctgggataa cggaggcttc atcggagatg atatcaccaa acatgttgct ggtgattata  13920
ataccattta ggtgggttgg gttcttaact aggatcatgg cggcagaatc aatcaattga  13980
tgttgaactt tcaatgtagg gaattcgttc ttgatggttt cctccacagt tttctccat  14040
aatcttgaag aggccaaaac attagcttta tccaaggacc aaataggcaa tggtggctca  14100
tgttgtaggg ccatgaaagc ggccattctt gtgattcttt gcacttctgg aacggtgtat  14160
tgttcactat cccaagcgac accatcacca tcgtcttcct ttctcttacc aaagtaaata  14220
cctcccacta attctctaac aacaacgaag tcagtacctt tagcaaattg tggcttgatt  14280
ggagataagt ctaaaagaga gtcggatgca aagttacatg gtcttaagtt ggcgtacaat  14340
tgaagttctt tacggatttt tagtaaacct tgttcaggtc taacactacc ggtaccccat  14400
ttaggaccac ccacagcacc taacaaaacg gcatcagcct tcttggaggc ttccagcgcc  14460
tcatctggaa gtggaacacc tgtagcatcg atagcagcac caccaattaa atgattttcg  14520
aaatcgaact tgacattgga acgaacatca gaaatagctt taagaacctt aatggcttcg  14580
gctgtgattt cttgaccaac gtggtcacct ggcaaaacga cgatcttctt aggggcagac  14640
attacaatgg tatatccttg aaatatatat aaaaaaaaaa aaaaaaaaaa aaaaaaaaaa  14700
tgcagcttct caatgatatt cgaatacgct ttgaggagat acagcctaat atccgacaaa  14760
ctgttttaca gatttacgat cgtacttgtt acccatcatt gaattttgaa catccgaacc  14820
tgggagtttt ccctgaaaca gatagtatat ttgaacctgt ataataatat atagtctagc  14880
gctttacgga agacaatgta tgtatttcgg ttcctggaga aactattgca tctattgcat  14940
aggtaatctt gcacgtcgca tccccggttc attttctgcg tttccatctt gcacttcaat  15000
agcatatctt tgttaacgaa gcatctgtgc ttcattttgt agaacaaaaa tgcaacgcga  15060
gagcgctaat ttttcaaaca aagaatctga gctgcatttt tacagaacag aaatgcaacg  15120
cgaaagcgct attttaccaa cgaagaatct gtgcttcatt tttgtaaaac aaaaatgcaa  15180
cgcgagagcg ctaatttttc aaacaaagaa tctgagctgc atttttacag aacagaaatg  15240
caacgcgaga gcgctatttt accaacaaag aatctatact tctttttgt tctacaaaaa  15300
tgcatcccga gagcgctatt tttctaacaa agcatcttag attacttttt ttctcctttg  15360
tgcgctctat aatgcagtct cttgataact ttttgcactg taggtccgtt aaggttagaa  15420
gaaggctact ttggtgtcta ttttctcttc cataaaaaaa gcctgactcc acttcccgcg  15480
tttactgatt actagcgaag ctgcgggtgc attttttcaa gataaaggca tccccgatta  15540
tattctatac cgatgtggat tgcgcatact ttgtgaacag aaagtgatag cgttgatgat  15600
tcttcattgg tcagaaaatt atgaacggtt tcttctattt tgtctctata tactacgtat  15660
```

aggaaatgtt tacattttcg tattgttttc gattcactct atgaatagtt cttactacaa 15720
tttttttgtc taaagagtaa tactagagat aaacataaaa aatgtagagg tcgagtttag 15780
atgcaagttc aaggagcgaa aggtggatgg gtaggttata tagggatata gcacagagat 15840
atatagcaaa gagatacttt tgagcaatgt ttgtggaagc ggtattcgca atattttagt 15900
agctcgttac agtccggtgc gtttttggtt ttttgaaagt gcgtcttcag agcgcttttg 15960
gttttcaaaa gcgctctgaa gttcctatac tttctagaga ataggaactt cggaatagga 16020
acttcaaagc gtttccgaaa acgagcgctt ccgaaaatgc aacgcgagct gcgcacatac 16080
agctcactgt tcacgtcgca cctatatctg cgtgttgcct gtatatatat atacatgaga 16140
agaacggcat agtgcgtgtt tatgcttaaa tgcgtactta tatgcgtcta tttatgtagg 16200
atgaaaggta gtctagtacc tcctgtgata ttatcccatt ccatgcgggg tatcgtatgc 16260
ttccttcagc actacccttt agctgttcta tatgctgcca ctcctcaatt ggattagtct 16320
catccttcaa tgctatcatt tcctttgata ttggatcata tgcatagtac cgagaaacta 16380
gaggatc 16387

<210> SEQ ID NO 30
<211> LENGTH: 448
<212> TYPE: DNA
<213> ORGANISM: Saccharomyces cerevisiae

<400> SEQUENCE: 30
cccattaccg acatttgggc gctatacgtg catatgttca tgtatgtatc tgtatttaaa 60
acacttttgt attatttttc ctcatatatg tgtataggtt tatacggatg atttaattat 120
tacttcacca ccctttattt caggctgata tcttagcctt gttactagtt agaaaaagac 180
atttttgctg tcagtcactg tcaagagatt cttttgctgg catttcttct agaagcaaaa 240
agagcgatgc gtcttttccg ctgaaccgtt ccagcaaaaa agactaccaa cgcaatatgg 300
attgtcagaa tcatataaaa gagaagcaaa taactccttg tcttgtatca attgcattat 360
aatatcttct tgttagtgca atatcatata gaagtcatcg aaatagatat taagaaaaac 420
aaactgtaca atcaatcaat caatcatc 448

<210> SEQ ID NO 31
<211> LENGTH: 1713
<212> TYPE: DNA
<213> ORGANISM: Bacillus subtilis

<400> SEQUENCE: 31
ttgacaaaag caacaaaaga acaaaaatcc cttgtgaaaa acagaggggc ggagcttgtt 60
gttgattgct tagtggagca aggtgtcaca catgtatttg gcattccagg tgcaaaaatt 120
gatgcggtat ttgacgcttt acaagataaa ggacctgaaa ttatcgttgc ccggcacgaa 180
caaaacgcag cattcatggc ccaagcagtc ggccgtttaa ctggaaaacc gggagtcgtg 240
ttagtcacat caggaccggg tgcctctaac ttggcaacag gcctgctgac agcgaacact 300
gaaggagacc ctgtcgttgc gcttgctgga aacgtgatcc gtgcagatcg tttaaaacgg 360
acacatcaat ctttggataa tgcggcgcta ttccagccga ttacaaaata cagtgtagaa 420
gttcaagatg taaaaaatat accggaagct gttacaaatg catttaggat agcgtcagca 480
gggcaggctg gggccgcttt tgtgagcttt ccgcaagatg ttgtgaatga agtcacaaat 540
acgaaaaacg tgcgtgctgt tgcagcgcca aaactcggtc ctgcagcaga tgatgcaatc 600
agtgcggcca tagcaaaaat ccaaacagca aaacttcctg tcgttttggt cggcatgaaa 660

-continued

```
ggcggaagac cggaagcaat taaagcggtt cgcaagcttt tgaaaaaggt tcagcttcca    720

tttgttgaaa catatcaagc tgccggtacc ctttctagag atttagagga tcaatatttt    780

ggccgtatcg gtttgttccg caaccagcct ggcgatttac tgctagagca ggcagatgtt    840

gttctgacga tcggctatga cccgattgaa tatgatccga aattctggaa tatcaatgga    900

gaccggacaa ttatccattt agacgagatt atcgctgaca ttgatcatgc ttaccagcct    960

gatcttgaat tgatcggtga cattccgtcc acgatcaatc atatcgaaca cgatgctgtg   1020

aaagtggaat ttgcagagcg tgagcagaaa atcctttctg atttaaaaca atatatgcat   1080

gaaggtgagc aggtgcctgc agattggaaa tcagacagag cgcaccctct tgaaatcgtt   1140

aaagagttgc gtaatgcagt cgatgatcat gttacagtaa cttgcgatat cggttcgcac   1200

gccatttgga tgtcacgtta tttccgcagc tacgagccgt taacattaat gatcagtaac   1260

ggtatgcaaa cactcggcgt tgcgcttcct tgggcaatcg gcgcttcatt ggtgaaaccg   1320

ggagaaaaag tggtttctgt ctctggtgac ggcggtttct tattctcagc aatggaatta   1380

gagacagcag ttcgactaaa agcaccaatt gtacacattg tatggaacga cagcacatat   1440

gacatggttg cattccagca attgaaaaaa tataaccgta catctgcggt cgatttcgga   1500

aatatcgata tcgtgaaata tgcggaaagc ttcggagcaa ctggcttgcg cgtagaatca   1560

ccagaccagc tggcagatgt tctgcgtcaa ggcatgaacg ctgaaggtcc tgtcatcatc   1620

gatgtcccgg ttgactacag tgataacatt aatttagcaa gtgacaagct tccgaaagaa   1680

ttcggggaac tcatgaaaac gaaagctctc tag                                1713
```

<210> SEQ ID NO 32
<211> LENGTH: 571
<212> TYPE: PRT
<213> ORGANISM: Bacillus subtilis

<400> SEQUENCE: 32

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190
```

-continued

```
Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570
```

<210> SEQ ID NO 33
<211> LENGTH: 250
<212> TYPE: DNA
<213> ORGANISM: Saccharomyces cerevisiae

<400> SEQUENCE: 33

```
ccgcaaatta aagccttcga gcgtcccaaa accttctcaa gcaaggtttt cagtataatg      60

ttacatgcgt acacgcgtct gtacagaaaa aaaagaaaaa tttgaaatat aaataacgtt     120

cttaatacta acataactat aaaaaaataa atagggacct agacttcagg ttgtctaact     180

ccttcctttt cggttagagc ggatgtgggg ggagggcgtg aatgtaagcg tgacataact     240

aattacatga                                                            250
```

<210> SEQ ID NO 34
<211> LENGTH: 1181
<212> TYPE: DNA
<213> ORGANISM: Saccharomyces cerevisiae

<400> SEQUENCE: 34

```
taaaacctct agtggagtag tagatgtaat caatgaagcg gaagccaaaa gaccagagta      60

gaggcctata gaagaaactg cgataccttt tgtgatggct aaacaaacag acatcttttt     120

atatgttttt acttctgtat atcgtgaagt agtaagtgat aagcgaattt ggctaagaac     180

gttgtaagtg aacaagggac ctcttttgcc tttcaaaaaa ggattaaatg gagttaatca     240

ttgagattta gttttcgtta gattctgtat ccctaaataa ctcccttacc cgacgggaag     300

gcacaaaaga cttgaataat agcaaacggc cagtagccaa gaccaaataa tactagagtt     360

aactgatggt cttaaacagg cattacgtgg tgaactccaa gaccaatata caaaatatcg     420

ataagttatt cttgcccacc aatttaagga gcctacatca ggacagtagt accattcctc     480

agagaagagg tatacataac aagaaaatcg cgtgaacacc ttatataact tagcccgtta     540

ttgagctaaa aaaccttgca aaatttccta tgaataagaa tacttcagac gtgataaaaa     600

tttactttct aactcttctc acgctgcccc tatctgttct tccgctctac cgtgagaaat     660

aaagcatcga gtacggcagt tcgctgtcac tgaactaaaa caataaggct agttcgaatg     720

atgaacttgc ttgctgtcaa acttctgagt tgccgctgat gtgacactgt gacaataaat     780

tcaaaccggt tatagcggtc tcctccggta ccggttctgc cacctccaat agagctcagt     840

aggagtcaga acctctgcgg tggctgtcag tgactcatcc gcgtttcgta agttgtgcgc     900

gtgcacattt cgcccgttcc cgctcatctt gcagcaggcg gaaattttca tcacgctgta     960

ggacgcaaaa aaaaaataat taatcgtaca agaatcttgg aaaaaaaatt gaaaaatttt    1020

gtataaaagg gatgacctaa cttgactcaa tggcttttac acccagtatt ttccctttcc    1080

ttgtttgtta caattataga agcaagacaa aaacatatag acaacctatt cctaggagtt    1140

atattttttt accctaccag caatataagt aaaaaactag t                        1181
```

<210> SEQ ID NO 35
<211> LENGTH: 759
<212> TYPE: DNA
<213> ORGANISM: Saccharomyces cerevisiae

<400> SEQUENCE: 35

```
ggccctgcag gcctatcaag tgctggaaac tttttctctt ggaatttttg caacatcaag      60

tcatagtcaa ttgaattgac ccaatttcac atttaagatt tttttttttt catccgacat     120

acatctgtac actaggaagc cctgtttttc tgaagcagct tcaaatatat atatttttta     180

catatttatt atgattcaat gaacaatcta attaaatcga aaacaagaac cgaaacgcga     240

ataaataatt tatttagatg gtgacaagtg tataagtcct catcgggaca gctacgattt     300

ctctttcggt tttggctgag ctactggttg ctgtgacgca gcggcattag cgcggcgtta     360

tgagctaccc tcgtggcctg aaagatggcg ggaataaagc ggaactaaaa attactgact     420
```

-continued

```
gagccatatt gaggtcaatt tgtcaactcg tcaagtcacg tttggtggac ggcccctttc    480

caacgaatcg tatatactaa catgcgcgcg cttcctatat acacatatac atatatatat    540

atatatatat gtgtgcgtgt atgtgtacac ctgtatttaa tttccttact cgcgggtttt    600

tctttttttct caattcttgg cttcctcttt ctcgagtata taatttttca ggtaaaattt    660

agtacgatag taaaatactt ctcgaactcg tcacatatac gtgtacataa tgtctgaacc    720

agctcaaaag aaacaaaagg ttgctaacaa ctctctaga                           759
```

<210> SEQ ID NO 36
<211> LENGTH: 643
<212> TYPE: DNA
<213> ORGANISM: Saccharomyces cerevisiae

<400> SEQUENCE: 36

```
gaaatgaata acaatactga cagtactaaa taattgccta cttggcttca catacgttgc     60

atacgtcgat atagataata atgataatga cagcaggatt atcgtaatac gtaatagttg    120

aaaatctcaa aaatgtgtgg gtcattacgt aaataatgat aggaatggga ttcttctatt    180

tttccttttt ccattctagc agccgtcggg aaaacgtggc atcctctctt tcgggctcaa    240

ttggagtcac gctgccgtga gcatcctctc tttccatatc taacaactga gcacgtaacc    300

aatggaaaag catgagctta gcgttgctcc aaaaaagtat tggatggtta ataccatttg    360

tctgttctct tctgactttg actcctcaaa aaaaaaaaat ctacaatcaa cagatcgctt    420

caattacgcc ctcacaaaaa ctttttttcct tcttcttcgc ccacgttaaa ttttatccct    480

catgttgtct aacggatttc tgcacttgat ttattataaa aagacaaaga cataatactt    540

ctctatcaat ttcagttatt gttcttcctt gcgttattct tctgttcttc tttttctttt    600

gtcatatata accataacca agtaatacat attcaaatct aga                      643
```

<210> SEQ ID NO 37
<211> LENGTH: 1014
<212> TYPE: DNA
<213> ORGANISM: artificial sequence
<220> FEATURE:
<223> OTHER INFORMATION: Pf5.IlvC-Z4B8 variant

<400> SEQUENCE: 37

```
atgaaggtgt tttacgataa agactgcgat ctgagcatca tccagggaaa gaaggttgct     60

attataggat atggttccca aggacacgca caagccttga acttgaaaga ttctggggtc    120

gacgtgacag taggtctgta taaaggtgct gctgatgcag caaaggctga agcacatggc    180

tttaaagtca cagatgttgc agcggctgtt gctggcgctg atttagtcat gattttaatt    240

ccagatgaat ttcaatcgca attgtacaaa aatgaaatag aaccaaacat taagaagggc    300

gctaccttgg ccttcagtca tggatttgcc attcattaca atcaagtagt ccccagggca    360

gatttggacg ttattatgat tgcacctaag gctccggggc atactgttag gagcgaattt    420

gttaagggtg gtggtattcc agatttgatc gctatatacc aagacgttag cggaaacgct    480

aagaatgtag ctttaagcta cgcagcagga gttggtggcg ggagaacggg tataatagaa    540

accactttta aagacgagac tgagacagat ttatttggag aacaagcggt tctgtgcgga    600

ggaactgttg aattggttaa agcaggcttt gagacgcttg tcgaagcagg gtacgctccc    660

gaaatggcat acttcgaatg tctacatgaa ttgaagttga tagtagactt aatgtatgaa    720

ggtggtatag ctaatatgaa ctattccatt tcaaataatg cagaatatgg tgagtatgtc    780

accggacctg aagtcattaa cgcagaatca agacaagcca tgagaaatgc cttgaaacgt    840
```

```
atccaggacg gtgaatacgc taagatgttc ataagtgaag gcgctacggg ttacccgagt     900

atgactgcta aaagaagaaa caatgcagca catggtatcg aaattattgg tgaacagtta     960

aggtctatga tgccctggat cggtgctaat aagatcgtag acaaggcgaa aaat          1014


<210> SEQ ID NO 38
<211> LENGTH: 338
<212> TYPE: PRT
<213> ORGANISM: artificial sequence
<220> FEATURE:
<223> OTHER INFORMATION: Pf5.IlvC-Z4B8 variant

<400> SEQUENCE: 38

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Ala Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn
```

<210> SEQ ID NO 39
<211> LENGTH: 1188
<212> TYPE: DNA
<213> ORGANISM: Saccharomyces cerevisiae

<400> SEQUENCE: 39
atgttgagaa ctcaagccgc cagattgatc tgcaactccc gtgtcatcac tgctaagaga 60
acctttgctt tggccacccg tgctgctgct tacagcagac cagctgcccg tttcgttaag 120
ccaatgatca ctacccgtgg tttgaagcaa atcaacttcg gtggtactgt tgaaaccgtc 180
tacgaaagag ctgactggcc aagagaaaag ttgttggact acttcaagaa cgacactttt 240
gctttgatcg gttacggttc ccaaggttac ggtcaaggtt tgaacttgag agacaacggt 300
ttgaacgtta tcattggtgt ccgtaaagat ggtgcttctt ggaaggctgc catcgaagac 360
ggttgggttc caggcaagaa cttgttcact gttgaagatg ctatcaagag aggtagttac 420
gttatgaact tgttgtccga tgccgctcaa tcagaaacct ggcctgctat caagccattg 480
ttgaccaagg gtaagacttt gtacttctcc cacggtttct ccccagtctt caaggacttg 540
actcacgttg aaccaccaaa ggacttagat gttatcttgg ttgctccaaa gggttccggt 600
agaactgtca gatctttgtt caaggaaggt cgtggtatta actcttctta cgccgtctgg 660
aacgatgtca ccggtaaggc tcacgaaaag gcccaagctt tggccgttgc cattggttcc 720
ggttacgttt accaaaccac tttcgaaaga gaagtcaact ctgacttgta cggtgaaaga 780
ggttgtttaa tgggtggtat ccacggtatg ttcttggctc aatacgacgt cttgagagaa 840
aacggtcact ccccatctga agctttcaac gaaaccgtcg aagaagctac ccaatctcta 900
tacccattga tcggtaagta cggtatggat tacatgtacg atgcttgttc caccaccgcc 960
agaagaggtg ctttggactg gtacccaatc ttcaagaatg ctttgaagcc tgttttccaa 1020
gacttgtacg aatctaccaa gaacggtacc gaaaccaaga gatctttgga attcaactct 1080
caacctgact acagagaaaa gctagaaaag gaattagaca ccatcagaaa catggaaatc 1140
tggaaggttg gtaaggaagt cagaaagttg agaccagaaa accaataa 1188

<210> SEQ ID NO 40
<211> LENGTH: 395
<212> TYPE: PRT
<213> ORGANISM: Saccharomyces cerevisiae

<400> SEQUENCE: 40

Met Leu Arg Thr Gln Ala Ala Arg Leu Ile Cys Asn Ser Arg Val Ile
1 5 10 15

Thr Ala Lys Arg Thr Phe Ala Leu Ala Thr Arg Ala Ala Ala Tyr Ser
20 25 30

Arg Pro Ala Ala Arg Phe Val Lys Pro Met Ile Thr Thr Arg Gly Leu
35 40 45

Lys Gln Ile Asn Phe Gly Gly Thr Val Glu Thr Val Tyr Glu Arg Ala
50 55 60

Asp Trp Pro Arg Glu Lys Leu Leu Asp Tyr Phe Lys Asn Asp Thr Phe
65 70 75 80

Ala Leu Ile Gly Tyr Gly Ser Gln Gly Tyr Gly Gln Gly Leu Asn Leu
85 90 95

Arg Asp Asn Gly Leu Asn Val Ile Ile Gly Val Arg Lys Asp Gly Ala
100 105 110

Ser Trp Lys Ala Ala Ile Glu Asp Gly Trp Val Pro Gly Lys Asn Leu
115 120 125

```
Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395


<210> SEQ ID NO 41
<211> LENGTH: 1017
<212> TYPE: DNA
<213> ORGANISM: artificial sequence
<220> FEATURE:
<223> OTHER INFORMATION: Pf5.IlvC-JEA1 variant

<400> SEQUENCE: 41

atgaaagttt tctacgataa agactgcgac ctgtcgatca tccaaggtaa gaaagttgcc      60

atcatcggct tcggttccca gggccacgct caagcactca acctgaagga ttccggcgta     120

gacgtgactg ttggcctgcc taaaggcttt gctgatgtag ccaaggctga agcccacggc     180

tttaaagtga ccgacgttgc tgcagccgtt gccggtgccg acttggtcat gatcctgatt     240

ccggacgagt tccagtccca gctgtacaag aacgaaatcg agccgaacat caagaagggc     300

gccactctgg ccttctccca cggcttcgcg atccactaca accaggttgt gcctcgtgcc     360

gacctcgacg tgatcatgat cgcgccgaag gctccaggcc acaccgtacg ttccgagttc     420

gtcaagggcg gaggtattcc tgacctgatc gcgatctacc aggacgtttc cggcaacgcc     480

aagaacgtcg ccctgtccta cgccgcaggc gtgggcggcg gccgtaccgg catcatcgaa     540
```

```
accaccttca aggacgagac tgaaaccgac ctgttcggtg agcaggctgt tctgtgtggc    600

ggtaccgtcg agctggtcaa agccggtttc gaaaccctgg ttgaagctgg ctacgctcca    660

gaaatggcct acttcgagtg cctgcacgaa ctgaagctga tcgttgacct catgtacgaa    720

ggcggtatcg ccaacatgaa ctactcgatc tccaacaacg ctgaatacgg cgagtacgtg    780

actggtccag aagtcatcaa cgccgaatcc cgtcaggcca tgcgcaatgc tctgaagcgc    840

atccaggacg gcgaatacgc gaagatgttc atcagcgaag gcgctaccgg ctacccatcg    900

atgaccgcca agcgtcgtaa caacgctgct cacggtatcg aaatcatcgg cgagcaactg    960

cgctcgatga tgccttggat cggtgccaac aaaatcgtcg acaaagccaa gaactaa      1017


<210> SEQ ID NO 42
<211> LENGTH: 338
<212> TYPE: PRT
<213> ORGANISM: artificial sequence
<220> FEATURE:
<223> OTHER INFORMATION: Pf5.IlvC-JEA1 variant

<400> SEQUENCE: 42

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Pro Lys
        35                  40                  45

Gly Phe Ala Asp Val Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285
```

```
Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 43
<211> LENGTH: 15539
<212> TYPE: DNA
<213> ORGANISM: artificial sequence
<220> FEATURE:
<223> OTHER INFORMATION: Synthetic construct

<400> SEQUENCE: 43

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

ttttttttt ccacctagcg gatgactctt ttttttttctt agcgattggc attatcacat    420

aatgaattat acattatata aagtaatgtg atttcttcga agaatatact aaaaaatgag    480

caggcaagat aaacgaaggc aaagatgaca gagcagaaag ccctagtaaa gcgtattaca    540

aatgaaacca agattcagat tgcgatctct ttaaagggtg gtcccctagc gatagagcac    600

tcgatcttcc cagaaaaaga ggcagaagca gtagcagaac aggccacaca atcgcaagtg    660

attaacgtcc acacaggtat agggtttctg gaccatatga tacatgctct ggccaagcat    720

tccggctggt cgctaatcgt tgagtgcatt ggtgacttac acatagacga ccatcacacc    780

actgaagact gcgggattgc tctcggtcaa gcttttaaag aggccctagg ggccgtgcgt    840

ggagtaaaaa ggtttggatc aggatttgcg cctttggatg aggcactttc cagagcggtg    900

gtagatcttt cgaacaggcc gtacgcagtt gtcgaacttg gtttgcaaag ggagaaagta    960

ggagatctct cttgcgagat gatcccgcat ttttcttgaaa gctttgcaga ggctagcaga   1020

attaccctcc acgttgattg tctgcgaggc aagaatgatc atcaccgtag tgagagtgcg   1080

ttcaaggctc ttgcggttgc cataagagaa gccacctcgc ccaatggtac caacgatgtt   1140

ccctccacca aaggtgttct tatgtagtga caccgattat ttaaagctgc agcatacgat   1200

atatatacat gtgtatatat gtatacctat gaatgtcagt aagtatgtat acgaacagta   1260

tgatactgaa gatgacaagg taatgcatca ttctatacgt gtcattctga acgaggcgcg   1320

ctttcctttt ttcttttttgc tttttctttt tttttctctt gaactcgacg gatctatgcg   1380

gtgtgaaata ccgcacagat gcgtaaggag aaaataccgc atcaggaaat tgtaagcgtt   1440

aatattttgt taaaattcgc gttaaatttt tgttaaatca gctcattttt taaccaatag   1500

gccgaaatcg gcaaaatccc ttataaatca aaagaataga ccgagatagg gttgagtgtt   1560

gttccagttt ggaacaagag tccactatta aagaacgtgg actccaacgt caaagggcga   1620

aaaaccgtct atcagggcga tggcccacta cgtgaaccat caccctaatc aagttttttg   1680

gggtcgaggt gccgtaaagc actaaatcgg aaccctaaag ggagcccccg atttagagct   1740

tgacggggaa agccggcgaa cgtggcgaga aaggaaggga agaaagcgaa aggagcgggc   1800
```

-continued

```
gctagggcgc tggcaagtgt agcggtcacg ctgcgcgtaa ccaccacacc cgccgcgctt   1860
aatgcgccgc tacagggcgc gtccattcgc cattcaggct gcgcaactgt tgggaagggc   1920
gcggtgcggg cctcttcgct attacgccag ctggcgaaag ggggatgtgc tgcaaggcga   1980
ttaagttggg taacgccagg gttttcccag tcacgacgtt gtaaaacgac ggccagtgag   2040
cgcgcgtaat acgactcact atagggcgaa ttgggtaccg ggccccccct cgaggtcgac   2100
ggcgcgccac tggtagagag cgactttgta tgccccaatt gcgaaacccg cgatatcctt   2160
ctcgattctt tagtacccga ccaggacaag gaaaaggagg tcgaaacgtt tttgaagaaa   2220
caagaggaac tacacggaag ctctaaagat ggcaaccagc cagaaactaa gaaaatgaag   2280
ttgatggatc caactggcac cgctggcttg aacaacaata ccagccttcc aacttctgta   2340
aataacggcg gtacgccagt gccaccagta ccgttacctt tcggtatacc tcctttcccc   2400
atgtttccaa tgcccttcat gcctccaacg gctactatca caaatcctca tcaagctgac   2460
gcaagcccta agaaatgaat aacaatactg acagtactaa ataattgcct acttggcttc   2520
acatacgttg catacgtcga tatagataat aatgataatg acagcaggat tatcgtaata   2580
cgtaatagct gaaaatctca aaaatgtgtg ggtcattacg taaataatga taggaatggg   2640
attcttctat ttttcctttt tccattctag cagccgtcgg gaaaacgtgg catcctctct   2700
ttcgggctca attggagtca cgctgccgtg agcatcctct ctttccatat ctaacaactg   2760
agcacgtaac caatggaaaa gcatgagctt agcgttgctc caaaaaagta ttggatggtt   2820
aataccattt gtctgttctc ttctgacttt gactcctcaa aaaaaaaaat ctacaatcaa   2880
cagatcgctt caattacgcc ctcacaaaaa ctttttttcct tcttcttcgc ccacgttaaa   2940
ttttatccct catgttgtct aacggatttc tgcacttgat ttattataaa aagacaaaga   3000
cataatactt ctctatcaat ttcagttatt gttcttcctt gcgttattct tctgttcttc   3060
tttttctttt gtcatatata accataacca agtaatacat attcaaacta gtatgactga   3120
caaaaaaact cttaaagact taagaaatcg tagttctgtt tacgattcaa tggttaaatc   3180
acctaatcgt gctatgttgc gtgcaactgg tatgcaagat gaagactttg aaaaacctat   3240
cgtcggtgtc atttcaactt gggctgaaaa cacaccttgt aatatccact tacatgactt   3300
tggtaaacta gccaaagtcg gtgttaagga agctggtgct tggccagttc agttcggaac   3360
aatcacggtt tctgatggaa tcgccatggg aacccaagga atgcgtttct ccttgacatc   3420
tcgtgatatt attgcagatt ctattgaagc agccatggga ggtcataatg cggatgcttt   3480
tgtagccatt ggcggttgtg ataaaaacat gcccggttct gttatcgcta tggctaacat   3540
ggatatccca gccatttttg cttacggcgg aacaattgca cctggtaatt tagacggcaa   3600
agatatcgat ttagtctctg tctttgaagg tgtcggccat tggaaccacg gcgatatgac   3660
caaagaagaa gttaaagctt tggaatgtaa tgcttgtccc ggtcctggag gctgcggtgg   3720
tatgtatact gctaacacaa tggcgacagc tattgaagtt ttgggactta gccttccggg   3780
ttcatcttct cacccggctg aatccgcaga aaagaaagca gatattgaag aagctggtcg   3840
cgctgttgtc aaaatgctcg aaatgggctt aaaaccttct gacattttaa cgcgtgaagc   3900
ttttgaagat gctattactg taactatggc tctgggaggt tcaaccaact caacccttca   3960
cctcttagct attgcccatg ctgctaatgt ggaattgaca cttgatgatt tcaatacttt   4020
ccaagaaaaa gttcctcatt tggctgattt gaaaccttct ggtcaatatg tattccaaga   4080
cctttacaag gtcggagggg taccagcagt tatgaaatat ctccttaaaa atggcttcct   4140
tcatggtgac cgtatcactt gtactggcaa aacagtcgct gaaaatttga aggcttttga   4200
```

tgatttaaca cctggtcaaa aggttattat gccgcttgaa aatcctaaac gtgaagatgg 4260
tccgctcatt attctccatg gtaacttggc tccagacggt gccgttgcca aagtttctgg 4320
tgtaaaagtg cgtcgtcatg tcggtcctgc taaggtcttt aattctgaag aagaagccat 4380
tgaagctgtc ttgaatgatg atattgttga tggtgatgtt gttgtcgtac gttttgtagg 4440
accaaagggc ggtcctggta tgcctgaaat gctttccctt tcatcaatga ttgttggtaa 4500
agggcaaggt gaaaaagttg cccttctgac agatggccgc ttctcaggtg gtacttatgg 4560
tcttgtcgtg ggtcatatcg ctcctgaagc acaagatggc ggtccaatcg cctacctgca 4620
aacaggagac atagtcacta ttgaccaaga cactaaggaa ttacactttg atatctccga 4680
tgaagagtta aaacatcgtc aagagaccat tgaattgcca ccgctctatt cacgcggtat 4740
ccttggtaaa tatgctcaca tcgtttcgtc tgcttctagg ggagccgtaa cagacttttg 4800
gaagcctgaa gaaactggca aaaaatgttg tcctggttgc tgtggttaag cggccgcgtt 4860
aattcaaatt aattgatata gtttttttaat gagtattgaa tctgtttaga aataatggaa 4920
tattatttt atttatttat ttatattatt ggtcggctct tttcttctga aggtcaatga 4980
caaaatgata tgaaggaaat aatgatttct aaaattttac aacgtaagat atttttacaa 5040
aagcctagct catcttttgt catgcactat tttactcacg cttgaaatta acggccagtc 5100
cactgcggag tcatttcaaa gtcatcctaa tcgatctatc gtttttgata gctcattttg 5160
gagttcgcga ttgtcttctg ttattcacaa ctgttttaat tttatttca ttctggaact 5220
cttcgagttc tttgtaaagt ctttcatagt agcttacttt atcctccaac atatttaact 5280
tcatgtcaat ttcggctctt aaattttcca catcatcaag ttcaacatca tcttttaact 5340
tgaatttatt ctctagctct tccaaccaag cctcattgct ccttgattta ctggtgaaaa 5400
gtgatacact ttgcgcgcaa tccaggtcaa aactttcctg caaagaattc accaatttct 5460
cgacatcata gtacaatttg ttttgttctc ccatcacaat ttaatatacc tgatggattc 5520
ttatgaagcg ctgggtaatg gacgtgtcac tctacttcgc ctttttccct actcctttta 5580
gtacggaaga caatgctaat aaataagagg gtaataataa tattattaat cggcaaaaaa 5640
gattaaacgc caagcgttta attatcagaa agcaaacgtc gtaccaatcc ttgaatgctt 5700
cccaattgta tattaagagt catcacagca acatattctt gttattaaat taattattat 5760
tgatttttga tattgtataa aaaaaccaaa tatgtataaa aaaagtgaat aaaaaatacc 5820
aagtatggag aaatatatta gaagtctata cgttaaacca cccgggcccc ccctcgaggt 5880
cgacggtatc gataagcttg atatcgaatt cctgcagccc gggggatcca ctagttctag 5940
agcggccgct ctagaactag taccacaggt gttgtcctct gaggacataa aatacacacc 6000
gagattcatc aactcattgc tggagttagc atatctacaa ttgggtgaaa tggggagcga 6060
tttgcaggca tttgctcggc atgccggtag aggtgtggtc aataagagcg acctcatgct 6120
atacctgaga aagcaacctg acctacagga aagagttact caagaataag aattttcgtt 6180
ttaaaaccta agagtcactt taaaatttgt atacacttat ttttttata acttatttaa 6240
taataaaaat cataaatcat aagaaattcg cttactctta attaatcaaa aagttaaaat 6300
tgtacgaata gattcaccac ttcttaacaa atcaaaccct tcattgattt tctcgaatgg 6360
caatacatgt gtaattaaag gatcaagagc aaacttcttc gccataaagt cggcaacaag 6420
ttttggaaca ctatccttgc tcttaaaacc gccaaatata gctcccttcc atgtacgacc 6480
gcttagcaac agcataggat tcatcgacaa attttgtgaa tcaggaggaa cacctacgat 6540
cacactgact ccatatgcct cttgacagca ggacaacgca gttaccatag tatcaagacg 6600

```
gcctataact tcaaaagaga aatcaactcc accgtttgac atttcagtaa ggacttcttg   6660
tattggtttc ttataatctt gagggttaac acattcagta gccccgacct ccttagcttt   6720
tgcaaatttg tccttattga tgtctacacc tataatcctc gctgcgcctg cagctttaca   6780
ccccataata acgcttagtc ctactcctcc taaaccgaat actgcacaag tcgaaccctg   6840
tgtaaccttt gcaactttaa ctgcggaacc gtaaccggtg gaaaatccgc accctatcaa   6900
gcaaactttt tccagtggtg aagctgcatc gattttagcg acagatatct cgtccaccac   6960
tgtgtattgg gaaaatgtag aagtaccaag gaaatggtgt ataggtttcc ctctgcatgt   7020
aaatctgctt gtaccatcct gcatagtacc tctaggcata gacaaatcat ttttaaggca   7080
gaaattaccc tcaggatgtt tgcagactct acacttacca cattgaggag tgaacagtgg   7140
gatcacttta tcaccaggac gaacagtggt aacaccttca cctatggatt caacgattcc   7200
ggcagcctcg tgtcccgcga ttactggcaa aggagtaact agagtgccac tcaccacatg   7260
gtcgtcggat ctacagattc cggtggcaac catcttgatt ctaacctcgt gtgcttttgg   7320
tggcgctact tctacttctt ctatgctaaa cggctttttc tcttcccaca aaactgccgc   7380
tttacactta ataactttac cggctgttga catcctcagc tagctattgt aatatgtgtg   7440
tttgtttgga ttattaagaa gaataattac aaaaaaaatt acaaaggaag gtaattacaa   7500
cagaattaag aaaggacaag aaggaggaag agaatcagtt cattatttct tctttgttat   7560
ataacaaacc caagtagcga tttggccata cattaaaagt tgagaaccac cctccctggc   7620
aacagccaca actcgttacc attgttcatc acgatcatga aactcgctgt cagctgaaat   7680
ttcacctcag tggatctctc tttttattct tcatcgttcc actaaccttt ttccatcagc   7740
tggcagggaa cggaaagtgg aatcccattt agcgagcttc ctcttttctt caagaaaaga   7800
cgaagcttgt gtgtgggtgc gcgcgctagt atctttccac attaagaaat ataccataaa   7860
ggttacttag acatcactat ggctatatat atatatatat atatatgtaa cttagcacca   7920
tcgcgcgtgc atcactgcat gtgttaaccg aaaagtttgg cgaacacttc accgacacgg   7980
tcatttagat ctgtcgtctg cattgcacgt cccttagcct taaatcctag gcgggagcat   8040
tctcgtgtaa ttgtgcagcc tgcgtagcaa ctcaacatag cgtagtctac ccagtttttc   8100
aagggtttat cgttagaaga ttctcccttt tcttcctgct cacaaatctt aaagtcatac   8160
attgcacgac taaatgcaag catgcggatc ccccgggctg caggaattcg atatcaagct   8220
tatcgatacc gtcgactggc cattaatctt tcccatatta gatttcgcca agccatgaaa   8280
gttcaagaaa ggtctttaga cgaattaccc ttcatttctc aaactggcgt caagggatcc   8340
tggtatggtt ttatcgtttt atttctggtt cttatagcat cgttttggac ttctctgttc   8400
ccattaggcg gttcaggagc cagcgcagaa tcattctttg aaggatactt atcctttcca   8460
attttgattg tctgttacgt tggacataaa ctgtatacta gaaattggac tttgatggtg   8520
aaactagaag atatggatct tgataccggc agaaaacaag tagatttgac tcttcgtagg   8580
gaagaaatga ggattgagcg agaaacatta gcaaaaagat ccttcgtaac aagattttta   8640
catttctggt gttgaaggga aagatatgag ctatacagcg gaatttccat atcactcaga   8700
ttttgttatc taatttttc cttcccacgt ccgcgggaat ctgtgtatat tactgcatct   8760
agatatatgt tatcttatct tggcgcgtac atttaatttt caacgtattc tataagaaat   8820
tgcgggagtt tttttcatgt agatgatact gactgcacgc aaatataggc atgatttata   8880
ggcatgattt gatggctgta ccgataggaa cgctaagagt aacttcagaa tcgttatcct   8940
ggcggaaaaa attcatttgt aaactttaaa aaaaaaagcc aatatcccca aaattattaa   9000
```

```
gagcgcctcc attattaact aaaatttcac tcagcatcca caatgtatca ggtatctact    9060
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaaagaa aatttattta aatgcaagat ttaaagtaaa ttcacggccc    9240
tgcaggcctc agctcttgtt ttgttctgca aataacttac ccatcttttt caaaacttta    9300
ggtgcaccct cctttgctag aataagttct atccaataca tcctatttgg atctgcttga    9360
gcttctttca tcacggatac gaattcattt tctgttctca caattttgga cacaactctg    9420
tcttccgttg ccccgaaact ttctggcagt tttgagtaat tccacatagg aatgtcatta    9480
taactctggt tcggaccatg aatttccctc tcaaccgtgt aaccatcgtt attaatgata    9540
aagcagattg ggtttatctt ctctctaatg gctagtccta attcttggac agtcagttgc    9600
aatgatccat ctccgataaa caataaatgt ctagattctt tatctgcaat ttggctgcct    9660
agagctgcgg ggaaagtgta tcctatagat ccccacaagg gttgaccaat aaaatgtgat    9720
ttcgatttca gaaatataga tgaggcaccg aagaaagaag tgccttgttc agccacgatc    9780
gtctcattac tttgggtcaa attttcgaca gcttgccaca gtctatcttg tgacaacagc    9840
gcgttagaag gtacaaaatc ttcttgcttt ttatctatgt acttgccttt atattcaatt    9900
tcggacaagt caagaagaga tgatatcagg gattcgaagt cgaaattttg gattctttcg    9960
ttgaaaattt taccttcatc gatattcaag gaaatcattt tattttcatt aagatggtga   10020
gtaaatgcac ccgtactaga atcggtaagc tttacaccca acataagaat aaaatcagca   10080
gattccacaa attccttcaa gtttggctct gacagagtac cgttgtaaat ccccaaaaat   10140
gagggcaatg cttcatcaac agatgattta ccaaagttca aagtagtaat aggtaactta   10200
gtctttgaaa taaactgagt aacagtcttc tctaggccga acgatataat ttcatggcct   10260
gtgattacaa ttggtttctt ggcattcttc agactttcct gtattttgtt cagaatctct   10320
tgatcagatg tattcgacgt ggaattttcc ttcttaagag gcaaggatgg tttttcagcc   10380
ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcatagga gcccgctaag ccattaactg cggataattc gccaacacca   10680
aatgtagtca agaatgccgc agcctttttc gttcttgcgt acccgtcggc catataggag   10740
gcatttaact cattagcatt tcccacccat ttcatatctt tgtgtgaaat aatttgatct   10800
agaaattgca aattgtagtc acctggtact ccgaatattt cttctatacc taattcgtgt   10860
aatctgtcca acagatagtc acctactgta tacattttgt ttactagttt atgtgtgttt   10920
attcgaaact aagttcttgg tgttttaaaa ctaaaaaaaa gactaactat aaaagtagaa   10980
tttaagaagt ttaagaaata gatttacaga attacaatca atacctaccg tctttatata   11040
cttattagtc aagtagggga ataatttcag ggaactggtt tcaacctttt ttttcagctt   11100
tttccaaatc agagagagca gaaggtaata gaaggtgtaa gaaaatgaga tagatacatg   11160
cgtgggtcaa ttgccttgtg tcatcattta ctccaggcag gttgcatcac tccattgagg   11220
ttgtgcccgt tttttgcctg tttgtgcccc tgttctctgt agttgcgcta agagaatgga   11280
cctatgaact gatggttggt gaagaaaaca atattttggt gctgggattc tttttttttc   11340
tggatgccag cttaaaaagc gggctccatt atatttagtg gatgccagga ataaactgtt   11400
```

cacccagaca cctacgatgt tatatattct gtgtaacccg cccccctattt tgggcatgta 11460
cgggttacag cagaattaaa aggctaattt tttgactaaa taaagttagg aaaatcacta 11520
ctattaatta tttacgtatt ctttgaaatg gcagtattga taatgataaa ctcgaactga 11580
aaaagcgtgt tttttattca aaatgattct aactccctta cgtaatcaag gaatcttttt 11640
gccttggcct ccgcgtcatt aaacttcttg ttgttgacgc taacattcaa cgctagtata 11700
tattcgtttt tttcaggtaa gttcttttca acgggtctta ctgatgaggc agtcgcgtct 11760
gaacctgtta agaggtcaaa tatgtcttct tgaccgtacg tgtcttgcat gttattagct 11820
ttgggaattt gcatcaagtc ataggaaaat ttaaatcttg gctctcttgg gctcaaggtg 11880
acaaggtcct cgaaaatagg gcgcgcccca ccgcggtgga gctccagctt ttgttccctt 11940
tagtgagggt taattgcgcg cttggcgtaa tcatggtcat agctgtttcc tgtgtgaaat 12000
tgttatccgc tcacaattcc acacaacata cgagccggaa gcataaagtg taaagcctgg 12060
ggtgcctaat gagtgagcta actcacatta attgcgttgc gctcactgcc cgctttccag 12120
tcgggaaacc tgtcgtgcca gctgcattaa tgaatcggcc aacgcgcggg gagaggcggt 12180
ttgcgtattg ggcgctcttc cgcttcctcg ctcactgact cgctgcgctc ggtcgttcgg 12240
ctgcggcgag cggtatcagc tcactcaaag gcggtaatac ggttatccac agaatcaggg 12300
gataacgcag gaaagaacat gtgagcaaaa ggccagcaaa aggccaggaa ccgtaaaaag 12360
gccgcgttgc tggcgttttt ccataggctc cgcccccctg acgagcatca caaaaatcga 12420
cgctcaagtc agaggtggcg aaacccgaca ggactataaa gataccaggc gtttccccct 12480
ggaagctccc tcgtgcgctc tcctgttccg accctgccgc ttaccggata cctgtccgcc 12540
tttctccctt cgggaagcgt ggcgctttct catagctcac gctgtaggta tctcagttcg 12600
gtgtaggtcg ttcgctccaa gctgggctgt gtgcacgaac cccccgttca gcccgaccgc 12660
tgcgccttat ccggtaacta tcgtcttgag tccaacccgg taagacacga cttatcgcca 12720
ctggcagcag ccactggtaa caggattagc agagcgaggt atgtaggcgg tgctacagag 12780
ttcttgaagt ggtggcctaa ctacggctac actagaagaa cagtatttgg tatctgcgct 12840
ctgctgaagc cagttacctt cggaaaaaga gttggtagct cttgatccgg caaacaaacc 12900
accgctggta gcggtggttt ttttgtttgc aagcagcaga ttacgcgcag aaaaaaagga 12960
tctcaagaag atcctttgat cttttctacg gggtctgacg ctcagtggaa cgaaaactca 13020
cgttaaggga ttttggtcat gagattatca aaaaggatct tcacctagat ccttttaaat 13080
taaaaatgaa gttttaaatc aatctaaagt atatatgagt aaacttggtc tgacagttac 13140
caatgcttaa tcagtgaggc acctatctca gcgatctgtc tatttcgttc atccatagtt 13200
gcctgactcc ccgtcgtgta gataactacg atacgggagg gcttaccatc tggccccagt 13260
gctgcaatga taccgcgaga cccacgctca ccggctccag atttatcagc aataaaccag 13320
ccagccggaa gggccgagcg cagaagtggt cctgcaactt tatccgcctc catccagtct 13380
attaattgtt gccgggaagc tagagtaagt agttcgccag ttaatagttt gcgcaacgtt 13440
gttgccattg ctacaggcat cgtggtgtca cgctcgtcgt ttggtatggc ttcattcagc 13500
tccggttccc aacgatcaag gcgagttaca tgatccccca tgttgtgcaa aaaagcggtt 13560
agctccttcg gtcctccgat cgttgtcaga agtaagttgg ccgcagtgtt atcactcatg 13620
gttatggcag cactgcataa ttctcttact gtcatgccat ccgtaagatg cttttctgtg 13680
actggtgagt actcaaccaa gtcattctga gaatagtgta tgcggcgacc gagttgctct 13740
tgcccggcgt caatacggga taataccgcg ccacatagca gaactttaaa agtgctcatc 13800

```
attggaaaac gttcttcggg gcgaaaactc tcaaggatct taccgctgtt gagatccagt  13860

tcgatgtaac ccactcgtgc acccaactga tcttcagcat cttttacttt caccagcgtt  13920

tctgggtgag caaaaacagg aaggcaaaat gccgcaaaaa agggaataag ggcgacacgg  13980

aaatgttgaa tactcatact cttccttttt caatattatt gaagcattta tcagggttat  14040

tgtctcatga gcggatacat atttgaatgt atttagaaaa ataaacaaat aggggttccg  14100

cgcacatttc cccgaaaagt gccacctgaa cgaagcatct gtgcttcatt ttgtagaaca  14160

aaaatgcaac gcgagagcgc taatttttca aacaaagaat ctgagctgca tttttacaga  14220

acagaaatgc aacgcgaaag cgctatttta ccaacgaaga atctgtgctt catttttgta  14280

aaacaaaaat gcaacgcgag agcgctaatt tttcaaacaa agaatctgag ctgcattttt  14340

acagaacaga aatgcaacgc gagagcgcta ttttaccaac aaagaatcta tacttctttt  14400

ttgttctaca aaaatgcatc ccgagagcgc tatttttcta acaaagcatc ttagattact  14460

tttttctcc tttgtgcgct ctataatgca gtctcttgat aactttttgc actgtaggtc  14520

cgttaaggtt agaagaaggc tactttggtg tctattttct cttccataaa aaaagcctga  14580

ctccacttcc cgcgtttact gattactagc gaagctgcgg gtgcattttt tcaagataaa  14640

ggcatccccg attatattct ataccgatgt ggattgcgca tactttgtga acagaaagtg  14700

atagcgttga tgattcttca ttggtcagaa aattatgaac ggtttcttct attttgtctc  14760

tatatactac gtataggaaa tgtttacatt ttcgtattgt tttcgattca ctctatgaat  14820

agttcttact acaatttttt tgtctaaaga gtaatactag agataaacat aaaaaatgta  14880

gaggtcgagt ttagatgcaa gttcaaggag cgaaaggtgg atgggtaggt tatataggga  14940

tatagcacag agatatatag caaagagata cttttgagca atgtttgtgg aagcggtatt  15000

cgcaatattt tagtagctcg ttacagtccg gtgcgttttt ggttttttga aagtgcgtct  15060

tcagagcgct tttggttttc aaaagcgctc tgaagttcct atactttcta gagaatagga  15120

acttcggaat aggaacttca aagcgtttcc gaaaacgagc gcttccgaaa atgcaacgcg  15180

agctgcgcac atacagctca ctgttcacgt cgcacctata tctgcgtgtt gcctgtatat  15240

atatatacat gagaagaacg gcatagtgcg tgtttatgct taaatgcgta cttatatgcg  15300

tctatttatg taggatgaaa ggtagtctag tacctcctgt gatattatcc cattccatgc  15360

ggggtatcgt atgcttcctt cagcactacc ctttagctgt tctatatgct gccactcctc  15420

aattggatta gtctcatcct tcaatgctat catttccttt gatattggat catactaaga  15480

aaccattatt atcatgacat taacctataa aaataggcgt atcacgaggc cctttcgtc   15539
```

<210> SEQ ID NO 44
<211> LENGTH: 1644
<212> TYPE: DNA
<213> ORGANISM: artificial sequence
<220> FEATURE:
<223> OTHER INFORMATION: codon optimized sequence

<400> SEQUENCE: 44

```
atgtatacag taggtgacta tctgttggac agattacacg aattaggtat agaagaaata     60

ttcggagtac caggtgacta caatttgcaa tttctagatc aaattatttc acacaaagat    120

atgaaatggg tgggaaatgc taatgagtta aatgcctcct atatggccga cgggtacgca    180

agaacgaaaa aggctgcggc attcttgact acatttggtg ttggcgaatt atccgcagtt    240

aatggcttag cgggctccta tgctgagaac ctgcctgttg ttgagatcgt gggatctcct    300

acctcgaaag tgcagaacga aggtaagttt gttcaccata cgttggctga tggtgatttc    360
```

aagcacttta tgaagatgca cgaaccggtt actgctgcca ggactttatt gacagccgag 420
aatgcaactg ttgaaattga tagagtgttg tctgccttac taaaggaaag aaagccggtt 480
tacatcaatt tacctgtaga tgtagctgcc gctaaggctg aaaaaccatc cttgcctctt 540
aagaaggaaa attccacgtc gaatacatct gatcaagaga ttctgaacaa aatacaggaa 600
agtctgaaga atgccaagaa accaattgta atcacaggcc atgaaattat atcgttcggc 660
ctagagaaga ctgttactca gtttatttca aagactaagt tacctattac tactttgaac 720
tttggtaaat catctgttga tgaagcattg ccctcatttt tggggattta caacggtact 780
ctgtcagagc caaacttgaa ggaatttgtg gaatctgctg attttattct tatgttgggt 840
gtaaagctta ccgattctag tacgggtgca tttactcacc atcttaatga aaataaaatg 900
atttccttga atatcgatga aggtaaaatt ttcaacgaaa gaatccaaaa tttcgacttc 960
gaatccctga tatcatctct tcttgacttg tccgaaattg aatataaagg caagtacata 1020
gataaaaagc aagaagattt tgtaccttct aacgcgctgt tgtcacaaga tagactgtgg 1080
caagctgtcg aaaatttgac ccaaagtaat gagacgatcg tggctgaaca aggcacttct 1140
ttcttcggtg cctcatctat atttctgaaa tcgaaatcac attttattgg tcaacccttg 1200
tggggatcta taggatacac tttccccgca gctctaggca gccaaattgc agataaagaa 1260
tctagacatt tattgtttat cggagatgga tcattgcaac tgactgtcca agaattagga 1320
ctagccatta gagagaagat aaacccaatc tgctttatca ttaataacga tggttacacg 1380
gttgagaggg aaattcatgg tccgaaccag agttataatg acattcctat gtggaattac 1440
tcaaaactgc cagaaagttt cggggcaacg gaagacagag ttgtgtccaa aattgtgaga 1500
acagaaaatg aattcgtatc cgtgatgaaa gaagctcaag cagatccaaa taggatgtat 1560
tggatagaac ttattctagc aaaggagggt gcacctaaag ttttgaaaaa gatgggtaag 1620
ttatttgcag aacaaaacaa gagc 1644

<210> SEQ ID NO 45
<211> LENGTH: 1125
<212> TYPE: DNA
<213> ORGANISM: artificial sequence
<220> FEATURE:
<223> OTHER INFORMATION: codon optimized sequence

<400> SEQUENCE: 45
atgtcaacag ccggtaaagt tattaagtgt aaagcggcag ttttgtggga agagaaaaag 60
ccgtttagca tagaagaagt agaagtagcg ccaccaaaag cacacgaggt tagaatcaag 120
atggttgcca ccggaatctg tagatccgac gaccatgtgg tgagtggcac tctagttact 180
cctttgccag taatcgcggg acacgaggct gccggaatcg ttgaatccat aggtgaaggt 240
gttaccactg ttcgtcctgg tgataaagtg atcccactgt tcactcctca atgtggtaag 300
tgtagagtct gcaaacatcc tgagggtaat ttctgcctta aaaatgattt gtctatgcct 360
agaggtacta tgcaggatgg tacaagcaga tttacatgca gagggaaacc tatacaccat 420
ttccttggta cttctacatt ttcccaatac acagtggtgg acgagatatc tgtcgctaaa 480
atcgatgcag cttcaccact ggaaaaagtt tgcttgatag ggtgcggatt ttccaccggt 540
tacggttccg cagttaaagt tgcaaaggtt acacagggtt cgacttgtgc agtattcggt 600
ttaggaggag taggactaag cgttattatg ggtgtaaag ctgcaggcgc agcgaggatt 660
ataggtgtag acatcaataa ggacaaattt gcaaaagcta aggaggtcgg ggctactgaa 720
tgtgttaacc ctcaagatta taagaaacca atacaagaag tccttactga aatgtcaaac 780

```
ggtggagttg atttctcttt tgaagttata ggccgtcttg atactatggt aactgcgttg    840

tcctgctgtc aagaggcata tggagtcagt gtgatcgtag gtgttcctcc tgattcacaa    900

aatttgtcga tgaatcctat gctgttgcta agcggtcgta catggaaggg agctatattt    960

ggcggtttta agagcaagga tagtgttcca aaacttgttg ccgactttat ggcgaagaag   1020

tttgctcttg atcctttaat tacacatgta ttgccattcg agaaaatcaa tgaagggttt   1080

gatttgttaa gaagtggtga atctattcgt acaattttaa ctttt                   1125


<210> SEQ ID NO 46
<211> LENGTH: 375
<212> TYPE: PRT
<213> ORGANISM: Equus caballus

<400> SEQUENCE: 46

Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320
```

```
Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375


<210> SEQ ID NO 47
<211> LENGTH: 548
<212> TYPE: PRT
<213> ORGANISM: Lactococcus lactis

<400> SEQUENCE: 47

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320
```

```
Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545
```

<210> SEQ ID NO 48
<211> LENGTH: 9089
<212> TYPE: DNA
<213> ORGANISM: artificial sequence
<220> FEATURE:
<223> OTHER INFORMATION: Synthetic construct

<400> SEQUENCE: 48

```
tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accataccac agcttttcaa ttcaattcat catttttttt ttattctttt ttttgatttc     240

ggtttctttg aaattttttt gattcggtaa tctccgaaca gaaggaagaa cgaaggaagg     300

agcacagact tagattggta tatatacgca tatgtagtgt tgaagaaaca tgaaattgcc     360

cagtattctt aacccaactg cacagaacaa aaacctgcag gaaacgaaga taaatcatgt     420

cgaaagctac atataaggaa cgtgctgcta ctcatcctag tcctgttgct gccaagctat     480

ttaatatcat gcacgaaaag caaacaaact tgtgtgcttc attggatgtt cgtaccacca     540

aggaattact ggagttagtt gaagcattag gtcccaaaat ttgtttacta aaaacacatg     600

tggatatctt gactgatttt tccatggagg gcacagttaa gccgctaaag gcattatccg     660

ccaagtacaa tttttactc ttcgaagaca gaaaatttgc tgacattggt aatacagtca     720
```

-continued

```
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg ggcccccct cgaggtcgac tggccattaa    2040
tctttcccat attagatttc gccaagccat gaaagttcaa gaaaggtctt tagacgaatt   2100
acccttcatt tctcaaactg gcgtcaaggg atcctggtat ggttttatcg ttttatttct   2160
ggttcttata gcatcgtttt ggacttctct gttcccatta ggcggttcag gagccagcgc   2220
agaatcattc tttgaaggat acttatcctt tccaattttg attgtctgtt acgttggaca   2280
taaactgtat actagaaatt ggactttgat ggtgaaacta gaagatatgg atcttgatac   2340
cggcagaaaa caagtagatt tgactcttcg tagggaagaa atgaggattg agcgagaaac   2400
attagcaaaa agatccttcg taacaagatt tttacatttc tggtgttgaa gggaaagata   2460
tgagctatac agcggaattt ccatatcact cagattttgt tatctaattt tttccttccc   2520
acgtccgcgg gaatctgtgt atattactgc atctagatat atgttatctt atcttggcgc   2580
gtacatttaa ttttcaacgt attctataag aaattgcggg agttttttc atgtagatga    2640
tactgactgc acgcaaatat aggcatgatt tataggcatg atttgatggc tgtaccgata   2700
ggaacgctaa gagtaacttc agaatcgtta tcctggcgga aaaaattcat ttgtaaactt   2760
taaaaaaaaa agccaatatc cccaaaatta ttaagagcgc ctccattatt aactaaaatt   2820
tcactcagca tccacaatgt atcaggtatc tactacagat attacatgtg gcgaaaaaga   2880
caagaacaat gcaatagcgc atcaagaaaa aacacaaagc tttcaatcaa tgaatcgaaa   2940
atgtcattaa aatagtatat aaattgaaac taagtcataa agctataaaa agaaaattta   3000
tttaaatgca agatttaaag taaattcacg gccctgcagg ccctaacctg ctaggacaca   3060
acgtctttgc ctggtaaagt ttctagctga cgtgattcct tcacctgtgg atccggcaat   3120
```

-continued

```
tgtaaaggtt gtgaaaccct cagcttcata accgacacct gcaaatgact ttgcattctt   3180
aacaaagata gttgtatcaa tttcacgttc gaatctatta aggttatcga tgttcttaga   3240
ataaatgtag gcggaatgtt ttctattctg ctcagctatc ttggcgtatt taatggcttc   3300
atcaatgtcc ttcactctaa ctataggcaa aattggcatc atcaactccg tcataacgaa   3360
cggatggttt gcgttgactt cacaaataat acactttaca ttacttggtg actctacatc   3420
tatttcatcc aaaaacagtt tagcgtcctt accaacccac ttcttattaa tgaaatattc   3480
ttgagtttca ttgttctttt gaagaacaag gtctatcagc ttggatactt ggtcttcatt   3540
gataatgacg gcgttgtttt tcaacatgtt agagatcaga tcatctgcaa cgttttcaaa   3600
cacgaacact tctttttccg cgatacaagg aagattgttg tcaaacgaac aaccttcaat   3660
aatgcttctg ccggccttct cgatatctgc tgtatcgtct acaataaccg gaggattacc   3720
cgcgccagct ccgatggcct ttttaccaga attaagaagg gtttttacca tacccgggcc   3780
acccgtaccg cacaacaatt ttatggatgg atgtttgata atagcgtcta aactttccat   3840
agttgggttc tttatagtag tgacaaggtt ttcaggtcca ccacagctaa ttatggcttt   3900
gtttatcatt tctactgcga aagcgacaca ctttttggcg catgggtgac cattaaatac   3960
aactgcattc cccgcagcta tcatacctat agaattgcag ataacggttt ctgttggatt   4020
cgtgcttgga gttatagcgc cgataactcc gtatggactc atttcaacca ctgttagtcc   4080
attatcgccg gaccatgctg ttgttgtcag atcttcagtg cctggggtat acttggccac   4140
taattcatgt ttcaagattt tatcctcata ccttcccatg tgggtttcct ccaggatcat   4200
tgtggctaag acctctttat tctgtaatgc ggcttttctt atttcggtga ttattttctc   4260
tctttgttcc tttgtgtagt gtagggaaag aatcttttgt gcatgtactg cagaagaaat   4320
ggcattctca acattttcaa atactccaaa acatgaagag ttatctttgt aattctttaa   4380
gttgatgttt tcaccattag tcttcacttt caagtctttg gtggttggga ttaaggtatc   4440
tttatccatg gtgtttgttt atgtgtgttt attcgaaact aagttcttgg tgttttaaaa   4500
ctaaaaaaaa gactaactat aaaagtagaa tttaagaagt ttaagaaata gatttacaga   4560
attacaatca atacctaccg tctttatata cttattagtc aagtagggga ataatttcag   4620
ggaactggtt tcaacctttt ttttcagctt tttccaaatc agagagagca gaaggtaata   4680
gaaggtgtaa gaaaatgaga tagatacatg cgtgggtcaa ttgccttgtg tcatcattta   4740
ctccaggcag gttgcatcac tccattgagg ttgtgcccgt tttttgcctg tttgtgcccc   4800
tgttctctgt agttgcgcta agagaatgga cctatgaact gatggttggt gaagaaaaca   4860
atattttggt gctgggattc tttttttttc tggatgccag cttaaaaagc gggctccatt   4920
atatttagtg gatgccagga ataaactgtt cacccagaca cctacgatgt tatatattct   4980
gtgtaacccg ccccctattt tgggcatgta cgggttacag cagaattaaa aggctaattt   5040
tttgactaaa taaagttagg aaaatcacta ctattaatta tttacgtatt ctttgaaatg   5100
gcagtattga taatgataaa ctcgaactga aaaagcgtgt tttttattca aaatgattct   5160
aactccctta cgtaatcaag gaatcttttt gccttggcct ccgcgtcatt aaacttcttg   5220
ttgttgacgc taacattcaa cgctagtata tattcgtttt tttcaggtaa gttcttttca   5280
acgggtctta ctgatgaggc agtcgcgtct gaacctgtta agaggtcaaa tatgtcttct   5340
tgaccgtacg tgtcttgcat gttattagct ttgggaattt gcatcaagtc ataggaaaat   5400
ttaaatcttg gctctcttgg gctcaaggtg acaaggtcct cgaaaatagg gcgcgcccca   5460
ccgcggtgga gctccagctt ttgttccctt tagtgagggt taattgcgcg cttggcgtaa   5520
```

-continued

```
tcatggtcat agctgtttcc tgtgtgaaat tgttatccgc tcacaattcc acacaacata   5580
ggagccggaa gcataaagtg taaagcctgg ggtgcctaat gagtgaggta actcacatta   5640
attgcgttgc gctcactgcc cgctttccag tcgggaaacc tgtcgtgcca gctgcattaa   5700
tgaatcggcc aacgcgcggg gagaggcggt ttgcgtattg ggcgctcttc cgcttcctcg   5760
ctcactgact cgctgcgctc ggtcgttcgg ctgcggcgag cggtatcagc tcactcaaag   5820
gcggtaatac ggttatccac agaatcaggg gataacgcag gaaagaacat gtgagcaaaa   5880
ggccagcaaa aggccaggaa ccgtaaaaag gccgcgttgc tggcgttttt ccataggctc   5940
cgcccccctg acgagcatca caaaaatcga cgctcaagtc agaggtggcg aaacccgaca   6000
ggactataaa gataccaggc gtttccccct ggaagctccc tcgtgcgctc tcctgttccg   6060
accctgccgc ttaccggata cctgtccgcc tttctccctt cgggaagcgt ggcgctttct   6120
catagctcac gctgtaggta tctcagttcg gtgtaggtcg ttcgctccaa gctgggctgt   6180
gtgcacgaac cccccgttca gcccgaccgc tgcgccttat ccggtaacta tcgtcttgag   6240
tccaacccgg taagacacga cttatcgcca ctggcagcag ccactggtaa caggattagc   6300
agagcgaggt atgtaggcgg tgctacagag ttcttgaagt ggtggcctaa ctacggctac   6360
actagaagga cagtatttgg tatctgcgct ctgctgaagc cagttacctt cggaaaaaga   6420
gttggtagct cttgatccgg caaacaaacc accgctggta gcggtggttt ttttgtttgc   6480
aagcagcaga ttacgcgcag aaaaaaagga tctcaagaag atcctttgat cttttctacg   6540
gggtctgacg ctcagtggaa cgaaaactca cgttaaggga ttttggtcat gagattatca   6600
aaaaggatct tcacctagat ccttttaaat taaaaatgaa gttttaaatc aatctaaagt   6660
atatatgagt aaacttggtc tgacagttac caatgcttaa tcagtgaggc acctatctca   6720
gcgatctgtc tatttcgttc atccatagtt gcctgactcc ccgtcgtgta gataactacg   6780
atacgggagg gcttaccatc tggccccagt gctgcaatga taccgcgaga cccacgctca   6840
ccggctccag atttatcagc aataaaccag ccagccggaa gggccgagcg cagaagtggt   6900
cctgcaactt tatccgcctc catccagtct attaattgtt gccgggaagc tagagtaagt   6960
agttcgccag ttaatagttt gcgcaacgtt gttgccattg ctacaggcat cgtggtgtca   7020
cgctcgtcgt ttggtatggc ttcattcagc tccggttccc aacgatcaag gcgagttaca   7080
tgatccccca tgttgtgcaa aaaagcggtt agctccttcg gtcctccgat cgttgtcaga   7140
agtaagttgg ccgcagtgtt atcactcatg gttatggcag cactgcataa ttctcttact   7200
gtcatgccat ccgtaagatg cttttctgtg actggtgagt actcaaccaa gtcattctga   7260
gaatagtgta tgcggcgacc gagttgctct tgcccggcgt caatacggga taataccgcg   7320
ccacatagca gaactttaaa agtgctcatc attggaaaac gttcttcggg gcgaaaactc   7380
tcaaggatct taccgctgtt gagatccagt tcgatgtaac ccactcgtgc acccaactga   7440
tcttcagcat cttttacttt caccagcgtt tctgggtgag caaaaacagg aaggcaaaat   7500
gccgcaaaaa agggaataag ggcgacacgg aaatgttgaa tactcatact cttccttttt   7560
caatattatt gaagcattta tcagggttat tgtctcatga gcggatacat atttgaatgt   7620
atttagaaaa ataaacaaat aggggttccg cgcacatttc cccgaaaagt gccacctgaa   7680
cgaagcatct gtgcttcatt ttgtagaaca aaaatgcaac gcgagagcgc taatttttca   7740
aacaaagaat ctgagctgca tttttacaga acagaaatgc aacgcgaaag cgctatttta   7800
ccaacgaaga atctgtgctt catttttgta aaacaaaaat gcaacgcgag agcgctaatt   7860
tttcaaacaa agaatctgag ctgcattttt acagaacaga aatgcaacgc gagagcgcta   7920
```

-continued

```
ttttaccaac aaagaatcta tacttctttt ttgttctaca aaaatgcatc ccgagagcgc   7980
tatttttcta acaaagcatc ttagattact ttttttctcc tttgtgcgct ctataatgca   8040
gtctcttgat aactttttgc actgtaggtc cgttaaggtt agaagaaggc tactttggtg   8100
tctattttct cttccataaa aaaagcctga ctccacttcc cgcgtttact gattactagc   8160
gaagctgcgg gtgcattttt tcaagataaa ggcatccccg attatattct ataccgatgt   8220
ggattgcgca tactttgtga acagaaagtg atagcgttga tgattcttca ttggtcagaa   8280
aattatgaac ggtttcttct attttgtctc tatatactac gtataggaaa tgtttacatt   8340
ttcgtattgt tttcgattca ctctatgaat agttcttact acaatttttt tgtctaaaga   8400
gtaatactag agataaacat aaaaaatgta gaggtcgagt ttagatgcaa gttcaaggag   8460
cgaaaggtgg atgggtaggt tatataggga tatagcacag agatatatag caaagagata   8520
cttttgagca atgtttgtgg aagcggtatt cgcaatattt tagtagctcg ttacagtccg   8580
gtgcgttttt ggtttttga aagtgcgtct tcagagcgct tttggttttc aaaagcgctc   8640
tgaagttcct atactttcta gagaatagga acttcggaat aggaacttca aagcgtttcc   8700
gaaaacgagc gcttccgaaa atgcaacgcg agctgcgcac atacagctca ctgttcacgt   8760
cgcacctata tctgcgtgtt gcctgtatat atatatacat gagaagaacg gcatagtgcg   8820
tgtttatgct taaatgcgta cttatatgcg tctatttatg taggatgaaa ggtagtctag   8880
tacctcctgt gatattatcc cattccatgc ggggtatcgt atgcttcctt cagcactacc   8940
ctttagctgt tctatatgct gccactcctc aattggatta gtctcatcct tcaatgctat   9000
catttccttt gatattggat catactaaga aaccattatt atcatgacat taacctataa   9060
aaataggcgt atcacgaggc cctttcgtc                                     9089
```

<210> SEQ ID NO 49
<211> LENGTH: 1023
<212> TYPE: DNA
<213> ORGANISM: Saccharomyces cerevisiae

<400> SEQUENCE: 49

```
caccgcggtg gggcgcgccc tattttcgag gaccttgtca ccttgagccc aagagagcca     60
agatttaaat tttcctatga cttgatgcaa attcccaaag ctaataacat gcaagacacg    120
tacggtcaag aagacatatt tgacctctta acaggttcag acgcgactgc ctcatcagta    180
agacccgttg aaaagaactt acctgaaaaa aacgaatata tactagcgtt gaatgttagc    240
gtcaacaaca agaagtttaa tgacgcggag gccaaggcaa aaagattcct tgattacgta    300
agggagttag aatcattttg aataaaaaac acgctttttc agttcgagtt tatcattatc    360
aatactgcca tttcaaagaa tacgtaaata attaatagta gtgattttcc taactttatt    420
tagtcaaaaa attagccttt taattctgct gtaacccgta catgcccaaa ataggggggcg    480
ggttacacag aatatataac atcgtaggtg tctgggtgaa cagtttattc ctggcatcca    540
ctaaatataa tggagcccgc tttttaagct ggcatccaga aaaaaaaaga atcccagcac    600
caaaatattg ttttcttcac caaccatcag ttcataggtc cattctctta gcgcaactac    660
agagaacagg ggcacaaaca ggcaaaaaac gggcacaacc tcaatggagt gatgcaacct    720
gcctggagta aatgatgaca caaggcaatt gacccacgca tgtatctatc tcattttctt    780
acaccttcta ttaccttctg ctctctctga tttggaaaaa gctgaaaaaa aaggttgaaa    840
ccagttccct gaaattattc ccctacttga ctaataagta tataaagacg gtaggtattg    900
attgtaattc tgtaaatcta tttcttaaac ttcttaaatt ctacttttat agttagtctt    960
```

tttttagtt ttaaaacacc aagaacttag tttcgaataa acacacataa actagtaaac 1020
aaa 1023

<210> SEQ ID NO 50
<211> LENGTH: 21
<212> TYPE: DNA
<213> ORGANISM: artificial sequence
<220> FEATURE:
<223> OTHER INFORMATION: Primer

<400> SEQUENCE: 50
caaaagctga gctccaccgc g 21

<210> SEQ ID NO 51
<211> LENGTH: 44
<212> TYPE: DNA
<213> ORGANISM: artificial sequence
<220> FEATURE:
<223> OTHER INFORMATION: Primer

<400> SEQUENCE: 51
gtttactagt ttatgtgtgt ttattcgaaa ctaagttctt ggtg 44

<210> SEQ ID NO 52
<211> LENGTH: 8994
<212> TYPE: DNA
<213> ORGANISM: artificial sequence
<220> FEATURE:
<223> OTHER INFORMATION: Synthetic construct

<400> SEQUENCE: 52
ctagttctag agcggccgcc accgcggtgg agctccagct tttgttccct ttagtgaggg 60
ttaattgcgc gcttggcgta atcatggtca tagctgtttc ctgtgtgaaa ttgttatccg 120
ctcacaattc cacacaacat aggagccgga agcataaagt gtaaagcctg gggtgcctaa 180
tgagtgaggt aactcacatt aattgcgttg cgctcactgc ccgctttcca gtcgggaaac 240
ctgtcgtgcc agctgcatta atgaatcggc caacgcgcgg ggagaggcgg tttgcgtatt 300
gggcgctctt ccgcttcctc gctcactgac tcgctgcgct cggtcgttcg gctgcggcga 360
gcggtatcag ctcactcaaa ggcggtaata cggttatcca cagaatcagg ggataacgca 420
ggaaagaaca tgtgagcaaa aggccagcaa aaggccagga accgtaaaaa ggccgcgttg 480
ctggcgtttt tccataggct ccgcccccct gacgagcatc acaaaaatcg acgctcaagt 540
cagaggtggc gaaacccgac aggactataa agataccagg cgtttccccc tggaagctcc 600
ctcgtgcgct ctcctgttcc gaccctgccg cttaccggat acctgtccgc ctttctccct 660
tcgggaagcg tggcgctttc tcatagctca cgctgtaggt atctcagttc ggtgtaggtc 720
gttcgctcca agctgggctg tgtgcacgaa ccccccgttc agcccgaccg ctgcgcctta 780
tccggtaact atcgtcttga gtccaacccg gtaagacacg acttatcgcc actggcagca 840
gccactggta acaggattag cagagcgagg tatgtaggcg gtgctacaga gttcttgaag 900
tggtggccta actacggcta cactagaagg acagtatttg gtatctgcgc tctgctgaag 960
ccagttacct tcggaaaaag agttggtagc tcttgatccg gcaaacaaac caccgctggt 1020
agcggtggtt tttttgtttg caagcagcag attacgcgca gaaaaaaagg atctcaagaa 1080
gatcctttga tcttttctac ggggtctgac gctcagtgga acgaaaactc acgttaaggg 1140
attttggtca tgagattatc aaaaaggatc ttcacctaga tccttttaaa ttaaaaatga 1200
agttttaaat caatctaaag tatatatgag taaacttggt ctgacagtta ccaatgctta 1260

-continued

```
atcagtgagg cacctatctc agcgatctgt ctatttcgtt catccatagt tgcctgactc   1320
cccgtcgtgt agataactac gatacgggag ggcttaccat ctggccccag tgctgcaatg   1380
ataccgcgag acccacgctc accggctcca gatttatcag caataaacca gccagccgga   1440
agggccgagc gcagaagtgg tcctgcaact ttatccgcct ccatccagtc tattaattgt   1500
tgccgggaag ctagagtaag tagttcgcca gttaatagtt tgcgcaacgt tgttgccatt   1560
gctacaggca tcgtggtgtc acgctcgtcg tttggtatgg cttcattcag ctccggttcc   1620
caacgatcaa ggcgagttac atgatccccc atgttgtgca aaaaagcggt tagctccttc   1680
ggtcctccga tcgttgtcag aagtaagttg gccgcagtgt tatcactcat ggttatggca   1740
gcactgcata attctcttac tgtcatgcca tccgtaagat gcttttctgt gactggtgag   1800
tactcaacca agtcattctg agaatagtgt atgcggcgac cgagttgctc ttgcccggcg   1860
tcaatacggg ataataccgc gccacatagc agaactttaa aagtgctcat cattggaaaa   1920
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga acgaagcatc tgtgcttcat tttgtagaac aaaaatgcaa   2280
cgcgagagcg ctaatttttc aaacaaagaa tctgagctgc atttttacag aacagaaatg   2340
caacgcgaaa gcgctatttt accaacgaag aatctgtgct tcatttttgt aaaacaaaaa   2400
tgcaacgcga gagcgctaat ttttcaaaca aagaatctga gctgcatttt tacagaacag   2460
aaatgcaacg cgagagcgct attttaccaa caaagaatct atacttcttt tttgttctac   2520
aaaaatgcat cccgagagcg ctatttttct aacaaagcat cttagattac tttttttctc   2580
ctttgtgcgc tctataatgc agtctcttga taactttttg cactgtaggt ccgttaaggt   2640
tagaagaagg ctactttggt gtctattttc tcttccataa aaaaagcctg actccacttc   2700
ccgcgtttac tgattactag cgaagctgcg ggtgcatttt ttcaagataa aggcatcccc   2760
gattatattc tataccgatg tggattgcgc atactttgtg aacagaaagt gatagcgttg   2820
atgattcttc attggtcaga aaattatgaa cggtttcttc tattttgtct ctatatacta   2880
cgtataggaa atgtttacat tttcgtattg ttttcgattc actctatgaa tagttcttac   2940
tacaattttt ttgtctaaag agtaatacta gagataaaca taaaaaatgt agaggtcgag   3000
tttagatgca agttcaagga gcgaaaggtg gatgggtagg ttatataggg atatagcaca   3060
gagatatata gcaaagagat acttttgagc aatgtttgtg gaagcggtat tcgcaatatt   3120
ttagtagctc gttacagtcc ggtgcgtttt tggttttttg aaagtgcgtc ttcagagcgc   3180
ttttggtttt caaaagcgct ctgaagttcc tatactttct agagaatagg aacttcggaa   3240
taggaacttc aaagcgtttc cgaaaacgag cgcttccgaa aatgcaacgc gagctgcgca   3300
catacagctc actgttcacg tcgcacctat atctgcgtgt tgcctgtata tatatataca   3360
tgagaagaac ggcatagtgc gtgtttatgc ttaaatgcgt acttatatgc gtctatttat   3420
gtaggatgaa aggtagtcta gtacctcctg tgatattatc ccattccatg cggggtatcg   3480
tatgcttcct tcagcactac cctttagctg ttctatatgc tgccactcct caattggatt   3540
agtctcatcc ttcaatgcta tcatttcctt tgatattgga tcatactaag aaaccattat   3600
tatcatgaca ttaacctata aaaataggcg tatcacgagg ccctttcgtc tcgcgcgttt   3660
```

```
cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
tttatttgtt gtattttttt ttttttagag aaaatcctcc aatatcaaat taggaatcgt   4020
agtttcatga ttttctgtta cacctaactt tttgtgtggt gccctcctcc ttgtcaatat   4080
taatgttaaa gtgcaattct ttttccttat cacgttgagc cattagtatc aatttgctta   4140
cctgtattcc tttactatcc tcctttttct ccttcttgat aaatgtatgt agattgcgta   4200
tatagtttcg tctaccctat gaacatattc cattttgtaa tttcgtgtcg tttctattat   4260
gaatttcatt tataaagttt atgtacaaat atcataaaaa aagagaatct ttttaagcaa   4320
ggattttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
aaatacctcc cactaattct ctgacaacaa cgaagtcagt acctttagca aattgtggct   5040
tgattggaga taagtctaaa agagagtcgg atgcaaagtt acatggtctt aagttggcgt   5100
acaattgaag ttctttacgg atttttagta aaccttgttc aggtctaaca ctaccggtac   5160
cccatttagg accagccaca gcacctaaca aaacggcatc aaccttcttg gaggcttcca   5220
gcgcctcatc tggaagtggg acacctgtag catcgatagc agcaccacca attaaatgat   5280
tttcgaaatc gaacttgaca ttggaacgaa catcagaaat agctttaaga accttaatgg   5340
cttcggctgt gatttcttga ccaacgtggt cacctggcaa aacgacgatc ttcttagggg   5400
cagacatagg ggcagacatt agaatggtat atccttgaaa tatatatata tattgctgaa   5460
atgtaaaagg taagaaaagt tagaaagtaa gacgattgct aaccacctat tggaaaaaac   5520
aataggtcct taaataatat tgtcaacttc aagtattgtg atgcaagcat ttagtcatga   5580
acgcttctct attctatatg aaaagccggt tccggcctct cacctttcct ttttctccca   5640
atttttcagt tgaaaaaggt atatgcgtca ggcgacctct gaaattaaca aaaaatttcc   5700
agtcatcgaa tttgattctg tgcgatagcg cccctgtgtg ttctcgttat gttgaggaaa   5760
aaaataatgg ttgctaagag attcgaactc ttgcatctta cgatacctga gtattcccac   5820
agttaactgc ggtcaagata tttcttgaat caggcgcctt agaccgctcg gccaaacaac   5880
caattacttg ttgagaaata gagtataatt atcctataaa tataacgttt ttgaacacac   5940
atgaacaagg aagtacagga caattgattt tgaagagaat gtggattttg atgtaattgt   6000
tgggattcca tttttaataa ggcaataata ttaggtatgt ggatatacta gaagttctcc   6060
```

```
tcgaccgtcg atatgcggtg tgaaataccg cacagatgcg taaggagaaa ataccgcatc   6120
aggaaattgt aaacgttaat attttgttaa aattcgcgtt aaatttttgt taaatcagct   6180
cattttttaa ccaataggcc gaaatcggca aaatccctta taaatcaaaa gaatagaccg   6240
agatagggtt gagtgttgtt ccagtttgga acaagagtcc actattaaag aacgtggact   6300
ccaacgtcaa agggcgaaaa accgtctatc agggcgatgg cccactacgt gaaccatcac   6360
cctaatcaag ttttttgggg tcgaggtgcc gtaaagcact aaatcggaac cctaaaggga   6420
gcccccgatt tagagcttga cggggaaagc cggcgaacgt ggcgagaaag gaagggaaga   6480
aagcgaaagg agcgggcgct agggcgctgg caagtgtagc ggtcacgctg cgcgtaacca   6540
ccacacccgc cgcgcttaat gcgccgctac agggcgcgtc gcgccattcg ccattcaggc   6600
tgcgcaactg ttgggaaggg cgatcggtgc gggcctcttc gctattacgc cagctggcga   6660
aagggggatg tgctgcaagg cgattaagtt gggtaacgcc agggttttcc cagtcacgac   6720
gttgtaaaac gacggccagt gagcgcgcgt aatacgactc actatagggc gaattgggta   6780
ccgggccccc cctcgaggtc gacggtatcg ataagcttga tatcgaattc ctgcagcccg   6840
ggggatccgc atgcttgcat ttagtcgtgc aatgtatgac tttaagattt gtgagcagga   6900
agaaaaggga gaatcttcta acgataaacc cttgaaaaac tgggtagact acgctatgtt   6960
gagttgctac gcaggctgca caattacacg agaatgctcc cgcctaggat ttaaggctaa   7020
gggacgtgca atgcagacga cagatctaaa tgaccgtgtc ggtgaagtgt tcgccaaact   7080
tttcggttaa cacatgcagt gatgcacgcg cgatggtgct aagttacata tatatatata   7140
tatatatata tagccatagt gatgtctaag taacctttat ggtatatttc ttaatgtgga   7200
aagatactag cgcgcgcacc cacacacaag cttcgtcttt tcttgaagaa aagaggaagc   7260
tcgctaaatg ggattccact ttccgttccc tgccagctga tggaaaaagg ttagtggaac   7320
gatgaagaat aaaaagagag atccactgag gtgaaatttc agctgacagc gagtttcatg   7380
atcgtgatga acaatggtaa cgagttgtgg ctgttgccag ggagggtggt tctcaacttt   7440
taatgtatgg ccaaatcgct acttgggttt gttatataac aaagaagaaa taatgaactg   7500
attctcttcc tccttcttgt cctttcttaa ttctgttgta attaccttcc tttgtaattt   7560
tttttgtaat tattcttctt aataatccaa acaaacacac atattacaat agctagctga   7620
ggatgaaggc attagtttat catggggatc acaaaatttc gttagaagac aaaccaaaac   7680
ccactctgca gaaaccaaca gacgttgtgg ttagggtgtt gaaaacaaca atttgcggta   7740
ctgacttggg aatatacaaa ggtaagaatc ctgaagtggc agatggcaga atcctgggtc   7800
atgagggcgt tggcgtcatt gaagaagtgg gcgaatccgt gacacaattc aaaaaggggg   7860
ataaagtttt aatctcctgc gttactagct gtggatcgtg tgattattgc aagaagcaac   7920
tgtattcaca ctgtagagac ggtggctgga ttttaggtta catgatcgac ggtgtccaag   7980
ccgaatacgt cagaatacca catgctgaca attcattgta taagatcccg caaactatcg   8040
atgatgaaat tgcagtacta ctgtccgata ttttacctac tggacatgaa attggtgttc   8100
aatatggtaa cgttcaacca ggcgatgctg tagcaattgt aggagcaggt cctgttggaa   8160
tgtcagtttt gttaactgct caattttact cgcctagtac cattattgtt atcgacatgg   8220
acgaaaaccg tttacaatta gcgaaggagc ttggggccac acacactatt aactccggta   8280
ctgaaaatgt tgtcgaagct gtgcatcgta tagcagccga aggagtggat gtagcaatag   8340
aagctgttgg tatacccgca acctgggaca tctgtcagga aattgtaaaa cccggcgctc   8400
atattgccaa cgtgggagtt catggtgtta aggtggactt tgaaattcaa aagttgtgga   8460
```

-continued

```
ttaagaatct aaccatcacc actggtttgg ttaacactaa tactacccca atgttgatga   8520

aggtagcctc tactgataaa ttgcctttaa agaaaatgat tactcacagg tttgagttag   8580

ctgaaatcga acacgcatat caggttttct tgaatggcgc taaagaaaaa gctatgaaga   8640

ttattctatc taatgcaggt gccgcctaat taattaagag taagcgaatt tcttatgatt   8700

tatgattttt attattaaat aagttataaa aaaaataagt gtatacaaat tttaaagtga   8760

ctcttaggtt ttaaaacgaa aattcttatt cttgagtaac tctttcctgt aggtcaggtt   8820

gctttctcag gtatagcatg aggtcgctct tattgaccac acctctaccg gcatgccgag   8880

caaatgcctg caaatcgctc cccatttcac ccaattgtag atatgctaac tccagcaatg   8940

agttgatgaa tctcggtgtg tattttatgt cctcagagga caacacctgt ggta         8994
```

```
<210> SEQ ID NO 53
<211> LENGTH: 753
<212> TYPE: DNA
<213> ORGANISM: Saccharomyces cerevisiae

<400> SEQUENCE: 53

gcatgcttgc atttagtcgt gcaatgtatg actttaagat ttgtgagcag gaagaaaagg     60

gagaatcttc taacgataaa cccttgaaaa actgggtaga ctacgctatg ttgagttgct    120

acgcaggctg cacaattaca cgagaatgct cccgcctagg atttaaggct aagggacgtg    180

caatgcagac gacagatcta aatgaccgtg tcggtgaagt gttcgccaaa cttttcggtt    240

aacacatgca gtgatgcacg cgcgatggtg ctaagttaca tatatatata tatagccata    300

gtgatgtcta agtaaccttt atggtatatt tcttaatgtg gaaagatact agcgcgcgca    360

cccacacaca agcttcgtct ttcttgaag aaaagaggaa gctcgctaaa tgggattcca     420

ctttccgttc cctgccagct gatggaaaaa ggttagtgga acgatgaaga ataaaaagag    480

agatccactg aggtgaaatt tcagctgaca gcgagtttca tgatcgtgat gaacaatggt    540

aacgagttgt ggctgttgcc agggagggtg gttctcaact tttaatgtat ggccaaatcg    600

ctacttgggt ttgttatata acaaagaaga aataatgaac tgattctctt cctccttctt    660

gtcctttctt aattctgttg taattacctt cctttgtaat ttttttgta attattcttc    720

ttaataatcc aaacaaacac acatattaca ata                                753
```

```
<210> SEQ ID NO 54
<211> LENGTH: 316
<212> TYPE: DNA
<213> ORGANISM: Saccharomyces cerevisiae

<400> SEQUENCE: 54

gagtaagcga atttcttatg atttatgatt tttattatta aataagttat aaaaaaaata     60

agtgtataca aattttaaag tgactcttag gttttaaaac gaaaattctt attcttgagt    120

aactctttcc tgtaggtcag gttgctttct caggtatagc atgaggtcgc tcttattgac    180

cacacctcta ccggcatgcc gagcaaatgc ctgcaaatcg ctccccattt cacccaattg    240

tagatatgct aactccagca atgagttgat gaatctcggt gtgtatttta tgtcctcaga    300

ggacaacacc tgtggt                                                   316
```

```
<210> SEQ ID NO 55
<211> LENGTH: 1047
<212> TYPE: DNA
<213> ORGANISM: Achromobacter xylosoxidans

<400> SEQUENCE: 55
```

-continued

```
atgaaagctc tggtttatca cggtgaccac aagatctcgc ttgaagacaa gcccaagccc      60

acccttcaaa agcccacgga tgtagtagta cgggttttga agaccacgat ctgcggcacg     120

gatctcggca tctacaaagg caagaatcca gaggtcgccg acgggcgcat cctgggccat     180

gaaggggtag gcgtcatcga ggaagtgggc gagagtgtca cgcagttcaa gaaaggcgac     240

aaggtcctga tttcctgcgt cacttcttgc ggctcgtgcg actactgcaa gaagcagctt     300

tactcccatt gccgcgacgg cgggtggatc ctgggttaca tgatcgatgg cgtgcaggcc     360

gaatacgtcc gcatcccgca tgccgacaac agcctctaca agatccccca gacaattgac     420

gacgaaatcg ccgtcctgct gagcgacatc ctgcccaccg gccacgaaat cggcgtccag     480

tatgggaatg tccagccggg cgatgcggtg gctattgtcg gcgcgggccc cgtcggcatg     540

tccgtactgt tgaccgccca gttctactcc ccctcgacca tcatcgtgat cgacatggac     600

gagaatcgcc tccagctcgc caaggagctc ggggcaacgc acaccatcaa ctccggcacg     660

gagaacgttg tcgaagccgt gcataggatt gcggcagagg gagtcgatgt tgcgatcgag     720

gcggtgggca taccggcgac ttgggacatc tgccaggaga tcgtcaagcc cggcgcgcac     780

atcgccaacg tcggcgtgca tggcgtcaag gttgacttcg agattcagaa gctctggatc     840

aagaacctga cgatcaccac gggactggtg aacacgaaca cgacgcccat gctgatgaag     900

gtcgcctcga ccgacaagct tccgttgaag aagatgatta cccatcgctt cgagctggcc     960

gagatcgagc acgcctatca ggtattcctc aatggcgcca aggagaaggc gatgaagatc    1020

atcctctcga acgcaggcgc tgcctga                                        1047
```

<210> SEQ ID NO 56
<211> LENGTH: 348
<212> TYPE: PRT
<213> ORGANISM: Achromobacter xylosoxidans

<400> SEQUENCE: 56

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190
```

```
Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345


<210> SEQ ID NO 57
<211> LENGTH: 39
<212> TYPE: DNA
<213> ORGANISM: artificial sequence
<220> FEATURE:
<223> OTHER INFORMATION: Primer

<400> SEQUENCE: 57

cacacatatt acaatagcta gctgaggatg aaagctctg                            39


<210> SEQ ID NO 58
<211> LENGTH: 39
<212> TYPE: DNA
<213> ORGANISM: artificial sequence
<220> FEATURE:
<223> OTHER INFORMATION: Primer

<400> SEQUENCE: 58

cagagctttc atcctcagct agctattgta atatgtgtg                            39


<210> SEQ ID NO 59
<211> LENGTH: 9491
<212> TYPE: DNA
<213> ORGANISM: artificial sequence
<220> FEATURE:
<223> OTHER INFORMATION: Synthetic construct

<400> SEQUENCE: 59

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accataaatt cccgttttaa gagcttggtg agcgctagga gtcactgcca ggtatcgttt     240

gaacacggca ttagtcaggg aagtcataac acagtccttt cccgcaattt tctttttcta     300

ttactcttgg cctcctctag tacactctat atttttttat gcctcggtaa tgattttcat     360

ttttttttt cccctagcgg atgactcttt ttttttctta gcgattggca ttatcacata     420

atgaattata cattatataa agtaatgtga tttcttcgaa gaatatacta aaaaatgagc     480
```

-continued

```
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
cctttttct ttttgctttt tcttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc atttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggcccccc ctcgaggtcg   2100
acggcgcgcc actggtagag agcgactttg tatgccccaa ttgcgaaacc cgcgatatcc   2160
ttctcgattc tttagtaccc gaccaggaca aggaaaagga ggtcgaaacg tttttgaaga   2220
aacaagagga actacacgga agctctaaag atggcaacca gccagaaact aagaaaatga   2280
agttgatgga tccaactggc accgctggct tgaacaacaa taccagcctt ccaacttctg   2340
taaataacgg cggtacgcca gtgccaccag taccgttacc tttcggtata cctcctttcc   2400
ccatgtttcc aatgcccttc atgcctccaa cggctactat cacaaatcct catcaagctg   2460
acgcaagccc taagaaatga ataacaatac tgacagtact aaataattgc ctacttggct   2520
tcacatacgt tgcatacgtc gatatagata ataatgataa tgacagcagg attatcgtaa   2580
tacgtaatag ttgaaaatct caaaaatgtg tgggtcatta cgtaaataat gataggaatg   2640
ggattcttct atttttcctt tttccattct agcagccgtc gggaaaacgt ggcatcctct   2700
ctttcgggct caattggagt cacgctgccg tgagcatcct ctctttccat atctaacaac   2760
tgagcacgta accaatggaa aagcatgagc ttagcgttgc tccaaaaaag tattggatgg   2820
ttaataccat ttgtctgttc tcttctgact ttgactcctc aaaaaaaaaa aatctacaat   2880
```

-continued

```
caacagatcg cttcaattac gccctcacaa aaactttttt ccttcttctt cgcccacgtt   2940
aaattttatc cctcatgttg tctaacggat ttctgcactt gatttattat aaaaagacaa   3000
agacataata cttctctatc aatttcagtt attgttcttc cttgcgttat tcttctgttc   3060
ttctttttct tttgtcatat ataaccataa ccaagtaata catattcaaa ctagtatgac   3120
tgacaaaaaa actcttaaag acttaagaaa tcgtagttct gtttacgatt caatggttaa   3180
atcacctaat cgtgctatgt tgcgtgcaac tggtatgcaa gatgaagact ttgaaaaacc   3240
tatcgtcggt gtcatttcaa cttgggctga aaacacacct tgtaatatcc acttacatga   3300
ctttggtaaa ctagccaaag tcggtgttaa ggaagctggt gcttggccag ttcagttcgg   3360
aacaatcacg gtttctgatg gaatcgccat gggaacccaa ggaatgcgtt tctccttgac   3420
atctcgtgat attattgcag attctattga agcagccatg ggaggtcata atgcggatgc   3480
ttttgtagcc attggcggtt gtgataaaaa catgcccggt tctgttatcg ctatggctaa   3540
catggatatc ccagccattt ttgcttacgg cggaacaatt gcacctggta atttagacgg   3600
caaagatatc gatttagtct ctgtctttga aggtgtcggc cattggaacc acggcgatat   3660
gaccaaagaa gaagttaaag ctttggaatg taatgcttgt cccggtcctg gaggctgcgg   3720
tggtatgtat actgctaaca caatggcgac agctattgaa gttttgggac ttagccttcc   3780
gggttcatct tctcacccgg ctgaatccgc agaaaagaaa gcagatattg aagaagctgg   3840
tcgcgctgtt gtcaaaatgc tcgaaatggg cttaaaacct tctgacattt taacgcgtga   3900
agcttttgaa gatgctatta ctgtaactat ggctctggga ggttcaacca actcaaccct   3960
tcacctctta gctattgccc atgctgctaa tgtggaattg acacttgatg atttcaatac   4020
tttccaagaa aaagttcctc atttggctga tttgaaacct tctggtcaat atgtattcca   4080
agacctttac aaggtcggag gggtaccagc agttatgaaa tatctcctta aaaatggctt   4140
ccttcatggt gaccgtatca cttgtactgg caaaacagtc gctgaaaatt tgaaggcttt   4200
tgatgattta acacctggtc aaaaggttat tatgccgctt gaaaatccta aacgtgaaga   4260
tggtccgctc attattctcc atggtaactt ggctccagac ggtgccgttg ccaaagtttc   4320
tggtgtaaaa gtgcgtcgtc atgtcggtcc tgctaaggtc tttaattctg aagaagaagc   4380
cattgaagct gtcttgaatg atgatattgt tgatggtgat gttgttgtcg tacgttttgt   4440
aggaccaaag ggcggtcctg gtatgcctga aatgctttcc ctttcatcaa tgattgttgg   4500
taaagggcaa ggtgaaaaag ttgcccttct gacagatggc cgcttctcag gtggtactta   4560
tggtcttgtc gtgggtcata tcgctcctga agcacaagat ggcggtccaa tcgcctacct   4620
gcaaacagga gacatagtca ctattgacca agacactaag gaattacact ttgatatctc   4680
cgatgaagag ttaaaacatc gtcaagagac cattgaattg ccaccgctct attcacgcgg   4740
tatccttggt aaatatgctc acatcgtttc gtctgcttct aggggagccg taacagactt   4800
ttggaagcct gaagaaactg gcaaaaaatg ttgtcctggt tgctgtggtt aagcggccgc   4860
gttaattcaa attaattgat atagtttttt aatgagtatt gaatctgttt agaaataatg   4920
gaatattatt tttatttatt tatttatatt attggtcggc tcttttcttc tgaaggtcaa   4980
tgacaaaatg atatgaagga aataatgatt tctaaaattt tacaacgtaa gatatttttta  5040
caaaagccta gctcatcttt tgtcatgcac tattttactc acgcttgaaa ttaacggcca   5100
gtccactgcg gagtcatttc aaagtcatcc taatcgatct atcgtttttg atagctcatt   5160
ttggagttcg cgattgtctt ctgttattca caactgtttt aatttttatt tcattctgga   5220
actcttcgag ttctttgtaa agtctttcat agtagcttac tttatcctcc aacatattta   5280
```

-continued

```
acttcatgtc aatttcggct cttaaatttt ccacatcatc aagttcaaca tcatctttta   5340
acttgaattt attctctagc tcttccaacc aagcctcatt gctccttgat ttactggtga   5400
aaagtgatac actttgcgcg caatccaggt caaaactttc ctgcaaagaa ttcaccaatt   5460
tctcgacatc atagtacaat ttgttttgtt ctcccatcac aatttaatat acctgatgga   5520
ttcttatgaa gcgctgggta atggacgtgt cactctactt cgcctttttc cctactcctt   5580
ttagtacgga agacaatgct aataaataag agggtaataa taatattatt aatcggcaaa   5640
aaagattaaa cgccaagcgt ttaattatca gaaagcaaac gtcgtaccaa tccttgaatg   5700
cttcccaatt gtatattaag agtcatcaca gcaacatatt cttgttatta aattaattat   5760
tattgatttt tgatattgta taaaaaaacc aaatatgtat aaaaaaagtg aataaaaaat   5820
accaagtatg gagaaatata ttagaagtct atacgttaaa ccaccgcggt ggagctccag   5880
cttttgttcc ctttagtgag ggttaattgc gcgcttggcg taatcatggt catagctgtt   5940
tcctgtgtga aattgttatc cgctcacaat tccacacaac ataggagccg gaagcataaa   6000
gtgtaaagcc tggggtgcct aatgagtgag gtaactcaca ttaattgcgt tgcgctcact   6060
gcccgctttc cagtcgggaa acctgtcgtg ccagctgcat taatgaatcg gccaacgcgc   6120
ggggagaggc ggtttgcgta ttgggcgctc ttccgcttcc tcgctcactg actcgctgcg   6180
ctcggtcgtt cggctgcggc gagcggtatc agctcactca aaggcggtaa tacggttatc   6240
cacagaatca ggggataacg caggaaagaa catgtgagca aaaggccagc aaaaggccag   6300
gaaccgtaaa aaggccgcgt tgctggcgtt tttccatagg ctccgccccc ctgacgagca   6360
tcacaaaaat cgacgctcaa gtcagaggtg gcgaaacccg acaggactat aaagatacca   6420
ggcgtttccc cctggaagct ccctcgtgcg ctctcctgtt ccgaccctgc cgcttaccgg   6480
atacctgtcc gcctttctcc cttcgggaag cgtggcgctt tctcatagct cacgctgtag   6540
gtatctcagt tcggtgtagg tcgttcgctc caagctgggc tgtgtgcacg aaccccccgt   6600
tcagcccgac cgctgcgcct tatccggtaa ctatcgtctt gagtccaacc cggtaagaca   6660
cgacttatcg ccactggcag cagccactgg taacaggatt agcagagcga ggtatgtagg   6720
cggtgctaca gagttcttga agtggtggcc taactacggc tacactagaa ggacagtatt   6780
tggtatctgc gctctgctga agccagttac cttcggaaaa agagttggta gctcttgatc   6840
cggcaaacaa accaccgctg gtagcggtgg tttttttgtt tgcaagcagc agattacgcg   6900
cagaaaaaaa ggatctcaag aagatccttt gatcttttct acggggtctg acgctcagtg   6960
gaacgaaaac tcacgttaag ggattttggt catgagatta tcaaaaagga tcttcaccta   7020
gatcctttta aattaaaaat gaagttttaa atcaatctaa agtatatatg agtaaacttg   7080
gtctgacagt taccaatgct taatcagtga ggcacctatc tcagcgatct gtctatttcg   7140
ttcatccata gttgcctgac tccccgtcgt gtagataact acgatacggg agggcttacc   7200
atctggcccc agtgctgcaa tgataccgcg agacccacgc tcaccggctc cagatttatc   7260
agcaataaac cagccagccg gaagggccga gcgcagaagt ggtcctgcaa ctttatccgc   7320
ctccatccag tctattaatt gttgccggga agctagagta agtagttcgc cagttaatag   7380
tttgcgcaac gttgttgcca ttgctacagg catcgtggtg tcacgctcgt cgtttggtat   7440
ggcttcattc agctccggtt cccaacgatc aaggcgagtt acatgatccc ccatgttgtg   7500
caaaaaagcg gttagctcct tcggtcctcc gatcgttgtc agaagtaagt tggccgcagt   7560
gttatcactc atggttatgg cagcactgca taattctctt actgtcatgc catccgtaag   7620
atgcttttct gtgactggtg agtactcaac caagtcattc tgagaatagt gtatgcggcg   7680
```

accgagttgc tcttgcccgg cgtcaatacg ggataatacc gcgccacata gcagaacttt 7740
aaaagtgctc atcattggaa aacgttcttc ggggcgaaaa ctctcaagga tcttaccgct 7800
gttgagatcc agttcgatgt aacccactcg tgcacccaac tgatcttcag catcttttac 7860
tttcaccagc gtttctgggt gagcaaaaac aggaaggcaa aatgccgcaa aaaagggaat 7920
aagggcgaca cggaaatgtt gaatactcat actcttcctt tttcaatatt attgaagcat 7980
ttatcagggt tattgtctca tgagcggata catatttgaa tgtatttaga aaaataaaca 8040
aataggggtt ccgcgcacat ttccccgaaa agtgccacct gaacgaagca tctgtgcttc 8100
attttgtaga acaaaaatgc aacgcgagag cgctaatttt tcaaacaaag aatctgagct 8160
gcatttttac agaacagaaa tgcaacgcga aagcgctatt ttaccaacga agaatctgtg 8220
cttcattttt gtaaaacaaa aatgcaacgc gagagcgcta atttttcaaa caaagaatct 8280
gagctgcatt tttacagaac agaaatgcaa cgcgagagcg ctattttacc aacaaagaat 8340
ctatacttct tttttgttct acaaaaatgc atcccgagag cgctattttt ctaacaaagc 8400
atcttagatt actttttttc tcctttgtgc gctctataat gcagtctctt gataactttt 8460
tgcactgtag gtccgttaag gttagaagaa ggctactttg gtgtctattt tctcttccat 8520
aaaaaaagcc tgactccact tcccgcgttt actgattact agcgaagctg cgggtgcatt 8580
ttttcaagat aaaggcatcc ccgattatat tctataccga tgtggattgc gcatactttg 8640
tgaacagaaa gtgatagcgt tgatgattct tcattggtca gaaaattatg aacggtttct 8700
tctattttgt ctctatatac tacgtatagg aaatgtttac attttcgtat tgttttcgat 8760
tcactctatg aatagttctt actacaattt ttttgtctaa agagtaatac tagagataaa 8820
cataaaaaat gtagaggtcg agtttagatg caagttcaag gagcgaaagg tggatgggta 8880
ggttatatag ggatatagca cagagatata tagcaaagag atacttttga gcaatgtttg 8940
tggaagcggt attcgcaata ttttagtagc tcgttacagt ccggtgcgtt tttggttttt 9000
tgaaagtgcg tcttcagagc gcttttggtt ttcaaaagcg ctctgaagtt cctatacttt 9060
ctagagaata ggaacttcgg aataggaact tcaaagcgtt tccgaaaacg agcgcttccg 9120
aaaatgcaac gcgagctgcg cacatacagc tcactgttca cgtcgcacct atatctgcgt 9180
gttgcctgta tatatatata catgagaaga acggcatagt gcgtgtttat gcttaaatgc 9240
gtacttatat gcgtctattt atgtaggatg aaaggtagtc tagtacctcc tgtgatatta 9300
tcccattcca tgcggggtat cgtatgcttc cttcagcact accctttagc tgttctatat 9360
gctgccactc ctcaattgga ttagtctcat ccttcaatgc tatcatttcc tttgatattg 9420
gatcatctaa gaaaccatta ttatcatgac attaacctat aaaaataggc gtatcacgag 9480
gccctttcgt c 9491

<210> SEQ ID NO 60
<211> LENGTH: 1000
<212> TYPE: DNA
<213> ORGANISM: Saccharomyces cerevisiae

<400> SEQUENCE: 60
gttaattcaa attaattgat atagtttttt aatgagtatt gaatctgttt agaaataatg 60
gaatattatt tttatttatt tatttatatt attggtcggc tcttttcttc tgaaggtcaa 120
tgacaaaatg atatgaagga aataatgatt tctaaaattt tacaacgtaa gatattttta 180
caaaagccta gctcatcttt tgtcatgcac tattttactc acgcttgaaa ttaacggcca 240
gtccactgcg gagtcatttc aaagtcatcc taatcgatct atcgtttttg atagctcatt 300

-continued

```
ttggagttcg cgattgtctt ctgttattca caactgtttt aatttttatt tcattctgga    360

actcttcgag ttctttgtaa agtctttcat agtagcttac tttatcctcc aacatattta    420

acttcatgtc aatttcggct cttaaatttt ccacatcatc aagttcaaca tcatctttta    480

acttgaattt attctctagc tcttccaacc aagcctcatt gctccttgat ttactggtga    540

aaagtgatac actttgcgcg caatccaggt caaaactttc ctgcaaagaa ttcaccaatt    600

tctcgacatc atagtacaat ttgttttgtt ctcccatcac aatttaatat acctgatgga    660

ttcttatgaa gcgctgggta atggacgtgt cactctactt cgcctttttc cctactcctt    720

ttagtacgga agacaatgct aataaataag agggtaataa taatattatt aatcggcaaa    780

aaagattaaa cgccaagcgt ttaattatca gaaagcaaac gtcgtaccaa tccttgaatg    840

cttcccaatt gtatattaag agtcatcaca gcaacatatt cttgttatta aattaattat    900

tattgatttt tgatattgta taaaaaaacc aaatatgtat aaaaaaagtg aataaaaaat    960

accaagtatg gagaaatata ttagaagtct atacgttaaa                         1000
```

<210> SEQ ID NO 61
<211> LENGTH: 244
<212> TYPE: DNA
<213> ORGANISM: Saccharomyces cerevisiae

<400> SEQUENCE: 61

```
attaaagcct tcgagcgtcc caaaaccttc tcaagcaagg ttttcagtat aatgttacat     60

gcgtacacgc gtctgtacag aaaaaaaaga aaaatttgaa atataaataa cgttcttaat    120

actaacataa ctataaaaaa ataaataggg acctagactt caggttgtct aactccttcc    180

ttttcggtta gagcggatgt ggggggaggg cgtgaatgta agcgtgacat aactaattac    240

atga                                                                244
```

<210> SEQ ID NO 62
<211> LENGTH: 1713
<212> TYPE: DNA
<213> ORGANISM: Streptococcus mutans

<400> SEQUENCE: 62

```
atgactgaca aaaaaactct taaagactta agaaatcgta gttctgttta cgattcaatg     60

gttaaatcac ctaatcgtgc tatgttgcgt gcaactggta tgcaagatga agactttgaa    120

aaacctatcg tcggtgtcat ttcaacttgg gctgaaaaca caccttgtaa tatccactta    180

catgactttg gtaaactagc caaagtcggt gttaaggaag ctggtgcttg gccagttcag    240

ttcggaacaa tcacggtttc tgatggaatc gccatgggaa cccaaggaat gcgtttctcc    300

ttgacatctc gtgatattat tgcagattct attgaagcag ccatgggagg tcataatgcg    360

gatgcttttg tagccattgg cggttgtgat aaaaacatgc ccggttctgt tatcgctatg    420

gctaacatgg atatcccagc catttttgct tacggcggaa caattgcacc tggtaattta    480

gacggcaaag atatcgattt agtctctgtc tttgaaggtg tcggccattg gaaccacggc    540

gatatgacca aagaagaagt taaagctttg gaatgtaatg cttgtcccgg tcctggaggc    600

tgcggtggta tgtatactgc taacacaatg gcgacagcta ttgaagtttt gggacttagc    660

cttccgggtt catcttctca cccggctgaa tccgcagaaa agaaagcaga tattgaagaa    720

gctggtcgcg ctgttgtcaa aatgctcgaa atgggcttaa aaccttctga cattttaacg    780

cgtgaagctt ttgaagatgc tattactgta actatggctc tgggaggttc aaccaactca    840

acccttcacc tcttagctat tgcccatgct gctaatgtgg aattgacact tgatgatttc    900
```

-continued

```
aatactttcc aagaaaaagt tcctcatttg gctgatttga aaccttctgg tcaatatgta    960

ttccaagacc tttacaaggt cggaggggta ccagcagtta tgaaatatct ccttaaaaat   1020

ggcttccttc atggtgaccg tatcacttgt actggcaaaa cagtcgctga aaatttgaag   1080

gcttttgatg atttaacacc tggtcaaaag gttattatgc cgcttgaaaa tcctaaacgt   1140

gaagatggtc cgctcattat tctccatggt aacttggctc cagacggtgc cgttgccaaa   1200

gtttctggtg taaaagtgcg tcgtcatgtc ggtcctgcta aggtctttaa ttctgaagaa   1260

gaagccattg aagctgtctt gaatgatgat attgttgatg gtgatgttgt tgtcgtacgt   1320

tttgtaggac caaagggcgg tcctggtatg cctgaaatgc tttccctttc atcaatgatt   1380

gttggtaaag ggcaaggtga aaaagttgcc cttctgacag atggccgctt ctcaggtggt   1440

acttatggtc ttgtcgtggg tcatatcgct cctgaagcac aagatggcgg tccaatcgcc   1500

tacctgcaaa caggagacat agtcactatt gaccaagaca ctaaggaatt acactttgat   1560

atctccgatg aagagttaaa acatcgtcaa gagaccattg aattgccacc gctctattca   1620

cgcggtatcc ttggtaaata tgctcacatc gtttcgtctg cttctagggg agccgtaaca   1680

gacttttgga agcctgaaga aactggcaaa aaa                                1713
```

<210> SEQ ID NO 63
<211> LENGTH: 571
<212> TYPE: PRT
<213> ORGANISM: Streptococcus mutans

<400> SEQUENCE: 63

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240
```

```
Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570
```

<210> SEQ ID NO 64
<211> LENGTH: 2145
<212> TYPE: DNA
<213> ORGANISM: artificial sequence
<220> FEATURE:
<223> OTHER INFORMATION: Synthetic construct

<400> SEQUENCE: 64

```
gcatgcttgc atttagtcgt gcaatgtatg actttaagat ttgtgagcag gaagaaaagg      60

gagaatcttc taacgataaa cccttgaaaa actgggtaga ctacgctatg ttgagttgct     120

acgcaggctg cacaattaca cgagaatgct cccgcctagg atttaaggct aagggacgtg     180
```

```
caatgcagac gacagatcta aatgaccgtg tcggtgaagt gttcgccaaa cttttcggtt    240
aacacatgca gtgatgcacg cgcgatggtg ctaagttaca tatatatata tatatatata    300
tatagccata gtgatgtcta agtaaccttt atggtatatt tcttaatgtg gaaagatact    360
agcgcgcgca cccacacaca agcttcgtct tttcttgaag aaaagaggaa gctcgctaaa    420
tgggattcca ctttccgttc cctgccagct gatggaaaaa ggttagtgga acgatgaaga    480
ataaaaagag agatccactg aggtgaaatt tcagctgaca gcgagtttca tgatcgtgat    540
gaacaatggt aacgagttgt ggctgttgcc agggagggtg gttctcaact tttaatgtat    600
ggccaaatcg ctacttgggt ttgttatata acaaagaaga aataatgaac tgattctctt    660
cctccttctt gtcctttctt aattctgttg taattacctt cctttgtaat tttttttgta    720
attattcttc ttaataatcc aaacaaacac acatattaca atagctagct gaggatgaag    780
gcattagttt atcatgggga tcacaaaatt tcgttagaag acaaaccaaa acccactctg    840
cagaaaccaa cagacgttgt ggttagggtg ttgaaaacaa caatttgcgg tactgacttg    900
ggaatataca aaggtaagaa tcctgaagtg gcagatggca gaatcctggg tcatgagggc    960
gttggcgtca ttgaagaagt gggcgaatcc gtgacacaat tcaaaaaggg ggataaagtt   1020
ttaatctcct gcgttactag ctgtggatcg tgtgattatt gcaagaagca actgtattca   1080
cactgtagag acggtggctg gattttaggt tacatgatcg acggtgtcca agccgaatac   1140
gtcagaatac cacatgctga caattcattg tataagatcc cgcaaactat cgatgatgaa   1200
attgcagtac tactgtccga tattttacct actggacatg aaattggtgt tcaatatggt   1260
aacgttcaac caggcgatgc tgtagcaatt gtaggagcag gtcctgttgg aatgtcagtt   1320
ttgttaactg ctcaatttta ctcgcctagt accattattg ttatcgacat ggacgaaaac   1380
cgtttacaat tagcgaagga gcttggggcc acacacacta ttaactccgg tactgaaaat   1440
gttgtcgaag ctgtgcatcg tatagcagcc gaaggagtgg atgtagcaat agaagctgtt   1500
ggtatacccg caacctggga catctgtcag gaaattgtaa aacccggcgc tcatattgcc   1560
aacgtgggag ttcatggtgt taaggtggac tttgaaattc aaaagttgtg gattaagaat   1620
ctaaccatca ccactggttt ggttaacact aatactaccc caatgttgat gaaggtagcc   1680
tctactgata aattgccttt aaagaaaatg attactcaca ggtttgagtt agctgaaatc   1740
gaacacgcat atcaggtttt cttgaatggc gctaaagaaa aagctatgaa gattattcta   1800
tctaatgcag gtgccgccta attaattaag agtaagcgaa tttcttatga tttatgattt   1860
ttattattaa ataagttata aaaaaaataa gtgtatacaa attttaaagt gactcttagg   1920
ttttaaaacg aaaattctta ttcttgagta actctttcct gtaggtcagg ttgctttctc   1980
aggtatagca tgaggtcgct cttattgacc acacctctac cggcatgccg agcaaatgcc   2040
tgcaaatcgc tccccatttc acccaattgt agatatgcta actccagcaa tgagttgatg   2100
aatctcggtg tgtattttat gtcctcagag gacaacacct gtggt                   2145
```

<210> SEQ ID NO 65
<211> LENGTH: 4280
<212> TYPE: DNA
<213> ORGANISM: artificial sequence
<220> FEATURE:
<223> OTHER INFORMATION: Synthetic construct

<400> SEQUENCE: 65

```
ggggatcctc tagagtcgac ctgcaggcat gcaagcttgg cgtaatcatg gtcatagctg     60
tttcctgtgt gaaattgtta tccgctcaca attccacaca acatacgagc cggaagcata    120
```

-continued

```
aagtgtaaag cctggggtgc ctaatgagtg agctaactca cattaattgc gttgcgctca    180
ctgcccgctt tccagtcggg aaacctgtcg tgccagctgc attaatgaat cggccaacgc    240
gcggggagag gcggtttgcg tattgggcgc tcttccgctt cctcgctcac tgactcgctg    300
cgctcggtcg ttcggctgcg gcgagcggta tcagctcact caaaggcggt aatacggtta    360
tccacagaat caggggataa cgcaggaaag aacatgtgag caaaaggcca gcaaaaggcc    420
aggaaccgta aaaaggccgc gttgctggcg tttttccata ggctccgccc ccctgacgag    480
catcacaaaa atcgacgctc aagtcagagg tggcgaaacc cgacaggact ataaagatac    540
caggcgtttc cccctggaag ctccctcgtg cgctctcctg ttccgaccct gccgcttacc    600
ggatacctgt ccgcctttct cccttcggga agcgtggcgc tttctcatag ctcacgctgt    660
aggtatctca gttcggtgta ggtcgttcgc tccaagctgg gctgtgtgca cgaacccccc    720
gttcagcccg accgctgcgc cttatccggt aactatcgtc ttgagtccaa cccggtaaga    780
cacgacttat cgccactggc agcagccact ggtaacagga ttagcagagc gaggtatgta    840
ggcggtgcta cagagttctt gaagtggtgg cctaactacg gctacactag aaggacagta    900
tttggtatct gcgctctgct gaagccagtt accttcggaa aaagagttgg tagctcttga    960
tccggcaaac aaaccaccgc tggtagcggt ggtttttttg tttgcaagca gcagattacg   1020
cgcagaaaaa aaggatctca agaagatcct ttgatctttt ctacggggtc tgacgctcag   1080
tggaacgaaa actcacgtta agggattttg gtcatgagat tatcaaaaag gatcttcacc   1140
tagatccttt taaattaaaa atgaagtttt aaatcaatct aaagtatata tgagtaaact   1200
tggtctgaca gttaccaatg cttaatcagt gaggcaccta tctcagcgat ctgtctattt   1260
cgttcatcca tagttgcctg actccccgtc gtgtagataa ctacgatacg ggagggctta   1320
ccatctggcc ccagtgctgc aatgataccg cgagacccac gctcaccggc tccagattta   1380
tcagcaataa accagccagc cggaagggcc gagcgcagaa gtggtcctgc aactttatcc   1440
gcctccatcc agtctattaa ttgttgccgg gaagctagag taagtagttc gccagttaat   1500
agtttgcgca acgttgttgc cattgctaca ggcatcgtgg tgtcacgctc gtcgtttggt   1560
atggcttcat tcagctccgg ttcccaacga tcaaggcgag ttacatgatc ccccatgttg   1620
tgcaaaaaag cggttagctc cttcggtcct ccgatcgttg tcagaagtaa gttggccgca   1680
gtgttatcac tcatggttat ggcagcactg cataattctc ttactgtcat gccatccgta   1740
agatgctttt ctgtgactgg tgagtactca accaagtcat tctgagaata gtgtatgcgg   1800
cgaccgagtt gctcttgccc ggcgtcaata cgggataata ccgcgccaca tagcagaact   1860
ttaaaagtgc tcatcattgg aaaacgttct tcggggcgaa aactctcaag gatcttaccg   1920
ctgttgagat ccagttcgat gtaacccact cgtgcaccca actgatcttc agcatctttt   1980
actttcacca gcgtttctgg gtgagcaaaa acaggaaggc aaaatgccgc aaaaaaggga   2040
ataagggcga cacggaaatg ttgaatactc atactcttcc tttttcaata ttattgaagc   2100
atttatcagg gttattgtct catgagcgga tacatatttg aatgtattta gaaaaataaa   2160
caaatagggg ttccgcgcac atttccccga aaagtgccac ctgacgtcta agaaaccatt   2220
attatcatga cattaaccta taaaaatagg cgtatcacga ggccctttcg tctcgcgcgt   2280
ttcggtgatg acggtgaaaa cctctgacac atgcagctcc cggagacggt cacagcttgt   2340
ctgtaagcgg atgccgggag cagacaagcc cgtcagggcg cgtcagcggg tgttggcggg   2400
tgtcggggct ggcttaacta tgcggcatca gagcagattg tactgagagt gcaccatatg   2460
cggtgtgaaa taccgcacag atgcgtaagg agaaaatacc gcatcaggcg ccattcgcca   2520
```

ttcaggctgc gcaactgttg ggaagggcga tcggtgcggg cctcttcgct attacgccag 2580
ctggcgaaag ggggatgtgc tgcaaggcga ttaagttggg taacgccagg gttttcccag 2640
tcacgacgtt gtaaaacgac ggccagtgaa ttcgagctcg gtacccccgg ctctgagaca 2700
gtagtaggtt agtcatcgct ctaccgacgc gcaggaaaag aaagaagcat tgcggattac 2760
gtattctaat gttcagcccg cggaacgcca gcaaatcacc acccatgcgc atgatactga 2820
gtcttgtaca cgctgggctt ccagtgtact gagagtgcac cataccacag cttttcaatt 2880
caattcatca tttttttttt attctttttt ttgatttcgg tttctttgaa atttttttga 2940
ttcggtaatc tccgaacaga aggaagaacg aaggaaggag cacagactta gattggtata 3000
tatacgcata tgtagtgttg aagaaacatg aaattgccca gtattcttaa cccaactgca 3060
cagaacaaaa acctgcagga aacgaagata aatcatgtcg aaagctacat ataaggaacg 3120
tgctgctact catcctagtc ctgttgctgc caagctattt aatatcatgc acgaaaagca 3180
aacaaacttg tgtgcttcat tggatgttcg taccaccaag gaattactgg agttagttga 3240
agcattaggt cccaaaattt gtttactaaa aacacatgtg gatatcttga ctgatttttc 3300
catggagggc acagttaagc cgctaaaggc attatccgcc aagtacaatt ttttactctt 3360
cgaagacaga aaatttgctg acattggtaa tacagtcaaa ttgcagtact ctgcgggtgt 3420
atacagaata gcagaatggg cagacattac gaatgcacac ggtgtggtgg gcccaggtat 3480
tgttagcggt ttgaagcagg cggcagaaga agtaacaaag gaacctagag gccttttgat 3540
gttagcagaa ttgtcatgca agggctccct atctactgga gaatatacta agggtactgt 3600
tgacattgcg aagagcgaca aagattttgt tatcggcttt attgctcaaa gagacatggg 3660
tggaagagat gaaggttacg attggttgat tatgacaccc ggtgtgggtt tagatgacaa 3720
gggagacgca ttgggtcaac agtatagaac cgtggatgat gtggtctcta caggatctga 3780
cattattatt gttggaagag gactatttgc aaagggaagg gatgctaagg tagagggtga 3840
acgttacaga aaagcaggct gggaagcata tttgagaaga tgcggccagc aaaactaaaa 3900
aactgtatta taagtaaatg catgtatact aaactcacaa attagagctt caatttaatt 3960
atatcagtta ttaccctatg cggtgtgaaa taccgcacag atgcgtaagg agaaaatacc 4020
gcatcaggaa attgtaaacg ttaatatttt gttaaaattc gcgttaaatt tttgttaaat 4080
cagctcattt tttaaccaat aggccgaaat cggcaaaatc ttcagcccgc ggaacgccag 4140
caaatcacca cccatgcgca tgatactgag tcttgtacac gctgggcttc cagtgatgat 4200
acaacgagtt agccaaggtg agcacggatg tctaaattag aattacgttt taatatcttt 4260
ttttccatat ctagggctag 4280

<210> SEQ ID NO 66
<211> LENGTH: 30
<212> TYPE: DNA
<213> ORGANISM: artificial sequence
<220> FEATURE:
<223> OTHER INFORMATION: Primer

<400> SEQUENCE: 66
gcatgcttgc atttagtcgt gcaatgtatg 30

<210> SEQ ID NO 67
<211> LENGTH: 54
<212> TYPE: DNA
<213> ORGANISM: artificial sequence
<220> FEATURE:
<223> OTHER INFORMATION: Primer

<400> SEQUENCE: 67
gaacattaga atacgtaatc cgcaatgcac tagtaccaca ggtgttgtcc tctg 54

<210> SEQ ID NO 68
<211> LENGTH: 54
<212> TYPE: DNA
<213> ORGANISM: artificial sequence
<220> FEATURE:
<223> OTHER INFORMATION: Primer

<400> SEQUENCE: 68
cagaggacaa cacctgtggt actagtgcat tgcggattac gtattctaat gttc 54

<210> SEQ ID NO 69
<211> LENGTH: 28
<212> TYPE: DNA
<213> ORGANISM: artificial sequence
<220> FEATURE:
<223> OTHER INFORMATION: Primer

<400> SEQUENCE: 69
caccttggct aactcgttgt atcatcac 28

<210> SEQ ID NO 70
<211> LENGTH: 100
<212> TYPE: DNA
<213> ORGANISM: artificial sequence
<220> FEATURE:
<223> OTHER INFORMATION: Primer

<400> SEQUENCE: 70
ttttaagccg aatgagtgac agaaaaagcc cacaacttat caagtgatat tgaacaaagg 60
gcgaaacttc gcatgcttgc atttagtcgt gcaatgtatg 100

<210> SEQ ID NO 71
<211> LENGTH: 98
<212> TYPE: DNA
<213> ORGANISM: artificial sequence
<220> FEATURE:
<223> OTHER INFORMATION: Primer

<400> SEQUENCE: 71
cccaattggt aaatattcaa caagagacgc gcagtacgta acatgcgaat tgcgtaattc 60
acggcgataa caccttggct aactcgttgt atcatcac 98

<210> SEQ ID NO 72
<211> LENGTH: 29
<212> TYPE: DNA
<213> ORGANISM: artificial sequence
<220> FEATURE:
<223> OTHER INFORMATION: Primer

<400> SEQUENCE: 72
caaaagccca tgtcccacac caaaggatg 29

<210> SEQ ID NO 73
<211> LENGTH: 26
<212> TYPE: DNA
<213> ORGANISM: artificial sequence
<220> FEATURE:
<223> OTHER INFORMATION: Primer

<400> SEQUENCE: 73
caccatcgcg cgtgcatcac tgcatg 26

<210> SEQ ID NO 74
<211> LENGTH: 28
<212> TYPE: DNA
<213> ORGANISM: artificial sequence
<220> FEATURE:
<223> OTHER INFORMATION: Primer

<400> SEQUENCE: 74
tcggtttttg caatatgacc tgtgggcc 28

<210> SEQ ID NO 75
<211> LENGTH: 22
<212> TYPE: DNA
<213> ORGANISM: artificial sequence
<220> FEATURE:
<223> OTHER INFORMATION: Primer

<400> SEQUENCE: 75
gagaagatgc ggccagcaaa ac 22

<210> SEQ ID NO 76
<211> LENGTH: 2745
<212> TYPE: DNA
<213> ORGANISM: artificial sequence
<220> FEATURE:
<223> OTHER INFORMATION: Synthetic construct

<400> SEQUENCE: 76
atgactgaca aaaaaactct taaagactta agaaatcgta gttctgttta cgattcaatg 60
gttaaatcac ctaatcgtgc tatgttgcgt gcaactggta tgcaagatga agactttgaa 120
aaacctatcg tcggtgtcat ttcaacttgg gctgaaaaca caccttgtaa tatccactta 180
catgactttg gtaaactagc caaagtcggt gttaaggaag ctggtgcttg gccagttcag 240
ttcggaacaa tcacggtttc tgatggaatc gccatgggaa cccaaggaat gcgtttctcc 300
ttgacatctc gtgatattat tgcagattct attgaagcag ccatgggagg tcataatgcg 360
gatgcttttg tagccattgg cggttgtgat aaaaacatgc ccggttctgt tatcgctatg 420
gctaacatgg atatcccagc catttttgct tacggcggaa caattgcacc tggtaattta 480
gacggcaaag atatcgattt agtctctgtc tttgaaggtg tcggccattg gaaccacggc 540
gatatgacca aagaagaagt taaagctttg gaatgtaatg cttgtcccgg tcctggaggc 600
tgcggtggta tgtatactgc taacacaatg gcgacagcta ttgaagtttt gggacttagc 660
cttccgggtt catcttctca cccggctgaa tccgcagaaa agaaagcaga tattgaagaa 720
gctggtcgcg ctgttgtcaa aatgctcgaa atgggcttaa aaccttctga cattttaacg 780
cgtgaagctt ttgaagatgc tattactgta actatggctc tgggaggttc aaccaactca 840
acccttcacc tcttagctat tgcccatgct gctaatgtgg aattgacact tgatgatttc 900
aatactttcc aagaaaaagt tcctcatttg gctgatttga aaccttctgg tcaatatgta 960
ttccaagacc tttacaaggt cggaggggta ccagcagtta tgaaatatct ccttaaaaat 1020
ggcttccttc atggtgaccg tatcacttgt actggcaaaa cagtcgctga aaatttgaag 1080
gcttttgatg atttaacacc tggtcaaaag gttattatgc cgcttgaaaa tcctaaacgt 1140
gaagatggtc cgctcattat tctccatggt aacttggctc cagacggtgc cgttgccaaa 1200
gtttctggtg taaaagtgcg tcgtcatgtc ggtcctgcta aggtctttaa ttctgaagaa 1260
gaagccattg aagctgtctt gaatgatgat attgttgatg gtgatgttgt tgtcgtacgt 1320
tttgtaggac caaagggcgg tcctggtatg cctgaaatgc tttccctttc atcaatgatt 1380

-continued

```
gttggtaaag ggcaaggtga aaaagttgcc cttctgacag atggccgctt ctcaggtggt   1440

acttatggtc ttgtcgtggg tcatatcgct cctgaagcac aagatggcgg tccaatcgcc   1500

tacctgcaaa caggagacat agtcactatt gaccaagaca ctaaggaatt acactttgat   1560

atctccgatg aagagttaaa acatcgtcaa gagaccattg aattgccacc gctctattca   1620

cgcggtatcc ttggtaaata tgctcacatc gtttcgtctg cttctagggg agccgtaaca   1680

gacttttgga agcctgaaga aactggcaaa aaatgttgtc ctggttgctg tggttaagcg   1740

gccgcgttaa ttcaaattaa ttgatatagt tttttaatga gtattgaatc tgtttagaaa   1800

taatggaata ttatttttat ttatttattt atattattgg tcggctcttt tcttctgaag   1860

gtcaatgaca aaatgatatg aaggaaataa tgatttctaa aattttacaa cgtaagatat   1920

ttttacaaaa gcctagctca tcttttgtca tgcactattt tactcacgct tgaaattaac   1980

ggccagtcca ctgcggagtc atttcaaagt catcctaatc gatctatcgt ttttgatagc   2040

tcattttgga gttcgcgatt gtcttctgtt attcacaact gttttaattt ttatttcatt   2100

ctggaactct tcgagttctt tgtaaagtct ttcatagtag cttactttat cctccaacat   2160

atttaacttc atgtcaattt cggctcttaa attttccaca tcatcaagtt caacatcatc   2220

ttttaacttg aatttattct ctagctcttc caaccaagcc tcattgctcc ttgatttact   2280

ggtgaaaagt gatacacttt gcgcgcaatc caggtcaaaa ctttcctgca aagaattcac   2340

caatttctcg acatcatagt acaatttgtt ttgttctccc atcacaattt aatatacctg   2400

atggattctt atgaagcgct gggtaatgga cgtgtcactc tacttcgcct ttttccctac   2460

tccttttagt acggaagaca atgctaataa ataagagggt aataataata ttattaatcg   2520

gcaaaaaaga ttaaacgcca agcgtttaat tatcagaaag caaacgtcgt accaatcctt   2580

gaatgcttcc caattgtata ttaagagtca tcacagcaac atattcttgt tattaaatta   2640

attattattg atttttgata ttgtataaaa aaaccaaata tgtataaaaa aagtgaataa   2700

aaaataccaa gtatggagaa atatattaga agtctatacg ttaaa                   2745
```

<210> SEQ ID NO 77
<211> LENGTH: 99
<212> TYPE: DNA
<213> ORGANISM: artificial sequence
<220> FEATURE:
<223> OTHER INFORMATION: Primer

<400> SEQUENCE: 77

```
tcctttctca attattattt tctactcata acctcacgca aaataacaca gtcaaatcaa     60

tcaaagtatg actgacaaaa aaactcttaa agacttaag                            99
```

<210> SEQ ID NO 78
<211> LENGTH: 77
<212> TYPE: DNA
<213> ORGANISM: artificial sequence
<220> FEATURE:
<223> OTHER INFORMATION: Primer

<400> SEQUENCE: 78

```
gaacattaga atacgtaatc cgcaatgctt ctttcttttc cgtttaacgt atagacttct     60

aatatatttc tccatac                                                    77
```

<210> SEQ ID NO 79
<211> LENGTH: 45
<212> TYPE: DNA
<213> ORGANISM: artificial sequence
<220> FEATURE:

<223> OTHER INFORMATION: Primer

<400> SEQUENCE: 79
aaacggaaaa gaaagaagca ttgcggatta cgtattctaa tgttc 45

<210> SEQ ID NO 80
<211> LENGTH: 88
<212> TYPE: DNA
<213> ORGANISM: artificial sequence
<220> FEATURE:
<223> OTHER INFORMATION: Primer

<400> SEQUENCE: 80
tatttttcgt tacataaaaa tgcttataaa actttaacta ataattagag attaaatcgc 60
caccttggct aactcgttgt atcatcac 88

<210> SEQ ID NO 81
<211> LENGTH: 2347
<212> TYPE: DNA
<213> ORGANISM: artificial sequence
<220> FEATURE:
<223> OTHER INFORMATION: Synthetic construct

<400> SEQUENCE: 81
gcattgcgga ttacgtattc taatgttcag gtgctggaag aagagctgct taaccgccgc 60
gcccagggtg aagatccacg ctactttacc ctgcgtcgtc tggatttcgg cggctgtcgt 120
ctttcgctgg caacgccggt tgatgaagcc tgggacggtc cgctctcctt aaacggtaaa 180
cgtatcgcca cctcttatcc tcacctgctc aagcgttatc tcgaccagaa aggcatctct 240
tttaaatcct gcttactgaa cggttctgtt gaagtcgccc cgcgtgccgg actggcggat 300
gcgatttgcg atctggtttc caccggtgcc acgctggaag ctaacggcct gcgcgaagtc 360
gaagttatct atcgctcgaa agcctgcctg attcaacgcg atggcgaaat ggaagaatcc 420
aaacagcaac tgatcgacaa actgctgacc cgtattcagg gtgtgatcca ggcgcgcgaa 480
tcaaaataca tcatgatgca cgcaccgacc gaacgtctgg atgaagtcat ggtacctact 540
gagagtgcac cataccacag cttttcaatt caattcatca tttttttttt attctttttt 600
ttgatttcgg tttctttgaa attttttttga ttcggtaatc tccgaacaga aggaagaacg 660
aaggaaggag cacagactta gattggtata tatacgcata tgtagtgttg aagaaacatg 720
aaattgccca gtattcttaa cccaactgca cagaacaaaa acctgcagga aacgaagata 780
aatcatgtcg aaagctacat ataaggaacg tgctgctact catcctagtc ctgttgctgc 840
caagctattt aatatcatgc acgaaaagca aacaaacttg tgtgcttcat tggatgttcg 900
taccaccaag gaattactgg agttagttga agcattaggt cccaaaattt gtttactaaa 960
aacacatgtg gatatcttga ctgatttttc catggagggc acagttaagc cgctaaaggc 1020
attatccgcc aagtacaatt ttttactctt cgaagacaga aaatttgctg acattggtaa 1080
tacagtcaaa ttgcagtact ctgcgggtgt atacagaata gcagaatggg cagacattac 1140
gaatgcacac ggtgtggtgg gcccaggtat tgttagcggt ttgaagcagg cggcagaaga 1200
agtaacaaag gaacctagag gcctttttgat gttagcagaa ttgtcatgca agggctccct 1260
atctactgga gaatatacta agggtactgt tgacattgcg aagagcgaca aagattttgt 1320
tatcggcttt attgctcaaa gagacatggg tggaagagat gaaggttacg attggttgat 1380
tatgacaccc ggtgtgggtt tagatgacaa gggagacgca ttgggtcaac agtatagaac 1440
cgtggatgat gtggtctcta caggatctga cattattatt gttggaagag gactatttgc 1500

-continued

```
aaagggaagg gatgctaagg tagagggtga acgttacaga aaagcaggct gggaagcata   1560

tttgagaaga tgcggccagc aaaactaaaa aactgtatta taagtaaatg catgtatact   1620

aaactcacaa attagagctt caatttaatt atatcagtta ttaccctatg cggtgtgaaa   1680

taccgcacag atgcgtaagg agaaaatacc gcatcaggaa attgtaaacg ttaatatttt   1740

gttaaaattc gcgttaaatt tttgttaaat cagctcattt tttaaccaat aggccgaaat   1800

cggcaaaatc tctagagtgc tggaagaaga gctgcttaac cgccgcgccc agggtgaaga   1860

tccacgctac tttaccctgc gtcgtctgga tttcggcggc tgtcgtcttt cgctggcaac   1920

gccggttgat gaagcctggg acggtccgct ctccttaaac ggtaaacgta tcgccacctc   1980

ttatcctcac ctgctcaagc gttatctcga ccagaaaggc atctctttta aatcctgctt   2040

actgaacggt tctgttgaag tcgccccgcg tgccggactg gcggatgcga tttgcgatct   2100

ggtttccacc ggtgccacgc tggaagctaa cggcctgcgc gaagtcgaag ttatctatcg   2160

ctcgaaagcc tgcctgattc aacgcgatgg cgaaatggaa gaatccaaac agcaactgat   2220

cgacaaactg ctgacccgta ttcagggtgt gatccaggcg cgcgaatcaa aatacatcat   2280

gatgcacgca ccgaccgaac gtctggatga agtcatccag tgatgataca acgagttagc   2340

caaggtg                                                             2347
```

<210> SEQ ID NO 82
<211> LENGTH: 27
<212> TYPE: DNA
<213> ORGANISM: artificial sequence
<220> FEATURE:
<223> OTHER INFORMATION: Primer

<400> SEQUENCE: 82

```
gacttttgga agcctgaaga aactggc                                         27
```

<210> SEQ ID NO 83
<211> LENGTH: 20
<212> TYPE: DNA
<213> ORGANISM: artificial sequence
<220> FEATURE:
<223> OTHER INFORMATION: Primer

<400> SEQUENCE: 83

```
cttggcagca acaggactag                                                 20
```

<210> SEQ ID NO 84
<211> LENGTH: 27
<212> TYPE: DNA
<213> ORGANISM: artificial sequence
<220> FEATURE:
<223> OTHER INFORMATION: Primer

<400> SEQUENCE: 84

```
gacttttgga agcctgaaga aactggc                                         27
```

<210> SEQ ID NO 85
<211> LENGTH: 20
<212> TYPE: DNA
<213> ORGANISM: artificial sequence
<220> FEATURE:
<223> OTHER INFORMATION: Primer

<400> SEQUENCE: 85

```
cttggcagca acaggactag                                                 20
```

<210> SEQ ID NO 86

<211> LENGTH: 26
<212> TYPE: DNA
<213> ORGANISM: artificial sequence
<220> FEATURE:
<223> OTHER INFORMATION: Primer

<400> SEQUENCE: 86
gacttgaata atgcagcggc gcttgc 26

<210> SEQ ID NO 87
<211> LENGTH: 30
<212> TYPE: DNA
<213> ORGANISM: artificial sequence
<220> FEATURE:
<223> OTHER INFORMATION: Primer

<400> SEQUENCE: 87
ccaccctctt caattagcta agatcatagc 30

<210> SEQ ID NO 88
<211> LENGTH: 25
<212> TYPE: DNA
<213> ORGANISM: artificial sequence
<220> FEATURE:
<223> OTHER INFORMATION: Primer

<400> SEQUENCE: 88
aaaaattgat tctcatcgta aatgc 25

<210> SEQ ID NO 89
<211> LENGTH: 20
<212> TYPE: DNA
<213> ORGANISM: artificial sequence
<220> FEATURE:
<223> OTHER INFORMATION: Primer

<400> SEQUENCE: 89
ctgcagcgag gagccgtaat 20

<210> SEQ ID NO 90
<211> LENGTH: 90
<212> TYPE: DNA
<213> ORGANISM: artificial sequence
<220> FEATURE:
<223> OTHER INFORMATION: Primer

<400> SEQUENCE: 90
atggttcatt taggtccaaa aaaaccacaa gccagaaagg gttccatggc cgatgtgcca 60
gcattgcgga ttacgtattc taatgttcag 90

<210> SEQ ID NO 91
<211> LENGTH: 91
<212> TYPE: DNA
<213> ORGANISM: artificial sequence
<220> FEATURE:
<223> OTHER INFORMATION: Primer

<400> SEQUENCE: 91
ttaagcaccg atgataccaa cggacttacc ttcagcaatt cttttttggg ccaaagcagc 60
caccttggct aactcgttgt atcatcactg g 91

<210> SEQ ID NO 92
<211> LENGTH: 24
<212> TYPE: DNA
<213> ORGANISM: artificial sequence
<220> FEATURE:

<223> OTHER INFORMATION: Primer

<400> SEQUENCE: 92
ctaggatgag tagcagcacg ttcc 24

<210> SEQ ID NO 93
<211> LENGTH: 26
<212> TYPE: DNA
<213> ORGANISM: artificial sequence
<220> FEATURE:
<223> OTHER INFORMATION: Primer

<400> SEQUENCE: 93
ccaattccgt gatgtctctt tgttgc 26

<210> SEQ ID NO 94
<211> LENGTH: 20
<212> TYPE: DNA
<213> ORGANISM: artificial sequence
<220> FEATURE:
<223> OTHER INFORMATION: Primer

<400> SEQUENCE: 94
gtgaacgagt tcacaaccgc 20

<210> SEQ ID NO 95
<211> LENGTH: 22
<212> TYPE: DNA
<213> ORGANISM: artificial sequence
<220> FEATURE:
<223> OTHER INFORMATION: Primer

<400> SEQUENCE: 95
gttcgttcca gaattatcac gc 22

<210> SEQ ID NO 96
<211> LENGTH: 41
<212> TYPE: DNA
<213> ORGANISM: artificial sequence
<220> FEATURE:
<223> OTHER INFORMATION: Primer

<400> SEQUENCE: 96
cactaaatct agaatggttc atttaggtcc aaaaaaacca c 41

<210> SEQ ID NO 97
<211> LENGTH: 40
<212> TYPE: DNA
<213> ORGANISM: Artificial sequence
<220> FEATURE:
<223> OTHER INFORMATION: Primer

<400> SEQUENCE: 97
tttgattgga tccggaagtg tagagagggt taaaattggc 40

<210> SEQ ID NO 98
<211> LENGTH: 600
<212> TYPE: DNA
<213> ORGANISM: Saccharomyces cerevisiae

<400> SEQUENCE: 98
ccgtgcaaaa actaactccg agcccgggca tgtcccgggt tagcgggccc aacaaaggcg 60
cttatctggt gggcttccgt agaagaaaaa aagctgttga gcgagctatt tcgggtatcc 120
cagccttctc tgcagaccgc cccagttggc ttggctctgg tgctgttcgt tagcatcaca 180
tcgcctgtga caggcagagg taataacggc ttaaggttct cttcgcatag tcggcagctt 240
tctttcggac gttgaacact caacaaacct tatctagtgc ccaaccaggt gtgcttctac 300
gagtcttgct cactcagaca cacctatccc tattgttacg gctatgggga tggcacacaa 360
aggtggaaat aatagtagtt aacaatatat gcagcaaatc atcggctcct ggctcatcga 420
gtcttgcaaa tcagcatata catatatata tgggggcaga tcttgattca tttattgttc 480
tatttccatc tttcctactt ctgtttccgt ttatattttg tattacgtag aatagaacat 540
catagtaata gatagttgtg gtgatcatat tataaacagc actaaaacat tacaacaaag 600

<210> SEQ ID NO 99
<211> LENGTH: 34
<212> TYPE: DNA
<213> ORGANISM: Artificial sequence
<220> FEATURE:
<223> OTHER INFORMATION: Primer

<400> SEQUENCE: 99
caacaaaagc ttccgtgcaa aaactaactc cgag 34

<210> SEQ ID NO 100
<211> LENGTH: 36
<212> TYPE: DNA
<213> ORGANISM: Artificial sequence
<220> FEATURE:
<223> OTHER INFORMATION: Primer

<400> SEQUENCE: 100
tttgattcta gactttgttg taatgtttta gtgctg 36

<210> SEQ ID NO 101
<211> LENGTH: 1765
<212> TYPE: DNA
<213> ORGANISM: Saccharomyces cerevisiae

<400> SEQUENCE: 101
atggttcatt taggtccaaa aaaaccacaa gccagaaagg gttccatggc cgatgtgcca 60
aaggaattga tgcaacaaat tgagaatttt gaaaaaattt tcactgttcc aactgaaact 120
ttacaagccg ttaccaagca cttcatttcc gaattggaaa agggtttgtc caagaagggt 180
ggtaacattc caatgattcc aggttgggtt atggatttcc caactggtaa ggaatccggt 240
gatttcttgg ccattgattt gggtggtacc aacttgagag ttgtcttagt caagttgggc 300
ggtgaccgta cctttgacac cactcaatct aagtacagat taccagatgc tatgagaact 360
actcaaaatc cagacgaatt gtgggaattt attgccgact ctttgaaagc ttttattgat 420
gagcaattcc cacaaggtat ctctgagcca attccattgg gtttcacctt ttctttccca 480
gcttctcaaa acaaaatcaa tgaaggtatc ttgcaaagat ggactaaagg ttttgatatt 540
ccaaacattg aaaaccacga tgttgttcca atgttgcaaa agcaaatcac taagaggaat 600
atcccaattg aagttgttgc tttgataaac gacactaccg gtactttggt tgcttcttac 660
tacactgacc cagaaactaa gatgggtgtt atcttcggta ctggtgtcaa tggtgcttac 720
tacgatgttt gttccgatat cgaaaagcta caaggaaaac tatctgatga cattccacca 780
tctgctccaa tggccatcaa ctgtgaatac ggttccttcg ataatgaaca tgtcgttttg 840
ccaagaacta aatacgatat caccattgat gaagaatctc caagaccagg ccaacaaacc 900
tttgaaaaaa tgtcttctgg ttactactta ggtgaaattt tgcgtttggc cttgatggac 960
atgtacaaac aaggtttcat cttcaagaac caagacttgt ctaagttcga caagcctttc 1020

```
gtcatggaca cttcttaccc agccagaatc gaggaagatc cattcgagaa cctagaagat   1080

accgatgact tgttccaaaa tgagttcggt atcaacacta ctgttcaaga acgtaaattg   1140

atcagacgtt tatctgaatt gattggtgct agagctgcta gattgtccgt ttgtggtatt   1200

gctgctatct gtcaaaagag aggttacaag accggtcaca tcgctgcaga cggttccgtt   1260

tacaacagat acccaggttt caaagaaaag gctgccaatg ctttgaagga catttacggc   1320

tggactcaaa cctcactaga cgactaccca atcaagattg ttcctgctga agatggttcc   1380

ggtgctggtg ccgctgttat tgctgctttg gcccaaaaaa gaattgctga aggtaagtcc   1440

gttggtatca tcggtgctta aacttaattt gtaaattaag tttgaacaac aagaaggtgc   1500

cctttttcta cttatgtgaa catgttttct atgatctttt tttttcttac ttttacaact   1560

gtgatattgt ataaactttg ttagaaattc acgggattta ttcgtgacga taaatattta   1620

tatagacaaa gaatatgacg atttatgaaa tctacatgat tttagtttct tttaacaatt   1680

gctcgttttt ttctcttgct taattttaaa tttttttggt agtaaaagat gcttatataa   1740

ggatttcgta tttattgttc aagta                                          1765
```

<210> SEQ ID NO 102
<211> LENGTH: 4236
<212> TYPE: DNA
<213> ORGANISM: artificial sequence
<220> FEATURE:
<223> OTHER INFORMATION: Synthetic construct

<400> SEQUENCE: 102

```
gatccgcatt gcggattacg tattctaatg ttcagataac ttcgtatagc atacattata     60

cgaagttatg cagattgtac tgagagtgca ccataccaca gcttttcaat tcaattcatc    120

attttttttt tattcttttt tttgatttcg gtttctttga aatttttttg attcggtaat    180

ctccgaacag aaggaagaac gaaggaagga gcacagactt agattggtat atatacgcat    240

atgtagtgtt gaagaaacat gaaattgccc agtattctta acccaactgc acagaacaaa    300

aacctgcagg aaacgaagat aaatcatgtc gaaagctaca tataaggaac gtgctgctac    360

tcatcctagt cctgttgctg ccaagctatt taatatcatg cacgaaaagc aaacaaactt    420

gtgtgcttca ttggatgttc gtaccaccaa ggaattactg gagttagttg aagcattagg    480

tcccaaaatt tgtttactaa aaacacatgt ggatatcttg actgattttt ccatggaggg    540

cacagttaag ccgctaaagg cattatccgc caagtacaat tttttactct tcgaagacag    600

aaaatttgct gacattggta atacagtcaa attgcagtac tctgcgggtg tatacagaat    660

agcagaatgg gcagacatta cgaatgcaca cggtgtggtg ggcccaggta ttgttagcgg    720

tttgaagcag gcggcagaag aagtaacaaa ggaacctaga ggccttttga tgttagcaga    780

attgtcatgc aagggctccc tatctactgg agaatatact aagggtactg ttgacattgc    840

gaagagcgac aaagatttg ttatcggctt tattgctcaa agagacatgg gtggaagaga    900

tgaaggttac gattggttga ttatgacacc cggtgtgggt ttagatgaca agggagacgc    960

attgggtcaa cagtatagaa ccgtggatga tgtggtctct acaggatctg acattattat   1020

tgttggaaga ggactatttg caaagggaag ggatgctaag gtagagggtg aacgttacag   1080

aaaagcaggc tgggaagcat atttgagaag atgcggccag caaaactaaa aaactgtatt   1140

ataagtaaat gcatgtatac taaactcaca aattagagct tcaatttaat tatatcagtt   1200

attaccctat gcggtgtgaa ataccgcaca gatgcgtaag gagaaaatac cgcatcagga   1260

aattgtaaac gttaatattt tgttaaaatt cgcgttaaat ttttgttaaa tcagctcatt   1320
```

-continued ttttaaccaa taggccgaaa tcggcaaaat cccttataaa tcaaaagaat agaccgagat 1380
agggttgagt gttgttccag tttggaacaa gagtccacta ttaaagaacg tggactccaa 1440
cgtcaaaggg cgaaaaaccg tctatcaggg cgatggccca ctacgtgaac catcacccta 1500
atcaagataa cttcgtatag catacattat acgaagttat ccagtgatga tacaacgagt 1560
tagccaaggt gaattcactg gccgtcgttt tacaacgtcg tgactgggaa aaccctggcg 1620
ttacccaact taatcgcctt gcagcacatc ccccctttcgc cagctggcgt aatagcgaag 1680
aggcccgcac cgatcgccct tcccaacagt tgcgcagcct gaatggcgaa tggcgcctga 1740
tgcggtattt tctccttacg catctgtgcg gtatttcaca ccgcatatgg tgcactctca 1800
gtacaatctg ctctgatgcc gcatagttaa gccagccccg acacccgcca acacccgctg 1860
acgcgccctg acgggcttgt ctgctcccgg catccgctta cagacaagct gtgaccgtct 1920
ccgggagctg catgtgtcag aggttttcac cgtcatcacc gaaacgcgcg agacgaaagg 1980
gcctcgtgat acgcctattt ttataggtta atgtcatgat aataatggtt tcttagacgt 2040
caggtggcac ttttcgggga aatgtgcgcg gaacccctat ttgtttattt ttctaaatac 2100
attcaaatat gtatccgctc atgagacaat aaccctgata aatgcttcaa taatattgaa 2160
aaaggaagag tatgagtatt caacatttcc gtgtcgccct tattcccttt tttgcggcat 2220
tttgccttcc tgtttttgct cacccagaaa cgctggtgaa agtaaaagat gctgaagatc 2280
agttgggtgc acgagtgggt tacatcgaac tggatctcaa cagcggtaag atccttgaga 2340
gttttcgccc cgaagaacgt tttccaatga tgagcacttt taaagttctg ctatgtggcg 2400
cggtattatc ccgtattgac gccgggcaag agcaactcgg tcgccgcata cactattctc 2460
agaatgactt ggttgagtac tcaccagtca cagaaaagca tcttacggat ggcatgacag 2520
taagagaatt atgcagtgct gccataacca tgagtgataa cactgcggcc aacttacttc 2580
tgacaacgat cggaggaccg aaggagctaa ccgctttttt gcacaacatg ggggatcatg 2640
taactcgcct tgatcgttgg gaaccggagc tgaatgaagc cataccaaac gacgagcgtg 2700
acaccacgat gcctgtagca atggcaacaa cgttgcgcaa actattaact ggcgaactac 2760
ttactctagc ttcccggcaa caattaatag actggatgga ggcggataaa gttgcaggac 2820
cacttctgcg ctcggccctt ccggctggct ggtttattgc tgataaatct ggagccggtg 2880
agcgtgggtc tcgcggtatc attgcagcac tggggccaga tggtaagccc tcccgtatcg 2940
tagttatcta cacgacgggg agtcaggcaa ctatggatga acgaaataga cagatcgctg 3000
agataggtgc ctcactgatt aagcattggt aactgtcaga ccaagtttac tcatatatac 3060
tttagattga tttaaaactt catttttaat ttaaaaggat ctaggtgaag atcctttttg 3120
ataatctcat gaccaaaatc ccttaacgtg agttttcgtt ccactgagcg tcagaccccg 3180
tagaaaagat caaaggatct tcttgagatc cttttttttct gcgcgtaatc tgctgcttgc 3240
aaacaaaaaa accaccgcta ccagcggtgg tttgtttgcc ggatcaagag ctaccaactc 3300
tttttccgaa ggtaactggc ttcagcagag cgcagatacc aaatactgtc cttctagtgt 3360
agccgtagtt aggccaccac ttcaagaact ctgtagcacc gcctacatac ctcgctctgc 3420
taatcctgtt accagtggct gctgccagtg gcgataagtc gtgtcttacc gggttggact 3480
caagacgata gttaccggat aaggcgcagc ggtcgggctg aacggggggt tcgtgcacac 3540
agcccagctt ggagcgaacg acctacaccg aactgagata cctacagcgt gagctatgag 3600
aaagcgccac gcttcccgaa gggagaaagg cggacaggta tccggtaagc ggcagggtcg 3660
gaacaggaga gcgcacgagg gagcttccag ggggaaacgc ctggtatctt tatagtcctg 3720
tcgggtttcg ccacctctga cttgagcgtc gatttttgtg atgctcgtca ggggggcgga 3780
gcctatggaa aaacgccagc aacgcggcct ttttacggtt cctggccttt tgctggcctt 3840
ttgctcacat gttctttcct gcgttatccc ctgattctgt ggataaccgt attaccgcct 3900
ttgagtgagc tgataccgct cgccgcagcc gaacgaccga gcgcagcgag tcagtgagcg 3960
aggaagcgga agagcgccca atacgcaaac cgcctctccc cgcgcgttgg ccgattcatt 4020
aatgcagctg gcacgacagg tttcccgact ggaaagcggg cagtgagcgc aacgcaatta 4080
atgtgagtta gctcactcat taggcacccc aggctttaca ctttatgctt ccggctcgta 4140
tgttgtgtgg aattgtgagc ggataacaat ttcacacagg aaacagctat gaccatgatt 4200
acgccaagct tgcatgcctg caggtcgact ctagag 4236

<210> SEQ ID NO 103
<211> LENGTH: 6649
<212> TYPE: DNA
<213> ORGANISM: artificial sequence
<220> FEATURE:
<223> OTHER INFORMATION: Synthetic construct

<400> SEQUENCE: 103
ctagactttg ttgtaatgtt ttagtgctgt ttataatatg atcaccacaa ctatctatta 60
ctatgatgtt ctattctacg taatacaaaa tataaacgga aacagaagta ggaaagatgg 120
aaatagaaca ataaatgaat caagatctgc cccatatat atatgtatat gctgatttgc 180
aagactcgat gagccaggag ccgatgattt gctgcatata ttgttaacta ctattatttc 240
cacctttgtg tgccatcccc atagccgtaa caatagggat aggtgtgtct gagtgagcaa 300
gactcgtaga agcacacctg gttgggcact agataaggtt tgttgagtgt tcaacgtccg 360
aaagaaagct gccgactatg cgaagagaac cttaagccgt tattacctct gcctgtcaca 420
ggcgatgtga tgctaacgaa cagcaccaga gccaagccaa ctggggcggt ctgcagagaa 480
ggctgggata cccgaaatag ctcgctcaac agcttttttt cttctacgga agcccaccag 540
ataagcgcct ttgttgggcc cgctaacccg ggacatgccc gggctcggag ttagtttttg 600
cacggaagct tggcgtaatc atggtcatag ctgtttcctg tgtgaaattg ttatccgctc 660
acaattccac acaacatacg agccggaagc ataaagtgta aagcctgggg tgcctaatga 720
gtgagctaac tcacattaat tgcgttgcgc tcactgcccg ctttccagtc gggaaacctg 780
tcgtgccagc tgcattaatg aatcggccaa cgcgcgggga gaggcggttt gcgtattggg 840
cgctcttccg cttcctcgct cactgactcg ctgcgctcgg tcgttcggct gcggcgagcg 900
gtatcagctc actcaaaggc ggtaatacgg ttatccacag aatcagggga taacgcagga 960
aagaacatgt gagcaaaagg ccagcaaaag gccaggaacc gtaaaaaggc cgcgttgctg 1020
gcgtttttcc ataggctccg cccccctgac gagcatcaca aaaatcgacg ctcaagtcag 1080
aggtggcgaa acccgacagg actataaaga taccaggcgt ttccccctgg aagctccctc 1140
gtgcgctctc ctgttccgac cctgccgctt accggatacc tgtccgcctt tctcccttcg 1200
ggaagcgtgg cgctttctca tagctcacgc tgtaggtatc tcagttcggt gtaggtcgtt 1260
cgctccaagc tgggctgtgt gcacgaaccc cccgttcagc ccgaccgctg cgccttatcc 1320
ggtaactatc gtcttgagtc caacccggta agacacgact tatcgccact ggcagcagcc 1380
actggtaaca ggattagcag agcgaggtat gtaggcggtg ctacagagtt cttgaagtgg 1440
tggcctaact acggctacac tagaaggaca gtatttggta tctgcgctct gctgaagcca 1500
gttaccttcg gaaaaagagt tggtagctct tgatccggca aacaaaccac cgctggtagc 1560

-continued

```
ggtggttttt ttgtttgcaa gcagcagatt acgcgcagaa aaaaaggatc tcaagaagat   1620
cctttgatct tttctacggg gtctgacgct cagtggaacg aaaactcacg ttaagggatt   1680
ttggtcatga gattatcaaa aaggatcttc acctagatcc ttttaaatta aaaatgaagt   1740
tttaaatcaa tctaaagtat atatgagtaa acttggtctg acagttacca atgcttaatc   1800
agtgaggcac ctatctcagc gatctgtcta tttcgttcat ccatagttgc ctgactcccc   1860
gtcgtgtaga taactacgat acgggagggc ttaccatctg gccccagtgc tgcaatgata   1920
ccgcgagacc cacgctcacc ggctccagat ttatcagcaa taaaccagcc agccggaagg   1980
gccgagcgca gaagtggtcc tgcaacttta tccgcctcca tccagtctat taattgttgc   2040
cgggaagcta gagtaagtag ttcgccagtt aatagtttgc gcaacgttgt tgccattgct   2100
acaggcatcg tggtgtcacg ctcgtcgttt ggtatggctt cattcagctc cggttcccaa   2160
cgatcaaggc gagttacatg atcccccatg ttgtgcaaaa aagcggttag ctccttcggt   2220
cctccgatcg ttgtcagaag taagttggcc gcagtgttat cactcatggt tatggcagca   2280
ctgcataatt ctcttactgt catgccatcc gtaagatgct tttctgtgac tggtgagtac   2340
tcaaccaagt cattctgaga atagtgtatg cggcgaccga gttgctcttg cccggcgtca   2400
atacgggata ataccgcgcc acatagcaga actttaaaag tgctcatcat tggaaaacgt   2460
tcttcggggc gaaaactctc aaggatctta ccgctgttga gatccagttc gatgtaaccc   2520
actcgtgcac ccaactgatc ttcagcatct tttactttca ccagcgtttc tgggtgagca   2580
aaaacaggaa ggcaaaatgc cgcaaaaaag ggaataaggg cgacacggaa atgttgaata   2640
ctcatactct tcctttttca atattattga agcatttatc agggttattg tctcatgagc   2700
ggatacatat ttgaatgtat ttagaaaaat aaacaaatag gggttccgcg cacatttccc   2760
cgaaaagtgc cacctgacgt ctaagaaacc attattatca tgacattaac ctataaaaat   2820
aggcgtatca cgaggccctt tcgtctcgcg cgtttcggtg atgacggtga aaacctctga   2880
cacatgcagc tcccggagac ggtcacagct tgtctgtaag cggatgccgg gagcagacaa   2940
gcccgtcagg gcgcgtcagc gggtgttggc gggtgtcggg gctggcttaa ctatgcggca   3000
tcagagcaga ttgtactgag agtgcaccat atgcggtgtg aaataccgca cagatgcgta   3060
aggagaaaat accgcatcag gcgccattcg ccattcaggc tgcgcaactg ttgggaaggg   3120
cgatcggtgc gggcctcttc gctattacgc cagctggcga aagggggatg tgctgcaagg   3180
cgattaagtt gggtaacgcc agggttttcc cagtcacgac gttgtaaaac gacggccagt   3240
gaattcacct tggctaactc gttgtatcat cactggataa cttcgtataa tgtatgctat   3300
acgaagttat cttgattagg gtgatggttc acgtagtggg ccatcgccct gatagacggt   3360
ttttcgccct ttgacgttgg agtccacgtt ctttaatagt ggactcttgt tccaaactgg   3420
aacaacactc aaccctatct cggtctattc ttttgattta taagggattt tgccgatttc   3480
ggcctattgg ttaaaaaatg agctgattta acaaaaattt aacgcgaatt ttaacaaaat   3540
attaacgttt acaatttcct gatgcggtat tttctcctta cgcatctgtg cggtatttca   3600
caccgcatag ggtaataact gatataatta aattgaagct ctaatttgtg agtttagtat   3660
acatgcattt acttataata cagtttttta gttttgctgg ccgcatcttc tcaaatatgc   3720
ttcccagcct gcttttctgt aacgttcacc ctctacctta gcatcccttc cctttgcaaa   3780
tagtcctctt ccaacaataa taatgtcaga tcctgtagag accacatcat ccacggttct   3840
atactgttga cccaatgcgt ctcccttgtc atctaaaccc acaccgggtg tcataatcaa   3900
ccaatcgtaa ccttcatctc ttccacccat gtctctttga gcaataaagc cgataacaaa   3960
```

-continued

```
atctttgtcg ctcttcgcaa tgtcaacagt acccttagta tattctccag tagataggga   4020
gcccttgcat gacaattctg ctaacatcaa aaggcctcta ggttcctttg ttacttcttc   4080
tgccgcctgc ttcaaaccgc taacaatacc tgggcccacc acaccgtgtg cattcgtaat   4140
gtctgcccat tctgctattc tgtatacacc cgcagagtac tgcaatttga ctgtattacc   4200
aatgtcagca aattttctgt cttcgaagag taaaaaattg tacttggcgg ataatgcctt   4260
tagcggctta actgtgccct ccatggaaaa atcagtcaag atatccacat gtgtttttag   4320
taaacaaatt ttgggaccta atgcttcaac taactccagt aattccttgg tggtacgaac   4380
atccaatgaa gcacacaagt ttgtttgctt ttcgtgcatg atattaaata gcttggcagc   4440
aacaggacta ggatgagtag cagcacgttc cttatatgta gctttcgaca tgatttatct   4500
tcgtttcctg caggtttttg ttctgtgcag ttgggttaag aatactgggc aatttcatgt   4560
ttcttcaaca ctacatatgc gtatatatac caatctaagt ctgtgctcct tccttcgttc   4620
ttccttctgt tcggagatta ccgaatcaaa aaaatttcaa agaaaccgaa atcaaaaaaa   4680
agaataaaaa aaaaatgatg aattgaattg aaaagctgtg gtatggtgca ctctcagtac   4740
aatctgcata acttcgtata atgtatgcta tacgaagtta tctgaacatt agaatacgta   4800
atccgcaatg cggatccgga agtgtagaga gggttaaaat tggcgtgcaa ttttatgaag   4860
aataaagaca tctagtcttt aaatacttga acaataaata cgaaatcctt atataagcat   4920
cttttactac caaaaaaatt taaaattaag caagagaaaa aaacgagcaa ttgttaaaag   4980
aaactaaaat catgtagatt tcataaatcg tcatattctt tgtctatata aatatttatc   5040
gtcacgaata aatcccgtga atttctaaca aagtttatac aatatcacag ttgtaaaagt   5100
aagaaaaaaa aagatcatag aaaacatgtt cacataagta gaaaaagggc accttcttgt   5160
tgttcaaact taatttacaa attaagttta agcaccgatg ataccaacgg acttaccttc   5220
agcaattctt ttttgggcca aagcagcaat aacagcggca ccagcaccgg aaccatcttc   5280
agcaggaaca atcttgattg ggtagtcgtc tagtgaggtt tgagtccagc cgtaaatgtc   5340
cttcaaagca ttggcagcct ttctttgaa acctgggtat ctgttgtaaa cggaaccgtc   5400
tgcagcgatg tgaccggtct tgtaacctct cttttgacag atagcagcaa taccacaaac   5460
ggacaatcta gcagctctag caccaatcaa ttcagataaa cgtctgatca atttacgttc   5520
ttgaacagta gtgttgatac cgaactcatt ttggaacaag tcatcggtat cttctaggtt   5580
ctcgaatgga tcttcctcga ttctggctgg gtaagaagtg tccatgacga aaggcttgtc   5640
gaacttagac aagtcttggt tcttgaagat gaaaccttgt ttgtacatgt ccatcaaggc   5700
caaacgcaaa atttcaccta agtagtaacc agaagacatt ttttcaaagg tttgttggcc   5760
tggtcttgga gattcttcat caatggtgat atcgtattta gttcttggca aaacgacatg   5820
ttcattatcg aaggaaccgt attcacagtt gatggccatt ggagcagatg gtggaatgtc   5880
atcagatagt tttccttgta gcttttcgat atcggaacaa acatcgtagt aagcaccatt   5940
gacaccagta ccgaagataa cacccatctt agtttctggg tcagtgtagt aagaagcaac   6000
caaagtaccg gtagtgtcgt ttatcaaagc aacaacttca attgggatat tcctcttagt   6060
gatttgcttt tgcaacattg gaacaacatc gtggttttca atgtttggaa tatcaaaacc   6120
tttagtccat ctttgcaaga taccttcatt gattttgttt tgagaagctg ggaaagaaaa   6180
ggtgaaaccc aatggaattg gctcagagat accttgtggg aattgctcat caataaaagc   6240
tttcaaagag tcggcaataa attcccacaa ttcgtctgga ttttgagtag ttctcatagc   6300
atctggtaat ctgtacttag attgagtggt gtcaaaggta cggtcaccgc ccaacttgac   6360
```

-continued

```
taagacaact ctcaagttgg taccacccaa atcaatggcc aagaaatcac cggattcctt   6420

accagttggg aaatccataa cccaacctgg aatcattgga atgttaccac ccttcttgga   6480

caaacccttt tccaattcgg aaatgaagtg cttggtaacg gcttgtaaag tttcagttgg   6540

aacagtgaaa attttttcaa aattctcaat ttgttgcatc aattcctttg gcacatcggc   6600

catggaaccc tttctggctt gtggtttttt tggacctaaa tgaaccatt               6649
```

<210> SEQ ID NO 104
<211> LENGTH: 38
<212> TYPE: DNA
<213> ORGANISM: Artificial sequence
<220> FEATURE:
<223> OTHER INFORMATION: Primer

<400> SEQUENCE: 104

```
cactaaatct agaatggttc gtttaggtcc aaagaagc                            38
```

<210> SEQ ID NO 105
<211> LENGTH: 42
<212> TYPE: DNA
<213> ORGANISM: artificial sequence
<220> FEATURE:
<223> OTHER INFORMATION: Primer

<400> SEQUENCE: 105

```
tttggatgga tccctattcg cctttaatac caacagactt ac                        42
```

<210> SEQ ID NO 106
<211> LENGTH: 6276
<212> TYPE: DNA
<213> ORGANISM: Artificial sequence
<220> FEATURE:
<223> OTHER INFORMATION: Synthetic construct

<400> SEQUENCE: 106

```
ctagactttg ttgtaatgtt ttagtgctgt ttataatatg atcaccacaa ctatctatta     60

ctatgatgtt ctattctacg taatacaaaa tataaacgga aacagaagta ggaaagatgg    120

aaatagaaca ataaatgaat caagatctgc ccccatatat atatgtatat gctgatttgc    180

aagactcgat gagccaggag ccgatgattt gctgcatata ttgttaacta ctattatttc    240

cacctttgtg tgccatcccc atagccgtaa caatagggat aggtgtgtct gagtgagcaa    300

gactcgtaga agcacacctg gttgggcact agataaggtt tgttgagtgt tcaacgtccg    360

aaagaaagct gccgactatg cgaagagaac cttaagccgt tattacctct gcctgtcaca    420

ggcgatgtga tgctaacgaa cagcaccaga gccaagccaa ctggggcggt ctgcagagaa    480

ggctgggata cccgaaatag ctcgctcaac agcttttttt cttctacgga agcccaccag    540

ataagcgcct ttgttgggcc cgctaacccg ggacatgccc gggctcggag ttagtttttg    600

cacggaagct tggcgtaatc atggtcatag ctgtttcctg tgtgaaattg ttatccgctc    660

acaattccac acaacatacg agccggaagc ataaagtgta aagcctgggg tgcctaatga    720

gtgagctaac tcacattaat tgcgttgcgc tcactgcccg ctttccagtc gggaaacctg    780

tcgtgccagc tgcattaatg aatcggccaa cgcgcgggga gaggcggttt gcgtattggg    840

cgctcttccg cttcctcgct cactgactcg ctgcgctcgg tcgttcggct gcggcgagcg    900

gtatcagctc actcaaaggc ggtaatacgg ttatccacag aatcagggga taacgcagga    960

aagaacatgt gagcaaaagg ccagcaaaag gccaggaacc gtaaaaaggc cgcgttgctg   1020

gcgtttttcc ataggctccg cccccctgac gagcatcaca aaaatcgacg ctcaagtcag   1080
```

-continued

```
aggtggcgaa acccgacagg actataaaga taccaggcgt ttccccctgg aagctccctc   1140
gtgcgctctc ctgttccgac cctgccgctt accggatacc tgtccgcctt tctcccttcg   1200
ggaagcgtgg cgctttctca tagctcacgc tgtaggtatc tcagttcggt gtaggtcgtt   1260
cgctccaagc tgggctgtgt gcacgaaccc cccgttcagc ccgaccgctg cgccttatcc   1320
ggtaactatc gtcttgagtc caacccggta agacacgact tatcgccact ggcagcagcc   1380
actggtaaca ggattagcag agcgaggtat gtaggcggtg ctacagagtt cttgaagtgg   1440
tggcctaact acggctacac tagaaggaca gtatttggta tctgcgctct gctgaagcca   1500
gttaccttcg gaaaaagagt tggtagctct tgatccggca aacaaaccac cgctggtagc   1560
ggtggttttt ttgtttgcaa gcagcagatt acgcgcagaa aaaaaggatc tcaagaagat   1620
cctttgatct tttctacggg gtctgacgct cagtggaacg aaaactcacg ttaagggatt   1680
ttggtcatga gattatcaaa aaggatcttc acctagatcc ttttaaatta aaaatgaagt   1740
tttaaatcaa tctaaagtat atatgagtaa acttggtctg acagttacca atgcttaatc   1800
agtgaggcac ctatctcagc gatctgtcta tttcgttcat ccatagttgc ctgactcccc   1860
gtcgtgtaga taactacgat acgggagggc ttaccatctg gccccagtgc tgcaatgata   1920
ccgcgagacc cacgctcacc ggctccagat ttatcagcaa taaaccagcc agccggaagg   1980
gccgagcgca gaagtggtcc tgcaacttta tccgcctcca tccagtctat taattgttgc   2040
cgggaagcta gagtaagtag ttcgccagtt aatagtttgc gcaacgttgt tgccattgct   2100
acaggcatcg tggtgtcacg ctcgtcgttt ggtatggctt cattcagctc cggttcccaa   2160
cgatcaaggc gagttacatg atcccccatg ttgtgcaaaa aagcggttag ctccttcggt   2220
cctccgatcg ttgtcagaag taagttggcc gcagtgttat cactcatggt tatggcagca   2280
ctgcataatt ctcttactgt catgccatcc gtaagatgct tttctgtgac tggtgagtac   2340
tcaaccaagt cattctgaga atagtgtatg cggcgaccga gttgctcttg cccggcgtca   2400
atacgggata ataccgcgcc acatagcaga actttaaaag tgctcatcat tggaaaacgt   2460
tcttcggggc gaaaactctc aaggatctta ccgctgttga gatccagttc gatgtaaccc   2520
actcgtgcac ccaactgatc ttcagcatct tttactttca ccagcgtttc tgggtgagca   2580
aaaacaggaa ggcaaaatgc cgcaaaaaag ggaataaggg cgacacggaa atgttgaata   2640
ctcatactct tcctttttca atattattga agcatttatc agggttattg tctcatgagc   2700
ggatacatat ttgaatgtat ttagaaaaat aaacaaatag gggttccgcg cacatttccc   2760
cgaaaagtgc cacctgacgt ctaagaaacc attattatca tgacattaac ctataaaaat   2820
aggcgtatca cgaggccctt tcgtctcgcg cgtttcggtg atgacggtga aaacctctga   2880
cacatgcagc tcccggagac ggtcacagct tgtctgtaag cggatgccgg gagcagacaa   2940
gcccgtcagg gcgcgtcagc gggtgttggc gggtgtcggg gctggcttaa ctatgcggca   3000
tcagagcaga ttgtactgag agtgcaccat atgcggtgtg aaataccgca cagatgcgta   3060
aggagaaaat accgcatcag gcgccattcg ccattcaggc tgcgcaactg ttgggaaggg   3120
cgatcggtgc gggcctcttc gctattacgc cagctggcga aagggggatg tgctgcaagg   3180
cgattaagtt gggtaacgcc agggttttcc cagtcacgac gttgtaaaac gacggccagt   3240
gaattcacct tggctaactc gttgtatcat cactggataa cttcgtataa tgtatgctat   3300
acgaagttat cttgattagg gtgatggttc acgtagtggg ccatcgccct gatagacggt   3360
ttttcgccct ttgacgttgg agtccacgtt ctttaatagt ggactcttgt tccaaactgg   3420
aacaacactc aaccctatct cggtctattc ttttgattta taagggattt tgccgatttc   3480
```

```
ggcctattgg ttaaaaaatg agctgattta acaaaaattt aacgcgaatt ttaacaaaat   3540
attaacgttt acaatttcct gatgcggtat tttctcctta cgcatctgtg cggtatttca   3600
caccgcatag ggtaataact gatataatta aattgaagct ctaatttgtg agtttagtat   3660
acatgcattt acttataata cagtttttta gttttgctgg ccgcatcttc tcaaatatgc   3720
ttcccagcct gcttttctgt aacgttcacc ctctacctta gcatcccttc cctttgcaaa   3780
tagtcctctt ccaacaataa taatgtcaga tcctgtagag accacatcat ccacggttct   3840
atactgttga cccaatgcgt ctcccttgtc atctaaaccc acaccgggtg tcataatcaa   3900
ccaatcgtaa ccttcatctc ttccacccat gtctctttga gcaataaagc cgataacaaa   3960
atctttgtcg ctcttcgcaa tgtcaacagt acccttagta tattctccag tagataggga   4020
gcccttgcat gacaattctg ctaacatcaa aaggcctcta ggttcctttg ttacttcttc   4080
tgccgcctgc ttcaaaccgc taacaatacc tgggcccacc acaccgtgtg cattcgtaat   4140
gtctgcccat tctgctattc tgtatacacc cgcagagtac tgcaatttga ctgtattacc   4200
aatgtcagca aattttctgt cttcgaagag taaaaaattg tacttggcgg ataatgcctt   4260
tagcggctta actgtgccct ccatggaaaa atcagtcaag atatccacat gtgtttttag   4320
taaacaaatt ttgggaccta atgcttcaac taactccagt aattccttgg tggtacgaac   4380
atccaatgaa gcacacaagt ttgtttgctt ttcgtgcatg atattaaata gcttggcagc   4440
aacaggacta ggatgagtag cagcacgttc cttatatgta gctttcgaca tgatttatct   4500
tcgtttcctg caggtttttg ttctgtgcag ttgggttaag aatactgggc aatttcatgt   4560
ttcttcaaca ctacatatgc gtatatatac caatctaagt ctgtgctcct tccttcgttc   4620
ttccttctgt tcggagatta ccgaatcaaa aaaatttcaa agaaaccgaa atcaaaaaaa   4680
agaataaaaa aaaaatgatg aattgaattg aaaagctgtg gtatggtgca ctctcagtac   4740
aatctgcata acttcgtata atgtatgcta tacgaagtta tctgaacatt agaatacgta   4800
atccgcaatg cggatcccta ttcgccttta ataccaacag acttaccggc agccaatctc   4860
ttttgagtca aacaagcaat gatagcagca ccaacaccgg aaccatcttc agcagccacc   4920
aattggattg ggtggtcttc catcttttcg acatcccagt tgtagatatc cttcaaggct   4980
tgagcggcct tttccttgta acctgggtat ctgttgaaga cagaaccatc agctgcaatg   5040
tgagcagtct tgtagcctct cttgtcacag atagcagaaa caccacaaac agtcaatctt   5100
gcagctcttg ttccgaccaa ttcggctaat tttctaatca actttctctc aacaacggta   5160
gtttcgatgt tcaagttagt cttgaacaga tcgtcagtgt cttccaagtt ttcgaatgga   5220
tcatcttcga tcttagatgg ataactggtg tccatgacgt aagcctcttt caacttggag   5280
atatcttggt ccttaaagat gaaaccactg tcgtacaagt ccaatagtac tagacgcatg   5340
atttcaccta gatagtaacc agaagtcatc ttttcgaaag cttgttgacc tggtcttgga   5400
gattcttcat cgattataac atcgtatttg gttcttggca acaccaaatg ttcgttatcg   5460
aaggaaccat attcacagtt gattgccatt ggagaatctg gaccgatatc ttctggcaac   5520
aaaccttcca atttctcaat accagaaaca acatcgtagt aagcaccgtt gacaccagta   5580
ccgataatga tacccatctt agtttgagga tcagtgtaca aagaggcaac caaggtacca   5640
gtggtatcgt tgatcaatcg aacgacattg attgggatat tcagcttttc aatctgttct   5700
tgtagcattg gaacaacatc gtgaccttca acaccttcaa tatcgaaacc cttggtccaa   5760
cgttgcaaca caccggaatt gatcttcttt tgagatgcag ggtatgagaa agtgaaaccc   5820
aatggcaatg gttcagaaac accatctggg taccattcat cgacgaattc cttcaaacac   5880
```

```
tttgcaataa atgaccacaa ttgttcagaa gtaccagttc tcaaatggtc tggtaatctg   5940

tacttgtttt gagtggtgtc gaaatcatga ttaccaccca atttaaccaa cacaactctc   6000

aagttggtac cacccaaatc aagagctaag aaatcaccag tttccttacc agttggatac   6060

tcaacaaccc aacctggaat cataggaatg ttaccaccct ttttggacaa acctttgtcc   6120

aattcactga tgaaatgctt gacaatgctt ctcatttttt ctgaagagac ggtgaacaaa   6180

gtttccaaac cgtggatttg ttccatcaaa ttagctggca catctgccat ggaccccttt   6240

ctggctggag gcttctttgg acctaaacga accatt                             6276


<210> SEQ ID NO 107
<211> LENGTH: 65
<212> TYPE: DNA
<213> ORGANISM: Artificial sequence
<220> FEATURE:
<223> OTHER INFORMATION: Primer

<400> SEQUENCE: 107

gtgagtatac gtgattaagc acacaaaggc agcttggagt cacacaggaa acagctatga     60

ccatg                                                                 65


<210> SEQ ID NO 108
<211> LENGTH: 66
<212> TYPE: DNA
<213> ORGANISM: Artificial sequence
<220> FEATURE:
<223> OTHER INFORMATION: Primer

<400> SEQUENCE: 108

gtgcacaaac aatacttaaa taaatactac tcagtaataa cgtcacgacg ttgtaaaacg     60

acggcc                                                                66


<210> SEQ ID NO 109
<211> LENGTH: 30
<212> TYPE: DNA
<213> ORGANISM: Artificial sequence
<220> FEATURE:
<223> OTHER INFORMATION: Primer

<400> SEQUENCE: 109

ctcttcaaca agtttgattc cattgcggtg                                      30


<210> SEQ ID NO 110
<211> LENGTH: 7523
<212> TYPE: DNA
<213> ORGANISM: artificial sequence
<220> FEATURE:
<223> OTHER INFORMATION: Synthetic construct

<400> SEQUENCE: 110

ccagcttttg ttccctttag tgagggttaa ttgcgcgctt ggcgtaatca tggtcatagc     60

tgtttcctgt gtgaaattgt tatccgctca caattccaca caacatagga gccggaagca    120

taaagtgtaa agcctggggt gcctaatgag tgaggtaact cacattaatt gcgttgcgct    180

cactgcccgc tttccagtcg ggaaacctgt cgtgccagct gcattaatga atcggccaac    240

gcgcggggag aggcggtttg cgtattgggc gctcttccgc ttcctcgctc actgactcgc    300

tgcgctcggt cgttcggctg cggcgagcgg tatcagctca ctcaaaggcg gtaatacggt    360

tatccacaga atcaggggat aacgcaggaa agaacatgtg agcaaaaggc cagcaaaagg    420

ccaggaaccg taaaaaggcc gcgttgctgg cgtttttcca taggctccgc ccccctgacg    480
```

-continued

```
agcatcacaa aaatcgacgc tcaagtcaga ggtggcgaaa cccgacagga ctataaagat    540
accaggcgtt tccccctgga agctccctcg tgcgctctcc tgttccgacc ctgccgctta    600
ccggatacct gtccgccttt ctcccttcgg gaagcgtggc gctttctcat agctcacgct    660
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt cctttttcaa tattattgaa   2100
gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa tttttcaaac aaagaatctg   2280
agctgcattt ttacagaaca gaaatgcaac gcgaaagcgc tattttacca acgaagaatc   2340
tgtgcttcat ttttgtaaaa caaaaatgca acgcgagagc gctaattttt caaacaaaga   2400
atctgagctg catttttaca gaacagaaat gcaacgcgag agcgctattt taccaacaaa   2460
gaatctatac ttcttttttg ttctacaaaa atgcatcccg agagcgctat ttttctaaca   2520
aagcatctta gattactttt tttctccttt gtgcgctcta taatgcagtc tcttgataac   2580
tttttgcact gtaggtccgt taaggttaga agaaggctac tttggtgtct attttctctt   2640
ccataaaaaa agcctgactc cacttcccgc gtttactgat tactagcgaa gctgcgggtg   2700
catttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
```

-continued

```
cgattcactc tatgaatagt tcttactaca attttttgt ctaaagagta atactagaga   2940
taaacataaa aaatgtagag gtcgagttta gatgcaagtt caaggagcga aaggtggatg   3000
ggtaggttat atagggatat agcacagaga tatatagcaa agagatactt ttgagcaatg   3060
tttgtggaag cggtattcgc aatattttag tagctcgtta cagtccggtg cgtttttggt   3120
tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt atatgcgtct atttatgtag gatgaaaggt agtctagtac ctcctgtgat   3420
attatcccat tccatgcggg gtatcgtatg cttccttcag cactaccctt tagctgttct   3480
atatgctgcc actcctcaat tggattagtc tcatccttca atgctatcat ttcctttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcatttttt tttttcccct agcggatgac tctttttttt tcttagcgat   4020
tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
aacgaggcgc gctttccttt ttttcttttg ctttttcttt ttttttctct tgaactcgac   4980
ggatctatgc ggtgtgaaat accgcacaga tgcgtaagga gaaaataccg catcaggaaa   5040
ttgtaaacgt taatattttg ttaaaattcg cgttaaattt ttgttaaatc agctcatttt   5100
ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280
```

-continued caagtttttt ggggtcgagg tgccgtaaag cactaaatcg gaaccctaaa gggagccccc 5340
gatttagagc ttgacgggga aagccggcga acgtggcgag aaaggaaggg aagaaagcga 5400
aaggagcggg cgctagggcg ctggcaagtg tagcggtcac gctgcgcgta accaccacac 5460
ccgccgcgct taatgcgccg ctacagggcg cgtcgcgcca ttcgccattc aggctgcgca 5520
actgttggga agggcgatcg gtgcgggcct cttcgctatt acgccagctg gcgaaagggg 5580
gatgtgctgc aaggcgatta agttgggtaa cgccagggtt ttcccagtca cgacgttgta 5640
aaacgacggc cagtgagcgc gcgtaatacg actcactata gggcgaattg ggtaccgggc 5700 ccccctcga ggtattagaa gccgccgagc gggcgacagc cctccgacgg aagactctcc 5760
tccgtgcgtc ctcgtcttca ccggtcgcgt tcctgaaacg cagatgtgcc tcgcgccgca 5820
ctgctccgaa caataaagat tctacaatac tagcttttat ggttatgaag aggaaaaatt 5880
ggcagtaacc tggccccaca aaccttcaaa ttaacgaatc aaattaacaa ccataggatg 5940
ataatgcgat tagtttttta gccttatttc tggggtaatt aatcagcgaa gcgatgattt 6000
ttgatctatt aacagatata taaatggaaa agctgcataa ccactttaac taatactttc 6060
aacattttca gtttgtatta cttcttattc aaatgtcata aaagtatcaa caaaaaattg 6120
ttaatatacc tctatacttt aacgtcaagg agaaaaaatgt ccaatttact gcccgtacac 6180
caaaatttgc ctgcattacc ggtcgatgca acgagtgatg aggttcgcaa gaacctgatg 6240
gacatgttca gggatcgcca ggcgttttct gagcatacct ggaaaatgct tctgtccgtt 6300
tgccggtcgt gggcggcatg gtgcaagttg aataaccgga aatggtttcc cgcagaacct 6360
gaagatgttc gcgattatct tctatatctt caggcgcgcg gtctggcagt aaaaactatc 6420
cagcaacatt tgggccagct aaacatgctt catcgtcggt ccgggctgcc acgaccaagt 6480
gacagcaatg ctgtttcact ggttatgcgg cggatccgaa aagaaaacgt tgatgccggt 6540
gaacgtgcaa aacaggctct agcgttcgaa cgcactgatt tcgaccaggt tcgttcactc 6600
atggaaaata gcgatcgctg ccaggatata cgtaatctgg catttctggg gattgcttat 6660
aacaccctgt tacgtatagc cgaaattgcc aggatcaggg ttaaagatat ctcacgtact 6720
gacggtggga gaatgttaat ccatattggc agaacgaaaa cgctggttag caccgcaggt 6780
gtagagaagg cacttagcct gggggtaact aaactggtcg agcgatggat ttccgtctct 6840
ggtgtagctg atgatccgaa taactacctg ttttgccggg tcagaaaaaa tggtgttgcc 6900
gcgccatctg ccaccagcca gctatcaact cgcgccctgg aagggatttt tgaagcaact 6960
catcgattga tttacggcgc taaggatgac tctggtcaga gatacctggc ctggtctgga 7020
cacagtgccc gtgtcggagc cgcgcgagat atggcccgcg ctggagtttc aataccggag 7080
atcatgcaag ctggtggctg gaccaatgta aatattgtca tgaactatat ccgtaacctg 7140
gatagtgaaa caggggcaat ggtgcgcctg ctggaagatg gcgattagga gtaagcgaat 7200
ttcttatgat ttatgatttt tattattaaa taagttataa aaaaaataag tgtatacaaa 7260
ttttaaagtg actcttaggt tttaaaacga aaattcttat tcttgagtaa ctctttcctg 7320
taggtcaggt tgctttctca ggtatagcat gaggtcgctc ttattgacca cacctctacc 7380
ggcatgccga gcaaatgcct gcaaatcgct ccccatttca cccaattgta gatatgctaa 7440
ctccagcaat gagttgatga atctcggtgt gtattttatg tcctcagagg acaacacctg 7500
tggtccgcca ccgcggtgga gct 7523

<210> SEQ ID NO 111
<211> LENGTH: 6747
<212> TYPE: DNA

<213> ORGANISM: Artificial sequence
<220> FEATURE:
<223> OTHER INFORMATION: Synthetic construct

<400> SEQUENCE: 111
ctagatgtat atgagatagt tgattgtatg cttggtatag cttgaaatat tgtgcagaaa 60
aagaaacaag gaagaaaggg aacgagaaca atgacgagga aacaaaagat taataattgc 120
aggtctattt atacttgata gcaagacagc aaactttttt ttatttcaaa ttcaagtaac 180
tggaaggaag gccgtatacc gttgctcatt agagagtagt gtgcgtgaat gaaggaagga 240
aaaagtttcg tgtgcttcga gatacccctc atcagctctg gaacaacgac atctgttggt 300
gctgtctttg tcgttaattt tttcctttag tgtcttccat catttttttg tcattgcgga 360
tatggtgaga caacaacggg ggagagagaa aagaaaaaaa aagaaaagaa gttgcatgcg 420
cctattatta cttcaataga tggcaaatgg aaaaagggta gtgaaacttc gatatgatga 480
tggctatcaa gtctagggct acagtattag ttcgttatgt accaccatca atgaggcagt 540
gtaattggtg tagtcttgtt tagcccatta tgtcttgtct ggtatctgtt ctattgtata 600
tctcccctcc gccacctaca tgttagggag accaacgaag gtattatagg aatcccgatg 660
tatgggtttg gttgccagaa aagaggaagt ccatattgta cacaagcttg gcgtaatcat 720
ggtcatagct gtttcctgtg tgaaattgtt atccgctcac aattccacac aacatacgag 780
ccggaagcat aaagtgtaaa gcctggggtg cctaatgagt gagctaactc acattaattg 840
cgttgcgctc actgcccgct ttccagtcgg gaaacctgtc gtgccagctg cattaatgaa 900
tcggccaacg cgcggggaga ggcggtttgc gtattgggcg ctcttccgct tcctcgctca 960
ctgactcgct gcgctcggtc gttcggctgc ggcgagcggt atcagctcac tcaaaggcgg 1020
taatacggtt atccacagaa tcaggggata acgcaggaaa gaacatgtga gcaaaaggcc 1080
agcaaaaggc caggaaccgt aaaaaggccg cgttgctggc gtttttccat aggctccgcc 1140
cccctgacga gcatcacaaa aatcgacgct caagtcagag gtggcgaaac ccgacaggac 1200
tataaagata ccaggcgttt ccccctggaa gctccctcgt gcgctctcct gttccgaccc 1260
tgccgcttac cggatacctg tccgcctttc tcccttcggg aagcgtggcg ctttctcata 1320
gctcacgctg taggtatctc agttcggtgt aggtcgttcg ctccaagctg ggctgtgtgc 1380
acgaaccccc cgttcagccc gaccgctgcg ccttatccgg taactatcgt cttgagtcca 1440
acccggtaag acacgactta tcgccactgg cagcagccac tggtaacagg attagcagag 1500
cgaggtatgt aggcggtgct acagagttct tgaagtggtg gcctaactac ggctacacta 1560
gaaggacagt atttggtatc tgcgctctgc tgaagccagt taccttcgga aaaagagttg 1620
gtagctcttg atccggcaaa caaaccaccg ctggtagcgg tggttttttt gtttgcaagc 1680
agcagattac gcgcagaaaa aaaggatctc aagaagatcc tttgatcttt tctacggggt 1740
ctgacgctca gtggaacgaa aactcacgtt aagggatttt ggtcatgaga ttatcaaaaa 1800
ggatcttcac ctagatcctt ttaaattaaa aatgaagttt taaatcaatc taaagtatat 1860
atgagtaaac ttggtctgac agttaccaat gcttaatcag tgaggcacct atctcagcga 1920
tctgtctatt tcgttcatcc atagttgcct gactccccgt cgtgtagata actacgatac 1980
gggagggctt accatctggc cccagtgctg caatgatacc gcgagaccca cgctcaccgg 2040
ctccagattt atcagcaata aaccagccag ccggaagggc cgagcgcaga agtggtcctg 2100
caactttatc cgcctccatc cagtctatta attgttgccg ggaagctaga gtaagtagtt 2160
cgccagttaa tagtttgcgc aacgttgttg ccattgctac aggcatcgtg gtgtcacgct 2220

-continued

```
cgtcgtttgg tatggcttca ttcagctccg gttcccaacg atcaaggcga gttacatgat   2280
cccccatgtt gtgcaaaaaa gcggttagct ccttcggtcc tccgatcgtt gtcagaagta   2340
agttggccgc agtgttatca ctcatggtta tggcagcact gcataattct cttactgtca   2400
tgccatccgt aagatgcttt tctgtgactg gtgagtactc aaccaagtca ttctgagaat   2460
agtgtatgcg gcgaccgagt tgctcttgcc cggcgtcaat acgggataat accgcgccac   2520
atagcagaac tttaaaagtg ctcatcattg gaaaacgttc ttcggggcga aaactctcaa   2580
ggatcttacc gctgttgaga tccagttcga tgtaacccac tcgtgcaccc aactgatctt   2640
cagcatcttt tactttcacc agcgtttctg ggtgagcaaa aacaggaagg caaaatgccg   2700
caaaaaaggg aataagggcg acacggaaat gttgaatact catactcttc ctttttcaat   2760
attattgaag catttatcag ggttattgtc tcatgagcgg atacatattt gaatgtattt   2820
agaaaaataa acaaataggg gttccgcgca catttccccg aaaagtgcca cctgacgtct   2880
aagaaaccat tattatcatg acattaacct ataaaaatag gcgtatcacg aggccctttc   2940
gtctcgcgcg tttcggtgat gacggtgaaa acctctgaca catgcagctc ccggagacgg   3000
tcacagcttg tctgtaagcg gatgccggga gcagacaagc ccgtcagggc gcgtcagcgg   3060
gtgttggcgg gtgtcggggc tggcttaact atgcggcatc agagcagatt gtactgagag   3120
tgcaccatat gcggtgtgaa ataccgcaca gatgcgtaag gagaaaatac cgcatcaggc   3180
gccattcgcc attcaggctg cgcaactgtt gggaagggcg atcggtgcgg gcctcttcgc   3240
tattacgcca gctggcgaaa gggggatgtg ctgcaaggcg attaagttgg gtaacgccag   3300
ggttttccca gtcacgacgt tgtaaaacga cggccagtga attcaccttg gctaactcgt   3360
tgtatcatca ctggataact tcgtataatg tatgctatac gaagttatct tgattagggt   3420
gatggttcac gtagtgggcc atcgccctga tagacggttt ttcgcccttt gacgttggag   3480
tccacgttct ttaatagtgg actcttgttc caaactggaa caacactcaa ccctatctcg   3540
gtctattctt ttgatttata agggattttg ccgatttcgg cctattggtt aaaaaatgag   3600
ctgatttaac aaaaatttaa cgcgaatttt aacaaaatat taacgtttac aatttcctga   3660
tgcggtattt tctccttacg catctgtgcg gtatttcaca ccgcataggg taataactga   3720
tataattaaa ttgaagctct aatttgtgag tttagtatac atgcatttac ttataataca   3780
gtttttagt  tttgctggcc gcatcttctc aaatatgctt cccagcctgc ttttctgtaa   3840
cgttcaccct ctaccttagc atcccttccc tttgcaaata gtcctcttcc aacaataata   3900
atgtcagatc ctgtagagac cacatcatcc acggttctat actgttgacc caatgcgtct   3960
cccttgtcat ctaaacccac accgggtgtc ataatcaacc aatcgtaacc ttcatctctt   4020
ccacccatgt ctctttgagc aataaagccg ataacaaaat ctttgtcgct cttcgcaatg   4080
tcaacagtac ccttagtata ttctccagta gatagggagc ccttgcatga caattctgct   4140
aacatcaaaa ggcctctagg ttcctttgtt acttcttctg ccgcctgctt caaaccgcta   4200
acaatacctg ggcccaccac accgtgtgca ttcgtaatgt ctgcccattc tgctattctg   4260
tatacacccg cagagtactg caatttgact gtattaccaa tgtcagcaaa ttttctgtct   4320
tcgaagagta aaaaattgta cttggcggat aatgccttta gcggcttaac tgtgccctcc   4380
atggaaaaat cagtcaagat atccacatgt gtttttagta aacaaatttt gggacctaat   4440
gcttcaacta actccagtaa ttccttggtg gtacgaacat ccaatgaagc acacaagttt   4500
gtttgctttt cgtgcatgat attaaatagc ttggcagcaa caggactagg atgagtagca   4560
gcacgttcct tatatgtagc tttcgacatg atttatcttc gtttcctgca ggtttttgtt   4620
```

-continued

```
ctgtgcagtt gggttaagaa tactgggcaa tttcatgttt cttcaacact acatatgcgt   4680

atatatacca atctaagtct gtgctccttc cttcgttctt ccttctgttc ggagattacc   4740

gaatcaaaaa aatttcaaag aaaccgaaat caaaaaaaag aataaaaaaa aaatgatgaa   4800

ttgaattgaa aagctgtggt atggtgcact ctcagtacaa tctgcataac ttcgtataat   4860

gtatgctata cgaagttatc tgaacattag aatacgtaat ccgcaatgcg gatccggaag   4920

tgtagagagg gttaaaattg gcgtgcaatt ttatgaagaa taaagacatc tagtctttaa   4980

atacttgaac aataaatacg aaatccttat ataagcatct tttactacca aaaaaattta   5040

aaattaagca agagaaaaaa acgagcaatt gttaaaagaa actaaaatca tgtagatttc   5100

ataaatcgtc atattctttg tctatataaa tatttatcgt cacgaataaa tcccgtgaat   5160

ttctaacaaa gtttatacaa tatcacagtt gtaaaagtaa gaaaaaaaaa gatcatagaa   5220

aacatgttca cataagtaga aaaagggcac cttcttgttg ttcaaactta atttacaaat   5280

taagtttaag caccgatgat accaacggac ttaccttcag caattctttt ttgggccaaa   5340

gcagcaataa cagcggcacc agcaccggaa ccatcttcag caggaacaat cttgattggg   5400

tagtcgtcta gtgaggtttg agtccagccg taaatgtcct tcaaagcatt ggcagccttt   5460

tctttgaaac ctgggtatct gttgtaaacg gaaccgtctg cagcgatgtg accggtcttg   5520

taacctctct tttgacagat agcagcaata ccacaaacgg acaatctagc agctctagca   5580

ccaatcaatt cagataaacg tctgatcaat ttacgttctt gaacagtagt gttgataccg   5640

aactcatttt ggaacaagtc atcggtatct tctaggttct cgaatggatc ttcctcgatt   5700

ctggctgggt aagaagtgtc catgacgaaa ggcttgtcga acttagacaa gtcttggttc   5760

ttgaagatga aaccttgttt gtacatgtcc atcaaggcca aacgcaaaat ttcacctaag   5820

tagtaaccag aagacatttt ttcaaaggtt tgttggcctg gtcttggaga ttcttcatca   5880

atggtgatat cgtatttagt tcttggcaaa acgacatgtt cattatcgaa ggaaccgtat   5940

tcacagttga tggccattgg agcagatggt ggaatgtcat cagatagttt tccttgtagc   6000

ttttcgatat cggaacaaac atcgtagtaa gcaccattga caccagtacc gaagataaca   6060

cccatcttag tttctgggtc agtgtagtaa gaagcaacca aagtaccggt agtgtcgttt   6120

atcaaagcaa caacttcaat tgggatattc ctcttagtga tttgcttttg caacattgga   6180

acaacatcgt ggttttcaat gtttggaata tcaaaacctt tagtccatct ttgcaagata   6240

ccttcattga ttttgttttg agaagctggg aaagaaaagg tgaaacccaa tggaattggc   6300

tcagagatac cttgtgggaa ttgctcatca ataaaagctt tcaaagagtc ggcaataaat   6360

tcccacaatt cgtctggatt ttgagtagtt ctcatagcat ctggtaatct gtacttagat   6420

tgagtggtgt caaaggtacg gtcaccgccc aacttgacta agacaactct caagttggta   6480

ccacccaaat caatggccaa gaaatcaccg gattccttac cagttgggaa atccataacc   6540

caacctggaa tcattggaat gttaccaccc ttcttggaca aaccctttc caattcggaa    6600

atgaagtgct tggtaacggc ttgtaaagtt tcagttggaa cagtgaaaat tttttcaaaa   6660

ttctcaattt gttgcatcaa ttcctttggc acatcggcca tggaaccctt tctggcttgt   6720

ggttttttg gacctaaatg aaccatt                                        6747
```

<210> SEQ ID NO 112
<211> LENGTH: 40
<212> TYPE: DNA
<213> ORGANISM: Artificial sequence
<220> FEATURE:
<223> OTHER INFORMATION: Primer

<400> SEQUENCE: 112
caacaaaagc ttgtgtacaa tatggacttc ctcttttctg 40

<210> SEQ ID NO 113
<211> LENGTH: 43
<212> TYPE: DNA
<213> ORGANISM: Artificial sequence
<220> FEATURE:
<223> OTHER INFORMATION: Primer

<400> SEQUENCE: 113
aagtttgtct agatgtatat gagatagttg attgtatgct tgg 43

<210> SEQ ID NO 114
<211> LENGTH: 1605
<212> TYPE: DNA
<213> ORGANISM: Yarrowia lipolytica

<400> SEQUENCE: 114
atggttcatc ttggtccccg aaaacccccg tcccgaaagg gctcaatggc agacgtcccg 60
cgggacctgc tggagcaaat ctcccagctt gaaaccatct tcaccgtttc gcccgaaaag 120
ctgcgtcaaa tcaccgacca ctttgtgtcc gagctcgcta aaggcctcac aaaggagggt 180
ggagatatcc ccatgaaccc cacctggatt ctgggatggc ccaccggaaa ggagagcggc 240
tgctatctgg ctctcgacat gggtggcacc aacctgcgag ttgtcaaggt gactctggac 300
ggcgaccgag gcttcgacgt catgcagtcc aagtaccaca tgccccccaa catcaaggtc 360
ggcaagcaag aggagctgtg ggagtacatt gccgaatgtc tgggcaagtt cttggccgac 420
aattatcctg aggctcttga tgcccatgag cgaggacgag atgtcgacag aaccgctgcg 480
cagagcttca ctcgagacaa gtctcctcct ccccacaacc agcacatttc gtgttctcct 540
ggcttcgaca tccacaagat tcctctcggt ttcacctttt catatccctg ctctcagccc 600
gccgtcaacc gaggtgtact gcagcgatgg accaagggtt tcgacattga gggagtcgag 660
ggcgaggacg tggtccccat gctggaagct gccctcgaaa gaaagaacat tcctatttcc 720
atcaccgccc tgatcaacga caccaccgga actatggtgg cctccaacta ccacgacccc 780
cagatcaagc tgggtaacat ctttggtact ggtgtcaacg ccgcctacta cgagaaggtc 840
aaggacattc ccaagctcaa gggtctcatc cccgacagca ttgatcccga gacccccatg 900
gccgtcaatt gcgagtatgg agccttcgac aatgagcaca aggttctccc tagaaccaag 960
tgggacatca tcatcgatga ggagtctccc cgacccggtc agcagacctt cgagaagatg 1020
agtgctggct actacctggg agaattgctt cgtctggttc ttctggacct gtacaaggac 1080
gggtttgtgt tcgagaacca gggcaagaac ggtcaggagc ttggaaacgg caacatcaac 1140
aagtcgtatt tcttcgacac ctctttcctg tctctgattg aggaggatcc ctgggagaac 1200
ttgactgatg tcgagattct cttcaaggag aagcttggta ttaacaccac tgagcccgag 1260
cgaaagctca ttcgtcgact ggccgagctc attggtactc gatccgctcg aatctctgcc 1320
tgtggtgtcg ctgccatctg taagaaggct ggctacaagg aggctcacgc tggagctgac 1380
ggatccgtgt tcaacaagta ccccggattc aaggagcgag gcgcccaggc tctcaacgag 1440
atttttgagt ggaacctgcc caaccctaag gaccacccca tcaaaatcgt tcccgctgag 1500
gatggtagcg gtgttggagc tgctctgtgc gctgctctca ccatcaagcg agtcaagcag 1560
ggtcttcccg ttggtgtcaa gcccggtgtc aagtacgata tttag 1605

<210> SEQ ID NO 115

<211> LENGTH: 534
<212> TYPE: PRT
<213> ORGANISM: Yarrowia lipolytica

<400> SEQUENCE: 115

```
Met Val His Leu Gly Pro Arg Lys Pro Pro Ser Arg Lys Gly Ser Met
1               5                   10                  15

Ala Asp Val Pro Arg Asp Leu Leu Glu Gln Ile Ser Gln Leu Glu Thr
            20                  25                  30

Ile Phe Thr Val Ser Pro Glu Lys Leu Arg Gln Ile Thr Asp His Phe
        35                  40                  45

Val Ser Glu Leu Ala Lys Gly Leu Thr Lys Glu Gly Gly Asp Ile Pro
    50                  55                  60

Met Asn Pro Thr Trp Ile Leu Gly Trp Pro Thr Gly Lys Glu Ser Gly
65                  70                  75                  80

Cys Tyr Leu Ala Leu Asp Met Gly Gly Thr Asn Leu Arg Val Val Lys
                85                  90                  95

Val Thr Leu Asp Gly Asp Arg Gly Phe Asp Val Met Gln Ser Lys Tyr
            100                 105                 110

His Met Pro Pro Asn Ile Lys Val Gly Lys Gln Glu Glu Leu Trp Glu
        115                 120                 125

Tyr Ile Ala Glu Cys Leu Gly Lys Phe Leu Ala Asp Asn Tyr Pro Glu
    130                 135                 140

Ala Leu Asp Ala His Glu Arg Gly Arg Asp Val Asp Arg Thr Ala Ala
145                 150                 155                 160

Gln Ser Phe Thr Arg Asp Lys Ser Pro Pro Pro His Asn Gln His Ile
                165                 170                 175

Ser Cys Ser Pro Gly Phe Asp Ile His Lys Ile Pro Leu Gly Phe Thr
            180                 185                 190

Phe Ser Tyr Pro Cys Ser Gln Pro Ala Val Asn Arg Gly Val Leu Gln
        195                 200                 205

Arg Trp Thr Lys Gly Phe Asp Ile Glu Gly Val Glu Gly Glu Asp Val
    210                 215                 220

Val Pro Met Leu Glu Ala Ala Leu Glu Arg Lys Asn Ile Pro Ile Ser
225                 230                 235                 240

Ile Thr Ala Leu Ile Asn Asp Thr Thr Gly Thr Met Val Ala Ser Asn
                245                 250                 255

Tyr His Asp Pro Gln Ile Lys Leu Gly Asn Ile Phe Gly Thr Gly Val
            260                 265                 270

Asn Ala Ala Tyr Tyr Glu Lys Val Lys Asp Ile Pro Lys Leu Lys Gly
        275                 280                 285

Leu Ile Pro Asp Ser Ile Asp Pro Glu Thr Pro Met Ala Val Asn Cys
    290                 295                 300

Glu Tyr Gly Ala Phe Asp Asn Glu His Lys Val Leu Pro Arg Thr Lys
305                 310                 315                 320

Trp Asp Ile Ile Ile Asp Glu Glu Ser Pro Arg Pro Gly Gln Gln Thr
                325                 330                 335

Phe Glu Lys Met Ser Ala Gly Tyr Tyr Leu Gly Glu Leu Leu Arg Leu
            340                 345                 350

Val Leu Leu Asp Leu Tyr Lys Asp Gly Phe Val Phe Glu Asn Gln Gly
        355                 360                 365

Lys Asn Gly Gln Glu Leu Gly Asn Gly Asn Ile Asn Lys Ser Tyr Phe
    370                 375                 380

Phe Asp Thr Ser Phe Leu Ser Leu Ile Glu Glu Asp Pro Trp Glu Asn
385                 390                 395                 400
```

```
Leu Thr Asp Val Glu Ile Leu Phe Lys Glu Lys Leu Gly Ile Asn Thr
                405                 410                 415

Thr Glu Pro Glu Arg Lys Leu Ile Arg Arg Leu Ala Glu Leu Ile Gly
            420                 425                 430

Thr Arg Ser Ala Arg Ile Ser Ala Cys Gly Val Ala Ala Ile Cys Lys
        435                 440                 445

Lys Ala Gly Tyr Lys Glu Ala His Ala Gly Ala Asp Gly Ser Val Phe
    450                 455                 460

Asn Lys Tyr Pro Gly Phe Lys Glu Arg Gly Ala Gln Ala Leu Asn Glu
465                 470                 475                 480

Ile Phe Glu Trp Asn Leu Pro Asn Pro Lys Asp His Pro Ile Lys Ile
                485                 490                 495

Val Pro Ala Glu Asp Gly Ser Gly Val Gly Ala Ala Leu Cys Ala Ala
            500                 505                 510

Leu Thr Ile Lys Arg Val Lys Gln Gly Leu Pro Val Gly Val Lys Pro
        515                 520                 525

Gly Val Lys Tyr Asp Ile
    530


<210> SEQ ID NO 116
<211> LENGTH: 1437
<212> TYPE: DNA
<213> ORGANISM: Schwanniomyces occidentalis

<400> SEQUENCE: 116

atggttcact taggtccaaa acctccacaa catagaaaag gatccttctt ggatgttcct     60

gaatatttgt tgaaggaatt gacagaactc gaaggattat taacagtttc aggtgaaaca    120

ttaaggaaga ttactgatca ctttatttca gaattggaaa aaggtttatc taaacaaggg    180

ggaaatattc ctatgattcc aggatgggtt atggacttcc caacaggaaa agaaatgggt    240

gattacttgg ctattgattt aggtggtact aatttgagag ttgttttagt taagttaggt    300

ggtaacaggg actttgacac tactcaatcc aagttcgcat tgccagaaaa catgagaact    360

gccaagtctg aagagttatg ggaatttatt gctgagtgtt tacaaaagtt cgtggaagaa    420

gaatttcgaa atggtgttct gtcaaattta ccattaggtt tcaccttttc atacccagca    480

tctcaaggtt ctatcaatga agggtatttg caaagatgga ccaaaggttt cgacattgaa    540

ggtgttgagg gacacgatgt tgttccaatg ttacaagctg caattgaaaa acgtaaggtt    600

ccaattgaag ttgttgcgtt aatcaatgac accacaggta ctttagttgc ttctatgtac    660

accgatccag aagctaaaat gggtttattt tccggtactg gttgtaatgg tgcttactac    720

gatgttgtcg ataacattcc aaaattagaa ggaaaggttc cagatgacat taaaagctct    780

tccccaatgg ccatcaactg tgaatacggt gctttcgata atgagcatat cattttgcct    840

agaactaaat acgatatcca aatcgatgaa gaatcaccaa gaccaggaca acaggctttc    900

gaaaagatga tctctggtta ctacttaggt gaagttttaa gattgatttt acttgattta    960

acctctaaac aattaatttt caaagaccaa gatttgtcta aattacaagt tccattcatt   1020

ttagatacct caatcccagc tagaattgaa gaagatccgt ttgaaaactt atctgatgtc   1080

caagaattat ttcaagaaat tttaggtatt caaactactt ctccagaaag aaaaatcatc   1140

cgtcgtctag cggaattgat cggtgaaaga tcagccagat tatcaatttg tggtattgct   1200

gctatttgca agaagagagg ctacaaaacc gctcattgtg ccgctgatgg ttcagtctac   1260

aacaaatacc caggtttcaa agaaagagct gctaaaggtt tgagagatat ctttcaatgg   1320
```

```
gaatctgaag aagatccaat tgtcattgtg cctgcagaag atggtttagg tgcaggtgcc   1380

gctatcattg ctgcattgac tgaaaaaaga ttaaaggatg gattaccgtt ggtatga      1437


<210> SEQ ID NO 117
<211> LENGTH: 478
<212> TYPE: PRT
<213> ORGANISM: Schwanniomyces occidentalis

<400> SEQUENCE: 117

Met Val His Leu Gly Pro Lys Pro Pro Gln His Arg Lys Gly Ser Phe
1               5                   10                  15

Leu Asp Val Pro Glu Tyr Leu Leu Lys Glu Leu Thr Glu Leu Glu Gly
            20                  25                  30

Leu Leu Thr Val Ser Gly Glu Thr Leu Arg Lys Ile Thr Asp His Phe
        35                  40                  45

Ile Ser Glu Leu Glu Lys Gly Leu Ser Lys Gln Gly Gly Asn Ile Pro
    50                  55                  60

Met Ile Pro Gly Trp Val Met Asp Phe Pro Thr Gly Lys Glu Met Gly
65                  70                  75                  80

Asp Tyr Leu Ala Ile Asp Leu Gly Gly Thr Asn Leu Arg Val Val Leu
                85                  90                  95

Val Lys Leu Gly Gly Asn Arg Asp Phe Asp Thr Thr Gln Ser Lys Phe
            100                 105                 110

Ala Leu Pro Glu Asn Met Arg Thr Ala Lys Ser Glu Glu Leu Trp Glu
        115                 120                 125

Phe Ile Ala Glu Cys Leu Gln Lys Phe Val Glu Glu Glu Phe Arg Asn
    130                 135                 140

Gly Val Leu Ser Asn Leu Pro Leu Gly Phe Thr Phe Ser Tyr Pro Ala
145                 150                 155                 160

Ser Gln Gly Ser Ile Asn Glu Gly Tyr Leu Gln Arg Trp Thr Lys Gly
                165                 170                 175

Phe Asp Ile Glu Gly Val Glu Gly His Asp Val Val Pro Met Leu Gln
            180                 185                 190

Ala Ala Ile Glu Lys Arg Lys Val Pro Ile Glu Val Val Ala Leu Ile
        195                 200                 205

Asn Asp Thr Thr Gly Thr Leu Val Ala Ser Met Tyr Thr Asp Pro Glu
    210                 215                 220

Ala Lys Met Gly Leu Phe Ser Gly Thr Gly Cys Asn Gly Ala Tyr Tyr
225                 230                 235                 240

Asp Val Val Asp Asn Ile Pro Lys Leu Glu Gly Lys Val Pro Asp Asp
                245                 250                 255

Ile Lys Ser Ser Ser Pro Met Ala Ile Asn Cys Glu Tyr Gly Ala Phe
            260                 265                 270

Asp Asn Glu His Ile Ile Leu Pro Arg Thr Lys Tyr Asp Ile Gln Ile
        275                 280                 285

Asp Glu Glu Ser Pro Arg Pro Gly Gln Gln Ala Phe Glu Lys Met Ile
    290                 295                 300

Ser Gly Tyr Tyr Leu Gly Glu Val Leu Arg Leu Ile Leu Leu Asp Leu
305                 310                 315                 320

Thr Ser Lys Gln Leu Ile Phe Lys Asp Gln Asp Leu Ser Lys Leu Gln
                325                 330                 335

Val Pro Phe Ile Leu Asp Thr Ser Ile Pro Ala Arg Ile Glu Glu Asp
            340                 345                 350

Pro Phe Glu Asn Leu Ser Asp Val Gln Glu Leu Phe Gln Glu Ile Leu
        355                 360                 365
```

```
Gly Ile Gln Thr Thr Ser Pro Glu Arg Lys Ile Ile Arg Arg Leu Ala
    370                 375                 380

Glu Leu Ile Gly Glu Arg Ser Ala Arg Leu Ser Ile Cys Gly Ile Ala
385                 390                 395                 400

Ala Ile Cys Lys Lys Arg Gly Tyr Lys Thr Ala His Cys Ala Ala Asp
                405                 410                 415

Gly Ser Val Tyr Asn Lys Tyr Pro Gly Phe Lys Glu Arg Ala Ala Lys
            420                 425                 430

Gly Leu Arg Asp Ile Phe Gln Trp Glu Ser Glu Glu Asp Pro Ile Val
        435                 440                 445

Ile Val Pro Ala Glu Asp Gly Leu Gly Ala Gly Ala Ala Ile Ile Ala
    450                 455                 460

Ala Leu Thr Glu Lys Arg Leu Lys Asp Gly Leu Pro Leu Val
465                 470                 475
```

<210> SEQ ID NO 118
<211> LENGTH: 1398
<212> TYPE: DNA
<213> ORGANISM: Homo sapiens

<400> SEQUENCE: 118

```
atgctggacg acagagccag gatggaggcc gccaagaagg agaaggtaga gcagatcctg      60

gcagagttcc agctgcagga ggaggacctg aagaaggtga tgagacggat gcagaaggag     120

atggaccgcg gcctgaggct ggagacccat gaagaggcca gtgtgaagat gctgcccacc     180

tacgtgcgct ccaccccaga aggctcagaa gtcggggact tcctctccct ggacctgggt     240

ggcactaact tcagggtgat gctggtgaag gtgggagaag gtgaggaggg gcagtggagc     300

gtgaagacca aacaccagat gtactccatc cccgaggacg ccatgaccgg cactgctgag     360

atgctcttcg actacatctc tgagtgcatc tccgacttcc tggacaagca tcagatgaaa     420

cacaagaagc tgcccctggg cttcaccttc tcctttcctg tgaggcacga agacatcgat     480

aagggcatcc ttctcaactg gaccaagggc ttcaaggcct caggagcaga agggaacaat     540

gtcgtggggc ttctgcgaga cgctatcaaa cggagagggg actttgaaat ggatgtggtg     600

gcaatggtga atgacacggt ggccacgatg atctcctgct actacgaaga ccatcagtgc     660

gaggtcggca tgatcgtggg cacgggctgc aatgcctgct acatggagga gatgcagaat     720

gtggagctgg tggaggggga cgagggccgc atgtgcgtca ataccgagtg gggcgccttc     780

ggggactccg gcgagctgga cgagttcctg ctggagtatg accgcctggt ggacgagagc     840

tctgcaaacc ccggtcagca gctgtatgag aagctcatag gtggcaagta catgggcgag     900

ctggtgcggc ttgtgctgct caggctcgtg gacgaaaacc tgctcttcca cggggaggcc     960

tccgagcagc tgcgcacacg cggagccttc gagacgcgct tcgtgtcgca ggtggagagc    1020

gacacgggcg accgcaagca gatctacaac atcctgagca cgctggggct gcgaccctcg    1080

accaccgact gcgacatcgt gcgccgcgcc tgcgagagcg tgtctacgcg cgctgcgcac    1140

atgtgctcgg cggggctggc gggcgtcatc aaccgcatgc gcgagagccg cagcgaggac    1200

gtaatgcgca tcactgtggg cgtggatggc tccgtgtaca agctgcaccc cagcttcaag    1260

gagcggttcc atgccagcgt gcgcaggctg acgcccagct gcgagatcac cttcatcgag    1320

tcggaggagg gcagtggccg ggcgcggccc ctggtctcgg cggtggcctg taagaaggcc    1380

tgtatgctgg gccagtga                                                  1398
```

<210> SEQ ID NO 119

-continued

<211> LENGTH: 465
<212> TYPE: PRT
<213> ORGANISM: Homo sapiens

<400> SEQUENCE: 119

```
Met Leu Asp Asp Arg Ala Arg Met Glu Ala Ala Lys Lys Glu Lys Val
1               5                   10                  15

Glu Gln Ile Leu Ala Glu Phe Gln Leu Gln Glu Glu Asp Leu Lys Lys
            20                  25                  30

Val Met Arg Arg Met Gln Lys Glu Met Asp Arg Gly Leu Arg Leu Glu
        35                  40                  45

Thr His Glu Glu Ala Ser Val Lys Met Leu Pro Thr Tyr Val Arg Ser
    50                  55                  60

Thr Pro Glu Gly Ser Glu Val Gly Asp Phe Leu Ser Leu Asp Leu Gly
65                  70                  75                  80

Gly Thr Asn Phe Arg Val Met Leu Val Lys Val Gly Glu Gly Glu Glu
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
        115                 120                 125

Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Ile Asp
145                 150                 155                 160

Lys Gly Ile Leu Leu Asn Trp Thr Lys Gly Phe Lys Ala Ser Gly Ala
                165                 170                 175

Glu Gly Asn Asn Val Val Gly Leu Leu Arg Asp Ala Ile Lys Arg Arg
            180                 185                 190

Gly Asp Phe Glu Met Asp Val Val Ala Met Val Asn Asp Thr Val Ala
        195                 200                 205

Thr Met Ile Ser Cys Tyr Tyr Glu Asp His Gln Cys Glu Val Gly Met
    210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
                245                 250                 255

Trp Gly Ala Phe Gly Asp Ser Gly Glu Leu Asp Glu Phe Leu Leu Glu
            260                 265                 270

Tyr Asp Arg Leu Val Asp Glu Ser Ser Ala Asn Pro Gly Gln Gln Leu
        275                 280                 285

Tyr Glu Lys Leu Ile Gly Gly Lys Tyr Met Gly Glu Leu Val Arg Leu
    290                 295                 300

Val Leu Leu Arg Leu Val Asp Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335

Gln Val Glu Ser Asp Thr Gly Asp Arg Lys Gln Ile Tyr Asn Ile Leu
            340                 345                 350

Ser Thr Leu Gly Leu Arg Pro Ser Thr Thr Asp Cys Asp Ile Val Arg
        355                 360                 365

Arg Ala Cys Glu Ser Val Ser Thr Arg Ala Ala His Met Cys Ser Ala
    370                 375                 380

Gly Leu Ala Gly Val Ile Asn Arg Met Arg Glu Ser Arg Ser Glu Asp
385                 390                 395                 400
```

```
Val Met Arg Ile Thr Val Gly Val Asp Gly Ser Val Tyr Lys Leu His
                405                 410                 415

Pro Ser Phe Lys Glu Arg Phe His Ala Ser Val Arg Arg Leu Thr Pro
            420                 425                 430

Ser Cys Glu Ile Thr Phe Ile Glu Ser Glu Glu Gly Ser Gly Arg Gly
        435                 440                 445

Ala Ala Leu Val Ser Ala Val Ala Cys Lys Lys Ala Cys Met Leu Gly
    450                 455                 460

Gln
465
```

<210> SEQ ID NO 120
<211> LENGTH: 1458
<212> TYPE: DNA
<213> ORGANISM: Saccharomyces cerevisiae

<400> SEQUENCE: 120

```
atggttcatt taggtccaaa gaaaccacag gctagaaagg gttccatggc tgatgtgccc     60

aaggaattga tggatgaaat tcatcagttg gaagatatgt ttacagttga cagcgagacc    120

ttgagaaagg ttgttaagca ctttatcgac gaattgaata aaggtttgac aaagaaggga    180

ggtaacattc caatgattcc cggttgggtc atggaattcc caacaggtaa agaatctggt    240

aactatttgg ccattgattt gggtggtact aacttaagag tcgtgttggt caagttgagc    300

ggtaaccata cctttgacac cactcaatcc aagtataaac taccacatga catgagaacc    360

actaagcacc aagaggagtt atggtccttt attgccgact ctttgaagga ctttatggtc    420

gagcaagaat tgctaaacac caaggacacc ttaccattag gtttcacctt ctcgtaccca    480

gcttcccaaa acaagattaa cgaaggtatt ttgcaaagat ggaccaaggg tttcgatatt    540

ccaaatgtcg aaggccacga tgtcgtccca ttgctacaaa acgaaatttc caagagagag    600

ttgcctattg aaattgtagc attgattaat gatactgttg gtactttaat tgcctcatac    660

tacactgacc cagagactaa gatgggtgtg attttcggta ctggtgtcaa cggtgctttc    720

tatgatgttg tttccgatat cgaaaagttg gagggcaaat tagcagacga tattccaagt    780

aactctccaa tggctatcaa ttgtgaatat ggttccttcg ataatgaaca tttggtcttg    840

ccaagaacca agtacgatgt tgctgtcgac gaacaatctc caagacctgg tcaacaagct    900

tttgaaaaga tgacctccgg ttactacttg ggtgaattgt tgcgtctagt gttacttgaa    960

ttaaacgaga agggcttgat gttgaaggat caagatctaa gcaagttgaa acaaccatac   1020

atcatggata cctcctaccc agcaagaatc gaggatgatc catttgaaaa cttggaagat   1080

actgatgaca tcttccaaaa ggactttggt gtcaagacca ctctgccaga acgtaagttg   1140

attagaagac tttgtgaatt gatcggtacc agagctgcta gattagctgt ttgtggtatt   1200

gccgctattt gccaaaagag aggttacaag actggtcaca ttgccgctga cggttctgtc   1260

tataacaaat acccaggttt caaggaagcc gccgctaagg gtttgagaga tatctatgga   1320

tggactggtg acgcaagcaa agatccaatt acgattgttc cagctgagga tggttcaggt   1380

gcaggtgctg ctgttattgc tgcattgtcc gaaaaaagaa ttgccgaagg taagtctctt   1440

ggtatcattg gcgcttaa                                                 1458
```

<210> SEQ ID NO 121
<211> LENGTH: 485
<212> TYPE: PRT
<213> ORGANISM: Saccharomyces cerevisiae

<400> SEQUENCE: 121

```
Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
            20                  25                  30

Met Phe Thr Val Asp Ser Glu Thr Leu Arg Lys Val Val Lys His Phe
        35                  40                  45

Ile Asp Glu Leu Asn Lys Gly Leu Thr Lys Lys Gly Gly Asn Ile Pro
    50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
    210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
    290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Asp Ile Phe Gln Lys Asp
        355                 360                 365

Phe Gly Val Lys Thr Thr Leu Pro Glu Arg Lys Leu Ile Arg Arg Leu
    370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415
```

-continued

```
Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Asp Ala Ser Lys Asp
        435                 440                 445

Pro Ile Thr Ile Val Pro Ala Glu Asp Gly Ser Gly Ala Gly Ala Ala
    450                 455                 460

Val Ile Ala Ala Leu Ser Glu Lys Arg Ile Ala Glu Gly Lys Ser Leu
465                 470                 475                 480

Gly Ile Ile Gly Ala
                485
```

<210> SEQ ID NO 122
<211> LENGTH: 1503
<212> TYPE: DNA
<213> ORGANISM: Saccharomyces cerevisiae

<400> SEQUENCE: 122

```
atgtcattcg acgacttaca caaagccact gagagagcgg tcatccaggc cgtggaccag      60

atctgcgacg atttcgaggt tacccccgag aagctggacg aattaactgc ttacttcatc     120

gaacaaatgg aaaaaggtct agctccacca aaggaaggcc acacattggc ctcggacaaa     180

ggtcttccta tgattccggc gttcgtcacc gggtcaccca acgggacgga gcgcggtgtt     240

ttactagccg ccgacctggg tggtaccaat ttccgtatat gttctgttaa cttgcatgga     300

gatcatactt tctccatgga gcaaatgaag tccaagattc ccgatgattt gctagacgat     360

gagaacgtca catctgacga cctgtttggg tttctagcac gtcgtacact ggcctttatg     420

aagaagtatc acccggacga gttggccaag ggtaaagacg ccaagcccat gaaactgggg     480

ttcactttct cataccctgt agaccagacc tctctaaact ccgggacatt gatccgttgg     540

accaagggtt tccgcatcgc ggacaccgtc ggaaaggatg tcgtgcaatt gtaccaggag     600

caattaagcg ctcagggtat gcctatgatc aaggttgttg cattaaccaa cgacaccgtc     660

ggaacgtacc tatcgcattg ctacacgtcc gataacacgg actcaatgac gtccggagaa     720

atctcggagc cggtcatcgg atgtattttc ggtaccggta ccaatgggtg ctatatggag     780

gagatcaaca agatcacgaa gttgccacag gagttgcgtg acaagttgat aaaggagggt     840

aagacacaca tgatcatcaa tgtcgaatgg gggtccttcg ataatgagct caagcacttg     900

cctactacta agtatgacgt cgtaattgac cagaaactgt caacgaaccc gggatttcac     960

ttgtttgaaa aacgtgtctc agggatgttc ttgggtgagg tgttgcgtaa cattttagtg    1020

gacttgcact cgcaaggctt gcttttgcaa cagtacaggt ccaaggaaca acttcctcgc    1080

cacttgacta cacctttcca gttgtcatcc gaagtgctgt cgcatattga aattgacgac    1140

tcgacaggtc tacgtgaaac agagttgtca ttattacaga gtctcagact gcccaccact    1200

ccaacagagc gtgttcaaat tcaaaaattg gtgcgcgcga tttctaggag atctgcgtat    1260

ttagccgccg tgccgcttgc cgcgatattg atcaagacaa atgctttgaa caagagatat    1320

catggtgaag tcgagatcgg ttgtgatggt tccgttgtgg aatactaccc cggtttcaga    1380

tctatgctga gacacgcctt agccttgtca cccttgggtg ccgagggtga gaggaaggtg    1440

cacttgaaga ttgccaagga tggttccgga gtgggtgccg ccttgtgtgc gcttgtagca    1500

tga                                                                  1503
```

<210> SEQ ID NO 123
<211> LENGTH: 500
<212> TYPE: PRT
<213> ORGANISM: Saccharomyces cerevisiae -continued

<400> SEQUENCE: 123

```
Met Ser Phe Asp Asp Leu His Lys Ala Thr Glu Arg Ala Val Ile Gln
1               5                   10                  15

Ala Val Asp Gln Ile Cys Asp Asp Phe Glu Val Thr Pro Glu Lys Leu
            20                  25                  30

Asp Glu Leu Thr Ala Tyr Phe Ile Glu Gln Met Glu Lys Gly Leu Ala
        35                  40                  45

Pro Pro Lys Glu Gly His Thr Leu Ala Ser Asp Lys Gly Leu Pro Met
    50                  55                  60

Ile Pro Ala Phe Val Thr Gly Ser Pro Asn Gly Thr Glu Arg Gly Val
65                  70                  75                  80

Leu Leu Ala Ala Asp Leu Gly Gly Thr Asn Phe Arg Ile Cys Ser Val
                85                  90                  95

Asn Leu His Gly Asp His Thr Phe Ser Met Glu Gln Met Lys Ser Lys
            100                 105                 110

Ile Pro Asp Asp Leu Leu Asp Asp Glu Asn Val Thr Ser Asp Asp Leu
        115                 120                 125

Phe Gly Phe Leu Ala Arg Arg Thr Leu Ala Phe Met Lys Lys Tyr His
    130                 135                 140

Pro Asp Glu Leu Ala Lys Gly Lys Asp Ala Lys Pro Met Lys Leu Gly
145                 150                 155                 160

Phe Thr Phe Ser Tyr Pro Val Asp Gln Thr Ser Leu Asn Ser Gly Thr
                165                 170                 175

Leu Ile Arg Trp Thr Lys Gly Phe Arg Ile Ala Asp Thr Val Gly Lys
            180                 185                 190

Asp Val Val Gln Leu Tyr Gln Glu Gln Leu Ser Ala Gln Gly Met Pro
        195                 200                 205

Met Ile Lys Val Val Ala Leu Thr Asn Asp Thr Val Gly Thr Tyr Leu
    210                 215                 220

Ser His Cys Tyr Thr Ser Asp Asn Thr Asp Ser Met Thr Ser Gly Glu
225                 230                 235                 240

Ile Ser Glu Pro Val Ile Gly Cys Ile Phe Gly Thr Gly Thr Asn Gly
                245                 250                 255

Cys Tyr Met Glu Glu Ile Asn Lys Ile Thr Lys Leu Pro Gln Glu Leu
            260                 265                 270

Arg Asp Lys Leu Ile Lys Glu Gly Lys Thr His Met Ile Ile Asn Val
        275                 280                 285

Glu Trp Gly Ser Phe Asp Asn Glu Leu Lys His Leu Pro Thr Thr Lys
    290                 295                 300

Tyr Asp Val Val Ile Asp Gln Lys Leu Ser Thr Asn Pro Gly Phe His
305                 310                 315                 320

Leu Phe Glu Lys Arg Val Ser Gly Met Phe Leu Gly Glu Val Leu Arg
                325                 330                 335

Asn Ile Leu Val Asp Leu His Ser Gln Gly Leu Leu Leu Gln Gln Tyr
            340                 345                 350

Arg Ser Lys Glu Gln Leu Pro Arg His Leu Thr Thr Pro Phe Gln Leu
        355                 360                 365

Ser Ser Glu Val Leu Ser His Ile Glu Ile Asp Asp Ser Thr Gly Leu
    370                 375                 380

Arg Glu Thr Glu Leu Ser Leu Leu Gln Ser Leu Arg Leu Pro Thr Thr
385                 390                 395                 400

Pro Thr Glu Arg Val Gln Ile Gln Lys Leu Val Arg Ala Ile Ser Arg
                405                 410                 415
```

```
Arg Ser Ala Tyr Leu Ala Ala Val Pro Leu Ala Ala Ile Leu Ile Lys
            420                 425                 430

Thr Asn Ala Leu Asn Lys Arg Tyr His Gly Glu Val Glu Ile Gly Cys
        435                 440                 445

Asp Gly Ser Val Val Glu Tyr Tyr Pro Gly Phe Arg Ser Met Leu Arg
    450                 455                 460

His Ala Leu Ala Leu Ser Pro Leu Gly Ala Glu Gly Glu Arg Lys Val
465                 470                 475                 480

His Leu Lys Ile Ala Lys Asp Gly Ser Gly Val Gly Ala Ala Leu Cys
                485                 490                 495

Ala Leu Val Ala
            500


<210> SEQ ID NO 124
<211> LENGTH: 1446
<212> TYPE: DNA
<213> ORGANISM: Kluyveromyces lactis

<400> SEQUENCE: 124

atgtcagatc ctaagttaac caaggcggtt gattctatat gcgatcagtt cattgttact      60

aaatcgaaga tatctcagtt gactgagtat ttcatcgatt gtatggaaaa gggattagaa     120

ccctgtgaat cagatatcag tcaaaacaaa gggttgccta tgattccgac gtttgtgact     180

gacaagccat ccggtcagga acatggagta accatgttgg cagctgattt aggtggtact     240

aatttcagag tttgctctgt ggaactatta ggtaatcatg aattcaagat tgaacaagag     300

aagtcaaaga ttccaacttt cttcttccag gacgatcatc atgttaccag taaggatttg     360

ttccaacata tggccctgat cacgcatcag tttttgacta aacatcataa ggatgtaatt     420

caagattaca aatggaaaat gggtttcact ttttcatatc cagtcgatca aacctccttg     480

agcagtggta agttgattag atggaccaag ggtttcaaga tcggtgatac tgttgggcaa     540

gacgttgttc aactgttcca acaagaattg aacgatattg ggttatcaaa tgttcatgtg     600

gttgcattga ctaatgacac tactggaacc ctattggctc gttgttacgc ttccagtgat     660

gcggcaagag ccatcaacga accagtaatt ggctgtatct ttggtactgg tacgaacggc     720

tgctacatgg aaaagcttga aaatattcac aaattggatc cagctagcag agaagaactt     780

ctgtctcagg ggaagaccca tatgtgcatc aataccgaat ggggctcttt tgataatgaa     840

ctaaatcatt tgcctactac aagttatgat attaagattg atcagcagtt ctccaccaat     900

cccgggttcc acttgtttga aaaaagggtc agtggtcttt atttgggtga aatacttcgt     960

aacatactac tagaccttga aaaacaagag ttattcgact tgaaggaatc tgttttaaag    1020

aacaatccct ttattttaac cacagaaact ttatcacata tcgaaattga taccgttgag    1080

aacgacttac aggacacaag ggatgctctt ttaaaggctg ctgacttgga gaccaccttc    1140

gaagaacgtg tcttgatcca aaaattggta agagctattt ccaggagagc tgcattctta    1200

gccgcagtgc caattgctgc aattttgatc aaaaccaacg ctttgaacca gagttatcac    1260

tgccaagtag aggttggttg tgacggtagt gtcgttgagc actatccagg attcagatct    1320

atgatgagac atgcattagc actttctcca attggccccg agggtgaacg tgatgtccat    1380

ctacgtatct ccaaggatgg ttccggtgtt ggcgctgctt tgtgtgcttt gcatgcaaat    1440

tattaa                                                                1446


<210> SEQ ID NO 125
<211> LENGTH: 481
```

<212> TYPE: PRT
<213> ORGANISM: Kluveromyces lactis

<400> SEQUENCE: 125

```
Met Ser Asp Pro Lys Leu Thr Lys Ala Val Asp Ser Ile Cys Asp Gln
1               5                   10                  15

Phe Ile Val Thr Lys Ser Lys Ile Ser Gln Leu Thr Glu Tyr Phe Ile
            20                  25                  30

Asp Cys Met Glu Lys Gly Leu Glu Pro Cys Glu Ser Asp Ile Ser Gln
        35                  40                  45

Asn Lys Gly Leu Pro Met Ile Pro Thr Phe Val Thr Asp Lys Pro Ser
    50                  55                  60

Gly Gln Glu His Gly Val Thr Met Leu Ala Ala Asp Leu Gly Gly Thr
65                  70                  75                  80

Asn Phe Arg Val Cys Ser Val Glu Leu Leu Gly Asn His Glu Phe Lys
                85                  90                  95

Ile Glu Gln Glu Lys Ser Lys Ile Pro Thr Phe Phe Phe Gln Asp Asp
            100                 105                 110

His His Val Thr Ser Lys Asp Leu Phe Gln His Met Ala Leu Ile Thr
        115                 120                 125

His Gln Phe Leu Thr Lys His His Lys Asp Val Ile Gln Asp Tyr Lys
    130                 135                 140

Trp Lys Met Gly Phe Thr Phe Ser Tyr Pro Val Asp Gln Thr Ser Leu
145                 150                 155                 160

Ser Ser Gly Lys Leu Ile Arg Trp Thr Lys Gly Phe Lys Ile Gly Asp
                165                 170                 175

Thr Val Gly Gln Asp Val Val Gln Leu Phe Gln Gln Glu Leu Asn Asp
            180                 185                 190

Ile Gly Leu Ser Asn Val His Val Val Ala Leu Thr Asn Asp Thr Thr
        195                 200                 205

Gly Thr Leu Leu Ala Arg Cys Tyr Ala Ser Ser Asp Ala Ala Arg Ala
    210                 215                 220

Ile Asn Glu Pro Val Ile Gly Cys Ile Phe Gly Thr Gly Thr Asn Gly
225                 230                 235                 240

Cys Tyr Met Glu Lys Leu Glu Asn Ile His Lys Leu Asp Pro Ala Ser
                245                 250                 255

Arg Glu Glu Leu Leu Ser Gln Gly Lys Thr His Met Cys Ile Asn Thr
            260                 265                 270

Glu Trp Gly Ser Phe Asp Asn Glu Leu Asn His Leu Pro Thr Thr Ser
        275                 280                 285

Tyr Asp Ile Lys Ile Asp Gln Gln Phe Ser Thr Asn Pro Gly Phe His
    290                 295                 300

Leu Phe Glu Lys Arg Val Ser Gly Leu Tyr Leu Gly Glu Ile Leu Arg
305                 310                 315                 320

Asn Ile Leu Leu Asp Leu Glu Lys Gln Glu Leu Phe Asp Leu Lys Glu
                325                 330                 335

Ser Val Leu Lys Asn Asn Pro Phe Ile Leu Thr Thr Glu Thr Leu Ser
            340                 345                 350

His Ile Glu Ile Asp Thr Val Glu Asn Asp Leu Gln Asp Thr Arg Asp
        355                 360                 365

Ala Leu Leu Lys Ala Ala Asp Leu Glu Thr Thr Phe Glu Glu Arg Val
    370                 375                 380

Leu Ile Gln Lys Leu Val Arg Ala Ile Ser Arg Arg Ala Ala Phe Leu
385                 390                 395                 400
```

```
Ala Ala Val Pro Ile Ala Ala Ile Leu Ile Lys Thr Asn Ala Leu Asn
                405                 410                 415

Gln Ser Tyr His Cys Gln Val Glu Val Gly Cys Asp Gly Ser Val Val
            420                 425                 430

Glu His Tyr Pro Gly Phe Arg Ser Met Met Arg His Ala Leu Ala Leu
        435                 440                 445

Ser Pro Ile Gly Pro Glu Gly Glu Arg Asp Val His Leu Arg Ile Ser
    450                 455                 460

Lys Asp Gly Ser Gly Val Gly Ala Ala Leu Cys Ala Leu His Ala Asn
465                 470                 475                 480

Tyr


<210> SEQ ID NO 126
<211> LENGTH: 1452
<212> TYPE: DNA
<213> ORGANISM: Hansenula polymorpha

<400> SEQUENCE: 126

atgagtatcg acgacaaacc gctgccagca gacctggcta aagagatcga gacctacaag      60

gagctgttct gggtgccaac cgagactctc cacaagatca tcgattactt catcgaggaa     120

ctcgagagag gtaacgcgga cggaacagat cctaccggta tccccatgaa ccctgcctgg     180

gtgttggaat acccgaacgg ttctgagacc ggcgattacc ttgccatcga cttgggagga     240

acaaaccttc gtgttgtcct tgctcacttg cttggagacc acaagttttc taccgaacaa     300

actaagtacc acatcccaag ccacatgaga acaaccaaga acagagacga gctgtttgag     360

ttcattgctc aatgtctgga agactttctt aagtcgaaac accctgacgg aattccatcg     420

gacgctgttt tccccttggg attcactttt tcgtacccag ccacgcaaaa cagcattttt     480

gagggtgttc tacagagatg gaccaaaggt tttgatattc ctaatgtcga gggccacgac     540

gtggtgcctc ttctgatgga acaggtcgag aagaaaggcc tgcctatcaa gattggtgcc     600

ctgatcaacg acaccagcgg aacccttgtt gcatcgagat acacagacga gctcacggag     660

atgggctgta tttttggtac tggtgtcaac ggagcatact acgaccgcat caagaacatc     720

cctaagctga agggaaagct ttacgacgat atcgacccag agtctccaat gctgatcaac     780

tgcgaatacg gttctttcga taatgcacac aaggttcttc caagaacgaa gttcgacatc     840

agaatcgacg acgagtctcc aagaccggga caacagtctt tcgagaaaat gacttccggc     900

tactacctag gagaacttct cagaatgatt atgctggaca cctacaaaaa gggactcatt     960

ttcaagagct acactgagtc ttcggagcag atcaagaacc tcgaaacccc atacttcctg    1020

gacacatctt tcctgtctat cgctgaggct gacgacaccc cttcattgag cgtcgtgtcg    1080

aatgagttct ccaacaaact cttcatcgac accactttcg aggagagact gtacgtgaga    1140

aagctgtcgc aatttatcgg aaccagagca gccagactct cgatttgtgg tatctctgcc    1200

gtgtgcaaaa agatgaacta caaaaagtgc cacgttgccg ctgacggatc cgtcttcctc    1260

aagtacccat acttcccaga aagggcagca cagggcctga gcgacgtgtt cggctgggat    1320

ggtatcgaca tgaaggacca ccctatccag atcaaacagg ccgaggacgg atctggtgtt    1380

ggtgccgcca tcattgctgc actttcgcat gccagaagag agaaaggtct gtctttgggt    1440

ctgaaaaaat aa                                                        1452


<210> SEQ ID NO 127
<211> LENGTH: 483
<212> TYPE: PRT
<213> ORGANISM: Hansenula polymorpha
```

<400> SEQUENCE: 127

Met Ser Ile Asp Asp Lys Pro Leu Pro Ala Asp Leu Ala Lys Glu Ile
1               5                   10                  15

Glu Thr Tyr Lys Glu Leu Phe Trp Val Pro Thr Glu Thr Leu His Lys
            20                  25                  30

Ile Ile Asp Tyr Phe Ile Glu Glu Leu Glu Arg Gly Asn Ala Asp Gly
        35                  40                  45

Thr Asp Pro Thr Gly Ile Pro Met Asn Pro Ala Trp Val Leu Glu Tyr
    50                  55                  60

Pro Asn Gly Ser Glu Thr Gly Asp Tyr Leu Ala Ile Asp Leu Gly Gly
65                  70                  75                  80

Thr Asn Leu Arg Val Val Leu Ala His Leu Leu Gly Asp His Lys Phe
                85                  90                  95

Ser Thr Glu Gln Thr Lys Tyr His Ile Pro Ser His Met Arg Thr Thr
            100                 105                 110

Lys Asn Arg Asp Glu Leu Phe Glu Phe Ile Ala Gln Cys Leu Glu Asp
        115                 120                 125

Phe Leu Lys Ser Lys His Pro Asp Gly Ile Pro Ser Asp Ala Val Phe
    130                 135                 140

Pro Leu Gly Phe Thr Phe Ser Tyr Pro Ala Thr Gln Asn Ser Ile Phe
145                 150                 155                 160

Glu Gly Val Leu Gln Arg Trp Thr Lys Gly Phe Asp Ile Pro Asn Val
                165                 170                 175

Glu Gly His Asp Val Val Pro Leu Leu Met Glu Gln Val Glu Lys Lys
            180                 185                 190

Gly Leu Pro Ile Lys Ile Gly Ala Leu Ile Asn Asp Thr Ser Gly Thr
        195                 200                 205

Leu Val Ala Ser Arg Tyr Thr Asp Glu Leu Thr Glu Met Gly Cys Ile
    210                 215                 220

Phe Gly Thr Gly Val Asn Gly Ala Tyr Tyr Asp Arg Ile Lys Asn Ile
225                 230                 235                 240

Pro Lys Leu Lys Gly Lys Leu Tyr Asp Asp Ile Asp Pro Glu Ser Pro
                245                 250                 255

Met Leu Ile Asn Cys Glu Tyr Gly Ser Phe Asp Asn Ala His Lys Val
            260                 265                 270

Leu Pro Arg Thr Lys Phe Asp Ile Arg Ile Asp Asp Glu Ser Pro Arg
        275                 280                 285

Pro Gly Gln Gln Ser Phe Glu Lys Met Thr Ser Gly Tyr Tyr Leu Gly
    290                 295                 300

Glu Leu Leu Arg Met Ile Met Leu Asp Thr Tyr Lys Lys Gly Leu Ile
305                 310                 315                 320

Phe Lys Ser Tyr Thr Glu Ser Ser Glu Gln Ile Lys Asn Leu Glu Thr
                325                 330                 335

Pro Tyr Phe Leu Asp Thr Ser Phe Leu Ser Ile Ala Glu Ala Asp Asp
            340                 345                 350

Thr Pro Ser Leu Ser Val Val Ser Asn Glu Phe Ser Asn Lys Leu Phe
        355                 360                 365

Ile Asp Thr Thr Phe Glu Glu Arg Leu Tyr Val Arg Lys Leu Ser Gln
    370                 375                 380

Phe Ile Gly Thr Arg Ala Ala Arg Leu Ser Ile Cys Gly Ile Ser Ala
385                 390                 395                 400

Val Cys Lys Lys Met Asn Tyr Lys Lys Cys His Val Ala Ala Asp Gly
                405                 410                 415

```
Ser Val Phe Leu Lys Tyr Pro Tyr Phe Pro Glu Arg Ala Ala Gln Gly
            420                 425                 430

Leu Ser Asp Val Phe Gly Trp Asp Gly Ile Asp Met Lys Asp His Pro
        435                 440                 445

Ile Gln Ile Lys Gln Ala Glu Asp Gly Ser Gly Val Gly Ala Ala Ile
    450                 455                 460

Ile Ala Ala Leu Ser His Ala Arg Arg Glu Lys Gly Leu Ser Leu Gly
465                 470                 475                 480

Leu Lys Lys


<210> SEQ ID NO 128
<211> LENGTH: 16387
<212> TYPE: DNA
<213> ORGANISM: artificial sequence
<220> FEATURE:
<223> OTHER INFORMATION: Synthetic construct

<400> SEQUENCE: 128

tcccattacc gacatttggg cgctatacgt gcatatgttc atgtatgtat ctgtatttaa     60

aacacttttg tattattttt cctcatatat gtgtataggt ttatacggat gatttaatta    120

ttacttcacc accctttatt tcaggctgat atcttagcct tgttactagt tagaaaaaga    180

catttttgct gtcagtcact gtcaagagat tcttttgctg gcatttcttc tagaagcaaa    240

aagagcgatg cgtcttttcc gctgaaccgt tccagcaaaa aagactacca acgcaatatg    300

gattgtcaga atcatataaa agagaagcaa ataactcctt gtcttgtatc aattgcatta    360

taatatcttc ttgttagtgc aatatcatat agaagtcatc gaaatagata ttaagaaaaa    420

caaactgtac aatcaatcaa tcaatcatcg ctgaggatgt tgacaaaagc aacaaaagaa    480

caaaaatccc ttgtgaaaaa cagaggggcg gagcttgttg ttgattgctt agtggagcaa    540

ggtgtcacac atgtatttgg cattccaggt gcaaaaattg atgcggtatt tgacgcttta    600

caagataaag gacctgaaat tatcgttgcc cggcacgaac aaaacgcagc attcatggcc    660

caagcagtcg gccgtttaac tggaaaaccg ggagtcgtgt tagtcacatc aggaccgggt    720

gcctctaact tggcaacagg cctgctgaca gcgaacactg aaggagaccc tgtcgttgcg    780

cttgctggaa acgtgatccg tgcagatcgt ttaaaacgga cacatcaatc tttggataat    840

gcggcgctat tccagccgat tacaaaatac agtgtagaag ttcaagatgt aaaaaatata    900

ccggaagctg ttacaaatgc atttaggata gcgtcagcag ggcaggctgg ggccgctttt    960

gtgagctttc cgcaagatgt tgtgaatgaa gtcacaaata cgaaaaacgt gcgtgctgtt   1020

gcagcgccaa aactcggtcc tgcagcagat gatgcaatca gtgcggccat agcaaaaatc   1080

caaacagcaa aacttcctgt cgttttggtc ggcatgaaag gcggaagacc ggaagcaatt   1140

aaagcggttc gcaagctttt gaaaaaggtt cagcttccat ttgttgaaac atatcaagct   1200

gccggtaccc tttctagaga tttagaggat caatattttg gccgtatcgg tttgttccgc   1260

aaccagcctg gcgatttact gctagagcag gcagatgttg ttctgacgat cggctatgac   1320

ccgattgaat atgatccgaa attctggaat atcaatggag accggacaat tatccattta   1380

gacgagatta tcgctgacat tgatcatgct taccagcctg atcttgaatt gatcggtgac   1440

attccgtcca cgatcaatca tatcgaacac gatgctgtga aagtggaatt tgcagagcgt   1500

gagcagaaaa tcctttctga tttaaaacaa tatatgcatg aaggtgagca ggtgcctgca   1560

gattggaaat cagacagagc gcaccctctt gaaatcgtta aagagttgcg taatgcagtc   1620

gatgatcatg ttacagtaac ttgcgatatc ggttcgcacg ccatttggat gtcacgttat   1680
```

-continued

```
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgctc tagaactagt accacaggtg   2460
ttgtcctctg aggacataaa atacacaccg agattcatca actcattgct ggagttagca   2520
tatctacaat tgggtgaaat ggggagcgat ttgcaggcat ttgctcggca tgccggtaga   2580
ggtgtggtca ataagagcga cctcatgcta tacctgagaa agcaacctga cctacaggaa   2640
agagttactc aagaataaga attttcgttt taaaacctaa gagtcacttt aaaatttgta   2700
tacacttatt ttttttataa cttatttaat aataaaaatc ataaatcata agaaattcgc   2760
ttactcttaa ttaatcaagc atctaaaaca caaccgttgg aagcgttgga aaccaactta   2820
gcatacttgg atagagtacc tcttgtgtaa cgaggtggag gtgcaaccca actttgttta   2880
cgttgagcca tttccttatc agagactaat aggtcaatct tgttattatc agcatcaatg   2940
ataatctcat cgccgtctct gaccaacccg ataggaccac cttcagcggc ttcgggaaca   3000
atgtggccga ttaagaaccc gtgagaacca ccagagaatc taccatcagt caacaatgca   3060
acatctttac ccaaaccgta acccatcaga gcagaggaag gctttagcat ttcaggcata   3120
cctggtgcac ctcttggacc ttcatatctg ataacaacaa cggttttttc acccttcttg   3180
atttcacctc tttccaaggc ttcaataaag gcaccttcct cttcgaacac acgtgctcta   3240
cccttgaagt aagtaccttc cttaccggta attttaccca cagctccacc tggtgccaat   3300
gaaccgtaca gaatttgcaa gtgaccgttg gccttgattg ggtgggagag tggcttaata   3360
atctcttgtc cttcaggtag gcttggtgct ttctttgcac gttctgccaa agtgtcaccg   3420
gtaacagtca ttgtgttacc gtgcaacatg ttgttttcat atagatactt aatcacagat   3480
tgggtaccac caacgttaat caaatcggcc atgacgtatt taccagaagg tttgaagtca   3540
ccgatcaatg gtgtagtatc actgattctt tggaaatcat ctggtgacaa cttgacaccc   3600
gcagagtgag caacagccac caaatgcaaa acagcattag tggacccacc ggttgcaacg   3660
acataagtaa tggcgttttc aaaagcctct tttgtgagga tatcacgagg taaaataccc   3720
aattccattg tcttcttgat gtattcacca atgttgtcac actcagctaa cttctccttg   3780
gaaacggctg ggaaggaaga ggagtttgga atggtcaaac ctagcacttc agcggcagaa   3840
gccattgtgt tggcagtata cataccacca caagaaccag gacctgggca tgcatgttcc   3900
acaacatctt ctctttcttc ttcagtgaat tgcttggaaa tatattcacc gtaggattgg   3960
aacgcagaga cgatatcgat gtttttagag atcctgttaa aacctctagt ggagtagtag   4020
atgtaatcaa tgaagcggaa gccaaaagac cagagtagag gcctatagaa gaaactgcga   4080
```

-continued

```
taccttttgt gatggctaaa caaacagaca tctttttata tgtttttact tctgtatatc   4140
gtgaagtagt aagtgataag cgaatttggc taagaacgtt gtaagtgaac aagggacctc   4200
ttttgccttt caaaaaagga ttaaatggag ttaatcattg agatttagtt ttcgttagat   4260
tctgtatccc taaataactc ccttacccga cgggaaggca caaaagactt gaataatagc   4320
aaacggccag tagccaagac caaataatac tagagttaac tgatggtctt aaacaggcat   4380
tacgtggtga actccaagac caatatacaa aatatcgata agttattctt gcccaccaat   4440
ttaaggagcc tacatcagga cagtagtacc attcctcaga gaagaggtat acataacaag   4500
aaaatcgcgt gaacacctta tataacttag cccgttattg agctaaaaaa ccttgcaaaa   4560
tttcctatga ataagaatac ttcagacgtg ataaaaattt actttctaac tcttctcacg   4620
ctgcccctat ctgttcttcc gctctaccgt gagaaataaa gcatcgagta cggcagttcg   4680
ctgtcactga actaaaacaa taaggctagt tcgaatgatg aacttgcttg ctgtcaaact   4740
tctgagttgc cgctgatgtg acactgtgac aataaattca aaccggttat agcggtctcc   4800
tccggtaccg gttctgccac ctccaataga gctcagtagg agtcagaacc tctgcggtgg   4860
ctgtcagtga ctcatccgcg tttcgtaagt tgtgcgcgtg cacatttcgc ccgttcccgc   4920
tcatcttgca gcaggcggaa attttcatca cgctgtagga cgcaaaaaaa aaataattaa   4980
tcgtacaaga atcttggaaa aaaaattgaa aaattttgta taaaagggat gacctaactt   5040
gactcaatgg cttttacacc cagtattttc cctttccttg tttgttacaa ttatagaagc   5100
aagacaaaaa catatagaca acctattcct aggagttata ttttttttacc ctaccagcaa   5160
tataagtaaa aaactagtat gaaagttttc tacgataaag actgcgacct gtcgatcatc   5220
caaggtaaga aagttgccat catcggcttc ggttcccagg gccacgctca agcactcaac   5280
ctgaaggatt ccggcgtaga cgtgactgtt ggcctgccta aaggctttgc tgatgtagcc   5340
aaggctgaag cccacggctt taaagtgacc gacgttgctg cagccgttgc cggtgccgac   5400
ttggtcatga tcctgattcc ggacgagttc cagtcccagc tgtacaagaa cgaaatcgag   5460
ccgaacatca agaagggcgc cactctggcc ttctcccacg gcttcgcgat ccactacaac   5520
caggttgtgc ctcgtgccga cctcgacgtg atcatgatcg cgccgaaggc tccaggccac   5580
accgtacgtt ccgagttcgt caagggcgga ggtattcctg acctgatcgc gatctaccag   5640
gacgtttccg gcaacgccaa gaacgtcgcc ctgtcctacg ccgcaggcgt gggcggcggc   5700
cgtaccggca tcatcgaaac caccttcaag gacgagactg aaaccgacct gttcggtgag   5760
caggctgttc tgtgtggcgg taccgtcgag ctggtcaaag ccggtttcga aaccctggtt   5820
gaagctggct acgctccaga aatggcctac ttcgagtgcc tgcacgaact gaagctgatc   5880
gttgacctca tgtacgaagg cggtatcgcc aacatgaact actcgatctc caacaacgct   5940
gaatacggcg agtacgtgac tggtccagaa gtcatcaacg ccgaatcccg tcaggccatg   6000
cgcaatgctc tgaagcgcat ccaggacggc gaatacgcga agatgttcat cagcgaaggc   6060
gctaccggct acccatcgat gaccgccaag cgtcgtaaca acgctgctca cggtatcgaa   6120
atcatcggcg agcaactgcg ctcgatgatg ccttggatcg gtgccaacaa aatcgtcgac   6180
aaagccaaga actaaggccc tgcaggccta tcaagtgctg gaaacttttt ctcttggaat   6240
ttttgcaaca tcaagtcata gtcaattgaa ttgacccaat ttcacattta agattttttt   6300
tttttcatcc gacatacatc tgtacactag gaagccctgt tttctgaag cagcttcaaa   6360
tatatatatt ttttacatat ttattatgat tcaatgaaca atctaattaa atcgaaaaca   6420
agaaccgaaa cgcgaataaa taatttattt agatggtgac aagtgtataa gtcctcatcg   6480
```

-continued

```
ggacagctac gatttctctt tcggttttgg ctgagctact ggttgctgtg acgcagcggc   6540

attagcgcgg cgttatgagc taccctcgtg gcctgaaaga tggcgggaat aaagcggaac   6600

taaaaattac tgactgagcc atattgaggt caatttgtca actcgtcaag tcacgtttgg   6660

tggacggccc ctttccaacg aatcgtatat actaacatgc gcgcgcttcc tatatacaca   6720

tatacatata tatatatata tatatgtgtg cgtgtatgtg tacacctgta tttaatttcc   6780

ttactcgcgg gtttttcttt tttctcaatt cttggcttcc tctttctcga gtatataatt   6840

tttcaggtaa aatttagtac gatagtaaaa tacttctcga actcgtcaca tatacgtgta   6900

cataatgtct gaaccagctc aaaagaaaca aaaggttgct aacaactctc tagagcggcc   6960

gcccgcaaat taaagccttc gagcgtccca aaaccttctc aagcaaggtt ttcagtataa   7020

tgttacatgc gtacacgcgt ctgtacagaa aaaaaagaaa aatttgaaat ataaataacg   7080

ttcttaatac taacataact ataaaaaaat aaatagggac ctagacttca ggttgtctaa   7140

ctccttcctt ttcggttaga gcggatgtgg ggggagggcg tgaatgtaag cgtgacataa   7200

ctaattacat gattaattaa ttattggttt tctggtctca actttctgac ttccttacca   7260

accttccaga tttccatgtt tctgatggtg tctaattcct tttctagctt ttctctgtag   7320

tcaggttgag agttgaattc caaagatctc ttggtttcgg taccgttctt ggtagattcg   7380

tacaagtctt ggaaaacagg cttcaaagca ttcttgaaga ttgggtacca gtccaaagca   7440

cctcttctgg cggtggtgga acaagcatcg tacatgtaat ccataccgta cttaccgatc   7500

aatgggtata gagattgggt agcttcttcg acggtttcgt tgaaagcttc agatggggag   7560

tgaccgtttt ctctcaagac gtcgtattga gccaagaaca taccgtggat accacccatt   7620

aaacaacctc tttcaccgta caagtcagag ttgacttctc tttcgaaagt ggtttggtaa   7680

acgtaaccgg aaccaatggc aacggccaaa gcttgggcct tttcgtgagc cttaccggtg   7740

acatcgttcc agacggcgta agaagagtta ataccacgac cttccttgaa caaagatctg   7800

acagttctac cggaaccctt tggagcaacc aagataacat ctaagtcctt tggtggttca   7860

acgtgagtca agtccttgaa gactggggag aaaccgtggg agaagtacaa agtcttaccc   7920

ttggtcaaca atggcttgat agcaggccag gtttctgatt gagcggcatc ggacaacaag   7980

ttcataacgt aactacctct cttgatagca tcttcaacag tgaacaagtt cttgcctgga   8040

acccaaccgt cttcgatggc agccttccaa gaagcaccat ctttacggac accaatgata   8100

acgttcaaac cgttgtctct caagttcaaa ccttgaccgt aaccttggga accgtaaccg   8160

atcaaagcaa aagtgtcgtt cttgaagtag tccaacaact tttctcttgg ccagtcagct   8220

ctttcgtaga cggtttcaac agtaccaccg aagttgattt gcttcaacat cctcagctct   8280

agatttgaat atgtattact tggttatggt tatatatgac aaaagaaaaa gaagaacaga   8340

agaataacgc aaggaagaac aataactgaa attgatagag aagtattatg tctttgtctt   8400

tttataataa atcaagtgca gaaatccgtt agacaacatg agggataaaa tttaacgtgg   8460

gcgaagaaga aggaaaaaag tttttgtgag ggcgtaattg aagcgatctg ttgattgtag   8520

attttttttt tttgaggagt caaagtcaga agagaacaga caaatggtat taaccatcca   8580

atacttttt ggagcaacgc taagctcatg cttttccatt ggttacgtgc tcagttgtta   8640

gatatggaaa gagaggatgc tcacggcagc gtgactccaa ttgagcccga aagagaggat   8700

gccacgtttt cccgacggct gctagaatgg aaaaaggaaa aatagaagaa tcccattcct   8760

atcattattt acgtaatgac ccacacattt ttgagatttt caactattac gtattacgat   8820

aatcctgctg tcattatcat tattatctat atcgacgtat gcaacgtatg tgaagccaag   8880
```

-continued

```
taggcaatta tttagtactg tcagtattgt tattcatttc agatctatcc gcggtggagc   8940
tcgaattcac tggccgtcgt tttacaacgt cgtgactggg aaaaccctgg cgttacccaa   9000
cttaatcgcc ttgcagcaca tccccctttc gccagctggc gtaatagcga agaggcccgc   9060
accgatcgcc cttcccaaca gttgcgcagc ctgaatggcg aatggcgcct gatgcggtat   9120
tttctcctta cgcatctgtg cggtatttca caccgcatac gtcaaagcaa ccatagtacg   9180
cgccctgtag cggcgcatta agcgcggcgg gtgtggtggt tacgcgcagc gtgaccgcta   9240
cacttgccag cgccttagcg cccgctcctt tcgctttctt cccttccttt ctcgccacgt   9300
tcgccggctt tccccgtcaa gctctaaatc gggggctccc tttagggttc cgatttagtg   9360
ctttacggca cctcgacccc aaaaaacttg atttgggtga tggttcacgt agtgggccat   9420
cgccctgata gacggttttt cgccctttga cgttggagtc cacgttcttt aatagtggac   9480
tcttgttcca aactggaaca acactcaact ctatctcggg ctattctttt gatttataag   9540
ggattttgcc gatttcggtc tattggttaa aaaatgagct gatttaacaa aaatttaacg   9600
cgaattttaa caaaatatta acgtttacaa ttttatggtg cactctcagt acaatctgct   9660
ctgatgccgc atagttaagc cagccccgac acccgccaac acccgctgac gcgccctgac   9720
gggcttgtct gctcccggca tccgcttaca gacaagctgt gaccgtctcc gggagctgca   9780
tgtgtcagag gttttcaccg tcatcaccga aacgcgcgag acgaaagggc ctcgtgatac   9840
gcctattttt ataggttaat gtcatgataa taatggtttc ttagacgtca ggtggcactt   9900
ttcggggaaa tgtgcgcgga acccctattt gtttattttt ctaaatacat tcaaatatgt   9960
atccgctcat gagacaataa ccctgataaa tgcttcaata atattgaaaa aggaagagta  10020
tgagtattca acatttccgt gtcgccctta ttcccttttt tgcggcattt tgccttcctg  10080
tttttgctca cccagaaacg ctggtgaaag taaaagatgc tgaagatcag ttgggtgcac  10140
gagtgggtta catcgaactg gatctcaaca gcggtaagat ccttgagagt tttcgccccg  10200
aagaacgttt tccaatgatg agcactttta aagttctgct atgtggcgcg gtattatccc  10260
gtattgacgc cgggcaagag caactcggtc gccgcataca ctattctcag aatgacttgg  10320
ttgagtactc accagtcaca gaaaagcatc ttacggatgg catgacagta agagaattat  10380
gcagtgctgc cataaccatg agtgataaca ctgcggccaa cttacttctg acaacgatcg  10440
gaggaccgaa ggagctaacc gcttttttgc acaacatggg ggatcatgta actcgccttg  10500
atcgttggga accggagctg aatgaagcca taccaaacga cgagcgtgac accacgatgc  10560
ctgtagcaat ggcaacaacg ttgcgcaaac tattaactgg cgaactactt actctagctt  10620
cccggcaaca attaatagac tggatggagg cggataaagt tgcaggacca cttctgcgct  10680
cggcccttcc ggctggctgg tttattgctg ataaatctgg agccggtgag cgtgggtctc  10740
gcggtatcat tgcagcactg gggccagatg gtaagccctc ccgtatcgta gttatctaca  10800
cgacggggag tcaggcaact atggatgaac gaaatagaca gatcgctgag ataggtgcct  10860
cactgattaa gcattggtaa ctgtcagacc aagtttactc atatatactt tagattgatt  10920
taaaacttca tttttaattt aaaaggatct aggtgaagat cctttttgat aatctcatga  10980
ccaaaatccc ttaacgtgag ttttcgttcc actgagcgtc agaccccgta gaaaagatca  11040
aaggatcttc ttgagatcct ttttttctgc gcgtaatctg ctgcttgcaa acaaaaaaac  11100
caccgctacc agcggtggtt tgtttgccgg atcaagagct accaactctt tttccgaagg  11160
taactggctt cagcagagcg cagataccaa atactgttct tctagtgtag ccgtagttag  11220
gccaccactt caagaactct gtagcaccgc ctacatacct cgctctgcta atcctgttac  11280
```

cagtggctgc tgccagtggc gataagtcgt gtcttaccgg gttggactca agacgatagt 11340
taccggataa ggcgcagcgg tcgggctgaa cggggggttc gtgcacacag cccagcttgg 11400
agcgaacgac ctacaccgaa ctgagatacc tacagcgtga gctatgagaa agcgccacgc 11460
ttcccgaagg gagaaaggcg gacaggtatc cggtaagcgg cagggtcgga acaggagagc 11520
gcacgaggga gcttccaggg ggaaacgcct ggtatcttta tagtcctgtc gggtttcgcc 11580
acctctgact tgagcgtcga tttttgtgat gctcgtcagg ggggcggagc ctatggaaaa 11640
acgccagcaa cgcggccttt ttacggttcc tggccttttg ctggcctttt gctcacatgt 11700
tctttcctgc gttatcccct gattctgtgg ataaccgtat taccgccttt gagtgagctg 11760
ataccgctcg ccgcagccga acgaccgagc gcagcgagtc agtgagcgag gaagcggaag 11820
agcgcccaat acgcaaaccg cctctccccg cgcgttggcc gattcattaa tgcagctggc 11880
acgacaggtt tcccgactgg aaagcgggca gtgagcgcaa cgcaattaat gtgagttagc 11940
tcactcatta ggcaccccag gctttacact ttatgcttcc ggctcgtatg ttgtgtggaa 12000
ttgtgagcgg ataacaattt cacacaggaa acagctatga ccatgattac gccaagcttt 12060
ttctttccaa tttttttttt ttcgtcatta taaaaatcat tacgaccgag attcccgggt 12120
aataactgat ataattaaat tgaagctcta atttgtgagt ttagtataca tgcatttact 12180
tataatacag ttttttagtt ttgctggccg catcttctca aatatgcttc ccagcctgct 12240
tttctgtaac gttcaccctc taccttagca tcccttccct ttgcaaatag tcctcttcca 12300
acaataataa tgtcagatcc tgtagagacc acatcatcca cggttctata ctgttgaccc 12360
aatgcgtctc ccttgtcatc taaacccaca ccgggtgtca taatcaacca atcgtaacct 12420
tcatctcttc cacccatgtc tctttgagca ataaagccga taacaaaatc tttgtcgctc 12480
ttcgcaatgt caacagtacc cttagtatat tctccagtag atagggagcc cttgcatgac 12540
aattctgcta acatcaaaag gcctctaggt tcctttgtta cttcttctgc cgcctgcttc 12600
aaaccgctaa caatacctgg gcccaccaca ccgtgtgcat tcgtaatgtc tgcccattct 12660
gctattctgt atacacccgc agagtactgc aatttgactg tattaccaat gtcagcaaat 12720
tttctgtctt cgaagagtaa aaaattgtac ttggcggata atgcctttag cggcttaact 12780
gtgccctcca tggaaaaatc agtcaagata tccacatgtg tttttagtaa acaaattttg 12840
ggacctaatg cttcaactaa ctccagtaat tccttggtgg tacgaacatc caatgaagca 12900
cacaagtttg tttgcttttc gtgcatgata ttaaatagct tggcagcaac aggactagga 12960
tgagtagcag cacgttcctt atatgtagct ttcgacatga tttatcttcg tttcctgcag 13020
gtttttgttc tgtgcagttg ggttaagaat actgggcaat ttcatgtttc ttcaacacta 13080
catatgcgta tatataccaa tctaagtctg tgctccttcc ttcgttcttc cttctgttcg 13140
gagattaccg aatcaaaaaa atttcaagga aaccgaaatc aaaaaaaaga ataaaaaaaa 13200
aatgatgaat tgaaaagctt gcatgcctgc aggtcgactc tagtatactc cgtctactgt 13260
acgatacact tccgctcagg tccttgtcct ttaacgaggc cttaccactc ttttgttact 13320
ctattgatcc agctcagcaa aggcagtgtg atctaagatt ctatcttcgc gatgtagtaa 13380
aactagctag accgagaaag agactagaaa tgcaaaaggc acttctacaa tggctgccat 13440
cattattatc cgatgtgacg ctgcattttt tttttttttt tttttttttt tttttttttt 13500
tttttttttt tttttttgta caaatatcat aaaaaaagag aatcttttta agcaaggatt 13560
ttcttaactt cttcggcgac agcatcaccg acttcggtgg tactgttgga accacctaaa 13620
tcaccagttc tgatacctgc atccaaaacc tttttaactg catcttcaat ggctttacct 13680

-continued

```
tcttcaggca agttcaatga caatttcaac atcattgcag cagacaagat agtggcgata  13740
gggttgacct tattctttgg caaatctgga gcggaaccat ggcatggttc gtacaaacca  13800
aatgcggtgt tcttgtctgg caaagaggcc aaggacgcag atggcaacaa acccaaggag  13860
cctgggataa cggaggcttc atcggagatg atatcaccaa acatgttgct ggtgattata  13920
ataccattta ggtgggttgg gttcttaact aggatcatgg cggcagaatc aatcaattga  13980
tgttgaactt tcaatgtagg gaattcgttc ttgatggttt cctccacagt ttttctccat  14040
aatcttgaag aggccaaaac attagcttta tccaaggacc aaataggcaa tggtggctca  14100
tgttgtaggg ccatgaaagc ggccattctt gtgattcttt gcacttctgg aacggtgtat  14160
tgttcactat cccaagcgac accatcacca tcgtcttcct ttctcttacc aaagtaaata  14220
cctcccacta attctctaac aacaacgaag tcagtacctt tagcaaattg tggcttgatt  14280
ggagataagt ctaaaagaga gtcggatgca aagttacatg gtcttaagtt ggcgtacaat  14340
tgaagttctt tacggatttt tagtaaacct tgttcaggtc taacactacc ggtaccccat  14400
ttaggaccac ccacagcacc taacaaaacg gcatcagcct tcttggaggc ttccagcgcc  14460
tcatctggaa gtggaacacc tgtagcatcg atagcagcac caccaattaa atgattttcg  14520
aaatcgaact tgacattgga acgaacatca gaaatagctt taagaacctt aatggcttcg  14580
gctgtgattt cttgaccaac gtggtcacct ggcaaaacga cgatcttctt aggggcagac  14640
attacaatgg tatatccttg aaatatatat aaaaaaaaaa aaaaaaaaaa aaaaaaaaaa  14700
tgcagcttct caatgatatt cgaatacgct ttgaggagat acagcctaat atccgacaaa  14760
ctgttttaca gatttacgat cgtacttgtt acccatcatt gaattttgaa catccgaacc  14820
tgggagtttt ccctgaaaca gatagtatat ttgaacctgt ataataatat atagtctagc  14880
gctttacgga agacaatgta tgtatttcgg ttcctggaga aactattgca tctattgcat  14940
aggtaatctt gcacgtcgca tccccggttc attttctgcg tttccatctt gcacttcaat  15000
agcatatctt tgttaacgaa gcatctgtgc ttcattttgt agaacaaaaa tgcaacgcga  15060
gagcgctaat ttttcaaaca aagaatctga gctgcatttt tacagaacag aaatgcaacg  15120
cgaaagcgct attttaccaa cgaagaatct gtgcttcatt tttgtaaaac aaaaatgcaa  15180
cgcgagagcg ctaatttttc aaacaaagaa tctgagctgc atttttacag aacagaaatg  15240
caacgcgaga gcgctatttt accaacaaag aatctatact tcttttttgt tctacaaaaa  15300
tgcatcccga gagcgctatt tttctaacaa agcatcttag attacttttt ttctcctttg  15360
tgcgctctat aatgcagtct cttgataact ttttgcactg taggtccgtt aaggttagaa  15420
gaaggctact ttggtgtcta ttttctcttc cataaaaaaa gcctgactcc acttcccgcg  15480
tttactgatt actagcgaag ctgcgggtgc attttttcaa gataaaggca tccccgatta  15540
tattctatac cgatgtggat tgcgcatact ttgtgaacag aaagtgatag cgttgatgat  15600
tcttcattgg tcagaaaatt atgaacggtt tcttctattt tgtctctata tactacgtat  15660
aggaaatgtt tacattttcg tattgttttc gattcactct atgaatagtt cttactacaa  15720
ttttttgtc taaagagtaa tactagagat aaacataaaa aatgtagagg tcgagtttag  15780
atgcaagttc aaggagcgaa aggtggatgg gtaggttata tagggatata gcacagagat  15840
atatagcaaa gagatacttt tgagcaatgt ttgtggaagc ggtattcgca atattttagt  15900
agctcgttac agtccggtgc gtttttggtt ttttgaaagt gcgtcttcag agcgcttttg  15960
gttttcaaaa gcgctctgaa gttcctatac tttctagaga ataggaactt cggaatagga  16020
acttcaaagc gtttccgaaa acgagcgctt ccgaaaatgc aacgcgagct gcgcacatac  16080
```

```
agctcactgt tcacgtcgca cctatatctg cgtgttgcct gtatatatat atacatgaga  16140

agaacggcat agtgcgtgtt tatgcttaaa tgcgtactta tatgcgtcta tttatgtagg  16200

atgaaaggta gtctagtacc tcctgtgata ttatcccatt ccatgcgggg tatcgtatgc  16260

ttccttcagc actacccttt agctgttcta tatgctgcca ctcctcaatt ggattagtct  16320

catccttcaa tgctatcatt tcctttgata ttggatcata tgcatagtac cgagaaacta  16380

gaggatc                                                            16387
```

<210> SEQ ID NO 129
<211> LENGTH: 26
<212> TYPE: DNA
<213> ORGANISM: artificial sequence
<220> FEATURE:
<223> OTHER INFORMATION: Primer

<400> SEQUENCE: 129

```
ccaggccaat tcaacagact gtcggc                                         26
```

<210> SEQ ID NO 130
<211> LENGTH: 476
<212> TYPE: PRT
<213> ORGANISM: Artificial sequence
<220> FEATURE:
<223> OTHER INFORMATION: Protein variant

<400> SEQUENCE: 130

```
Met Val His Leu Gly Pro Ala Asp Val Pro Lys Glu Leu Met Gln Gln
1               5                   10                  15

Ile Glu Asn Phe Glu Lys Ile Phe Thr Val Pro Thr Glu Thr Leu Gln
            20                  25                  30

Ala Val Thr Lys His Phe Ile Ser Glu Leu Glu Lys Gly Leu Ser Lys
        35                  40                  45

Lys Gly Gly Asn Ile Pro Met Ile Pro Gly Trp Val Met Asp Phe Pro
    50                  55                  60

Thr Gly Lys Glu Ser Gly Asp Phe Leu Ala Ile Asp Leu Gly Gly Thr
65                  70                  75                  80

Asn Leu Arg Val Val Leu Val Lys Leu Gly Gly Asp Arg Thr Phe Asp
                85                  90                  95

Thr Thr Gln Ser Lys Tyr Arg Leu Pro Asp Ala Met Arg Thr Thr Gln
            100                 105                 110

Asn Pro Asp Glu Leu Trp Glu Phe Ile Ala Asp Ser Leu Lys Ala Phe
        115                 120                 125

Ile Asp Glu Gln Phe Pro Gln Gly Ile Ser Glu Pro Ile Pro Leu Gly
    130                 135                 140

Phe Thr Phe Ser Phe Pro Ala Ser Gln Asn Lys Ile Asn Glu Gly Ile
145                 150                 155                 160

Leu Gln Arg Trp Thr Lys Gly Phe Asp Ile Pro Asn Ile Glu Asn His
                165                 170                 175

Asp Val Val Pro Met Leu Gln Lys Gln Ile Thr Lys Arg Asn Ile Pro
            180                 185                 190

Ile Glu Val Val Ala Leu Ile Asn Asp Thr Thr Gly Thr Leu Val Ala
        195                 200                 205

Ser Tyr Tyr Thr Asp Pro Glu Thr Lys Met Gly Val Ile Phe Gly Thr
    210                 215                 220

Gly Val Asn Gly Ala Tyr Tyr Asp Val Cys Ser Asp Ile Glu Lys Leu
225                 230                 235                 240
```

```
Gln Gly Lys Leu Ser Asp Asp Ile Pro Pro Ser Ala Pro Met Ala Ile
                245                 250                 255

Asn Cys Glu Tyr Gly Ser Phe Asp Asn Glu His Val Val Leu Pro Arg
            260                 265                 270

Thr Lys Tyr Asp Ile Thr Ile Asp Glu Glu Ser Pro Arg Pro Gly Gln
        275                 280                 285

Gln Thr Phe Glu Lys Met Ser Ser Gly Tyr Tyr Leu Gly Glu Ile Leu
    290                 295                 300

Arg Leu Ala Leu Met Asp Met Tyr Lys Gln Gly Phe Ile Phe Lys Asn
305                 310                 315                 320

Gln Asp Leu Ser Lys Phe Asp Lys Pro Phe Val Met Asp Thr Ser Tyr
                325                 330                 335

Pro Ala Arg Ile Glu Glu Asp Pro Phe Glu Asn Leu Glu Asp Thr Asp
            340                 345                 350

Asp Leu Phe Gln Asn Glu Phe Gly Ile Asn Thr Thr Val Gln Glu Arg
        355                 360                 365

Lys Leu Ile Arg Arg Leu Ser Glu Leu Ile Gly Ala Arg Ala Ala Arg
    370                 375                 380

Leu Ser Val Cys Gly Ile Ala Ala Ile Cys Gln Lys Arg Gly Tyr Lys
385                 390                 395                 400

Thr Gly His Ile Ala Ala Asp Gly Ser Val Tyr Asn Arg Tyr Pro Gly
                405                 410                 415

Phe Lys Glu Lys Ala Ala Asn Ala Leu Lys Asp Ile Tyr Gly Trp Thr
            420                 425                 430

Gln Thr Ser Leu Asp Asp Tyr Pro Ile Lys Ile Val Pro Ala Glu Asp
        435                 440                 445

Gly Ser Gly Ala Gly Ala Ala Val Ile Ala Ala Leu Ala Gln Lys Arg
    450                 455                 460

Ile Ala Glu Gly Lys Ser Val Gly Ile Ile Gly Ala
465                 470                 475
```

<210> SEQ ID NO 131
<211> LENGTH: 723
<212> TYPE: DNA
<213> ORGANISM: Saccharomyces cerevisiae

<400> SEQUENCE: 131

```
caacaaaagc ttgtgtacaa tatggacttc ctcttttctg gcaaccaaac ccatacatcg     60

ggattcctat aataccttcg ttggtctccc taacatgtag gtggcggagg ggagatatac    120

aatagaacag ataccagaca agacataatg ggctaaacaa gactacacca attacactgc    180

ctcattgatg gtggtacata acgaactaat actgtagccc tagacttgat agccatcatc    240

atatcgaagt ttcactaccc tttttccatt tgccatctat tgaagtaata ataggcgcat    300

gcaacttctt ttcttttttt ttcttttctc tctcccccgt tgttgtctca ccatatccgc    360

aatgacaaaa aaatgatgga agacactaaa ggaaaaaatt aacgacaaag acagcaccaa    420

cagatgtcgt tgttccagag ctgatgaggg gtatctcgaa gcacacgaaa ctttttcctt    480

ccttcattca cgcacactac tctctaatga gcaacggtat acggccttcc ttccagttac    540

ttgaatttga aataaaaaaa agtttgctgt cttgctatca agtataaata gacctgcaat    600

tattaatctt ttgtttcctc gtcattgttc tcgttccctt tcttccttgt ttctttttct    660

gcacaatatt tcaagctata ccaagcatac aatcaactat ctcatataca tctagacaaa    720

ctt                                                                  723
```

<210> SEQ ID NO 132
<211> LENGTH: 1747
<212> TYPE: DNA
<213> ORGANISM: artificial sequence
<220> FEATURE:
<223> OTHER INFORMATION: Synthetic construct

<400> SEQUENCE: 132
atggtacatt taggtccagc agatgtgccc aaggaattga tgcagcaaat tgaaaatttt 60
gagaagatct ttacagtgcc tactgaaacc ctccaggctg tcaccaagca tttcatttca 120
gaactggaaa agggtttgtc taaaaagggg ggtaatatcc caatgattcc aggttgggta 180
atggattttc ctacaggaaa ggaatccggt gatttttgg caatagacct aggaggcaca 240
aacttaaggg ttgtacttgt taagttaggc ggtgatcgta cgtttgatac gacacaatcg 300
aaatataggt taccagatgc gatgagaact actcagaatc ctgacgaact atgggagttc 360
atcgcagact cattaaaagc attcatcgac gaacagttcc cccagggtat cagcgaacct 420
attccactag gtttcacttt ctcttttcct gcctctcaaa acaagatcaa cgaaggcatt 480
ctacaaagat ggacaaaggg cttcgatata cctaacatcg aaaatcacga cgttgtgcct 540
atgctacaga agcagattac taaaagaaat attcctattg aagttgttgc tctaattaac 600
gatactacag gcacgctcgt tgcctcgtac tacactgacc ctgaaacgaa aatgggcgtt 660
attttcggta ctggtgttaa tggagcctac tacgatgtct gttcggatat cgaaaaactg 720
caaggaaaac tatccgatga cattccacct tccgcgccta tggcaataaa ttgtgaatac 780
ggatcttttg ataatgaaca cgttgttcta cctagaacta aatatgatat aactatcgat 840
gaagaaagtc caagacctgg acaacaaaca ttcgaaaaga tgtcgtcagg ttactactta 900
ggtgagatat tgagactggc tttgatggat atgtacaaac agggttttat cttcaagaat 960
caagacttga gtaaattcga caagccattt gttatggata cttcatatcc tgctagaata 1020
gaagaagatc ccttcgaaaa cttggaagac acagatgatc ttttccaaaa cgaatttgga 1080
attaatacca ccgtacaaga aagaaagttg ataagacgtt tgtctgaact tatcggagct 1140
agggccgcaa gactgagtgt gtgtggtata gctgctattt gccaaaagag gggatataaa 1200
actggtcaca ttgctgctga tggtagcgtt tacaatagat acccaggatt taaggaaaaa 1260
gcagccaatg ctctaaaaga tatatacggt tggactcaaa cctcactcga tgattaccct 1320
attaaaattg ttccggctga ggatggctcc ggtgctggag ccgcagttat tgcagctttg 1380
gcacagaaaa ggatagcgga aggtaaaagt gtaggtatta ttggtgcgtg agagtaagcg 1440
aatttcttat gatttatgat ttttattatt aaataagtta taaaaaaaat aagtgtatac 1500
aaattttaaa gtgactctta ggttttaaaa cgaaaattct tattcttgag taactctttc 1560
ctgtaggtca ggttgctttc tcaggtatag catgaggtcg ctcttattga ccacacctct 1620
accggcatgc cgagcaaatg cctgcaaatc gctccccatt tcacccaatt gtagatatgc 1680
taactccagc aatgagttga tgaatctcgg tgtgtatttt atgtcctcag aggacaacac 1740
ctgtggt 1747

<210> SEQ ID NO 133
<211> LENGTH: 35
<212> TYPE: DNA
<213> ORGANISM: artificial sequence
<220> FEATURE:
<223> OTHER INFORMATION: primer

<400> SEQUENCE: 133
tcatctaaag cttatggtac atttaggtcc agcag 35

<210> SEQ ID NO 134
<211> LENGTH: 39
<212> TYPE: DNA
<213> ORGANISM: artificial sequence
<220> FEATURE:
<223> OTHER INFORMATION: primer

<400> SEQUENCE: 134
tatttagtgg atccaccaca ggtgttgtcc tctgaggac 39

<210> SEQ ID NO 135
<211> LENGTH: 92
<212> TYPE: DNA
<213> ORGANISM: artificial sequence
<220> FEATURE:
<223> OTHER INFORMATION: primer

<400> SEQUENCE: 135
tttttctttg aaaaggttgt aggaatataa ttctccacac ataataagta cgctaattaa 60
ataaaatggt acatttaggt ccagcagatg tg 92

<210> SEQ ID NO 136
<211> LENGTH: 96
<212> TYPE: DNA
<213> ORGANISM: artificial sequence
<220> FEATURE:
<223> OTHER INFORMATION: primer

<400> SEQUENCE: 136
aacatgttca cataagtaga aaaagggcac cttcttgttg ttcaaactta atttacaaat 60
taagtcacct tggctaactc gttgtatcat cactgg 96

<210> SEQ ID NO 137
<211> LENGTH: 30
<212> TYPE: DNA
<213> ORGANISM: artificial sequence
<220> FEATURE:
<223> OTHER INFORMATION: primer

<400> SEQUENCE: 137
gcatatttga gaagatgcgg ccagcaaaac 30

<210> SEQ ID NO 138
<211> LENGTH: 30
<212> TYPE: DNA
<213> ORGANISM: artificial sequence
<220> FEATURE:
<223> OTHER INFORMATION: primer

<400> SEQUENCE: 138
gaagtgtaga gagggttaaa attggcgtgc 30

<210> SEQ ID NO 139
<211> LENGTH: 5959
<212> TYPE: DNA
<213> ORGANISM: artificial sequence
<220> FEATURE:
<223> OTHER INFORMATION: Synthetic construct

<400> SEQUENCE: 139
agcttatggt acatttaggt ccagcagatg tgcccaagga attgatgcag caaattgaaa 60
attttgagaa gatctttaca gtgcctactg aaaccctcca ggctgtcacc aagcatttca 120
tttcagaact ggaaaagggt ttgtctaaaa agggggtaa tatcccaatg attccaggtt 180

-continued

```
gggtaatgga ttttcctaca ggaaaggaat ccggtgattt tttggcaata gacctaggag    240
gcacaaactt aagggttgta cttgttaagt taggcggtga tcgtacgttt gatacgacac    300
aatcgaaata taggttacca gatgcgatga gaactactca gaatcctgac gaactatggg    360
agttcatcgc agactcatta aaagcattca tcgacgaaca gttcccccag ggtatcagcg    420
aacctattcc actaggtttc actttctctt ttcctgcctc tcaaaacaag atcaacgaag    480
gcattctaca aagatggaca aagggcttcg atatacctaa catcgaaaat cacgacgttg    540
tgcctatgct acagaagcag attactaaaa gaaatattcc tattgaagtt gttgctctaa    600
ttaacgatac tacaggcacg ctcgttgcct cgtactacac tgaccctgaa acgaaaatgg    660
gcgttatttt cggtactggt gttaatggag cctactacga tgtctgttcg gatatcgaaa    720
aactgcaagg aaaactatcc gatgacattc caccttccgc gcctatggca ataaattgtg    780
aatacggatc ttttgataat gaacacgttg ttctacctag aactaaatat gatataacta    840
tcgatgaaga aagtccaaga cctggacaac aaacattcga aaagatgtcg tcaggttact    900
acttaggtga gatattgaga ctggctttga tggatatgta caaacagggt tttatcttca    960
agaatcaaga cttgagtaaa ttcgacaagc catttgttat ggatacttca tatcctgcta   1020
gaatagaaga agatcccttc gaaaacttgg aagacacaga tgatcttttc caaaacgaat   1080
ttggaattaa taccaccgta caagaaagaa agttgataag acgtttgtct gaacttatcg   1140
gagctagggc cgcaagactg agtgtgtgtg gtatagctgc tatttgccaa aagaggggat   1200
ataaaactgg tcacattgct gctgatggta gcgtttacaa tagataccca ggatttaagg   1260
aaaaagcagc caatgctcta aaagatatat acggttggac tcaaacctca ctcgatgatt   1320
accctattaa aattgttccg gctgaggatg gctccggtgc tggagccgca gttattgcag   1380
ctttggcaca gaaaaggata gcggaaggta aaagtgtagg tattattggt gcgtgagagt   1440
aagcgaattt cttatgattt atgattttta ttattaaata agttataaaa aaaataagtg   1500
tatacaaatt ttaaagtgac tcttaggttt taaaacgaaa attcttattc ttgagtaact   1560
ctttcctgta ggtcaggttg ctttctcagg tatagcatga ggtcgctctt attgaccaca   1620
cctctaccgg catgccgagc aaatgcctgc aaatcgctcc ccatttcacc caattgtaga   1680
tatgctaact ccagcaatga gttgatgaat ctcggtgtgt attttatgtc ctcagaggac   1740
aacacctgtg gtggatccgc attgcggatt acgtattcta atgttcagat aacttcgtat   1800
agcatacatt atacgaagtt atgcagattg tactgagagt gcaccatacc acagcttttc   1860
aattcaattc atcatttttt ttttattctt ttttttgatt tcggtttctt tgaaattttt   1920
ttgattcggt aatctccgaa cagaaggaag aacgaaggaa ggagcacaga cttagattgg   1980
tatatatacg catatgtagt gttgaagaaa catgaaattg cccagtattc ttaacccaac   2040
tgcacagaac aaaaacctgc aggaaacgaa gataaatcat gtcgaaagct acatataagg   2100
aacgtgctgc tactcatcct agtcctgttg ctgccaagct atttaatatc atgcacgaaa   2160
agcaaacaaa cttgtgtgct tcattggatg ttcgtaccac caaggaatta ctggagttag   2220
ttgaagcatt aggtcccaaa atttgtttac taaaaacaca tgtggatatc ttgactgatt   2280
tttccatgga gggcacagtt aagccgctaa aggcattatc cgccaagtac aatttttttac   2340
tcttcgaaga cagaaaattt gctgacattg gtaatacagt caaattgcag tactctgcgg   2400
gtgtatacag aatagcagaa tgggcagaca ttacgaatgc acacggtgtg gtgggcccag   2460
gtattgttag cggtttgaag caggcggcag aagaagtaac aaaggaacct agaggccttt   2520
tgatgttagc agaattgtca tgcaagggct ccctatctac tggagaatat actaagggta   2580
```

-continued ctgttgacat tgcgaagagc gacaaagatt ttgttatcgg ctttattgct caaagagaca 2640
tgggtggaag agatgaaggt tacgattggt tgattatgac acccggtgtg ggtttagatg 2700
acaagggaga cgcattgggt caacagtata gaaccgtgga tgatgtggtc tctacaggat 2760
ctgacattat tattgttgga agaggactat ttgcaaaggg aagggatgct aaggtagagg 2820
gtgaacgtta cagaaaagca ggctgggaag catatttgag aagatgcggc cagcaaaact 2880
aaaaaactgt attataagta aatgcatgta tactaaactc acaaattaga gcttcaattt 2940
aattatatca gttattaccc tatgcggtgt gaaataccgc acagatgcgt aaggagaaaa 3000
taccgcatca ggaaattgta aacgttaata ttttgttaaa attcgcgtta aatttttgtt 3060
aaatcagctc atttttaac caataggccg aaatcggcaa aatcccttat aaatcaaaag 3120
aatagaccga gatagggttg agtgttgttc cagtttggaa caagagtcca ctattaaaga 3180
acgtggactc caacgtcaaa gggcgaaaaa ccgtctatca gggcgatggc ccactacgtg 3240
aaccatcacc ctaatcaaga taacttcgta tagcatacat tatacgaagt tatccagtga 3300
tgatacaacg agttagccaa ggtgaattca ctggccgtcg ttttacaacg tcgtgactgg 3360
gaaaaccctg gcgttaccca acttaatcgc cttgcagcac atcccccttt cgccagctgg 3420
cgtaatagcg aagaggcccg caccgatcgc ccttcccaac agttgcgcag cctgaatggc 3480
gaatggcgcc tgatgcggta ttttctcctt acgcatctgt gcggtatttc acaccgcata 3540
tggtgcactc tcagtacaat ctgctctgat gccgcatagt taagccagcc ccgacacccg 3600
ccaacacccg ctgacgcgcc ctgacgggct tgtctgctcc cggcatccgc ttacagacaa 3660
gctgtgaccg tctccgggag ctgcatgtgt cagaggtttt caccgtcatc accgaaacgc 3720
gcgagacgaa agggcctcgt gatacgccta tttttatagg ttaatgtcat gataataatg 3780
gtttcttaga cgtcaggtgg cacttttcgg ggaaatgtgc gcggaacccc tatttgttta 3840
tttttctaaa tacattcaaa tatgtatccg ctcatgagac aataaccctg ataaatgctt 3900
caataatatt gaaaaaggaa gagtatgagt attcaacatt tccgtgtcgc ccttattccc 3960
ttttttgcgg cattttgcct tcctgttttt gctcacccag aaacgctggt gaaagtaaaa 4020
gatgctgaag atcagttggg tgcacgagtg ggttacatcg aactggatct caacagcggt 4080
aagatccttg agagttttcg ccccgaagaa cgttttccaa tgatgagcac ttttaaagtt 4140
ctgctatgtg gcgcggtatt atcccgtatt gacgccgggc aagagcaact cggtcgccgc 4200
atacactatt ctcagaatga cttggttgag tactcaccag tcacagaaaa gcatcttacg 4260
gatggcatga cagtaagaga attatgcagt gctgccataa ccatgagtga taacactgcg 4320
gccaacttac ttctgacaac gatcggagga ccgaaggagc taaccgcttt tttgcacaac 4380
atgggggatc atgtaactcg ccttgatcgt tgggaaccgg agctgaatga agccatacca 4440
aacgacgagc gtgacaccac gatgcctgta gcaatggcaa caacgttgcg caaactatta 4500
actggcgaac tacttactct agcttcccgg caacaattaa tagactggat ggaggcggat 4560
aaagttgcag gaccacttct gcgctcggcc cttccggctg gctggtttat tgctgataaa 4620
tctggagccg gtgagcgtgg gtctcgcggt atcattgcag cactggggcc agatggtaag 4680
ccctcccgta tcgtagttat ctacacgacg gggagtcagg caactatgga tgaacgaaat 4740
agacagatcg ctgagatagg tgcctcactg attaagcatt ggtaactgtc agaccaagtt 4800
tactcatata tactttagat tgatttaaaa cttcattttt aatttaaaag gatctaggtg 4860
aagatccttt ttgataatct catgaccaaa atcccttaac gtgagttttc gttccactga 4920
gcgtcagacc ccgtagaaaa gatcaaagga tcttcttgag atcctttttt tctgcgcgta 4980

```
atctgctgct tgcaaacaaa aaaaccaccg ctaccagcgg tggtttgttt gccggatcaa   5040
gagctaccaa ctctttttcc gaaggtaact ggcttcagca gagcgcagat accaaatact   5100
gtccttctag tgtagccgta gttaggccac cacttcaaga actctgtagc accgcctaca   5160
tacctcgctc tgctaatcct gttaccagtg gctgctgcca gtggcgataa gtcgtgtctt   5220
accgggttgg actcaagacg atagttaccg gataaggcgc agcggtcggg ctgaacgggg   5280
ggttcgtgca cacagcccag cttggagcga acgacctaca ccgaactgag atacctacag   5340
cgtgagctat gagaaagcgc cacgcttccc gaagggagaa aggcggacag gtatccggta   5400
agcggcaggg tcggaacagg agagcgcacg agggagcttc cagggggaaa cgcctggtat   5460
ctttatagtc ctgtcgggtt tcgccacctc tgacttgagc gtcgattttt gtgatgctcg   5520
tcaggggggc ggagcctatg gaaaaacgcc agcaacgcgg cctttttacg gttcctggcc   5580
ttttgctggc cttttgctca catgttcttt cctgcgttat cccctgattc tgtggataac   5640
cgtattaccg cctttgagtg agctgatacc gctcgccgca gccgaacgac cgagcgcagc   5700
gagtcagtga gcgaggaagc ggaagagcgc ccaatacgca aaccgcctct ccccgcgcgt   5760
tggccgattc attaatgcag ctggcacgac aggtttcccg actggaaagc gggcagtgag   5820
cgcaacgcaa ttaatgtgag ttagctcact cattaggcac cccaggcttt acactttatg   5880
cttccggctc gtatgttgtg tggaattgtg agcggataac aatttcacac aggaaacagc   5940
tatgaccatg attacgcca                                                5959
```

<210> SEQ ID NO 140
<211> LENGTH: 500
<212> TYPE: DNA
<213> ORGANISM: Saccharomyces cerevisiae

<400> SEQUENCE: 140

```
cttttaacat ttgggcgaga ccactcttga tcttaaagtc ttctccagtc atcgtgataa     60
ttaactgaat attagtactg tgtatatttg ctagtcgttc ctaaaggttt ctccaacaat    120
accatagact tcgtccatag ctctcagcgt cctcctattt atatcgaaaa tggtacttcg    180
cagccagaat tacagacgta actaacggtg cggcagagtg tgtcagagtc atgaagaaat    240
ggcggcgcta cctgaaaagt agtgaaaaag cccggctttc aacccttacc cttgtcggct    300
gagtcattat gtcatgatga gctattccaa ctagtgccat aaattccaac tgagtcagta    360
aacggcattt atcagcaata actggtcacg aactctttga atgttttatt ctttcttcca    420
aaaatcacgt tgatgccacc aggttttttt ttcttattat ttcatttcgt taaatagaaa    480
gaaaaaccat atcttaaagt                                                500
```

<210> SEQ ID NO 141
<211> LENGTH: 500
<212> TYPE: DNA
<213> ORGANISM: Saccharomyces cerevisiae

<400> SEQUENCE: 141

```
ccccaattac tttcatcgac tttccggaca ttgtactgtg ggttttgtgc atactttaag     60
atatggtttt tctttctatt taacgaaatg aaataataag aaaaaaaaac ctggtggcat    120
caacgtgatt tttggaagaa agaataaaac attcaaagag ttcgtgacca gttattgctg    180
ataaatgccg tttactgact cagttggaat ttatggcact agttggaata gctcatcatg    240
acataatgac tcagccgaca agggtaaggg ttgaaagccg ggctttttca ctacttttca    300
ggtagcgccg ccatttcttc atgactctga cacactctgc cgcaccgtta gttacgtctg    360
```

taattctggc tgcgaagtac cattttcgat ataaatagga ggacgctgag agctatggac 420
gaagtctatg gtattgttgg agaaaccttt aggaacgact agcaaatata cacagtacta 480
atattcagtt aattatcacg 500

<210> SEQ ID NO 142
<211> LENGTH: 9333
<212> TYPE: DNA
<213> ORGANISM: Artificial sequence
<220> FEATURE:
<223> OTHER INFORMATION: Synthetic construct

<400> SEQUENCE: 142
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataccac agcttttcaa ttcaattcat cattttttt ttattctttt ttttgatttc 240
ggtttctttg aaattttttt gattcggtaa tctccgaaca gaaggaagaa cgaaggaagg 300
agcacagact tagattggta tatatacgca tatgtagtgt tgaagaaaca tgaaattgcc 360
cagtattctt aacccaactg cacagaacaa aaacctgcag gaaacgaaga taaatcatgt 420
cgaaagctac atataaggaa cgtgctgcta ctcatcctag tcctgttgct gccaagctat 480
ttaatatcat gcacgaaaag caaacaaact tgtgtgcttc attggatgtt cgtaccacca 540
aggaattact ggagttagtt gaagcattag gtcccaaaat ttgtttacta aaaacacatg 600
tggatatctt gactgatttt tccatggagg gcacagttaa gccgctaaag gcattatccg 660
ccaagtacaa tttttactc ttcgaagaca gaaaatttgc tgacattggt aatacagtca 720
aattgcagta ctctgcgggt gtatacagaa tagcagaatg ggcagacatt acgaatgcac 780
acggtgtggt gggcccaggt attgttagcg gtttgaagca ggcggcagaa gaagtaacaa 840
aggaacctag aggccttttg atgttagcag aattgtcatg caagggctcc ctatctactg 900
gagaatatac taagggtact gttgacattg cgaagagcga caaagatttt gttatcggct 960
ttattgctca aagagacatg ggtggaagag atgaaggtta cgattggttg attatgacac 1020
ccggtgtggg tttagatgac aagggagacg cattgggtca acagtataga accgtggatg 1080
atgtggtctc tacaggatct gacattatta ttgttggaag aggactattt gcaaagggaa 1140
gggatgctaa ggtagagggt gaacgttaca gaaaagcagg ctgggaagca tatttgagaa 1200
gatgcggcca gcaaaactaa aaaactgtat tataagtaaa tgcatgtata ctaaactcac 1260
aaattagagc ttcaatttaa ttatatcagt tattacccta tgcggtgtga aataccgcac 1320
agatgcgtaa ggagaaaata ccgcatcagg aaattgtaaa cgttaatatt ttgttaaaat 1380
tcgcgttaaa tttttgttaa atcagctcat tttttaacca ataggccgaa atcggcaaaa 1440
tcccttataa atcaaaagaa tagaccgaga tagggttgag tgttgttcca gtttggaaca 1500
agagtccact attaaagaac gtggactcca acgtcaaagg gcgaaaaacc gtctatcagg 1560
gcgatggccc actacgtgaa ccatcaccct aatcaagttt tttggggtcg aggtgccgta 1620
aagcactaaa tcggaaccct aaagggagcc cccgatttag agcttgacgg ggaaagccgg 1680
cgaacgtggc gagaaaggaa gggaagaaag cgaaaggagc gggcgctagg gcgctggcaa 1740
gtgtagcggt cacgctgcgc gtaaccacca cacccgccgc gcttaatgcg ccgctacagg 1800
gcgcgtcgcg ccattcgcca ttcaggctgc gcaactgttg ggaagggcga tcggtgcggg 1860
cctcttcgct attacgccag ctggcgaaag ggggatgtgc tgcaaggcga ttaagttggg 1920

-continued

```
taacgccagg gttttcccag tcacgacgtt gtaaaacgac ggccagtgag cgcgcgtaat   1980
acgactcact atagggcgaa ttgggtaccg ggccccccct cgaggtcgac tggccattaa   2040
tctttcccat attagatttc gccaagccat gaaagttcaa gaaaggtctt tagacgaatt   2100
acccttcatt tctcaaactg gcgtcaaggg atcctggtat ggttttatcg ttttatttct   2160
ggttcttata gcatcgtttt ggacttctct gttcccatta ggcggttcag gagccagcgc   2220
agaatcattc tttgaaggat acttatcctt tccaattttg attgtctgtt acgttggaca   2280
taaactgtat actagaaatt ggactttgat ggtgaaacta gaagatatgg atcttgatac   2340
cggcagaaaa caagtagatt tgactcttcg tagggaagaa atgaggattg agcgagaaac   2400
attagcaaaa agatccttcg taacaagatt tttacatttc tggtgttgaa gggaaagata   2460
tgagctatac agcggaattt ccatatcact cagattttgt tatctaattt tttccttccc   2520
acgtccgcgg gaatctgtgt atattactgc atctagatat atgttatctt atcttggcgc   2580
gtacatttaa ttttcaacgt attctataag aaattgcggg agttttttttc atgtagatga   2640
tactgactgc acgcaaatat aggcatgatt tataggcatg atttgatggc tgtaccgata   2700
ggaacgctaa gagtaacttc agaatcgtta tcctggcgga aaaaattcat ttgtaaactt   2760
taaaaaaaaa agccaatatc cccaaaatta ttaagagcgc ctccattatt aactaaaatt   2820
tcactcagca tccacaatgt atcaggtatc tactacagat attacatgtg gcgaaaaaga   2880
caagaacaat gcaatagcgc atcaagaaaa aacacaaagc tttcaatcaa tgaatcgaaa   2940
atgtcattaa aatagtatat aaattgaaac taagtcataa agctataaaa agaaaattta   3000
tttaaatgca agatttaaag taaattcacg gccctgcagg cctcagctct tgttttgttc   3060
tgcaaataac ttacccatct ttttcaaaac tttaggtgca ccctcctttg ctagaataag   3120
ttctatccaa tacatcctat ttggatctgc ttgagcttct ttcatcacgg atacgaattc   3180
attttctgtt ctcacaattt tggacacaac tctgtcttcc gttgccccga aactttctgg   3240
cagttttgag taattccaca taggaatgtc attataactc tggttcggac catgaatttc   3300
cctctcaacc gtgtaaccat cgttattaat gataaagcag attgggttta tcttctctct   3360
aatggctagt cctaattctt ggacagtcag ttgcaatgat ccatctccga taaacaataa   3420
atgtctagat tctttatctg caatttggct gcctagagct gcggggaaag tgtatcctat   3480
agatccccac aagggttgac caataaaatg tgatttcgat ttcagaaata tagatgaggc   3540
accgaagaaa gaagtgcctt gttcagccac gatcgtctca ttactttggg tcaaattttc   3600
gacagcttgc cacagtctat cttgtgacaa cagcgcgtta gaaggtacaa aatcttcttg   3660
ctttttatct atgtacttgc ctttatattc aatttcggac aagtcaagaa gagatgatat   3720
cagggattcg aagtcgaaat tttggattct ttcgttgaaa attttacctt catcgatatt   3780
caaggaaatc attttatttt cattaagatg gtgagtaaat gcacccgtac tagaatcggt   3840
aagctttaca cccaacataa gaataaaatc agcagattcc acaaattcct tcaagtttgg   3900
ctctgacaga gtaccgttgt aaatccccaa aaatgagggc aatgcttcat caacagatga   3960
tttaccaaag ttcaaagtag taataggtaa cttagtcttt gaaataaact gagtaacagt   4020
cttctctagg ccgaacgata taatttcatg gcctgtgatt acaattggtt tcttggcatt   4080
cttcagactt tcctgtattt tgttcagaat ctcttgatca gatgtattcg acgtggaatt   4140
ttccttctta agaggcaagg atggtttttc agccttagcg gcagctacat ctacaggtaa   4200
attgatgtaa accggctttc tttcctttag taaggcagac aacactctat caatttcaac   4260
agttgcattc tcggctgtca ataaagtcct ggcagcagta accggttcgt gcatcttcat   4320
```

```
aaagtgcttg aaatcaccat cagccaacgt atggtgaaca aacttacctt cgttctgcac   4380
tttcgaggta ggagatccca cgatctcaac aacaggcagg ttctcagcat aggagcccgc   4440
taagccatta actgcggata attcgccaac accaaatgta gtcaagaatg ccgcagcctt   4500
tttcgttctt gcgtacccgt cggccatata ggaggcattt aactcattag catttcccac   4560
ccatttcata tctttgtgtg aaataatttg atctagaaat tgcaaattgt agtcacctgg   4620
tactccgaat atttcttcta tacctaattc gtgtaatctg tccaacagat agtcacctac   4680
tgtatacatt ttgtttacta gtttatgtgt gtttattcga aactaagttc ttggtgtttt   4740
aaaactaaaa aaaagactaa ctataaaagt agaatttaag aagtttaaga aatagattta   4800
cagaattaca atcaatacct accgtcttta tatacttatt agtcaagtag gggaataatt   4860
tcagggaact ggtttcaacc tttttttca gctttttcca aatcagagag agcagaaggt   4920
aatagaaggt gtaagaaaat gagatagata catgcgtggg tcaattgcct tgtgtcatca   4980
tttactccag gcaggttgca tcactccatt gaggttgtgc ccgtttttg cctgtttgtg   5040
cccctgttct ctgtagttgc gctaagagaa tggacctatg aactgatggt tggtgaagaa   5100
aacaatattt tggtgctggg attctttttt tttctggatg ccagcttaaa aagcgggctc   5160
cattatattt agtggatgcc aggaataaac tgttcaccca gacacctacg atgttatata   5220
ttctgtgtaa cccgccccct atttgggca tgtacgggtt acagcagaat taaaaggcta   5280
attttttgac taaataaagt taggaaaatc actactatta attatttacg tattctttga   5340
aatggcagta ttgataatga taaactcgaa ctgaaaaagc gtgtttttta ttcaaaatga   5400
ttctaactcc cttacgtaat caaggaatct ttttgccttg gcctccgcgt cattaaactt   5460
cttgttgttg acgctaacat tcaacgctag tatatattcg tttttttcag gtaagttctt   5520
ttcaacgggt cttactgatg aggcagtcgc gtctgaacct gttaagaggt caaatatgtc   5580
ttcttgaccg tacgtgtctt gcatgttatt agctttggga atttgcatca agtcatagga   5640
aaatttaaat cttggctctc ttgggctcaa ggtgacaagg tcctcgaaaa tagggcgcgc   5700
cccaccgcgg tggagctcca gcttttgttc cctttagtga gggttaattg cgcgcttggc   5760
gtaatcatgg tcatagctgt ttcctgtgtg aaattgttat ccgctcacaa ttccacacaa   5820
cataggagcc ggaagcataa agtgtaaagc ctggggtgcc taatgagtga ggtaactcac   5880
attaattgcg ttgcgctcac tgcccgcttt ccagtcggga aacctgtcgt gccagctgca   5940
ttaatgaatc ggccaacgcg cggggagagg cggtttgcgt attgggcgct cttccgcttc   6000
ctcgctcact gactcgctgc gctcggtcgt tcggctgcgg cgagcggtat cagctcactc   6060
aaaggcggta atacggttat ccacagaatc aggggataac gcaggaaaga acatgtgagc   6120
aaaaggccag caaaaggcca ggaaccgtaa aaaggccgcg ttgctggcgt ttttccatag   6180
gctccgcccc cctgacgagc atcacaaaaa tcgacgctca agtcagaggt ggcgaaaccc   6240
gacaggacta taaagatacc aggcgtttcc ccctggaagc tccctcgtgc gctctcctgt   6300
tccgaccctg ccgcttaccg gatacctgtc cgcctttctc ccttcgggaa gcgtggcgct   6360
ttctcatagc tcacgctgta ggtatctcag ttcggtgtag gtcgttcgct ccaagctggg   6420
ctgtgtgcac gaaccccccg ttcagcccga ccgctgcgcc ttatccggta actatcgtct   6480
tgagtccaac ccggtaagac acgacttatc gccactggca gcagccactg gtaacaggat   6540
tagcagagcg aggtatgtag gcggtgctac agagttcttg aagtggtggc ctaactacgg   6600
ctacactaga aggacagtat ttggtatctg cgctctgctg aagccagtta ccttcggaaa   6660
aagagttggt agctcttgat ccggcaaaca aaccaccgct ggtagcggtg gtttttttgt   6720
```

-continued

```
ttgcaagcag cagattacgc gcagaaaaaa aggatctcaa gaagatcctt tgatcttttc   6780
tacggggtct gacgctcagt ggaacgaaaa ctcacgttaa gggattttgg tcatgagatt   6840
atcaaaaagg atcttcacct agatcctttt aaattaaaaa tgaagtttta aatcaatcta   6900
aagtatatat gagtaaactt ggtctgacag ttaccaatgc ttaatcagtg aggcacctat   6960
ctcagcgatc tgtctatttc gttcatccat agttgcctga ctccccgtcg tgtagataac   7020
tacgatacgg gagggcttac catctggccc cagtgctgca atgataccgc gagacccacg   7080
ctcaccggct ccagatttat cagcaataaa ccagccagcc ggaagggccg agcgcagaag   7140
tggtcctgca actttatccg cctccatcca gtctattaat tgttgccggg aagctagagt   7200
aagtagttcg ccagttaata gtttgcgcaa cgttgttgcc attgctacag gcatcgtggt   7260
gtcacgctcg tcgtttggta tggcttcatt cagctccggt tcccaacgat caaggcgagt   7320
tacatgatcc cccatgttgt gcaaaaaagc ggttagctcc ttcggtcctc cgatcgttgt   7380
cagaagtaag ttggccgcag tgttatcact catggttatg gcagcactgc ataattctct   7440
tactgtcatg ccatccgtaa gatgcttttc tgtgactggt gagtactcaa ccaagtcatt   7500
ctgagaatag tgtatgcggc gaccgagttg ctcttgcccg gcgtcaatac gggataatac   7560
cgcgccacat agcagaactt taaaagtgct catcattgga aaacgttctt cggggcgaaa   7620
actctcaagg atcttaccgc tgttgagatc cagttcgatg taacccactc gtgcacccaa   7680
ctgatcttca gcatctttta ctttcaccag cgtttctggg tgagcaaaaa caggaaggca   7740
aaatgccgca aaaaagggaa taagggcgac acggaaatgt tgaatactca tactcttcct   7800
ttttcaatat tattgaagca tttatcaggg ttattgtctc atgagcggat acatatttga   7860
atgtatttag aaaaataaac aaataggggt tccgcgcaca tttccccgaa aagtgccacc   7920
tgaacgaagc atctgtgctt cattttgtag aacaaaaatg caacgcgaga gcgctaattt   7980
ttcaaacaaa gaatctgagc tgcattttta cagaacagaa atgcaacgcg aaagcgctat   8040
tttaccaacg aagaatctgt gcttcatttt tgtaaaacaa aaatgcaacg cgagagcgct   8100
aatttttcaa acaaagaatc tgagctgcat ttttacagaa cagaaatgca acgcgagagc   8160
gctattttac caacaaagaa tctatacttc ttttttgttc tacaaaaatg catcccgaga   8220
gcgctatttt tctaacaaag catcttagat tacttttttt ctcctttgtg cgctctataa   8280
tgcagtctct tgataacttt ttgcactgta ggtccgttaa ggttagaaga aggctacttt   8340
ggtgtctatt ttctcttcca taaaaaaagc ctgactccac ttcccgcgtt tactgattac   8400
tagcgaagct gcgggtgcat tttttcaaga taaaggcatc cccgattata ttctataccg   8460
atgtggattg cgcatacttt gtgaacagaa agtgatagcg ttgatgattc ttcattggtc   8520
agaaaattat gaacggtttc ttctattttg tctctatata ctacgtatag gaaatgttta   8580
cattttcgta ttgttttcga ttcactctat gaatagttct tactacaatt tttttgtcta   8640
aagagtaata ctagagataa acataaaaaa tgtagaggtc gagtttagat gcaagttcaa   8700
ggagcgaaag gtggatgggt aggttatata gggatatagc acagagatat atagcaaaga   8760
gatacttttg agcaatgttt gtggaagcgg tattcgcaat attttagtag ctcgttacag   8820
tccggtgcgt ttttggtttt ttgaaagtgc gtcttcagag cgcttttggt tttcaaaagc   8880
gctctgaagt tcctatactt tctagagaat aggaacttcg gaataggaac ttcaaagcgt   8940
ttccgaaaac gagcgcttcc gaaaatgcaa cgcgagctgc gcacatacag ctcactgttc   9000
acgtcgcacc tatatctgcg tgttgcctgt atatatatat acatgagaag aacggcatag   9060
tgcgtgttta tgcttaaatg cgtacttata tgcgtctatt tatgtaggat gaaaggtagt   9120
```

ctagtacctc ctgtgatatt atcccattcc atgcggggta tcgtatgctt ccttcagcac 9180
taccctttag ctgttctata tgctgccact cctcaattgg attagtctca tccttcaatg 9240
ctatcatttc ctttgatatt ggatcatact aagaaaccat tattatcatg acattaacct 9300
ataaaaatag gcgtatcacg aggccctttc gtc 9333

<210> SEQ ID NO 143
<211> LENGTH: 9075
<212> TYPE: DNA
<213> ORGANISM: Artificial sequence
<220> FEATURE:
<223> OTHER INFORMATION: Synthetic construct

<400> SEQUENCE: 143
ctagttctag agcggccgcc accgcggtgg agctccagct tttgttccct ttagtgaggg 60
ttaattgcgc gcttggcgta atcatggtca tagctgtttc ctgtgtgaaa ttgttatccg 120
ctcacaattc cacacaacat aggagccgga agcataaagt gtaaagcctg gggtgcctaa 180
tgagtgaggt aactcacatt aattgcgttg cgctcactgc ccgctttcca gtcgggaaac 240
ctgtcgtgcc agctgcatta atgaatcggc caacgcgcgg ggagaggcgg tttgcgtatt 300
gggcgctctt ccgcttcctc gctcactgac tcgctgcgct cggtcgttcg gctgcggcga 360
gcggtatcag ctcactcaaa ggcggtaata cggttatcca cagaatcagg ggataacgca 420
ggaaagaaca tgtgagcaaa aggccagcaa aaggccagga accgtaaaaa ggccgcgttg 480
ctggcgtttt tccataggct ccgcccccct gacgagcatc acaaaaatcg acgctcaagt 540
cagaggtggc gaaacccgac aggactataa agataccagg cgtttccccc tggaagctcc 600
ctcgtgcgct ctcctgttcc gaccctgccg cttaccggat acctgtccgc ctttctccct 660
tcgggaagcg tggcgctttc tcatagctca cgctgtaggt atctcagttc ggtgtaggtc 720
gttcgctcca agctgggctg tgtgcacgaa ccccccgttc agcccgaccg ctgcgcctta 780
tccggtaact atcgtcttga gtccaacccg gtaagacacg acttatcgcc actggcagca 840
gccactggta acaggattag cagagcgagg tatgtaggcg gtgctacaga gttcttgaag 900
tggtggccta actacggcta cactagaagg acagtatttg gtatctgcgc tctgctgaag 960
ccagttacct tcggaaaaag agttggtagc tcttgatccg gcaaacaaac caccgctggt 1020
agcggtggtt tttttgtttg caagcagcag attacgcgca gaaaaaaagg atctcaagaa 1080
gatcctttga tcttttctac ggggtctgac gctcagtgga acgaaaactc acgttaaggg 1140
attttggtca tgagattatc aaaaaggatc ttcacctaga tccttttaaa ttaaaaatga 1200
agttttaaat caatctaaag tatatatgag taaacttggt ctgacagtta ccaatgctta 1260
atcagtgagg cacctatctc agcgatctgt ctatttcgtt catccatagt tgcctgactc 1320
cccgtcgtgt agataactac gatacgggag ggcttaccat ctggccccag tgctgcaatg 1380
ataccgcgag acccacgctc accggctcca gatttatcag caataaacca gccagccgga 1440
agggccgagc gcagaagtgg tcctgcaact ttatccgcct ccatccagtc tattaattgt 1500
tgccgggaag ctagagtaag tagttcgcca gttaatagtt tgcgcaacgt tgttgccatt 1560
gctacaggca tcgtggtgtc acgctcgtcg tttggtatgg cttcattcag ctccggttcc 1620
caacgatcaa ggcgagttac atgatccccc atgttgtgca aaaaagcggt tagctccttc 1680
ggtcctccga tcgttgtcag aagtaagttg gccgcagtgt tatcactcat ggttatggca 1740
gcactgcata attctcttac tgtcatgcca tccgtaagat gcttttctgt gactggtgag 1800
tactcaacca agtcattctg agaatagtgt atgcggcgac cgagttgctc ttgcccggcg 1860

```
tcaatacggg ataataccgc gccacatagc agaactttaa aagtgctcat cattggaaaa   1920
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga acgaagcatc tgtgcttcat tttgtagaac aaaaatgcaa   2280
cgcgagagcg ctaatttttc aaacaaagaa tctgagctgc atttttacag aacagaaatg   2340
caacgcgaaa gcgctatttt accaacgaag aatctgtgct tcatttttgt aaaacaaaaa   2400
tgcaacgcga gagcgctaat ttttcaaaca aagaatctga gctgcatttt tacagaacag   2460
aaatgcaacg cgagagcgct attttaccaa caaagaatct atacttcttt tttgttctac   2520
aaaaatgcat cccgagagcg ctatttttct aacaaagcat cttagattac tttttttctc   2580
ctttgtgcgc tctataatgc agtctcttga taactttttg cactgtaggt ccgttaaggt   2640
tagaagaagg ctactttggt gtctattttc tcttccataa aaaaagcctg actccacttc   2700
ccgcgtttac tgattactag cgaagctgcg ggtgcatttt ttcaagataa aggcatcccc   2760
gattatattc tataccgatg tggattgcgc atactttgtg aacagaaagt gatagcgttg   2820
atgattcttc attggtcaga aaattatgaa cggtttcttc tattttgtct ctatatacta   2880
cgtataggaa atgtttacat tttcgtattg ttttcgattc actctatgaa tagttcttac   2940
tacaattttt ttgtctaaag agtaatacta gagataaaca taaaaaatgt agaggtcgag   3000
tttagatgca agttcaagga gcgaaaggtg gatgggtagg ttatataggg atatagcaca   3060
gagatatata gcaaagagat acttttgagc aatgtttgtg gaagcggtat tcgcaatatt   3120
ttagtagctc gttacagtcc ggtgcgtttt tggttttttg aaagtgcgtc ttcagagcgc   3180
ttttggtttt caaaagcgct ctgaagttcc tatactttct agagaatagg aacttcggaa   3240
taggaacttc aaagcgtttc cgaaaacgag cgcttccgaa aatgcaacgc gagctgcgca   3300
catacagctc actgttcacg tcgcacctat atctgcgtgt tgcctgtata tatatataca   3360
tgagaagaac ggcatagtgc gtgtttatgc ttaaatgcgt acttatatgc gtctatttat   3420
gtaggatgaa aggtagtcta gtacctcctg tgatattatc ccattccatg cggggtatcg   3480
tatgcttcct tcagcactac cctttagctg ttctatatgc tgccactcct caattggatt   3540
agtctcatcc ttcaatgcta tcatttcctt tgatattgga tcatactaag aaaccattat   3600
tatcatgaca ttaacctata aaaataggcg tatcacgagg ccctttcgtc tcgcgcgttt   3660
cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
tttatttgtt gtattttttt ttttttagag aaaatcctcc aatatcaaat taggaatcgt   4020
agtttcatga ttttctgtta cacctaactt tttgtgtggt gccctcctcc ttgtcaatat   4080
taatgttaaa gtgcaattct ttttccttat cacgttgagc cattagtatc aatttgctta   4140
cctgtattcc tttactatcc tcctttttct ccttcttgat aaatgtatgt agattgcgta   4200
tatagtttcg tctaccctat gaacatattc cattttgtaa tttcgtgtcg tttctattat   4260
```

-continued

```
gaatttcatt tataaagttt atgtacaaat atcataaaaa aagagaatct ttttaagcaa   4320
ggattttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
aaatacctcc cactaattct ctgacaacaa cgaagtcagt acctttagca aattgtggct   5040
tgattggaga taagtctaaa agagagtcgg atgcaaagtt acatggtctt aagttggcgt   5100
acaattgaag ttctttacgg atttttagta aaccttgttc aggtctaaca ctaccggtac   5160
cccatttagg accagccaca gcacctaaca aaacggcatc aaccttcttg gaggcttcca   5220
gcgcctcatc tggaagtggg acacctgtag catcgatagc agcaccacca attaaatgat   5280
tttcgaaatc gaacttgaca ttggaacgaa catcagaaat agctttaaga accttaatgg   5340
cttcggctgt gatttcttga ccaacgtggt cacctggcaa aacgacgatc ttcttagggg   5400
cagacatagg ggcagacatt agaatggtat atccttgaaa tatatatata tattgctgaa   5460
atgtaaaagg taagaaaagt tagaaagtaa gacgattgct aaccacctat tggaaaaaac   5520
aataggtcct taaataatat tgtcaacttc aagtattgtg atgcaagcat ttagtcatga   5580
acgcttctct attctatatg aaaagccggt tccggcctct cacctttcct ttttctccca   5640
atttttcagt tgaaaaaggt atatgcgtca ggcgacctct gaaattaaca aaaaatttcc   5700
agtcatcgaa tttgattctg tgcgatagcg cccctgtgtg ttctcgttat gttgaggaaa   5760
aaaataatgg ttgctaagag attcgaactc ttgcatctta cgatacctga gtattcccac   5820
agttaactgc ggtcaagata tttcttgaat caggcgcctt agaccgctcg gccaaacaac   5880
caattacttg ttgagaaata gagtataatt atcctataaa tataacgttt ttgaacacac   5940
atgaacaagg aagtacagga caattgattt tgaagagaat gtggattttg atgtaattgt   6000
tgggattcca tttttaataa ggcaataata ttaggtatgt ggatatacta gaagttctcc   6060
tcgaccgtcg atatgcggtg tgaaataccg cacagatgcg taaggagaaa ataccgcatc   6120
aggaaattgt aaacgttaat attttgttaa aattcgcgtt aaatttttgt taaatcagct   6180
cattttttaa ccaataggcc gaaatcggca aaatccctta taaatcaaaa gaatagaccg   6240
agatagggtt gagtgttgtt ccagtttgga acaagagtcc actattaaag aacgtggact   6300
ccaacgtcaa agggcgaaaa accgtctatc agggcgatgg cccactacgt gaaccatcac   6360
cctaatcaag ttttttgggg tcgaggtgcc gtaaagcact aaatcggaac cctaaaggga   6420
gcccccgatt tagagcttga cggggaaagc cggcgaacgt ggcgagaaag gaagggaaga   6480
aagcgaaagg agcgggcgct agggcgctgg caagtgtagc ggtcacgctg cgcgtaacca   6540
ccacacccgc cgcgcttaat gcgccgctac agggcgcgtc gcgccattcg ccattcaggc   6600
tgcgcaactg ttgggaaggg cgatcggtgc gggcctcttc gctattacgc cagctggcga   6660
```

-continued aaggggggatg tgctgcaagg cgattaagtt gggtaacgcc agggttttcc cagtcacgac 6720
gttgtaaaac gacggccagt gagcgcgcgt aatacgactc actatagggc gaattgggta 6780
ccgggccccc cctcgaggtc gacggtatcg ataagcttga tatcgaattc ctgcagcccg 6840
ggggatccgc atgcttgcat ttagtcgtgc aatgtatgac tttaagattt gtgagcagga 6900
agaaaaggga gaatcttcta acgataaacc cttgaaaaac tgggtagact acgctatgtt 6960
gagttgctac gcaggctgca caattacacg agaatgctcc cgcctaggat ttaaggctaa 7020
gggacgtgca atgcagacga cagatctaaa tgaccgtgtc ggtgaagtgt tcgccaaact 7080
tttcggttaa cacatgcagt gatgcacgcg cgatggtgct aagttacata tatatatata 7140
tatatatata tagccatagt gatgtctaag taacctttat ggtatatttc ttaatgtgga 7200
aagatactag cgcgcgcacc cacacacaag cttcgtcttt tcttgaagaa aagaggaagc 7260
tcgctaaatg ggattccact ttccgttccc tgccagctga tggaaaaagg ttagtggaac 7320
gatgaagaat aaaaagagag atccactgag gtgaaatttc agctgacagc gagtttcatg 7380
atcgtgatga acaatggtaa cgagttgtgg ctgttgccag ggagggtggt tctcaacttt 7440
taatgtatgg ccaaatcgct acttgggttt gttatataac aaagaagaaa taatgaactg 7500
attctcttcc tccttcttgt cctttcttaa ttctgttgta attaccttcc tttgtaattt 7560
tttttgtaat tattcttctt aataatccaa acaaacacac atattacaat agctagctga 7620
ggatgtcaac agccggtaaa gttattaagt gtaaagcggc agttttgtgg gaagagaaaa 7680
agccgtttag catagaagaa gtagaagtag cgccaccaaa agcacacgag gttagaatca 7740
agatggttgc caccggaatc tgtagatccg acgaccatgt ggtgagtggc actctagtta 7800
ctcctttgcc agtaatcgcg ggacacgagg ctgccggaat cgttgaatcc ataggtgaag 7860
gtgttaccac tgttcgtcct ggtgataaag tgatcccact gttcactcct caatgtggta 7920
agtgtagagt ctgcaaacat cctgagggta atttctgcct taaaaatgat ttgtctatgc 7980
ctagaggtac tatgcaggat ggtacaagca gatttacatg cagagggaaa cctatacacc 8040
atttccttgg tacttctaca ttttcccaat acacagtggt ggacgagata tctgtcgcta 8100
aaatcgatgc agcttcacca ctggaaaaag tttgcttgat agggtgcgga ttttccaccg 8160
gttacggttc cgcagttaaa gttgcaaagg ttacacaggg ttcgacttgt gcagtattcg 8220
gtttaggagg agtaggacta agcgttatta tggggtgtaa agctgcaggc gcagcgagga 8280
ttataggtgt agacatcaat aaggacaaat ttgcaaaagc taaggaggtc ggggctactg 8340
aatgtgttaa ccctcaagat tataagaaac caatacaaga agtccttact gaaatgtcaa 8400
acggtggagt tgatttctct tttgaagtta taggccgtct tgatactatg gtaactgcgt 8460
tgtcctgctg tcaagaggca tatggagtca gtgtgatcgt aggtgttcct cctgattcac 8520
aaaatttgtc gatgaatcct atgctgttgc taagcggtcg tacatggaag ggagctatat 8580
ttggcggttt taagagcaag gatagtgttc caaaacttgt tgccgacttt atggcgaaga 8640
agtttgctct tgatccttta attacacatg tattgccatt cgagaaaatc aatgaagggt 8700
ttgatttgtt aagaagtggt gaatctattc gtacaatttt aactttttga ttaattaaga 8760
gtaagcgaat ttcttatgat ttatgatttt tattattaaa taagttataa aaaaaataag 8820
tgtatacaaa ttttaaagtg actcttaggt tttaaaacga aaattcttat tcttgagtaa 8880
ctctttcctg taggtcaggt tgctttctca ggtatagcat gaggtcgctc ttattgacca 8940
cacctctacc ggcatgccga gcaaatgcct gcaaatcgct ccccatttca cccaattgta 9000
gatatgctaa ctccagcaat gagttgatga atctcggtgt gtattttatg tcctcagagg 9060
acaacacctg tggta 9075

<210> SEQ ID NO 144
<211> LENGTH: 11367
<212> TYPE: DNA
<213> ORGANISM: Artificial sequence
<220> FEATURE:
<223> OTHER INFORMATION: Synthetic construct

<400> SEQUENCE: 144
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatagcca tcctcatgaa aactgtgtaa cataataacc gaagtgtcga aaaggtggca 240
ccttgtccaa ttgaacacgc tcgatgaaaa aaataagata tatataaggt taagtaaagc 300
gtctgttaga aaggaagttt ttcctttttc ttgctctctt gtcttttcat ctactatttc 360
cttcgtgtaa tacagggtcg tcagatacat agatacaatt ctattacccc catccataca 420
atgccatctc atttcgatac tgttcaacta cacgccggcc aagagaaccc tggtgacaat 480
gctcacagat ccagagctgt accaatttac gccaccactt cttatgtttt cgaaaactct 540
aagcatggtt cgcaattgtt tggtctagaa gttccaggtt acgtctattc ccgtttccaa 600
aacccaacca gtaatgtttt ggaagaaaga attgctgctt tagaaggtgg tgctgctgct 660
ttggctgttt cctccggtca agccgctcaa acccttgcca tccaaggttt ggcacacact 720
ggtgacaaca tcgtttccac ttcttactta tacggtggta cttataacca gttcaaaatc 780
tcgttcaaaa gatttggtat cgaggctaga tttgttgaag gtgacaatcc agaagaattc 840
gaaaaggtct ttgatgaaag aaccaaggct gtttatttgg aaaccattgg taatccaaag 900
tacaatgttc cggattttga aaaaattgtt gcaattgctc acaaacacgg tattccagtt 960
gtcgttgaca acacatttgg tgccggtggt tacttctgtc agccaattaa atacggtgct 1020
gatattgtaa cacattctgc taccaaatgg attggtggtc atggtactac tatcggtggt 1080
attattgttg actctggtaa gttcccatgg aaggactacc cagaaaagtt ccctcaattc 1140
tctcaacctg ccgaaggata tcacggtact atctacaatg aagcctacgg taacttggca 1200
tacatcgttc atgttagaac tgaactatta agagatttgg gtccattgat gaacccattt 1260
gcctctttct tgctactaca aggtgttgaa acattatctt tgagagctga aagacacggt 1320
gaaaatgcat tgaagttagc caaatggtta gaacaatccc catacgtatc ttgggtttca 1380
taccctggtt tagcatctca ttctcatcat gaaaatgcta agaagtatct atctaacggt 1440
ttcggtggtg tcttatcttt cggtgtaaaa gacttaccaa atgccgacaa ggaaactgac 1500
ccattcaaac tttctggtgc tcaagttgtt gacaatttaa agcttgcctc taacttggcc 1560
aatgttggtg atgccaagac cttagtcatt gctccatact tcactaccca caaacaatta 1620
aatgacaaag aaaagttggc atctggtgtt accaaggact taattcgtgt ctctgttggt 1680
atcgaattta ttgatgacat tattgcagac ttccagcaat cttttgaaac tgttttcgct 1740
ggccaaaaac catgagtgtg cgtaatgagt tgtaaaatta tgtataaacc tactttctct 1800
cacaagttat gcggtgtgaa ataccgcaca gatgcgtaag gagaaaatac cgcatcagga 1860
aattgtaaac gttaatattt tgttaaaatt cgcgttaaat ttttgttaaa tcagctcatt 1920
ttttaaccaa taggccgaaa tcggcaaaat cccttataaa tcaaaagaat agaccgagat 1980
agggttgagt gttgttccag tttggaacaa gagtccacta ttaaagaacg tggactccaa 2040

-continued

```
cgtcaaaggg cgaaaaaccg tctatcaggg cgatggccca ctacgtgaac catcacccta   2100
atcaagtttt ttggggtcga ggtgccgtaa agcactaaat cggaacccta aagggagccc   2160
ccgatttaga gcttgacggg gaaagccggc gaacgtggcg agaaaggaag ggaagaaagc   2220
gaaaggagcg ggcgctaggg cgctggcaag tgtagcggtc acgctgcgcg taaccaccac   2280
acccgccgcg cttaatgcgc cgctacaggg cgcgtcgcgc cattcgccat tcaggctgcg   2340
caactgttgg gaagggcgat cggtgcgggc ctcttcgcta ttacgccagc tggcgaaagg   2400
gggatgtgct gcaaggcgat taagttgggt aacgccaggg ttttcccagt cacgacgttg   2460
taaaacgacg gccagtgagc gcgcgtaata cgactcacta tagggcgaat tgggtaccgg   2520
gccccccctc gaggtcgacg gtatcgataa gcttgatatc gaattcctgc agcccggggg   2580
atccactagt tctagagcgg ccgctctaga actagtacca caggtgttgt cctctgagga   2640
cataaaatac acaccgagat tcatcaactc attgctggag ttagcatatc tacaattggg   2700
tgaaatgggg agcgatttgc aggcatttgc tcggcatgcc ggtagaggtg tggtcaataa   2760
gagcgacctc atgctatacc tgagaaagca acctgaccta caggaaagag ttactcaaga   2820
ataagaattt tcgttttaaa acctaagagt cactttaaaa tttgtataca cttatttttt   2880
ttataactta tttaataata aaaatcataa atcataagaa attcgcttac tcttaattaa   2940
tcaaaaagtt aaaattgtac gaatagattc accacttctt aacaaatcaa acccttcatt   3000
gattttctcg aatggcaata catgtgtaat taaaggatca agagcaaact tcttcgccat   3060
aaagtcggca acaagttttg gaacactatc cttgctctta aaaccgccaa atatagctcc   3120
cttccatgta cgaccgctta gcaacagcat aggattcatc gacaaatttt gtgaatcagg   3180
aggaacacct acgatcacac tgactccata tgcctcttga cagcaggaca acgcagttac   3240
catagtatca agacggccta taacttcaaa agagaaatca actccaccgt ttgacatttc   3300
agtaaggact tcttgtattg gtttcttata atcttgaggg ttaacacatt cagtagcccc   3360
gacctcctta gcttttgcaa atttgtcctt attgatgtct acacctataa tcctcgctgc   3420
gcctgcagct ttacacccca taataacgct tagtcctact cctcctaaac cgaatactgc   3480
acaagtcgaa ccctgtgtaa cctttgcaac tttaactgcg gaaccgtaac cggtggaaaa   3540
tccgcaccct atcaagcaaa ctttttccag tggtgaagct gcatcgattt tagcgacaga   3600
tatctcgtcc accactgtgt attgggaaaa tgtagaagta ccaaggaaat ggtgtatagg   3660
tttccctctg catgtaaatc tgcttgtacc atcctgcata gtacctctag gcatagacaa   3720
atcattttta aggcagaaat taccctcagg atgtttgcag actctacact taccacattg   3780
aggagtgaac agtgggatca ctttatcacc aggacgaaca gtggtaacac cttcacctat   3840
ggattcaacg attccggcag cctcgtgtcc cgcgattact ggcaaaggag taactagagt   3900
gccactcacc acatggtcgt cggatctaca gattccggtg gcaaccatct tgattctaac   3960
ctcgtgtgct tttggtggcg ctacttctac ttcttctatg ctaaacggct ttttctcttc   4020
ccacaaaact gccgctttac acttaataac tttaccggct gttgacatcc tcagctagct   4080
attgtaatat gtgtgtttgt ttggattatt aagaagaata attacaaaaa aaattacaaa   4140
ggaaggtaat tacaacagaa ttaagaaagg acaagaagga ggaagagaat cagttcatta   4200
tttcttcttt gttatataac aaacccaagt agcgatttgg ccatacatta aaagttgaga   4260
accaccctcc ctggcaacag ccacaactcg ttaccattgt tcatcacgat catgaaactc   4320
gctgtcagct gaaatttcac ctcagtggat ctctcttttt attcttcatc gttccactaa   4380
cctttttcca tcagctggca gggaacggaa agtggaatcc catttagcga gcttcctctt   4440
```

-continued

```
ttcttcaaga aaagacgaag cttgtgtgtg ggtgcgcgcg ctagtatctt tccacattaa   4500
gaaatatacc ataaaggtta cttagacatc actatggcta tatatatata tatatatata   4560
tatgtaactt agcaccatcg cgcgtgcatc actgcatgtg ttaaccgaaa agtttggcga   4620
acacttcacc gacacggtca tttagatctg tcgtctgcat tgcacgtccc ttagccttaa   4680
atcctaggcg ggagcattct cgtgtaattg tgcagcctgc gtagcaactc aacatagcgt   4740
agtctaccca gtttttcaag ggtttatcgt tagaagattc tcccttttct tcctgctcac   4800
aaatcttaaa gtcatacatt gcacgactaa atgcaagcat gcggatcccc cgggctgcag   4860
gaattcgata tcaagcttat cgataccgtc gactggccat taatctttcc catattagat   4920
ttcgccaagc catgaaagtt caagaaaggt ctttagacga attacccttc atttctcaaa   4980
ctggcgtcaa gggatcctgg tatggtttta tcgttttatt tctggttctt atagcatcgt   5040
tttggacttc tctgttccca ttaggcggtt caggagccag cgcagaatca ttctttgaag   5100
gatacttatc ctttccaatt ttgattgtct gttacgttgg acataaactg tatactagaa   5160
attggacttt gatggtgaaa ctagaagata tggatcttga taccggcaga aaacaagtag   5220
atttgactct tcgtagggaa gaaatgagga ttgagcgaga aacattagca aaaagatcct   5280
tcgtaacaag atttttacat ttctggtgtt gaagggaaag atatgagcta tacagcggaa   5340
tttccatatc actcagattt tgttatctaa ttttttcctt cccacgtccg cgggaatctg   5400
tgtatattac tgcatctaga tatatgttat cttatcttgg cgcgtacatt taattttcaa   5460
cgtattctat aagaaattgc gggagttttt ttcatgtaga tgatactgac tgcacgcaaa   5520
tataggcatg atttataggc atgatttgat ggctgtaccg ataggaacgc taagagtaac   5580
ttcagaatcg ttatcctggc ggaaaaaatt catttgtaaa ctttaaaaaa aaaagccaat   5640
atccccaaaa ttattaagag cgcctccatt attaactaaa atttcactca gcatccacaa   5700
tgtatcaggt atctactaca gatattacat gtggcgaaaa agacaagaac aatgcaatag   5760
cgcatcaaga aaaaacacaa agctttcaat caatgaatcg aaaatgtcat taaaatagta   5820
tataaattga aactaagtca taaagctata aaaagaaaat ttatttaaat gcaagattta   5880
aagtaaattc acggccctgc aggcctcagc tcttgttttg ttctgcaaat aacttaccca   5940
tctttttcaa aactttaggt gcaccctcct ttgctagaat aagttctatc caatacatcc   6000
tatttggatc tgcttgagct tctttcatca cggatacgaa ttcattttct gttctcacaa   6060
ttttggacac aactctgtct tccgttgccc cgaaactttc tggcagtttt gagtaattcc   6120
acataggaat gtcattataa ctctggttcg gaccatgaat ttccctctca accgtgtaac   6180
catcgttatt aatgataaag cagattgggt ttatcttctc tctaatggct agtcctaatt   6240
cttggacagt cagttgcaat gatccatctc cgataaacaa taaatgtcta gattctttat   6300
ctgcaatttg gctgcctaga gctgcgggga aagtgtatcc tatagatccc cacaagggtt   6360
gaccaataaa atgtgatttc gatttcagaa atatagatga ggcaccgaag aaagaagtgc   6420
cttgttcagc cacgatcgtc tcattacttt gggtcaaatt ttcgacagct tgccacagtc   6480
tatcttgtga caacagcgcg ttagaaggta caaaatcttc ttgcttttta tctatgtact   6540
tgcctttata ttcaatttcg gacaagtcaa gaagagatga tatcagggat tcgaagtcga   6600
aattttggat tctttcgttg aaaattttac cttcatcgat attcaaggaa atcattttat   6660
tttcattaag atggtgagta aatgcacccg tactagaatc ggtaagcttt acacccaaca   6720
taagaataaa atcagcagat tccacaaatt ccttcaagtt tggctctgac agagtaccgt   6780
tgtaaatccc caaaaatgag ggcaatgctt catcaacaga tgatttacca aagttcaaag   6840
```

```
tagtaatagg taacttagtc tttgaaataa actgagtaac agtcttctct aggccgaacg   6900
atataatttc atggcctgtg attacaattg gtttcttggc attcttcaga ctttcctgta   6960
ttttgttcag aatctcttga tcagatgtat tcgacgtgga attttccttc ttaagaggca   7020
aggatggttt ttcagcctta gcggcagcta catctacagg taaattgatg taaaccggct   7080
ttctttcctt tagtaaggca gacaacactc tatcaatttc aacagttgca ttctcggctg   7140
tcaataaagt cctggcagca gtaaccggtt cgtgcatctt cataaagtgc ttgaaatcac   7200
catcagccaa cgtatggtga acaaacttac cttcgttctg cactttcgag gtaggagatc   7260
ccacgatctc aacaacaggc aggttctcag cataggagcc cgctaagcca ttaactgcgg   7320
ataattcgcc aacaccaaat gtagtcaaga atgccgcagc ctttttcgtt cttgcgtacc   7380
cgtcggccat ataggaggca tttaactcat tagcatttcc cacccatttc atatctttgt   7440
gtgaaataat ttgatctaga aattgcaaat tgtagtcacc tggtactccg aatatttctt   7500
ctatacctaa ttcgtgtaat ctgtccaaca gatagtcacc tactgtatac attttgttta   7560
ctagtttatg tgtgtttatt cgaaactaag ttcttggtgt tttaaaacta aaaaaaagac   7620
taactataaa agtagaattt aagaagttta agaaatagat ttacagaatt acaatcaata   7680
cctaccgtct ttatatactt attagtcaag taggggaata atttcaggga actggtttca   7740
acctttttt tcagcttttt ccaaatcaga gagagcagaa ggtaatagaa ggtgtaagaa   7800
aatgagatag atacatgcgt gggtcaattg ccttgtgtca tcatttactc caggcaggtt   7860
gcatcactcc attgaggttg tgcccgtttt ttgcctgttt gtgcccctgt tctctgtagt   7920
tgcgctaaga gaatggacct atgaactgat ggttggtgaa gaaaacaata ttttggtgct   7980
gggattcttt ttttttctgg atgccagctt aaaaagcggg ctccattata tttagtggat   8040
gccaggaata aactgttcac ccagacacct acgatgttat atattctgtg taacccgccc   8100
cctattttgg gcatgtacgg gttacagcag aattaaaagg ctaatttttt gactaaataa   8160
agttaggaaa atcactacta ttaattattt acgtattctt tgaaatggca gtattgataa   8220
tgataaactc gaactgaaaa agcgtgtttt ttattcaaaa tgattctaac tcccttacgt   8280
aatcaaggaa tctttttgcc ttggcctccg cgtcattaaa cttcttgttg ttgacgctaa   8340
cattcaacgc tagtatatat tcgttttttt caggtaagtt cttttcaacg ggtcttactg   8400
atgaggcagt cgcgtctgaa cctgttaaga ggtcaaatat gtcttcttga ccgtacgtgt   8460
cttgcatgtt attagctttg ggaatttgca tcaagtcata ggaaaattta aatcttggct   8520
ctcttgggct caaggtgaca aggtcctcga aaatagggcg cgccccaccg cggtggagct   8580
cagcttttgt tccctttagt gagggttaat tgcgcgcttg gcgtaatcat ggtcatagct   8640
gtttcctgtg tgaaattgtt atccgctcac aattccacac aacatacgag ccggaagcat   8700
aaagtgtaaa gcctggggtg cctaatgagt gagctaactc acattaattg cgttgcgctc   8760
actgcccgct ttccagtcgg gaaacctgtc gtgccagctg cattaatgaa tcggccaacg   8820
cgcggggaga ggcggtttgc gtattgggcg ctcttccgct tcctcgctca ctgactcgct   8880
gcgctcggtc gttcggctgc ggcgagcggt atcagctcac tcaaaggcgg taatacggtt   8940
atccacagaa tcaggggata acgcaggaaa gaacatgtga gcaaaaggcc agcaaaaggc   9000
caggaaccgt aaaaaggccg cgttgctggc gtttttccat aggctccgcc cccctgacga   9060
gcatcacaaa aatcgacgct caagtcagag gtggcgaaac ccgacaggac tataaagata   9120
ccaggcgttt ccccctggaa gctccctcgt gcgctctcct gttccgaccc tgccgcttac   9180
cggatacctg tccgcctttc tcccttcggg aagcgtggcg ctttctcata gctcacgctg   9240
```

```
taggtatctc agttcggtgt aggtcgttcg ctccaagctg ggctgtgtgc acgaaccccc   9300
cgttcagccc gaccgctgcg ccttatccgg taactatcgt cttgagtcca acccggtaag   9360
acacgactta tcgccactgg cagcagccac tggtaacagg attagcagag cgaggtatgt   9420
aggcggtgct acagagttct tgaagtggtg gcctaactac ggctacacta gaaggacagt   9480
atttggtatc tgcgctctgc tgaagccagt taccttcgga aaaagagttg gtagctcttg   9540
atccggcaaa caaaccaccg ctggtagcgg tggttttttt gtttgcaagc agcagattac   9600
gcgcagaaaa aaaggatctc aagaagatcc tttgatcttt tctacggggt ctgacgctca   9660
gtggaacgaa aactcacgtt aagggatttt ggtcatgaga ttatcaaaaa ggatcttcac   9720
ctagatcctt ttaaattaaa aatgaagttt taaatcaatc taaagtatat atgagtaaac   9780
ttggtctgac agttaccaat gcttaatcag tgaggcacct atctcagcga tctgtctatt   9840
tcgttcatcc atagttgcct gactccccgt cgtgtagata actacgatac gggagggctt   9900
accatctggc cccagtgctg caatgatacc gcgagaccca cgctcaccgg ctccagattt   9960
atcagcaata aaccagccag ccggaagggc cgagcgcaga agtggtcctg caactttatc  10020
cgcctccatc cagtctatta attgttgccg ggaagctaga gtaagtagtt cgccagttaa  10080
tagtttgcgc aacgttgttg ccattgctac aggcatcgtg gtgtcacgct cgtcgtttgg  10140
tatggcttca ttcagctccg gttcccaacg atcaaggcga gttacatgat cccccatgtt  10200
gtgcaaaaaa gcggttagct ccttcggtcc tccgatcgtt gtcagaagta agttggccgc  10260
agtgttatca ctcatggtta tggcagcact gcataattct cttactgtca tgccatccgt  10320
aagatgcttt tctgtgactg gtgagtactc aaccaagtca ttctgagaat agtgtatgcg  10380
gcgaccgagt tgctcttgcc cggcgtcaat acgggataat accgcgccac atagcagaac  10440
tttaaaagtg ctcatcattg gaaaacgttc ttcggggcga aaactctcaa ggatcttacc  10500
gctgttgaga tccagttcga tgtaacccac tcgtgcaccc aactgatctt cagcatcttt  10560
tactttcacc agcgtttctg ggtgagcaaa aacaggaagg caaaatgccg caaaaaaggg  10620
aataagggcg acacggaaat gttgaatact catactcttc ctttttcaat attattgaag  10680
catttatcag ggttattgtc tcatgagcgg atacatattt gaatgtattt agaaaaataa  10740
acaaataggg gttccgcgca catttccccg aaaagtgcca cctgggtcct tttcatcacg  10800
tgctataaaa ataattataa tttaaatttt ttaatataaa tatataaatt aaaaatagaa  10860
agtaaaaaaa gaaattaaag aaaaaatagt ttttgttttc cgaagatgta aaagactcta  10920
gggggatcgc caacaaatac taccttttat cttgctcttc ctgctctcag gtattaatgc  10980
cgaattgttt catcttgtct gtgtagaaga ccacacacga aaatcctgtg attttacatt  11040
ttacttatcg ttaatcgaat gtatatctat ttaatctgct tttcttgtct aataaatata  11100
tatgtaaagt acgctttttg ttgaaatttt ttaaaccttt gtttattttt ttttcttcat  11160
tccgtaactc ttctaccttc tttatttact ttctaaaatc caaatacaaa acataaaaat  11220
aaataaacac agagtaaatt cccaaattat tccatcatta aaagatacga ggcgcgtgta  11280
agttacaggc aagcgatccg tcctaagaaa ccattattat catgacatta acctataaaa  11340
ataggcgtat cacgaggccc tttcgtc                                      11367
```